US010882902B2

United States Patent
Grimm et al.

(10) Patent No.: US 10,882,902 B2
(45) Date of Patent: Jan. 5, 2021

(54) HUMAN ISLET AMYLOID POLYPEPTIDE (HIAPP) SPECIFIC ANTIBODIES AND USES THEREOF

(71) Applicant: Neurimmune Holding AG, Schlieren (CH)

(72) Inventors: Jan Grimm, Dubendorf (CH); Fabrice Heitz, Bartenheim (FR); Feng Chen, Zurich (CH); Ioana Combaluzier, Urdorf (CH)

(73) Assignee: Neurimmune Holding AG, Schlieren (CH)

( * ) Notice: Subject to any disclaimer, the term of this patent is extended or adjusted under 35 U.S.C. 154(b) by 93 days.

(21) Appl. No.: 16/058,630

(22) Filed: Aug. 8, 2018

(65) Prior Publication Data

US 2018/0346558 A1  Dec. 6, 2018

Related U.S. Application Data

(60) Continuation of application No. 15/258,883, filed on Sep. 7, 2016, now Pat. No. 10,072,074, which is a division of application No. 14/427,575, filed as application No. PCT/EP2013/068907 on Sep. 12, 2013, now Pat. No. 9,475,866.

(60) Provisional application No. 61/700,110, filed on Sep. 12, 2012.

(30) Foreign Application Priority Data

Sep. 12, 2012 (EP) .................................... 12184134

(51) Int. Cl.
| | |
|---|---|
| C07K 16/18 | (2006.01) |
| A61K 47/68 | (2017.01) |
| G01N 33/577 | (2006.01) |
| G01N 33/68 | (2006.01) |
| C07K 14/47 | (2006.01) |
| C07K 7/06 | (2006.01) |
| G01N 33/543 | (2006.01) |
| A61K 39/00 | (2006.01) |

(52) U.S. Cl.
CPC ................ *C07K 16/18* (2013.01); *C07K 7/06* (2013.01); *C07K 14/4711* (2013.01); *G01N 33/54306* (2013.01); *G01N 33/577* (2013.01); *G01N 33/6893* (2013.01); *A61K 47/6843* (2017.08); *A61K 2039/505* (2013.01); *C07K 2317/21* (2013.01); *C07K 2317/24* (2013.01); *C07K 2317/33* (2013.01); *C07K 2317/34* (2013.01); *C07K 2317/54* (2013.01); *C07K 2317/55* (2013.01); *C07K 2317/565* (2013.01); *C07K 2317/622* (2013.01); *C07K 2317/92* (2013.01); *G01N 2333/47* (2013.01); *G01N 2333/4709* (2013.01); *G01N 2800/042* (2013.01); *G01N 2800/52* (2013.01); *G01N 2800/56* (2013.01)

(58) Field of Classification Search
CPC ................ C07K 16/18; C07K 14/4711; C07K 2317/21; C07K 2317/24; C07K 2317/34; C07K 2317/54; C07K 2317/55; C07K 2317/565; C07K 2317/622; C07K 2317/92; G01N 33/54306; G01N 33/577; G01N 33/6896; G01N 2333/47; G01N 2333/4709; G01N 2800/042; G01N 2800/52; G01N 2800/56
See application file for complete search history.

(56) References Cited

U.S. PATENT DOCUMENTS

| | | | |
|---|---|---|---|
| 5,716,619 A | 2/1998 | Cooper et al. | |
| 7,138,501 B2 * | 11/2006 | Ruben | .............. C07K 14/70575 530/388.23 |
| 8,119,130 B2 * | 2/2012 | Barry | ...................... A61P 37/00 424/130.1 |
| 9,475,866 B2 | 10/2016 | Grimm et al. | |
| 2008/0004211 A1 | 1/2008 | Fraser | |
| 2008/0213262 A1 | 9/2008 | Jaikaran | |
| 2011/0038790 A1 | 2/2011 | Schenk et al. | |
| 2015/0210759 A1 | 7/2015 | Grimm et al. | |

FOREIGN PATENT DOCUMENTS

| | | |
|---|---|---|
| EP | 0289287 A2 | 11/1988 |
| WO | 2003063760 A2 | 8/2003 |
| WO | WO-03/080672 A1 | 10/2003 |

(Continued)

OTHER PUBLICATIONS

Tamura, et al. "Structural Correlates of an Anticarcinoma Antibody: Identification of Specificity-Determining Residues (SDRs) and Development of a Minimally Immunogenic Antibody Variant by Retention of SDRs Only," The Journal of Immunology, 2000, 164: 1432-1441.
Westermark et al. "Pro Islet Amyloid Polypeptide (ProIAPP) Immunoreactivity in the Islets of Langerhans" Upsala J Med Sci 105: 2, 97-106, 2000.
Paul WE, editor. Fundamental Immunology, Third Edition, Raven Press, New York, 1993, pp. 292-295, Chapter 9.
Rudikoff S et al. Single amino acid substitution altering antigen-binding specificity. Proc. Natl. Acad. Sci. USA, 1982, 79:1979-1983.

(Continued)

*Primary Examiner* — Kimberly Ballard
(74) *Attorney, Agent, or Firm* — Clark & Elbing LLP; Susan M. Michaud

(57) ABSTRACT

Provided are novel human islet amyloid polypeptide, also known as amylin and IAPP and proIAPP respectively, specific antibodies as well as fragments, derivatives and variants thereof as well as methods related thereto. Assays, kits, and solid supports related to antibodies specific for IAPP and/or proIAPP are also disclosed. The antibody, immunoglobulin chain(s), as well as binding fragments, derivatives and variants thereof can be used in pharmaceutical and diagnostic compositions for IAPP and/or proIAPP targeted immunotherapy and diagnostics, respectively.

16 Claims, 18 Drawing Sheets

Specification includes a Sequence Listing.

(56) References Cited

FOREIGN PATENT DOCUMENTS

| WO | 2003092619 A2 | 11/2003 |
| WO | 2005000193 A2 | 1/2005 |
| WO | WO-2006/077442 A2 | 7/2006 |
| WO | 2011151833 A1 | 12/2011 |

OTHER PUBLICATIONS

Vajdos et al., "Comprehensive functional maps of the antigen-binding site of an anti-ErbB2 antibody obtained with shotgun scanning mutagenesis," J Mol Biol. 320(2):415-28 (2002).

International Search Report for International Application No. PCT/EP2013/068907, dated Oct. 17, 2013 (6 pages).

Lin et al., "Toxic human islet amyloid polypeptide (h-IAPP) oligomers are intracellular, and vaccination to induce anti-toxic oligomer antibodies does not prevent h-IAPP-induced beta-cell apoptosis in h-IAPP transgenic mice," Diabetes. 56(5):1324-32 (2007).

Ma et al., "Altered immunoreactivity of islet amyloid polypeptide (IAPP) may reflect major modifications of the IAPP molecule in amyloidogenesis," Diabetoloqia. 40(7):793-801 (1997).

Ma et al., "Amyloid in human islets of Langerhans: immunologic evidence that islet amyloid polypeptide is modified in amyloidogenesis," Pancreas. 21(2):212-8 (2000).

Phelps et al., "Development and characterization of monoclonal antibodies specific for amylin," Hybridoma. 15 (5):379-86 (1996).

Tomita, "Islet amyloid polypeptide in pancreatic islets from type 2 diabetic subjects," Islets. 4(3):223-32 (2012).

International Preliminary Report on Patentability and Written Opinion for International Application No. PCT/EP2013/068907, dated Mar. 26, 2015 (9 pages).

Bram Y et al. Apoptosis induced by islet amyloid polypeptide soluble oligomers is neutralized by diabetes-associated specific antibodies. Scientific Reports, 4:4267, pp. 1-9. (Year: 2014).

Padlan et al. Proc. Natl. Acad. Sci. USA, 1989, 86:5938-5942.

Hatami et al., "Monoclonal antibodies against AB42 fibrils distinguish multiple aggregation state polymorphisms in vitro and in Alzheimer disease brain," J Biol Chem. 289(46):32131-43 (2014) (14 pages).

Kayed et al., "Fibril specific, conformation dependent antibodies recognize a generic epitope common to amyloid fibrils and fibrillar oligomers that is absent in prefibrillar oligomers," Mal Neurodegener. 2:18 (2007) (11 pages).

Lippow et al., "Computational design of antibody-affinity improvement beyond in vivo maturation," available in PMC Jan. 7, 2010, published in final edited form as: Nat Biotechnol. 25(10):1171-6 (2007) (14 pages).

Rajpal et al., "A general method for greatly improving the affinity of antibodies by using combinatorial libraries," Proc Natl Acad Sci U S A. 102(24):8466-71 (2005).

Getts et al., "Have we overestimated the benefit of human(ized) antibodies?" MAbs. 2(6):682-94 (2010).

Heyl et al., "Liposome Damage and Modeling of Fragments of Human Islet Amyloid Polypeptide (IAPP) Support a Two-Step Model of Membrane Destruction," Int. J. Pept. Res. Ther. 16(1):43-54 (2010).

Notice of Allowance for Patent and English Translation for Korean Application No. 10-2015-7009218 dated Apr. 28, 2020 (4 pages).

* cited by examiner

A   NI-203.9A2-VH  (variable heavy chain sequence VH) (SEQ ID NO: 12)
```
FR1-------------------------CDR1------FR2------------CDR2---------------
EVQLVESGGGLVQPGGSLRLSCAASGFTFSTFAMSWVRQAPGKGLEWVSTISGSGDNTYYADSLKG FR3-------------------------------------CDR3---------JH----------
RFTISRDNSKNTLYLQVNSLRPEDTAVYYCAKSPSSLLATYFDYWGQGTLVTVSS
```

NI-203.9A2-VH  (variable heavy chain sequence VH after PIMC) (SEQ ID NO: 162)
```
FR1-------------------------CDR1------FR2------------CDR2---------------
EVQLLESGGGLVQPGGSLRLSCAASGFTFSTFAMSWVRQAPGKGLEWVSTISGSGDNTYYADSLKG FR3-------------------------------------CDR3---------JH----------
RFTISRDNSKNTLYLQVNSLRPEDTAVYYCAKSPSSLLATYFDYWGQGTLVTVSS
```

NI-203.9A2-VK  (variable light chain sequence VK) (SEQ ID NO: 14)
```
FR1----------------------CDR1--------FR2-------------CDR2---FR3---------
EIVLTQSPSTLSASVGDRVTITCRASESINSWLAWYQQKPGKGPKLLIYKASSLQSGVPSRFSGSGS ------------------------CDR3-----JK---------
GTEFTLTISSLQPDDFATYYCQQHNSYWTFGQGTKVEIK
```

NI-203.9A2-VK  (variable light chain sequence VK after PIMC) (SEQ ID NO: 163)
```
FR1----------------------CDR1--------FR2-------------CDR2---FR3---------
DIQMTQSPSTLSASVGDRVTITCRASESINSWLAWYQQKPGKGPKLLIYKASSLQSGVPSRFSGSGS ------------------------CDR3-----JK---------
GTEFTLTISSLQPDDFATYYCQQHNSYWTFGQGTKVEIK
```

B   NI-203.19H8-VH  (variable heavy chain sequence VH) (SEQ ID NO: 16)
```
FR1-------------------------CDR1------FR2------------CDR2---------------
EVQLVESGGGVVQPGTSLRLSCAASGFTFSSYGMHWVRQAPGKGLEWVAIIWYDGSKEYYADSLKG FR3-------------------------------------CDR3-----------JH----------
RVTISRDNSENTLYLQLHTLRVEDTAVYFCARTIASATVDHGMDVWGQGTLVTVSS
```

NI-203.19H8-VK  (variable light chain sequence VK) (SEQ ID NO: 18)
```
FR1----------------------CDR1--------FR2-------------CDR2---FR3---------
DVVMTQSPSSVSASVGDRVTITCRASHDISTWLAWYQQRPGKAPNLLIFGASRLQSGVSPRFSGSGS ------------------------CDR3------JK---------
GTDFTLTISSLQPEDFATYYCQQTNNFPPTFGQGTRLEIK
```

Fig. 1

C    NI-203.26C11-VH  (variable heavy chain sequence VH) (SEQ ID NO: 20)

```
FR1------------------------CDR1---------FR2------------CDR2-------------
QVQLQESGPGLVKPSQTLSLTCTVSGGSISSGNYYWTWIRQPAGKGLEWIGHIYSSGTTNYNPSLES

FR3--------------------------------CDR3-------JH---------
RVTISVDTSKNQFSLSLNSVTAADTAVYYCARPLATVPDAFNIWGQGTMVTVSS
```

NI-203.26C11-VK  (variable light chain sequence VK) (SEQ ID NO: 22)

```
FR1-----------------CDR1-----------FR2-------------CDR2---FR3----
EIVMTQSPDSLAVSLGERATIKCKSSQSVLYSNKNFLAWYQQKPGQPPKLLIYWASTRESGVPDRFS

----------------------------CDR3-----JK---------
GSGSGTDFTLTISSLQAEDVAVYYCQQYYSNPNTFGQGTKVEIK
```

D    NI-203.8E3-VH  (variable heavy chain sequence VH) (SEQ ID NO: 24)

```
FR1-----------------------CDR1-------FR2-----------CDR2--------------
QVQLVQSGAEVKKPGSSVKVSCKASGGTFSSHTISWVRQAPGQGLEWMGGIIPIFGTANYAQKFQD

FR3--------------------------------CDR3-----------JH---------
RVTVTADKSTNTAYMELSSLRPEDTAVYYCAKGELEPRILYYYGMDVWGRGTTVTVSS
```

NI-203.8E3-VK  (variable light chain sequence VK) (SEQ ID NO: 26)

```
FR1-----------------CDR1-------------FR2--------------CDR2---FR3---
DVVMTQSPLSLPVTLGQPASISCRSSQSLVYSDGNTYLNWFHQRPGQSPRRLIYKVSNRDSGVPDRF

-----------------------------CDR3-----JK---------
SGSGSGTDFTLKISRVEAEDVGVYYCMQGSNWPGTFGQGTKVEIK
```

E    NI-203.11B12-VH  (variable heavy chain sequence VH) (SEQ ID NO: 28)

```
FR1-----------------------CDR1-------FR2--------------CDR2-------------
QVQLVQSGAEVKKPGASMKVSCKASGYTFTNYYLHWVRQAPGQGLEWMGIINPSAGSTSYAQKFQG

FR3--------------------------------CDR3-----------JH---------
RVTMTRDTSTSTVYMELSSLKSEDTAVYYCARDSAGIQIWFRDAFDIWGQGTMVTVSS
```

NI-203.11B12-VL  (variable light chain sequence VL) (SEQ ID NO: 30)

```
FR1-----------------CDR1---------FR2-------------CDR2---FR3---------
QPVLTQPPSASASLGSSVKLTCTLNSGHSSYTIAWHQQQPGKAPRYLMKVEHNGNYNKGSLPDRFS

-----------------------------CDR3-----JK---------
GSSSGADRYLAISNLQSEDEADYYCETWDTSTRVFGGGTKLTVL
```

Fig. 1 (continued)

F      NI-203.205F8-VH  (variable heavy chain sequence VH) (SEQ ID NO: 32)
```
FR1---------------------------CDR1--------FR2-------------CDR2------------
QVQLQESGPGLVKPSETLSLTCTVSGDSVSSGSYYWSWIRQPPGKGLEWIGYIYYSGSTNYNPSLKS FR3-----------------------------------CDR3--------------JH---------
RVTISVDTSKNQFSLKLSSVTAADTAVYSCARVPYGYGYRGYDGAWYFDYWGQGTLVTVSS
```

NI-203.205F8-VK  (variable light chain sequence VK) (SEQ ID NO: 34)
```
FR1----------------------------CDR1--------FR2-------------CDR2---FR3--------
EIVLTQSPATLSLSPGERATLSCRASQSVSSYLAWYQQKPGQAPRLLIYDASNRATGIPARFSGSGS -----------------------CDR3-----JK---------
GTDFTLTISSLEPEDFAVYYCQQRSNRFTFGPGTKVDIK
```

G      NI-203.9B3-VH  (variable heavy chain sequence VH) (SEQ ID NO: 36)
```
FR1---------------------------CDR1-------FR2------------CDR2--------------
EVQLVESGGGVVQPGGSLRLSCAASGFTFSSYGMHWVRQAPGKGLEWVAVIWYDGTKKYYADSVKG FR3-------------------------------CDR3-------JH---------
RFTTSRDNSKNTLSLQMNSLRAEDSAVYYCARGFSSSWEFGFWGQGTLVTVSS
```

NI-203.9B3-VL  (variable light chain sequence VL) (SEQ ID NO: 38)
```
FR1---------------------CDR1----------FR2---------------CDR2---FR3------
QSALTQPPSASGSPGQSVTISCTGTSGYIYGYNYVSWYQQHPGKAPKVMIYEVTKRPSGVPDRFSG -----------------------------CDR3---------JK---------
SKSGNTASLTVSGLQAEDEAVYYCASYAGSNNVVFGGGTKLTVL
```

H      NI-203.19F2-VH  (variable heavy chain sequence VH) (SEQ ID NO: 64)
```
FR1--------------------------CDR1------FR2------------CDR2--------------
EVQLVQSGAEVRKPGSSVKVSCKASGGNFLSYSISWVRQAPGQGLEWMGGIIPIFGTPNYAQKFQG FR3-------------------------------CDR3---------------JH---------
RVTITADKSTRTAYMELSSLRFDDTAVYYCADATRPGTAASGFYYYGMDVWGQGTTVTVSS
```

NI-203.19F2-VK  (variable light chain sequence VK) (SEQ ID NO: 66)
```
FR1----------------------------CDR1-------FR2-------------CDR2---FR3--------
EIVMTQSPDTLSVSPGERATLSCRASQSVNNNLAWFQQKPGQAPRLLIYGASTRATGIPARFSGSGS -----------------------------CDR3------JK---------
GTEFTLTISSLQSEDFAVYFCQQSHNWPTFGPGTKVDIK
```

Fig. 1 (continued)

NI-203.15C7-VH  (variable heavy chain sequence VH) (SEQ ID NO: 68)

```
FR1-----------------------CDR1-------FR2-----------CDR2--------------
EVQLVETGGGVVQPGMSLKLSCAASGFTFSTYTMHWVRQAPGKGLEWVSFISYDGRDKYYADSVKG

FR3-------------------------------------CDR3-----------JH----------
RFTISRDNSKNMLYLQMNSLRDEDMAVYYCATLQVWQLYDYYGMDVWGQGTTVTVSS
```

NI-203.15C7-VL  (variable light chain sequence VL) (SEQ ID NO: 70)

```
FR1------------------------CDR1----------FR2---------------CDR2----FR3---------
QSVLTQPPSVSAAPGQKVTISCSGSSSNIGNNYVSWYQQLPGTAPKLLIYNSDKRPSGIPDRFSASKS

-------------------------CDR3--------JK---------
GTSATLGITGLQTGDEADYYCATWDTRLSAGVFGGGTKLTVL
```

Fig. 1 (continued)

A        NI-203.1D10-VH (variable heavy chain sequence VH) (SEQ ID NO: 40)

```
FR1--------------------------CDR1--------FR2--------------CDR2--------------
EVQLVQSGAEVKKPGESLRISCKASGYSFTNSWIAWVRQMPGKGLDYVGIIYPGDSDTKYGPSFQG

FR3--------------------------------------CDR3--------JH----------
HVTISADNFANTAYLQWSSLKASDTAIYYCARRAAAAINWFDSWGQGTLVTVSS
```

NI-203.1D10-VK (variable light chain sequence VK) (SEQ ID NO: 42)

```
FR1-----------------------CDR1-------------FR2-------------CDR2---FR3---
DIQLTQSPLSLSVTPGEPASISCRSSQSLLHPNGNDYLDWYVQKPGQSPQIVIYMGSNRAAGVPDRF

-------------------------------CDR3-----JK---------
SGSGSGTDFTLKISRVEAEDVGTYYCLQALRGYTFGQGTKVEIK
```

B        NI-203.2A11-VH (variable heavy chain sequence VH) (SEQ ID NO: 44)

```
FR1----------------------------CDR1--------FR2-------------CDR2----------------
QVQLVESGGGVVQPGGSLRLSCVASGFTFSSYGMHWVRQAPGKGLEWVAFVRYDGSNKYYADSVKG

FR3--------------------------------------CDR3--------JH----------
RFTISRDNSKNSLSLQMNSLRTEDTAVYYCAKEQEDHKEAFDYWGQGTLVTVSS
```

NI-203.2A11-VK (variable light chain sequence VK) (SEQ ID NO: 46)

```
FR1------------------------CDR1-------FR2---------------CDR2---FR3---------
EIVMTQSPATLSVSPGERATLSCRASQRVTTIAWYQQKPGQAPRLLIYGASSRATDIPARFSGSGS

---------------------------CDR3---------JK------------
GTDFTLTISSLQSEDFAVYYCQQYNQWPLTFGGGTKLEIK
```

C        NI-203.10C4-VH (variable heavy chain sequence VH) (SEQ ID NO: 48)

```
FR1----------------------------CDR1--------FR2-------------CDR2----------------
EVQLVESGAEVRKPGASVRVSCQTSGYSVTDYYLHWVRQAPGQGLEWMGVMNPSNGNVGYPQKFQG

FR3--------------------------------------CDR3--------------JH----------
RVTMTADTSTGTVYMVLTGLTAGDTAVYYCARGGSTPGQEVRSPHVLDLWGQGTLVTVSS
```

NI-203.10C4-VH (variable heavy chain sequence VH after PIMC) (SEQ ID NO: 164)

```
FR1----------------------------CDR1--------FR2-------------CDR2----------------
QVQLVQSGAEVRKPGASVRVSCQTSGYSVTDYYLHWVRQAPGQGLEWMGVMNPSNGNVGYPQKFQG

FR3--------------------------------------CDR3--------------JH----------
RVTMTADTSTGTVYMVLTGLTAGDTAVYYCARGGSTPGQEVRSPHVLDLWGQGTLVTVSS
```

Fig. 2

NI-203.10C4-VK  (variable light chain sequence VK) (SEQ ID NO: 50)
```
FR1------------------------CDR1---------------FR2-------------CDR2----FR3----
DVVMTQSPLSLSVTPGQPASISCRSDESLLHSDGRTYLYWYLQKPGQPPQLLIYEVSNRFSGVPNRF ----------------------------CDR3------JK--------
SGSGSGTDFTLKISRVEAEDVGVYYCMQGVHFPQTFGQGTKLEIK
```

NI-203.10C4-VK  (variable light chain sequence VK after PIMC) (SEQ ID NO: 165)
```
FR1------------------------CDR1---------------FR2-------------CDR2----FR3----
DIVMTQTPLSLSVTPGQPASISCRSDESLLHSDGRTYLYWYLQKPGQPPQLLIYEVSNRFSGVPNRF ----------------------------CDR3------JK--------
SGSGSGTDFTLKISRVEAEDVGVYYCMQGVHFPQTFGQGTKLEIK
```

D  NI-203.20H9-VH  (variable heavy chain sequence VH) (SEQ ID NO: 52)
```
FR1-----------------------------CDR1-------FR2-------------CDR2----------------
QVQLVQSGSELKKPGASVKVSCKASGYIFSKHGINWVRQAPGQGLEWIGWINTNTGNPTYAQDFTG FR3-----------------------------------CDR3---------JH----------
RFVFSLDTSVSTAYLEISSLKAEDTAVYYCARESEPIFGVIYYMDVWGKGTTVTVSS
```

NI-203.20H9-VK  (variable light chain sequence VK) (SEQ ID NO: 54)
```
FR1------------------------CDR1---------FR2--------------CDR2----FR3----------
DIQMTQSPSSLSASVGDSVTITCRASQSISTNLNWYQKKPGQAPTVLIYAASSLQGGVPSRFRGRGS ------------------CDR3--------JK--------
GTYFTLTISGLQPEDFATYYCQHNYNDLWTFGQGTKVEIK
```

E  NI-203.26D2-VH  (variable heavy chain sequence VH) (SEQ ID NO: 56)
```
FR1-------------------------------CDR1-------FR2--------------CDR2-------------
QVQLVESGGGVVQPGGSLRLSCAASGFTFRTCGMHWVRQAPGKGLEWVAFVRSDGTTRYYADSLMG FR3------------------------------CDR3---------JH----------
RFTISRDNSKNSLYLQMNSLRPEDTALYYCAREKEDHREAFDYWGQGTLVTVSS
```

NI-203.26D2-VK  (variable light chain sequence VK) (SEQ ID NO: 58)
```
FR1------------------------CDR1-------FR2---------------CDR2----FR3---------
EIVMTQSPATLSVSPGERATLSCRASQRVSTVAWYQQKPGQAPRLLIYDASTRATDIPARFSGSGS ----------------------------CDR3------JK--------
GTDFTLTISTLQSEDSAVYYCQQYNRWPLTFGGGTKVEIK
```

Fig. 2 (continued)

F       NI-203.60H3-VH  (variable heavy chain sequence VH) (SEQ ID NO: 60)
FR1———————————————————CDR1——————FR2——————————CDR2——————————
EVQLVESGGGLARPGGSLRLSCAVAGFTFSGYEMNWVRQAPGKGLEWISYISGPGDVIYYADSVKG FR3————————————————————————CDR3——————JH————————
RFTISRDNAKNSLFLQMNSLRAEDTAVYYCTRVPPDISYGFDYWGQGTLVTVSS

NI-203.60H3-VK  (variable light chain sequence VK) (SEQ ID NO: 62)
FR1——————————————————CDR1——————FR2——————————CDR2———FR3————————
DIQMTQSPSSLSASVRDSVTITCRASQSISTYLNWYQQKPGKAPNLLIHDTDILQSGVPSRFSGTGS ————————————————————CDR3——————JK——————————
GTDFTLTISGLQPEDFATYYCQQSYSTPPTFGQGTKLEIK

Fig. 2 (continued)

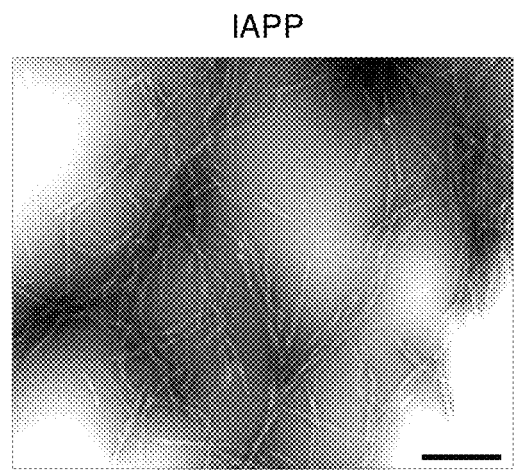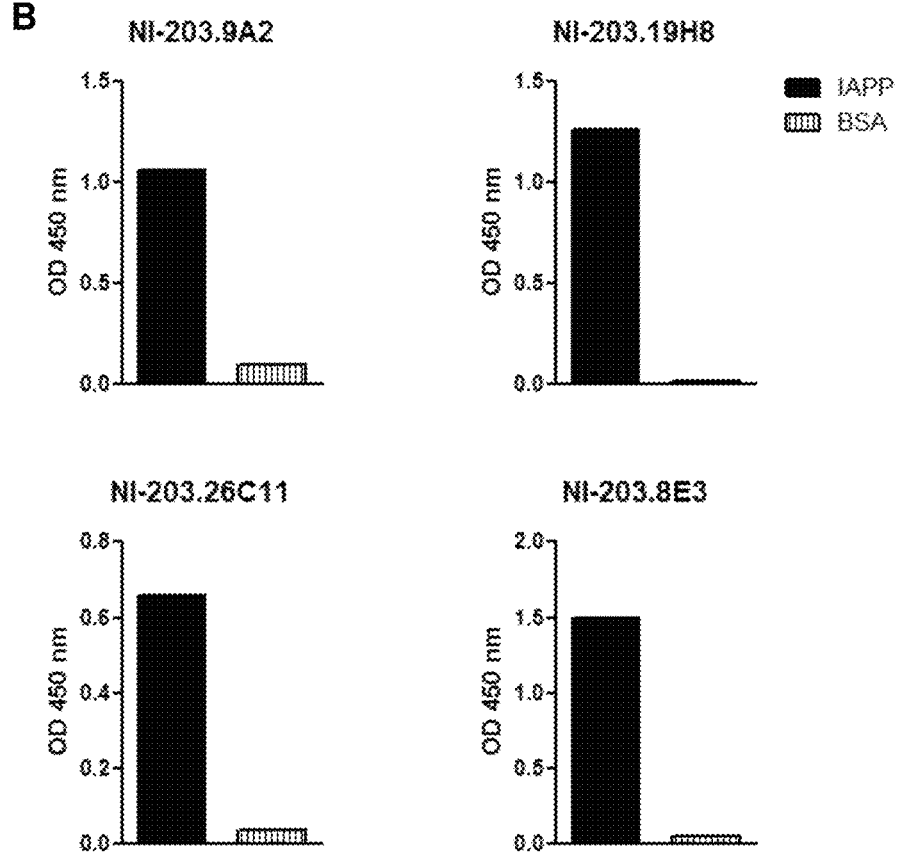
Fig. 3

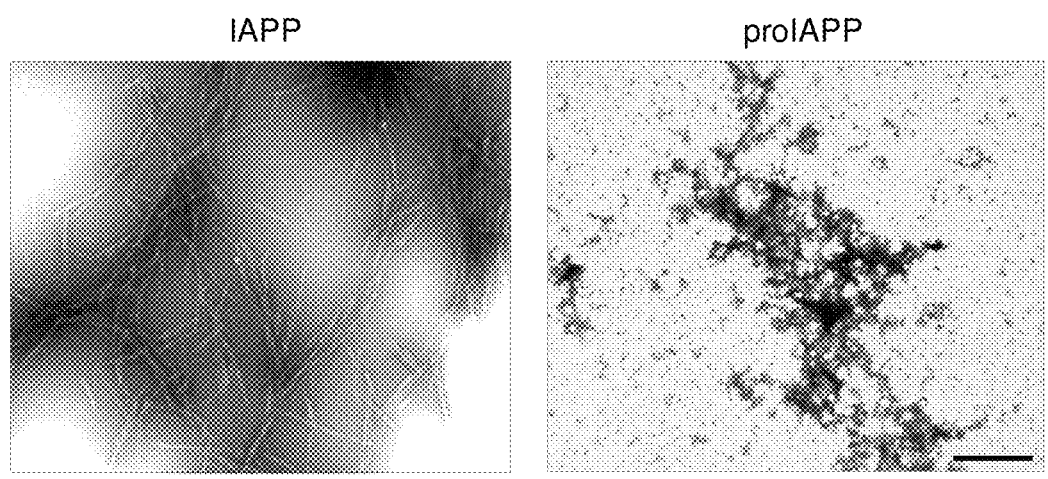
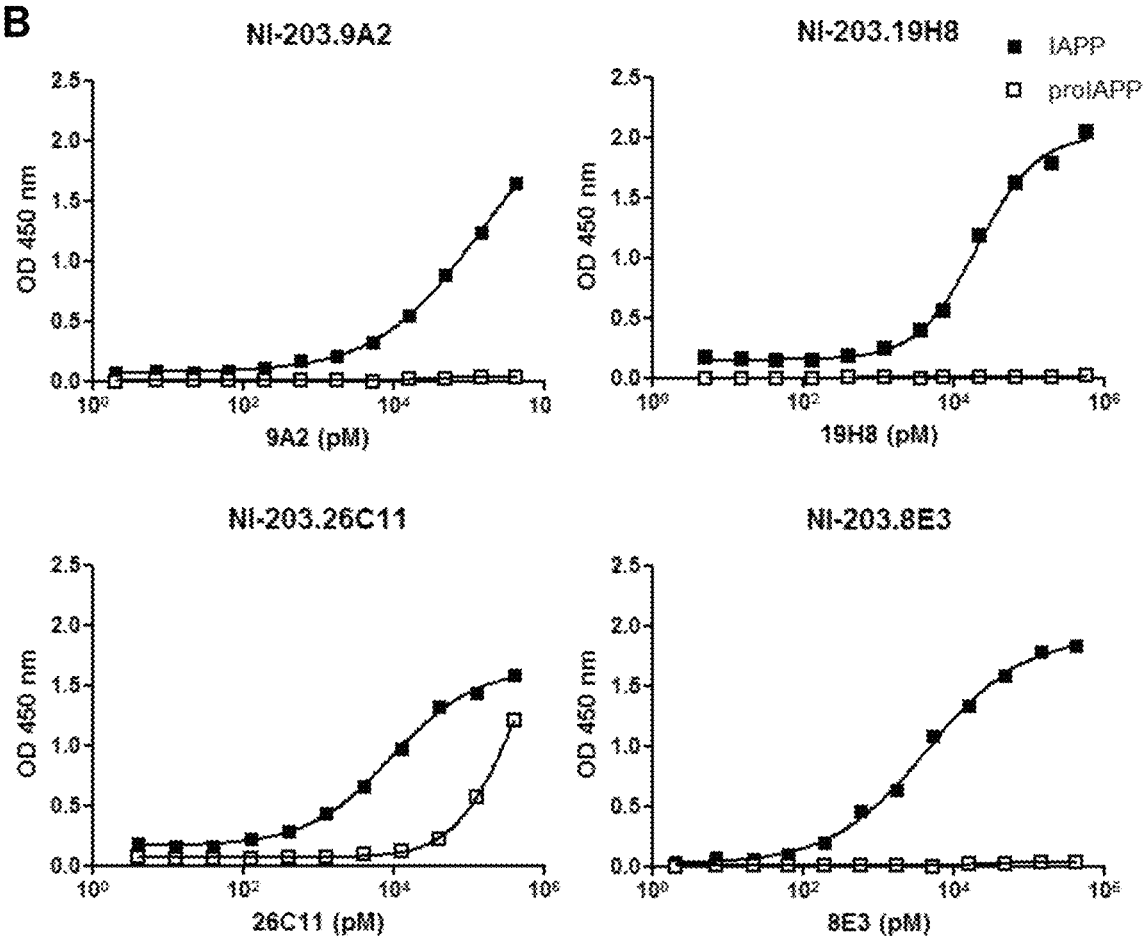
Fig. 4

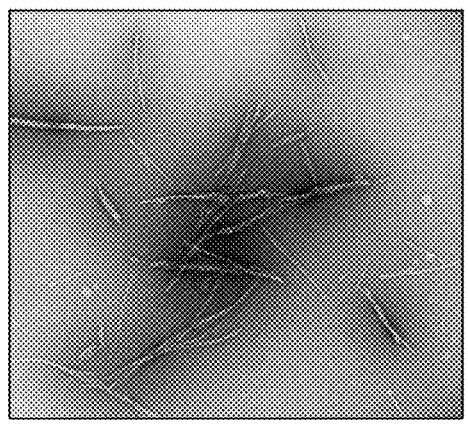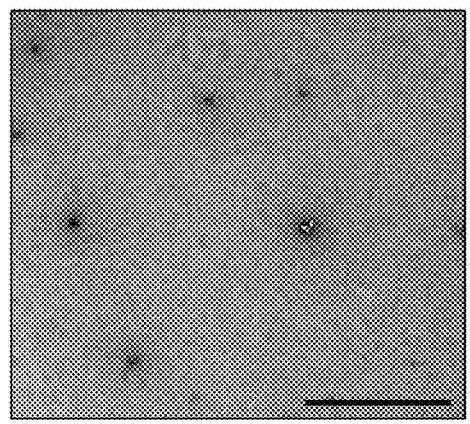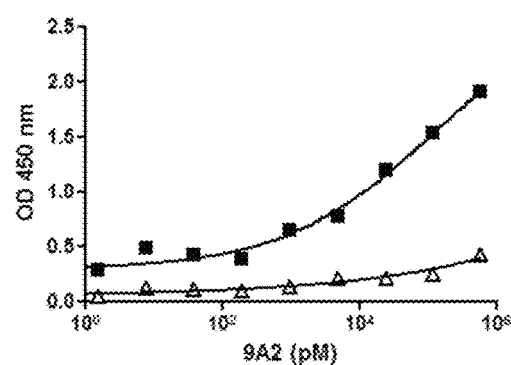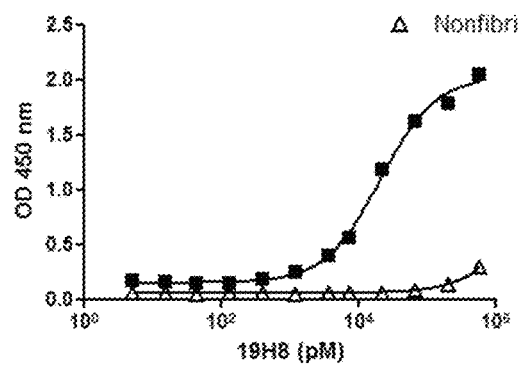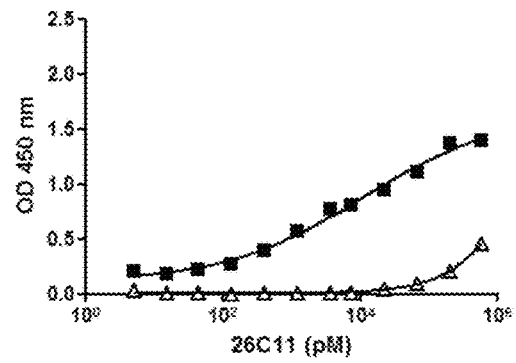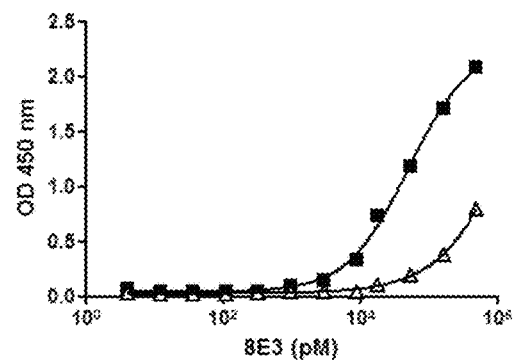
Fig. 5

A
NI-203.19H8 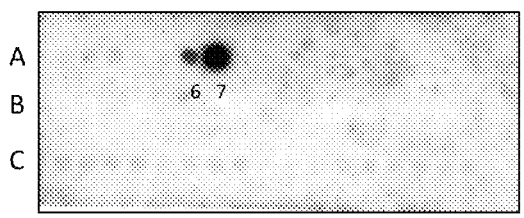 NI-203.26C11 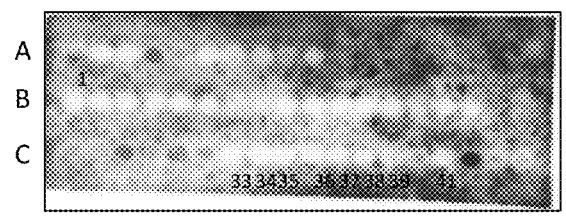
Ilary Ab 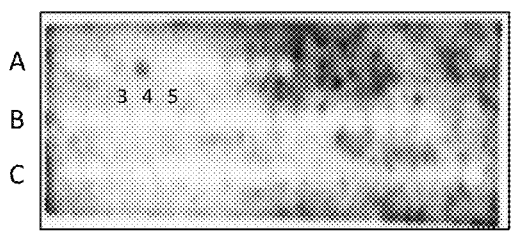
B
Human IAPP: 1-KCNTATCATQRLANFLVHSSNNFGAILSSTNVGSNTY-37 (SEQ ID NO: 1)
| Antibody | Binding epitope |
|---|---|
| NI-203.9A2 | NI |
| NI-203.19H8 | 19-SSNNFGA-25 (SEQ ID NO:4) |
| NI-203.26C11 | N-Terminal: 2-CNTATCA-8 (SEQ ID NO:5) |
| NI-203.8E3 | NI |
| NI-203.19F2 | NI |
| NI-203.15C7 | 10-QRLANFLVHS-19 (SEQ ID NO:71) |
Fig. 6

SEQUENCE LISTING

```
<160> NUMBER OF SEQ ID NOS: 165

<210> SEQ ID NO 1
<211> LENGTH: 37
<212> TYPE: PRT
<213> ORGANISM: Homo sapiens
<220> FEATURE:
<221> NAME/KEY: PEPTIDE
<222> LOCATION: (1)..(37)
<223> OTHER INFORMATION: The amino acid sequence of 37 aa of human IAPP
      with a disulfide bridge between cysteine residues 2 and 7 and an
      amidated C-terminus
<220> FEATURE:
<221> NAME/KEY: DISULFID
<222> LOCATION: (2)..(7)
<223> OTHER INFORMATION: Disulfide bridge between cysteine residues 2
      and 7

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 89
<212> TYPE: PRT
<213> ORGANISM: Homo sapiens
<220> FEATURE:
<221> NAME/KEY: PEPTIDE
<222> LOCATION: (1)..(89)
<223> OTHER INFORMATION: 89 amino acid precursor of hIAPP produced in
      pancreatic beta-cells
<300> PUBLICATION INFORMATION:
<308> DATABASE ACCESSION NUMBER: UniProtID/P10997
<309> DATABASE ENTRY DATE: 1989-07-01
<313> RELEVANT RESIDUES IN SEQ ID NO: (1)..(89)

<400> SEQUENCE: 2

Met Gly Ile Leu Lys Leu Gln Val Phe Leu Ile Val Leu Ser Val Ala
1               5                   10                  15

Leu Asn His Leu Lys Ala Thr Pro Ile Glu Ser His Gln Val Glu Lys
            20                  25                  30

Arg Lys Cys Asn Thr Ala Thr Cys Ala Thr Gln Arg Leu Ala Asn Phe
        35                  40                  45
```

```
Leu Val His Ser Ser Asn Asn Phe Gly Ala Ile Leu Ser Ser Thr Asn
 50                  55                  60

Val Gly Ser Asn Thr Tyr Gly Lys Arg Asn Ala Val Glu Val Leu Lys
 65                  70                  75                  80

Arg Glu Pro Leu Asn Tyr Leu Pro Leu
                 85

<210> SEQ ID NO 3
<211> LENGTH: 67
<212> TYPE: PRT
<213> ORGANISM: Homo sapiens
<220> FEATURE:
<221> NAME/KEY: PEPTIDE
<222> LOCATION: (1)..(67)
<223> OTHER INFORMATION: PreproIAPP is rapidly cleaved after translation
      into proislet amyloid polypeptide (proIAPP)

<400> SEQUENCE: 3

Thr Pro Ile Glu Ser His Gln Val Glu Lys Arg Lys Cys Asn Thr Ala
 1               5                  10                  15

Thr Cys Ala Thr Gln Arg Leu Ala Asn Phe Leu Val His Ser Ser Asn
                 20                  25                  30

Asn Phe Gly Ala Ile Leu Ser Ser Thr Asn Val Gly Ser Asn Thr Tyr
             35                  40                  45

Gly Lys Arg Asn Ala Val Glu Val Leu Lys Arg Glu Pro Leu Asn Tyr
         50                  55                  60

Leu Pro Leu
 65

<210> SEQ ID NO 4
<211> LENGTH: 7
<212> TYPE: PRT
<213> ORGANISM: Artificial Sequence
<220> FEATURE:
<223> OTHER INFORMATION: linear epitope recognized by antibody
      NI-203.19H8
<220> FEATURE:
<221> NAME/KEY: PEPTIDE
<222> LOCATION: (1)..(7)
<223> OTHER INFORMATION: unique linear epitope recognized by antibody
      NI-203.19H8

<400> SEQUENCE: 4

Ser Ser Asn Asn Phe Gly Ala
 1               5

<210> SEQ ID NO 5
<211> LENGTH: 7
<212> TYPE: PRT
<213> ORGANISM: Artificial Sequence
<220> FEATURE:
<223> OTHER INFORMATION: unique linear epitope recognized by antibody
      NI-203.26C11
<220> FEATURE:
<221> NAME/KEY: PEPTIDE
<222> LOCATION: (1)..(7)
<223> OTHER INFORMATION: unique linear epitope recognized by antibody
      NI-203.26C11

<400> SEQUENCE: 5

Cys Asn Thr Ala Thr Cys Ala
 1               5

<210> SEQ ID NO 6
<211> LENGTH: 10
<212> TYPE: PRT
```

```
<213> ORGANISM: Artificial Sequence
<220> FEATURE:
<223> OTHER INFORMATION: peptide 6 of the pepscan covering aa 16-25 of
      IAPP
<220> FEATURE:
<221> NAME/KEY: PEPTIDE
<222> LOCATION: (1)..(10)
<223> OTHER INFORMATION: peptide 6 of the pepscan covering aa 16-25 of
      IAPP

<400> SEQUENCE: 6

Leu Val His Ser Ser Asn Asn Phe Gly Ala
1               5                   10

<210> SEQ ID NO 7
<211> LENGTH: 22
<212> TYPE: PRT
<213> ORGANISM: Artificial Sequence
<220> FEATURE:
<223> OTHER INFORMATION: synthetic peptide derived from human proIAPP
      (N-terminal fragment)
<220> FEATURE:
<221> NAME/KEY: PEPTIDE
<222> LOCATION: (1)..(22)
<223> OTHER INFORMATION: synthetic peptide derived from human proIAPP
      (N-terminal fragment)

<400> SEQUENCE: 7

Thr Pro Ile Glu Ser His Gln Val Glu Lys Arg Lys Cys Asn Thr Ala
1               5                   10                  15

Thr Cys Ala Thr Gln Arg
            20

<210> SEQ ID NO 8
<211> LENGTH: 10
<212> TYPE: PRT
<213> ORGANISM: Artificial Sequence
<220> FEATURE:
<223> OTHER INFORMATION: peptide 7 of the pepscan comprising aa 19-28 of
      hIAPP
<220> FEATURE:
<221> NAME/KEY: PEPTIDE
<222> LOCATION: (1)..(10)
<223> OTHER INFORMATION: peptide 7 of the pepscan comprising aa 19-28 of
      hIAPP

<400> SEQUENCE: 8

Ser Ser Asn Asn Phe Gly Ala Ile Leu Ser
1               5                   10

<210> SEQ ID NO 9
<211> LENGTH: 10
<212> TYPE: PRT
<213> ORGANISM: Artificial Sequence
<220> FEATURE:
<223> OTHER INFORMATION: peptide 1 of the pepscan comprising aa 1-10 of
      huamn IAPP
<220> FEATURE:
<221> NAME/KEY: PEPTIDE
<222> LOCATION: (1)..(10)
<223> OTHER INFORMATION: peptide 1 of the pepscan comprising aa 1-10 of
      huamn IAPP

<400> SEQUENCE: 9

Lys Cys Asn Thr Ala Thr Cys Ala Thr Gln
1               5                   10

<210> SEQ ID NO 10
<211> LENGTH: 10
<212> TYPE: PRT
```

```
<213> ORGANISM: Artificial Sequence
<220> FEATURE:
<223> OTHER INFORMATION: peptide 2 of the pepscan comprising aa 4-13 of
      huamn IAPP
<220> FEATURE:
<221> NAME/KEY: PEPTIDE
<222> LOCATION: (1)..(10)
<223> OTHER INFORMATION: peptide 2 of the pepscan comprising aa 4-13 of
      huamn IAPP

<400> SEQUENCE: 10

Thr Ala Thr Cys Ala Thr Gln Arg Leu Ala
1               5                   10

<210> SEQ ID NO 11
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-203.9A2-VH variable heavy chain (VH)
      sequence, wherein Val at position 5 can also be Leu
<220> FEATURE:
<221> NAME/KEY: V_region
<222> LOCATION: (76)..(93)
<223> OTHER INFORMATION: complementarity determining region (CDR) VH-
      CDR1
<220> FEATURE:
<221> NAME/KEY: V_region
<222> LOCATION: (148)..(197)
<223> OTHER INFORMATION: complementarity determining region (CDR) VH-
      CDR2
<220> FEATURE:
<221> NAME/KEY: V_region
<222> LOCATION: (295)..(330)
<223> OTHER INFORMATION: complementarity determining region (CDR) VH-
      CDR3

<400> SEQUENCE: 11 gag gtg cag ctg gtg gag tct ggg gga ggc ttg gta cag cct ggg ggg       48
Glu Val Gln Leu Val Glu Ser Gly Gly Gly Leu Val Gln Pro Gly Gly
1               5                   10                  15 tcc ctg agg ctc tcc tgt gca gcc tct gga ttc acg ttt agc acc ttt       96
Ser Leu Arg Leu Ser Cys Ala Ala Ser Gly Phe Thr Phe Ser Thr Phe
            20                  25                  30 gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45 tca act att agt ggt agt ggt gat aat aca tac tat gca gac tcc ctg      192
Ser Thr Ile Ser Gly Ser Gly Asp Asn Thr Tyr Tyr Ala Asp Ser Leu
    50                  55                  60 aag ggc cgg ttc acc atc tcc aga gac aat tcc aag aac aca cta tat      240
Lys Gly Arg Phe Thr Ile Ser Arg Asp Asn Ser Lys Asn Thr Leu Tyr
65                  70                  75                  80 ctg caa gtg aac agc ctg aga ccc gag gac acg gcc gtt tat tac tgt      288
Leu Gln Val Asn Ser Leu Arg Pro Glu Asp Thr Ala Val Tyr Tyr Cys
                85                  90                  95 gcg aaa agt ccc tcg tca ctt ctg gcc acc tac ttt gac tac tgg ggc      336
Ala Lys Ser Pro Ser Ser Leu Leu Ala Thr Tyr Phe Asp Tyr Trp Gly
            100                 105                 110 cag gga acc ctg gtc acc gtc tcc tcg                                  363
Gln Gly Thr Leu Val Thr Val Ser Ser
        115                 120

<210> SEQ ID NO 12
<211> LENGTH: 121
<212> TYPE: PRT
```

<213> ORGANISM: Homo sapiens

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Ala Met Ser Trp Val Arg Gln Ala Pro Gly Lys Gly Leu Glu Trp Val
        35                  40                  45

Ser Thr Ile Ser Gly Ser Gly Asp Asn Thr Tyr Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Pro Glu Asp Thr Ala Val Tyr Tyr Cys
                85                  90                  95

Ala Lys Ser Pro Ser Ser Leu Leu Ala Thr Tyr Phe Asp Tyr Trp Gly
            100                 105                 110

Gln Gly Thr Leu Val Thr Val Ser Ser
        115                 120

<210> SEQ ID NO 13
<211> LENGTH: 318
<212> TYPE: DNA
<213> ORGANISM: Homo sapiens
<220> FEATURE:
<221> NAME/KEY: CDS
<222> LOCATION: (1)..(318)
<223> OTHER INFORMATION: NI-203.9A2-VL variable light chain (VK)
      sequence, wherein Glu at position 1 can also be Asp, Val at
      position 3 can also be Gln and Leu at position 4 can also be Met
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (147)..(168)
<223> OTHER INFORMATION: complementarity determining region (CDR)
      VK-CDR2
<220> FEATURE:
<221> NAME/KEY: V_region
<222> LOCATION: (265)..(288)
<223> OTHER INFORMATION: complementarity determining region (CDR)
      VK-CDR3

<400> SEQUENCE: 13 gaa att gtg ttg aca cag tct cct tcc acc ctg tct gca tct gta gga    48
Glu Ile Val Leu Thr Gln Ser Pro Ser Thr Leu Ser Ala Ser Val Gly
1               5                   10                  15 gac aga gtc acc atc act tgc cgg gcc agt gag agt att aat agc tgg    96
Asp Arg Val Thr Ile Thr Cys Arg Ala Ser Glu Ser Ile Asn Ser Trp
            20                  25                  30 ttg gcc tgg tat cag cag aaa cca ggg aaa ggc cct aag ctc ctg atc   144
Leu Ala Trp Tyr Gln Gln Lys Pro Gly Lys Gly Pro Lys Leu Leu Ile
        35                  40                  45 tat aag gcg tct agt tta caa agt ggg gtc cca tca agg ttc agc ggc   192
Tyr Lys Ala Ser Ser Leu Gln Ser Gly Val Pro Ser Arg Phe Ser Gly
    50                  55                  60 agt gga tct ggg aca gaa ttc act ctc acc atc agc agc ctg cag cct   240
Ser Gly Ser Gly Thr Glu Phe Thr Leu Thr Ile Ser Ser Leu Gln Pro
65                  70                  75                  80 gat gat ttt gca act tat tac tgc caa cag cac aat agt tat tgg acg   288
Asp Asp Phe Ala Thr Tyr Tyr Cys Gln Gln His Asn Ser Tyr Trp Thr

```
                      85                  90                  95
ttc ggc caa ggg acc aag gtg gaa atc aaa                              318
Phe Gly Gln Gly Thr Lys Val Glu Ile Lys
            100                 105

<210> SEQ ID NO 14
<211> LENGTH: 106
<212> TYPE: PRT
<213> ORGANISM: Homo sapiens

<400> SEQUENCE: 14

Glu Ile Val Leu Thr Gln Ser Pro Ser Thr Leu Ser Ala Ser Val Gly
1               5                   10                  15

Asp Arg Val Thr Ile Thr Cys Arg Ala Ser Glu Ser Ile Asn Ser Trp
            20                  25                  30

Leu Ala Trp Tyr Gln Gln Lys Pro Gly Lys Pro Lys Leu Leu Ile
        35                  40                  45

Tyr Lys Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln His Asn Ser Tyr Trp Thr
                85                  90                  95

Phe Gly Gln Gly Thr Lys Val Glu Ile Lys
            100                 105

<210> SEQ ID NO 15
<211> LENGTH: 366
<212> TYPE: DNA
<213> ORGANISM: Homo sapiens
<220> FEATURE:
<221> NAME/KEY: CDS
<222> LOCATION: (1)..(366)
<223> OTHER INFORMATION: NI-203.19H8-VH variable heavy chain (VH)
      sequence
<220> FEATURE:
<221> NAME/KEY: V_region
<222> LOCATION: (76)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(333)
<223> OTHER INFORMATION: complementarity determining region (CDR)
      VH-CDR3

<400> SEQUENCE: 15 gag gtg cag ctg gtg gag tct ggg gga ggc gtg gtc cag cct ggg acg    48
Glu Val Gln Leu Val Glu Ser Gly Gly Gly Val Val Gln Pro Gly Thr
1               5                   10                  15 tcc ctg aga ctc tcc tgt gca gcg tct ggg ttc acc ttc agc agt tat    96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggc ctg gag tgg gtg   144
Gly Met His Trp Val Arg Gln Ala Pro Gly Lys Gly Leu Glu Trp Val
        35                  40                  45 gca att ata tgg tat gat gga agt aag gaa tat tat gca gac tcc ctg   192
Ala Ile Ile Trp Tyr Asp Gly Ser Lys Glu Tyr Tyr Ala Asp Ser Leu
50                  55                  60
```

```
aag ggc cga gtc acc atc tcc aga gac aat tcc gag aac act ctc tat    240
Lys Gly Arg Val Thr Ile Ser Arg Asp Asn Ser Glu Asn Thr Leu Tyr
 65                  70                  75                  80 ctg caa ctg cac acc ctg aga gtc gag gac acg gct gtg tat ttc tgt    288
Leu Gln Leu His Thr Leu Arg Val Glu Asp Thr Ala Val Tyr Phe Cys
                 85                  90                  95 gcg agg aca atc gca tcg gcc acc gtg gac cac ggt atg gac gtc tgg    336
Ala Arg Thr Ile Ala Ser Ala Thr Val Asp His Gly Met Asp Val Trp
                100                 105                 110 ggc caa ggc acc ctg gtc acc gtc tcc tcg                            366
Gly Gln Gly Thr Leu Val Thr Val Ser Ser
            115                 120

<210> SEQ ID NO 16
<211> LENGTH: 122
<212> TYPE: PRT
<213> ORGANISM: Homo sapiens

<400> SEQUENCE: 16

Glu Val Gln Leu Val Glu Ser Gly Gly Gly Val Val Gln Pro Gly Thr
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ile Ile Trp Tyr Asp Gly Ser Lys Glu Tyr Tyr Ala Asp Ser Leu
     50                  55                  60

Lys Gly Arg Val Thr Ile Ser Arg Asp Asn Ser Glu Asn Thr Leu Tyr
 65                  70                  75                  80

Leu Gln Leu His Thr Leu Arg Val Glu Asp Thr Ala Val Tyr Phe Cys
                 85                  90                  95

Ala Arg Thr Ile Ala Ser Ala Thr Val Asp His Gly Met Asp Val Trp
                100                 105                 110

Gly Gln Gly Thr Leu Val Thr Val Ser Ser
            115                 120

<210> SEQ ID NO 17
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-203.19H8-VL variable light chain (VK)
      sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (147)..(168)
<223> OTHER INFORMATION: complementarity determining region (CDR)
      VK-CDR2
<220> FEATURE:
<221> NAME/KEY: V_region
<222> LOCATION: (265)..(291)
<223> OTHER INFORMATION: complementarity determining region (CDR)
      VK-CDR3

<400> SEQUENCE: 17 gat gtt gtg atg act cag tct cct tcg tcc gtg tct gca tct gta gga    48
Asp Val Val Met Thr Gln Ser Pro Ser Ser Val Ser Ala Ser Val Gly
 1               5                  10                  15
```

```
gac aga gtc acc atc act tgt cgg gcg agt cac gat att agc acc tgg      96
Asp Arg Val Thr Ile Thr Cys Arg Ala Ser His Asp Ile Ser Thr Trp
        20                  25                  30 tta gcc tgg tat cag cag aga cca ggg aaa gcc cct aac ctc ctg atc     144
Leu Ala Trp Tyr Gln Gln Arg Pro Gly Lys Ala Pro Asn Leu Leu Ile
    35                  40                  45 ttt gga gca tcg agg ttg caa agt ggg gtc tca cca agg ttc agc ggc     192
Phe Gly Ala Ser Arg Leu Gln Ser Gly Val Ser Pro Arg Phe Ser Gly
50                  55                  60 agt gga tct ggg aca gat ttc act ctc acc atc agc agc ctg cag cct     240
Ser Gly Ser Gly Thr Asp Phe Thr Leu Thr Ile Ser Ser Leu Gln Pro
65                  70                  75                  80 gaa gat ttt gca act tac tat tgt caa cag act aac aat ttc cct ccc     288
Glu Asp Phe Ala Thr Tyr Tyr Cys Gln Gln Thr Asn Asn Phe Pro Pro
                85                  90                  95 acc ttc ggc caa ggg aca cga ctg gag att aaa                         321
Thr Phe Gly Gln Gly Thr Arg Leu Glu Ile Lys
            100                 105

<210> SEQ ID NO 18
<211> LENGTH: 107
<212> TYPE: PRT
<213> ORGANISM: Homo sapiens

<400> SEQUENCE: 18

Asp Val Val Met Thr Gln Ser Pro Ser Ser Val Ser Ala Ser Val Gly
1               5                   10                  15

Asp Arg Val Thr Ile Thr Cys Arg Ala Ser His Asp Ile Ser Thr Trp
            20                  25                  30

Leu Ala Trp Tyr Gln Gln Arg Pro Gly Lys Ala Pro Asn Leu Leu Ile
        35                  40                  45

Phe Gly Ala Ser Arg Leu Gln Ser Gly Val Ser Pro Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Asn Phe Pro Pro
                85                  90                  95

Thr Phe Gly Gln Gly Thr Arg Leu Glu Ile Lys
            100                 105

<210> SEQ ID NO 19
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-203.26C11-VH variable heavy chain (VH)
      sequence
<220> FEATURE:
<221> NAME/KEY: V_region
<222> LOCATION: (76)..(111)
<223> OTHER INFORMATION: complementarity determining region (CDR)
      VH-CDR1
<220> FEATURE:
<221> NAME/KEY: V_region
<222> LOCATION: (154)..(201)
<223> OTHER INFORMATION: complementarity determining region (CDR)
      VH-CDR2
<220> FEATURE:
<221> NAME/KEY: V_region
<222> LOCATION: (298)..(330)
<223> OTHER INFORMATION: complementarity determining region (CDR)
      VH-CDR3
```

<400> SEQUENCE: 19

```
cag gtg cag ctg cag gag tcg ggc cca gga ttg gtg aag cct tct cag        48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt        96
Thr Leu Ser Leu Thr Cys Thr Val Ser Gly Gly Ser Ile Ser Ser Gly
            20                  25                  30 aat tac tac tgg acc tgg atc cgg cag ccc gcc ggg aag gga ctg gag       144
Asn Tyr Tyr Trp Thr Trp Ile Arg Gln Pro Ala Gly Lys Gly Leu Glu
        35                  40                  45 tgg att ggg cat atc tat tcc agt ggg acc acc aat tac aac ccc tcc       192
Trp Ile Gly His Ile Tyr Ser Ser Gly Thr Thr Asn Tyr Asn Pro Ser
    50                  55                  60 ctc gag agt cga gtc acc att tca gta gac acg tcc aag aac cag ttc       240
Leu Glu Ser Arg Val Thr Ile Ser Val Asp Thr Ser Lys Asn Gln Phe
65                  70                  75                  80 tcc ctg agc ctg aac tct gtg acc gcc gca gac acg gcc gtt tat tac       288
Ser Leu Ser Leu Asn Ser Val Thr Ala Ala Asp Thr Ala Val Tyr Tyr
                85                  90                  95 tgt gcg aga cca ctg gct aca gtt ccg gat gct ttt aat atc tgg ggc       336
Cys Ala Arg Pro Leu Ala Thr Val Pro Asp Ala Phe Asn Ile Trp Gly
            100                 105                 110 caa ggg aca atg gtc acc gtc tct tcg                                   363
Gln Gly Thr Met Val Thr Val Ser Ser
        115                 120
```

<210> SEQ ID NO 20
<211> LENGTH: 121
<212> TYPE: PRT
<213> ORGANISM: Homo sapiens

<400> SEQUENCE: 20

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asn Tyr Tyr Trp Thr Trp Ile Arg Gln Pro Ala Gly Lys Gly Leu Glu
        35                  40                  45

Trp Ile Gly His Ile Tyr Ser Ser Gly Thr Thr Asn Tyr Asn Pro Ser
    50                  55                  60

Leu Glu Ser Arg Val Thr Ile Ser Val Asp Thr Ser Lys Asn Gln Phe
65                  70                  75                  80

Ser Leu Ser Leu Asn Ser Val Thr Ala Ala Asp Thr Ala Val Tyr Tyr
                85                  90                  95

Cys Ala Arg Pro Leu Ala Thr Val Pro Asp Ala Phe Asn Ile Trp Gly
            100                 105                 110

Gln Gly Thr Met Val Thr Val Ser Ser
        115                 120
```

<210> SEQ ID NO 21
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-203.26C11-VL variable light chain (VK)
      sequence
<220> FEATURE:
<221> NAME/KEY: V_region

```
<222> LOCATION: (70)..(114)
<223> OTHER INFORMATION: complementarity determining region (CDR)
      VK-CDR1
<220> FEATURE:
<221> NAME/KEY: V_region
<222> LOCATION: (160)..(180)
<223> OTHER INFORMATION: complementarity determining region (CDR)
      VK-CDR2
<220> FEATURE:
<221> NAME/KEY: V_region
<222> LOCATION: (277)..(303)
<223> OTHER INFORMATION: complementarity determining region (CDR)
      VK-CDR3

<400> SEQUENCE: 21 gaa att gtg atg act cag tct cca gac tcc ctg gct gtg tct ctg ggc      48
Glu Ile Val Met Thr Gln Ser Pro Asp Ser Leu Ala Val Ser Leu Gly
1               5                   10                  15 gag agg gcc acc atc aag tgc aag tcc agc cag agt gtt tta tac agc      96
Glu Arg Ala Thr Ile Lys Cys Lys Ser Ser Gln Ser Val Leu Tyr Ser
            20                  25                  30 aat aag aac ttc tta gct tgg tac cag cag aaa cca gga cag cct cct     144
Asn Lys Asn Phe Leu Ala Trp Tyr Gln Gln Lys Pro Gly Gln Pro Pro
        35                  40                  45 aaa tta ctc att tac tgg gca tct act cgg gaa tcc ggg gtc cct gac     192
Lys Leu Leu Ile Tyr Trp Ala Ser Thr Arg Glu Ser Gly Val Pro Asp
50                  55                  60 cga ttc agt ggc agc ggg tct ggg aca gat ttc act ctc acc atc agc     240
Arg Phe Ser Gly Ser Gly Ser Gly Thr Asp Phe Thr Leu Thr Ile Ser
65                  70                  75                  80 agc ctg cag gct gaa gat gtg gca gtt tat tac tgt cag cag tat tat     288
Ser Leu Gln Ala Glu Asp Val Ala Val Tyr Tyr Cys Gln Gln Tyr Tyr
                85                  90                  95 agt aat cct aac act ttt ggc cag ggg acc aag gtg gag atc aaa         333
Ser Asn Pro Asn Thr Phe Gly Gln Gly Thr Lys Val Glu Ile Lys
            100                 105                 110

<210> SEQ ID NO 22
<211> LENGTH: 111
<212> TYPE: PRT
<213> ORGANISM: Homo sapiens

<400> SEQUENCE: 22

Glu Ile Val Met Thr Gln Ser Pro Asp Ser Leu Ala Val Ser Leu Gly
1               5                   10                  15

Glu Arg Ala Thr Ile Lys Cys Lys Ser Ser Gln Ser Val Leu Tyr Ser
            20                  25                  30

Asn Lys Asn Phe Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Ser Asn Pro Asn Thr Phe Gly Gln Gly Thr Lys Val Glu Ile Lys
            100                 105                 110

<210> SEQ ID NO 23
<211> LENGTH: 372
<212> TYPE: DNA
<213> ORGANISM: Homo sapiens
<220> FEATURE:
```

```
<221> NAME/KEY: CDS
<222> LOCATION: (1)..(372)
<223> OTHER INFORMATION: NI-203.8E3-VH variable heavy chain (VH)
      sequence
<220> FEATURE:
<221> NAME/KEY: V_region
<222> LOCATION: (76)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(339)
<223> OTHER INFORMATION: complementarity determining region (CDR)
      VH-CDR3

<400> SEQUENCE: 23 cag gtg cag ctg gtg cag tct ggg gct gaa gtg aag aaa cct ggg tcc      48
Gln Val Gln Leu Val Gln Ser Gly Ala Glu Val Lys Lys Pro Gly Ser
1               5                   10                  15 tcg gtg aag gtc tcc tgc aag gct tct gga ggc acc ttc agt agt cac      96
Ser Val Lys Val Ser Cys Lys Ala Ser Gly Gly Thr Phe Ser Ser His
            20                  25                  30 act atc agc tgg gtg cga cag gcc cct ggg caa ggg ctt gag tgg atg     144
Thr Ile Ser Trp Val Arg Gln Ala Pro Gly Gln Gly Leu Glu Trp Met
        35                  40                  45 gga ggg atc atc ccc atc ttt ggt aca gca aac tac gca cag aag ttt     192
Gly Gly Ile Ile Pro Ile Phe Gly Thr Ala Asn Tyr Ala Gln Lys Phe
    50                  55                  60 cag gac aga gtc acg gtt acc gcg gac aaa tcc acg aat aca gcc tac     240
Gln Asp Arg Val Thr Val Thr Ala Asp Lys Ser Thr Asn Thr Ala Tyr
65                  70                  75                  80 atg gag ttg agt agc ctc aga cct gag gac acg gcc gtg tat tac tgt     288
Met Glu Leu Ser Ser Leu Arg Pro Glu Asp Thr Ala Val Tyr Tyr Cys
                85                  90                  95 gcg aag ggg gaa ctg gaa cca cga atc ctc tac tac tac ggt atg gac     336
Ala Lys Gly Glu Leu Glu Pro Arg Ile Leu Tyr Tyr Tyr Gly Met Asp
            100                 105                 110 gtc tgg ggc cga ggg acc acg gtc acc gtc tcc tcg                     372
Val Trp Gly Arg Gly Thr Thr Val Thr Val Ser Ser
        115                 120

<210> SEQ ID NO 24
<211> LENGTH: 124
<212> TYPE: PRT
<213> ORGANISM: Homo sapiens

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
            20                  25                  30

Thr Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Asp Arg Val Thr Val Thr Ala Asp Lys Ser Thr Asn Thr Ala Tyr
65                  70                  75                  80

Met Glu Leu Ser Ser Leu Arg Pro Glu Asp Thr Ala Val Tyr Tyr Cys
                85                  90                  95
```

```
Ala Lys Gly Glu Leu Glu Pro Arg Ile Leu Tyr Tyr Gly Met Asp
            100                 105                 110

Val Trp Gly Arg Gly Thr Thr Val Thr Val Ser Ser
            115                 120
```

<210> SEQ ID NO 25
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-203.8E3-VK variable light chain (VK)
      sequence
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
<222> LOCATION: (163)..(183)
<223> OTHER INFORMATION: complementarity determining region (CDR)
      VK-CDR2
<220> FEATURE:
<221> NAME/KEY: V_region
<222> LOCATION: (280)..(306)
<223> OTHER INFORMATION: complementarity determining region (CDR)
      VK-CDR3

<400> SEQUENCE: 25

```
gat gtt gtg atg act cag tct cca ctc tcc ctg ccc gtc acc ctt gga    48
Asp Val Val Met Thr Gln Ser Pro Leu Ser Leu Pro Val Thr Leu Gly
1               5                   10                  15 cag ccg gcc tcc atc tcc tgc agg tct agt caa agc ctc gta tac agt    96
Gln Pro Ala Ser Ile Ser Cys Arg Ser Ser Gln Ser Leu Val Tyr Ser
            20                  25                  30 gat gga aac acc tac ttg aat tgg ttt cac cag agg cca ggc caa tct   144
Asp Gly Asn Thr Tyr Leu Asn Trp Phe His Gln Arg Pro Gly Gln Ser
        35                  40                  45 cca agg cgg cta att tat aag gtt tct aat cgt gac tct ggg gtc cca   192
Pro Arg Arg Leu Ile Tyr Lys Val Ser Asn Arg Asp Ser Gly Val Pro
    50                  55                  60 gac aga ttc agc ggc agt ggg tca ggc act gat ttc aca ctg aaa atc   240
Asp Arg Phe Ser Gly Ser Gly Ser Gly Thr Asp Phe Thr Leu Lys Ile
65                  70                  75                  80 agc agg gtg gag gct gag gat gtt ggg gtt tat tac tgc atg caa ggt   288
Ser Arg Val Glu Ala Glu Asp Val Gly Val Tyr Tyr Cys Met Gln Gly
                85                  90                  95 tca aat tgg cca ggg acg ttc ggc caa ggg acc aag gtg gaa atc aaa   336
Ser Asn Trp Pro Gly Thr Phe Gly Gln Gly Thr Lys Val Glu Ile Lys
            100                 105                 110
```

<210> SEQ ID NO 26
<211> LENGTH: 112
<212> TYPE: PRT
<213> ORGANISM: Homo sapiens

<400> SEQUENCE: 26

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe His Gln Arg Pro Gly Gln Ser
        35                  40                  45
```

```
Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ser Asn Trp Pro Gly Thr Phe Gly Gln Gly Thr Lys Val Glu Ile Lys
            100                 105                 110

<210> SEQ ID NO 27
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: NI-203.11B12-VH variable heavy chain (VH)
      sequence
<220> FEATURE:
<221> NAME/KEY: V_region
<222> LOCATION: (76)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(339)
<223> OTHER INFORMATION: complementarity determining region (CDR)
      VH-CDR3

<400> SEQUENCE: 27 cag gtg cag ctg gtg caa tct ggg gct gag gtg aag aag cct ggg gcc    48
Gln Val Gln Leu Val Gln Ser Gly Ala Glu Val Lys Lys Pro Gly Ala
1               5                   10                  15 tca atg aag gtt tcc tgc aag gca tct gga tac acc ttc acc aac tac    96
Ser Met Lys Val Ser Cys Lys Ala Ser Gly Tyr Thr Phe Thr Asn Tyr
                20                  25                  30 tat tta cac tgg gtg cga cag gcc cct gga caa gga ctt gag tgg atg   144
Tyr Leu His Trp Val Arg Gln Ala Pro Gly Gln Gly Leu Glu Trp Met
            35                  40                  45 gga ata atc aac cct agt gct ggt agc aca agc tac gca cag aag ttc   192
Gly Ile Ile Asn Pro Ser Ala Gly Ser Thr Ser Tyr Ala Gln Lys Phe
        50                  55                  60 cag ggc aga gtc acc atg acc agg gac acg tcc acg agc aca gtc tac   240
Gln Gly Arg Val Thr Met Thr Arg Asp Thr Ser Thr Ser Thr Val Tyr
65                  70                  75                  80 atg gaa ctg agc agc ctg aaa tct gaa gac acg gcc gtc tat tac tgt   288
Met Glu Leu Ser Ser Leu Lys Ser Glu Asp Thr Ala Val Tyr Tyr Cys
                85                  90                  95 gcg aga gat tcc gct ggg ata cag ata tgg ttc agg gat gct ttt gat   336
Ala Arg Asp Ser Ala Gly Ile Gln Ile Trp Phe Arg Asp Ala Phe Asp
            100                 105                 110 atc tgg ggc caa ggg aca atg gtc acc gtc tct tcg                   372
Ile Trp Gly Gln Gly Thr Met Val Thr Val Ser Ser
        115                 120

<210> SEQ ID NO 28
<211> LENGTH: 124
<212> TYPE: PRT
<213> ORGANISM: Homo sapiens
```

<400> SEQUENCE: 28

```
Gln Val Gln Leu Val Gln Ser Gly Ala Glu Val Lys Lys Pro Gly Ala
1               5                   10                  15

Ser Met Lys Val Ser Cys Lys Ala Ser Gly Tyr Thr Phe Thr Asn Tyr
            20                  25                  30

Tyr Leu His Trp Val Arg Gln Ala Pro Gly Gln Gly Leu Glu Trp Met
        35                  40                  45

Gly Ile Ile Asn Pro Ser Ala Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Lys Ser Glu Asp Thr Ala Val Tyr Tyr Cys
                85                  90                  95

Ala Arg Asp Ser Ala Gly Ile Gln Ile Trp Phe Arg Asp Ala Phe Asp
            100                 105                 110

Ile Trp Gly Gln Gly Thr Met Val Thr Val Ser Ser
        115                 120
```

<210> SEQ ID NO 29
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-203.11B12-VL variable light chain (VL)
      sequence
<220> FEATURE:
<221> NAME/KEY: V_region
<222> LOCATION: (67)..(102)
<223> OTHER INFORMATION: complementarity determining region (CDR)
      VL-CDR1
<220> FEATURE:
<221> NAME/KEY: V_region
<222> LOCATION: (148)..(168)
<223> OTHER INFORMATION: complementarity determining region (CDR)
      VL-CDR2
<220> FEATURE:
<221> NAME/KEY: V_region
<222> LOCATION: (277)..(303)
<223> OTHER INFORMATION: complementarity determining region (CDR)
      VL-CDR3

<400> SEQUENCE: 29

```
cag cct gtg ctg act cag cca ccc tct gcc tct gct tcc ctg gga tcc      48
Gln Pro Val Leu Thr Gln Pro Pro Ser Ala Ser Ala Ser Leu Gly Ser
1               5                   10                  15 tcg gtc aag ctc acc tgc act ctg aac agt ggg cac agt agc tac acc      96
Ser Val Lys Leu Thr Cys Thr Leu Asn Ser Gly His Ser Ser Tyr Thr
            20                  25                  30 atc gca tgg cat cag cag cag cca ggg aag gcc cct cgg tac ttg atg     144
Ile Ala Trp His Gln Gln Gln Pro Gly Lys Ala Pro Arg Tyr Leu Met
        35                  40                  45 aag gtt gaa cat aat gga aac tac aac aag ggg agc gga ctt cct gat     192
Lys Val Glu His Asn Gly Asn Tyr Asn Lys Gly Ser Gly Leu Pro Asp
    50                  55                  60 cgc ttc tca ggc tcc agc tct ggg gct gac cgc tac ctc gcc atc tcc     240
Arg Phe Ser Gly Ser Ser Ser Gly Ala Asp Arg Tyr Leu Ala Ile Ser
65                  70                  75                  80 aac ctc cag tct gag gat gag gct gat tat tac tgt gag acc tgg gac     288
Asn Leu Gln Ser Glu Asp Glu Ala Asp Tyr Tyr Cys Glu Thr Trp Asp
                85                  90                  95 act agc act agg gtc ttc ggc gga ggg acc aag ctg acc gtc cta          333
Thr Ser Thr Arg Val Phe Gly Gly Gly Thr Lys Leu Thr Val Leu
```

```
Thr Ser Thr Arg Val Phe Gly Gly Gly Thr Lys Leu Thr Val Leu
            100                 105                 110

<210> SEQ ID NO 30
<211> LENGTH: 111
<212> TYPE: PRT
<213> ORGANISM: Homo sapiens

<400> SEQUENCE: 30

Gln Pro Val Leu Thr Gln Pro Pro Ser Ala Ser Ala Ser Leu Gly Ser
1               5                   10                  15

Ser Val Lys Leu Thr Cys Thr Leu Asn Ser Gly His Ser Ser Tyr Thr
            20                  25                  30

Ile Ala Trp His Gln Gln Pro Gly Lys Ala Pro Arg Tyr Leu Met
        35                  40                  45

Lys Val Glu His Asn Gly Asn Tyr Asn Lys Gly Ser Gly Leu Pro Asp
50                  55                  60

Arg Phe Ser Gly Ser Ser Ser Gly Ala Asp Arg Tyr Leu Ala Ile Ser
65                  70                  75                  80

Asn Leu Gln Ser Glu Asp Glu Ala Asp Tyr Tyr Cys Glu Thr Trp Asp
                85                  90                  95

Thr Ser Thr Arg Val Phe Gly Gly Gly Thr Lys Leu Thr Val Leu
            100                 105                 110

<210> SEQ ID NO 31
<211> LENGTH: 384
<212> TYPE: DNA
<213> ORGANISM: Homo sapiens
<220> FEATURE:
<221> NAME/KEY: CDS
<222> LOCATION: (1)..(384)
<223> OTHER INFORMATION: NI-203.205F8-VH variable heavy chain (VH)
      sequence
<220> FEATURE:
<221> NAME/KEY: V_region
<222> LOCATION: (76)..(105)
<223> OTHER INFORMATION: complementarity determining region (CDR)
      VH-CDR1
<220> FEATURE:
<221> NAME/KEY: V_region
<222> LOCATION: (157)..(201)
<223> OTHER INFORMATION: complementarity determining region (CDR)
      VH-CDR2
<220> FEATURE:
<221> NAME/KEY: V_region
<222> LOCATION: (298)..(351)
<223> OTHER INFORMATION: complementarity determining region (CDR)
      VH-CDR3

<400> SEQUENCE: 31 cag gtg cag ctg cag gag tcg ggc ccc gga ctg gtg aag cct tcg gag      48
Gln Val Gln Leu Gln Glu Ser Gly Pro Gly Leu Val Lys Pro Ser Glu
1               5                   10                  15 acc ctg tcc ctc acc tgc act gtc tct ggt gac tcc gtc agc agt ggt      96
Thr Leu Ser Leu Thr Cys Thr Val Ser Gly Asp Ser Val Ser Ser Gly
            20                  25                  30 agt tac tac tgg agc tgg atc cgg cag ccc cca ggg aag gga ctg gag     144
Ser Tyr Tyr Trp Ser Trp Ile Arg Gln Pro Pro Gly Lys Gly Leu Glu
        35                  40                  45 tgg att ggg tat atc tat tac agt ggg agc acc aac tac aac ccc tcc     192
Trp Ile Gly Tyr Ile Tyr Tyr Ser Gly Ser Thr Asn Tyr Asn Pro Ser
50                  55                  60 ctc aag agt cga gtc acc ata tca gta gac acg tcc aag aac cag ttc     240
Leu Lys Ser Arg Val Thr Ile Ser Val Asp Thr Ser Lys Asn Gln Phe
65                  70                  75                  80
```

```
tcc ctg aag ctg agc tct gtg acc gct gcg gac acg gcc gta tat tcc    288
Ser Leu Lys Leu Ser Ser Val Thr Ala Ala Asp Thr Ala Val Tyr Ser
            85                  90                  95 tgt gcg aga gtc ccc tat ggt tac gga tat agg ggc tac gat ggg gct    336
Cys Ala Arg Val Pro Tyr Gly Tyr Gly Tyr Arg Gly Tyr Asp Gly Ala
        100                 105                 110 tgg tac ttt gac tac tgg ggc cag gga acc ctg gtc acc gtc tcc tcg    384
Trp Tyr Phe Asp Tyr Trp Gly Gln Gly Thr Leu Val Thr Val Ser Ser
        115                 120                 125
```

<210> SEQ ID NO 32
<211> LENGTH: 128
<212> TYPE: PRT
<213> ORGANISM: Homo sapiens

<400> SEQUENCE: 32

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Ser
            85                  90                  95

Cys Ala Arg Val Pro Tyr Gly Tyr Gly Tyr Arg Gly Tyr Asp Gly Ala
        100                 105                 110

Trp Tyr Phe Asp Tyr Trp Gly Gln Gly Thr Leu Val Thr Val Ser Ser
        115                 120                 125
```

<210> SEQ ID NO 33
<211> LENGTH: 318
<212> TYPE: DNA
<213> ORGANISM: Homo sapiens
<220> FEATURE:
<221> NAME/KEY: CDS
<222> LOCATION: (1)..(318)
<223> OTHER INFORMATION: NI-203.205F8-VL variable light chain (VK)
      sequence
<220> FEATURE:
<221> NAME/KEY: V_region
<222> LOCATION: (69)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(288)
<223> OTHER INFORMATION: complementarity determining region (CDR)
      VK-CDR3

<400> SEQUENCE: 33

```
gaa att gtg ttg aca cag tct cca gcc acc ctg tct ttg tct cca ggg    48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt agc agc tac    96
Glu Arg Ala Thr Leu Ser Cys Arg Ala Ser Gln Ser Val Ser Ser Tyr
```

|  |  |  |  |  |  |  |  |  |  |  |  |  |  |  |  |
|---|---|---|---|---|---|---|---|---|---|---|---|---|---|---|---|

```
                    20                  25                  30
tta gcc tgg tac caa cag aaa cct ggc cag gct ccc agg ctc ctc atc       144
Leu Ala Trp Tyr Gln Gln Lys Pro Gly Gln Ala Pro Arg Leu Leu Ile
         35                  40                  45 tat gat gca tcc aac agg gcc act ggc atc cca gcc agg ttc agt ggc       192
Tyr Asp Ala Ser Asn Arg Ala Thr Gly Ile Pro Ala Arg Phe Ser Gly
 50                  55                  60 agt ggg tct ggg aca gac ttc act ctc acc atc agc agc cta gag cct       240
Ser Gly Ser Gly Thr Asp Phe Thr Leu Thr Ile Ser Ser Leu Glu Pro
 65                  70                  75                  80 gaa gat ttt gca gtt tat tac tgt cag cag cgt agc aac cgg ttc act       288
Glu Asp Phe Ala Val Tyr Tyr Cys Gln Gln Arg Ser Asn Arg Phe Thr
                 85                  90                  95 ttc ggc cct ggg acc aaa gtg gat atc aaa                               318
Phe Gly Pro Gly Thr Lys Val Asp Ile Lys
            100                 105

<210> SEQ ID NO 34
<211> LENGTH: 106
<212> TYPE: PRT
<213> ORGANISM: Homo sapiens

<400> SEQUENCE: 34

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Arg Phe Thr
                85                  90                  95

Phe Gly Pro Gly Thr Lys Val Asp Ile Lys
            100                 105

<210> SEQ ID NO 35
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: NI-203.9B3-VH variable heavy chain (VH)
      sequence
<220> FEATURE:
<221> NAME/KEY: V_region
<222> LOCATION: (76)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(324)
<223> OTHER INFORMATION: complementarity determining region (CDR)
      VH-CDR3

<400> SEQUENCE: 35
```

```
gag gtg cag ctg gtg gag tct ggg gga ggc gtg gtc cag cct ggg ggg       48
Glu Val Gln Leu Val Glu Ser Gly Gly Gly Val Val Gln Pro Gly Gly
1               5                   10                  15 tcc ctg aga ctc tcc tgt gca gcg tca gga ttc acc ttc agt agc tat       96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggg ctg gag tgg gtg      144
Gly Met His Trp Val Arg Gln Ala Pro Gly Lys Gly Leu Glu Trp Val
        35                  40                  45 gca gtt atc tgg tat gat gga act aag aag tac tat gca gac tcc gtg      192
Ala Val Ile Trp Tyr Asp Gly Thr Lys Lys Tyr Tyr Ala Asp Ser Val
    50                  55                  60 aag ggc cga ttc acc acc tcc aga gac aat tcc aag aat acg ctg tct      240
Lys Gly Arg Phe Thr Thr Ser Arg Asp Asn Ser Lys Asn Thr Leu Ser
65                  70                  75                  80 ctg caa atg aac agc ctg aga gcc gag gac tcg gct gtg tat tac tgt      288
Leu Gln Met Asn Ser Leu Arg Ala Glu Asp Ser Ala Val Tyr Tyr Cys
                85                  90                  95 gcg aga ggc ttt agc agc agc tgg gag ttt ggg ttc tgg ggc cag gga      336
Ala Arg Gly Phe Ser Ser Ser Trp Glu Phe Gly Phe Trp Gly Gln Gly
            100                 105                 110 acc ctg gtc acc gtc tcc tcg                                          357
Thr Leu Val Thr Val Ser Ser
        115

<210> SEQ ID NO 36
<211> LENGTH: 119
<212> TYPE: PRT
<213> ORGANISM: Homo sapiens

<400> SEQUENCE: 36

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Thr Lys Lys Tyr Tyr Ala Asp Ser Val
    50                  55                  60

Lys Gly Arg Phe Thr Thr Ser Arg Asp Asn Ser Lys Asn Thr Leu Ser
65                  70                  75                  80

Leu Gln Met Asn Ser Leu Arg Ala Glu Asp Ser Ala Val Tyr Tyr Cys
                85                  90                  95

Ala Arg Gly Phe Ser Ser Ser Trp Glu Phe Gly Phe Trp Gly Gln Gly
            100                 105                 110

Thr Leu Val Thr Val Ser Ser
        115

<210> SEQ ID NO 37
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-203.9B3-VL variable light chain (VL)
      sequence
<220> FEATURE:
<221> NAME/KEY: V_region
<222> LOCATION: (67)..(108)
<223> OTHER INFORMATION: complementarity determining region (CDR)
      VL-CDR1
```

```
<220> FEATURE:
<221> NAME/KEY: V_region
<222> LOCATION: (154)..(174)
<223> OTHER INFORMATION: complementarity determining region (CDR)
      VL-CDR2
<220> FEATURE:
<221> NAME/KEY: V_region
<222> LOCATION: (271)..(300)
<223> OTHER INFORMATION: complementarity determining region (CDR)
      VL-CDR3

<400> SEQUENCE: 37 cag tct gcc ctg act cag cct ccc tcc gcg tcc ggg tct cct gga cag         48
Gln Ser Ala Leu Thr Gln Pro Pro Ser Ala Ser Gly Ser Pro Gly Gln
1               5                   10                  15 tca gtc acc atc tcc tgc act gga acc agc ggt tac att tat ggt tat         96
Ser Val Thr Ile Ser Cys Thr Gly Thr Ser Gly Tyr Ile Tyr Gly Tyr
            20                  25                  30 aac tat gtc tcc tgg tac caa cag cac ccc ggc aaa gcc ccc aaa gtc        144
Asn Tyr Val Ser Trp Tyr Gln Gln His Pro Gly Lys Ala Pro Lys Val
        35                  40                  45 atg att tat gag gtc act aag cgg ccc tca ggg gtc cct gat cgc ttc        192
Met Ile Tyr Glu Val Thr Lys Arg Pro Ser Gly Val Pro Asp Arg Phe
50                  55                  60 tct ggc tcc aag tct ggc aac acg gcc tcc ctg acc gtc tct ggg ctc        240
Ser Gly Ser Lys Ser Gly Asn Thr Ala Ser Leu Thr Val Ser Gly Leu
65                  70                  75                  80 cag gct gag gat gag gct gtt tat tac tgc gcc tca tat gca ggc agc        288
Gln Ala Glu Asp Glu Ala Val Tyr Tyr Cys Ala Ser Tyr Ala Gly Ser
                85                  90                  95 aac aat gta gta ttc ggc gga ggg acc aag ctg acc gtc cta                330
Asn Asn Val Val Phe Gly Gly Gly Thr Lys Leu Thr Val Leu
            100                 105                 110

<210> SEQ ID NO 38
<211> LENGTH: 110
<212> TYPE: PRT
<213> ORGANISM: Homo sapiens

<400> SEQUENCE: 38

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Gly Tyr Ile Tyr Gly Tyr
            20                  25                  30

Asn Tyr Val Ser Trp Tyr Gln Gln His Pro Gly Lys Ala Pro Lys Val
        35                  40                  45

Met Ile Tyr Glu Val Thr Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Val Tyr Tyr Cys Ala Ser Tyr Ala Gly Ser
                85                  90                  95

Asn Asn Val Val Phe Gly Gly Gly Thr Lys Leu Thr Val Leu
            100                 105                 110

<210> SEQ ID NO 39
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-203.1D10-VH variable heavy chain (VH)
```

```
                                  sequence
<220> FEATURE:
<221> NAME/KEY: V_region
<222> LOCATION: (76)..(105)
<223> OTHER INFORMATION: complementarity determining region (CDR)
      VH-CDR1
<220> FEATURE:
<221> NAME/KEY: V_region
<222> LOCATION: (151)..(198)
<223> OTHER INFORMATION: complementarity determining region (CDR)
      VH-CDR2
<220> FEATURE:
<221> NAME/KEY: V_region
<222> LOCATION: (295)..(327)
<223> OTHER INFORMATION: complementarity determining region (CDR)
      VH-CDR3

<400> SEQUENCE: 39 gag gtg cag ctg gtg cag tct ggc gca gaa gtg aag aag ccc ggg gag        48
Glu Val Gln Leu Val Gln Ser Gly Ala Glu Val Lys Lys Pro Gly Glu
1               5                   10                  15 tct ctc aga atc tcc tgt aag gct tct gga tac agc ttc acc aac tct        96
Ser Leu Arg Ile Ser Cys Lys Ala Ser Gly Tyr Ser Phe Thr Asn Ser
            20                  25                  30 tgg atc gcc tgg gtg cgc cag atg ccc ggg aaa ggc ctg gac tac gtg       144
Trp Ile Ala Trp Val Arg Gln Met Pro Gly Lys Gly Leu Asp Tyr Val
        35                  40                  45 ggt atc atc tat cct ggt gac tct gat acc aag tat ggc ccg tcc ttc       192
Gly Ile Ile Tyr Pro Gly Asp Ser Asp Thr Lys Tyr Gly Pro Ser Phe
    50                  55                  60 caa ggc cac gtc act atc tca gcc gac aac ttc gcc aac acc gcc tac       240
Gln Gly His Val Thr Ile Ser Ala Asp Asn Phe Ala Asn Thr Ala Tyr
65                  70                  75                  80 ctg cag tgg agc agc ctg aag gcc tcc gac acc gcc atc tat tat tgt       288
Leu Gln Trp Ser Ser Leu Lys Ala Ser Asp Thr Ala Ile Tyr Tyr Cys
                85                  90                  95 gcg aga cgg gca gca gcg gct att aac tgg ttc gac tcc tgg ggc cag       336
Ala Arg Arg Ala Ala Ala Ala Ile Asn Trp Phe Asp Ser Trp Gly Gln
            100                 105                 110 gga acc ctg gtc acc gtc tcc tcg                                        360
Gly Thr Leu Val Thr Val Ser Ser
        115                 120

<210> SEQ ID NO 40
<211> LENGTH: 120
<212> TYPE: PRT
<213> ORGANISM: Homo sapiens

<400> SEQUENCE: 40

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Asn Ser
            20                  25                  30

Trp Ile Ala Trp Val Arg Gln Met Pro Gly Lys Gly Leu Asp Tyr Val
        35                  40                  45

Gly Ile Ile Tyr Pro Gly Asp Ser Asp Thr Lys Tyr Gly Pro Ser Phe
    50                  55                  60

Gln Gly His Val Thr Ile Ser Ala Asp Asn Phe Ala Asn Thr Ala Tyr
65                  70                  75                  80

Leu Gln Trp Ser Ser Leu Lys Ala Ser Asp Thr Ala Ile Tyr Tyr Cys
                85                  90                  95

Ala Arg Arg Ala Ala Ala Ala Ile Asn Trp Phe Asp Ser Trp Gly Gln
            100                 105                 110
```

```
Gly Thr Leu Val Thr Val Ser Ser
        115                 120

<210> SEQ ID NO 41
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: NI-203.1D10-VL variable light chain (VK)
      sequence
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
<222> LOCATION: (163)..(183)
<223> OTHER INFORMATION: complementarity determining region (CDR)
      VK-CDR2
<220> FEATURE:
<221> NAME/KEY: V_region
<222> LOCATION: (280)..(303)
<223> OTHER INFORMATION: complementarity determining region (CDR)
      VK-CDR3

<400> SEQUENCE: 41 gac atc cag ttg acc cag tct cca ctc tcc ctg tcc gtc acc cct gga        48
Asp Ile Gln Leu Thr Gln Ser Pro Leu Ser Leu Ser Val Thr Pro Gly
1               5                   10                  15 gag ccg gcc tcc atc tcc tgc agg tct agc cag agc ctc ctg cat cct        96
Glu Pro Ala Ser Ile Ser Cys Arg Ser Ser Gln Ser Leu Leu His Pro
            20                  25                  30 aat gga aac gac tat ttg gat tgg tac gtg cag aag cca ggg cag tct       144
Asn Gly Asn Asp Tyr Leu Asp Trp Tyr Val Gln Lys Pro Gly Gln Ser
        35                  40                  45 cca cag atc gtg atc tac atg ggt tct aat cgg gcc gcc ggg gtc cct       192
Pro Gln Ile Val Ile Tyr Met Gly Ser Asn Arg Ala Ala Gly Val Pro
    50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
65                  70                  75                  80 agc aga gtg gag gct gag gat gtt ggg act tat tac tgc ctg caa gct       288
Ser Arg Val Glu Ala Glu Asp Val Gly Thr Tyr Tyr Cys Leu Gln Ala
                85                  90                  95 cta cgc ggg tac act ttt ggc cag ggg acc aag gtg gaa atc aaa           333
Leu Arg Gly Tyr Thr Phe Gly Gln Gly Thr Lys Val Glu Ile Lys
            100                 105                 110

<210> SEQ ID NO 42
<211> LENGTH: 111
<212> TYPE: PRT
<213> ORGANISM: Homo sapiens

<400> SEQUENCE: 42

Asp Ile Gln Leu Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Pro
            20                  25                  30

Asn Gly Asn Asp Tyr Leu Asp Trp Tyr Val Gln Lys Pro Gly Gln Ser
        35                  40                  45

Pro Gln Ile Val Ile Tyr Met Gly Ser Asn Arg Ala Ala Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Thr Tyr Tyr Cys Leu Gln Ala
                 85                  90                  95

Leu Arg Gly Tyr Thr Phe Gly Gln Gly Thr Lys Val Glu Ile Lys
            100                 105                 110

<210> SEQ ID NO 43
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-203.2A11-VH variable heavy chain (VH)
      sequence
<220> FEATURE:
<221> NAME/KEY: V_region
<222> LOCATION: (76)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(327)
<223> OTHER INFORMATION: complementarity determining region (CDR)
      VH-CDR3

<400> SEQUENCE: 43 cag gtg cag ctg gtg gag tct ggg gga ggc gtg gtc cag cct ggg ggg      48
Gln Val Gln Leu Val Glu Ser Gly Gly Gly Val Val Gln Pro Gly Gly
 1               5                  10                  15 tcc ctg aga ctc tcc tgt gta gcg tct gga ttc acc ttc agc agt tat      96
Ser Leu Arg Leu Ser Cys Val Ala Ser Gly Phe Thr Phe Ser Ser Tyr
             20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
         35                  40                  45 gca ttt gta cgg tat gat gga agt aat aag tac tat gca gac tcc gtg     192
Ala Phe Val Arg Tyr Asp Gly Ser Asn Lys Tyr Tyr Ala Asp Ser Val
     50                  55                  60 aag ggc cga ttc acc atc tcc aga gac aat tcc aag aac tcg ctg tct     240
Lys Gly Arg Phe Thr Ile Ser Arg Asp Asn Ser Lys Asn Ser Leu Ser
 65                  70                  75                  80 ctt caa atg aac agt ctg aga act gaa gac acg gct gta tat tac tgc     288
Leu Gln Met Asn Ser Leu Arg Thr Glu Asp Thr Ala Val Tyr Tyr Cys
                 85                  90                  95 gcg aaa gaa cag gag gac cac aag gaa gct ttt gac tac tgg ggc cag     336
Ala Lys Glu Gln Glu Asp His Lys Glu Ala Phe Asp Tyr Trp Gly Gln
            100                 105                 110 gga acc ctg gtc acc gtc tcc tcg                                     360
Gly Thr Leu Val Thr Val Ser Ser
        115                 120

<210> SEQ ID NO 44
<211> LENGTH: 120
<212> TYPE: PRT
<213> ORGANISM: Homo sapiens

<400> SEQUENCE: 44

Gln Val Gln Leu Val Glu Ser Gly Gly Gly Val Val Gln Pro Gly Gly
```

```
                1               5                  10                  15
              Ser Leu Arg Leu Ser Cys Val Ala Ser Gly Phe Thr Phe Ser Ser Tyr
                            20                  25                  30

Gly Met His Trp Val Arg Gln Ala Pro Gly Lys Gly Leu Glu Trp Val
                            35                  40                  45

Ala Phe Val Arg Tyr Asp Gly Ser Asn Lys Tyr Tyr Ala Asp Ser Val
                            50                  55                  60

Lys Gly Arg Phe Thr Ile Ser Arg Asp Asn Ser Lys Asn Ser Leu Ser
               65                70                  75                  80

Leu Gln Met Asn Ser Leu Arg Thr Glu Asp Thr Ala Val Tyr Tyr Cys
                            85                  90                  95

Ala Lys Glu Gln Glu Asp His Lys Glu Ala Phe Asp Tyr Trp Gly Gln
                            100                 105                 110

Gly Thr Leu Val Thr Val Ser Ser
                            115                 120

<210> SEQ ID NO 45
<211> LENGTH: 318
<212> TYPE: DNA
<213> ORGANISM: Homo sapiens
<220> FEATURE:
<221> NAME/KEY: CDS
<222> LOCATION: (1)..(318)
<223> OTHER INFORMATION: NI-203.2A11-VL variable light chain (VK)
      sequence
<220> FEATURE:
<221> NAME/KEY: V_region
<222> LOCATION: (70)..(99)
<223> OTHER INFORMATION: complementarity determining region (CDR)
      VK-CDR1
<220> FEATURE:
<221> NAME/KEY: V_region
<222> LOCATION: (145)..(165)
<223> OTHER INFORMATION: complementarity determining region (CDR)
      VK-CDR2
<220> FEATURE:
<221> NAME/KEY: V_region
<222> LOCATION: (262)..(288)
<223> OTHER INFORMATION: complementarity determining region (CDR)
      VK-CDR3

<400> SEQUENCE: 45 gaa att gtg atg aca cag tct cca gcc acc ctg tct gtg tct cca ggg        48
Glu Ile Val Met Thr Gln Ser Pro Ala Thr Leu Ser Val Ser Pro Gly
 1               5                  10                  15 gaa aga gcc acc ctc tcc tgc agg gcc agt cag aga gtt acc acc ata        96
Glu Arg Ala Thr Leu Ser Cys Arg Ala Ser Gln Arg Val Thr Thr Ile
                20                  25                  30 gcc tgg tac cag cag aaa cct ggc cag gct ccc agg ctc ctc atc tat       144
Ala Trp Tyr Gln Gln Lys Pro Gly Gln Ala Pro Arg Leu Leu Ile Tyr
            35                  40                  45 ggt gca tcc agc agg gcc act gat att ccc gcc agg ttc agt ggc agt       192
Gly Ala Ser Ser Arg Ala Thr Asp Ile Pro Ala Arg Phe Ser Gly Ser
     50                  55                  60 ggg tct ggg aca gac ttc act ctc acc atc agc agt ctg cag tct gaa       240
Gly Ser Gly Thr Asp Phe Thr Leu Thr Ile Ser Ser Leu Gln Ser Glu
 65                70                  75                  80 gac ttt gca gtt tat tac tgt cag cag tat aac cag tgg ccc ctc act       288
Asp Phe Ala Val Tyr Tyr Cys Gln Gln Tyr Asn Gln Trp Pro Leu Thr
                85                  90                  95 ttc ggc gga ggg acc aag ctg gag atc aaa                               318
Phe Gly Gly Gly Thr Lys Leu Glu Ile Lys
            100                 105
```

<210> SEQ ID NO 46
<211> LENGTH: 106
<212> TYPE: PRT
<213> ORGANISM: Homo sapiens

<400> SEQUENCE: 46

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Arg Val Thr Thr Ile
            20                  25                  30

Ala Trp Tyr Gln Gln Lys Pro Gly Gln Ala Pro Arg Leu Leu Ile Tyr
        35                  40                  45

Gly Ala Ser Ser Arg Ala Thr Asp Ile Pro Ala Arg Phe Ser Gly Ser
    50                  55                  60

Gly Ser Gly Thr Asp Phe Thr Leu Thr Ile Ser Ser Leu Gln Ser Glu
65                  70                  75                  80

Asp Phe Ala Val Tyr Tyr Cys Gln Gln Tyr Asn Gln Trp Pro Leu Thr
                85                  90                  95

Phe Gly Gly Gly Thr Lys Leu Glu Ile Lys
            100                 105
```

<210> SEQ ID NO 47
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION: NI-203.10C4-VH variable heavy chain (VH) sequence, wherein Glu at positions 1 and 6 can also be Gln
<220> FEATURE:
<221> NAME/KEY: V_region
<222> LOCATION: (76)..(105)
<223> OTHER INFORMATION: complementarity determining region (CDR) VH-CDR1
<220> FEATURE:
<221> NAME/KEY: V_region
<222> LOCATION: (148)..(198)
<223> OTHER INFORMATION: complementarity determining region (CDR) VH-CDR2
<220> FEATURE:
<221> NAME/KEY: V_region
<222> LOCATION: (295)..(345)
<223> OTHER INFORMATION: complementarity determining region (CDR) VH-CDR3

<400> SEQUENCE: 47

```
gag gtg cag ctg gtg gag tct ggg gct gaa gtg agg aag cct ggg gcc      48
Glu Val Gln Leu Val Glu Ser Gly Ala Glu Val Arg Lys Pro Gly Ala
1               5                   10                  15 tca gtg agg gtc tcc tgc cag aca tct gga tac agc gtc acc gac tac      96
Ser Val Arg Val Ser Cys Gln Thr Ser Gly Tyr Ser Val Thr Asp Tyr
            20                  25                  30 tat cta cac tgg gtg cga cag gcc cct gga cag ggc ctt gag tgg atg     144
Tyr Leu His Trp Val Arg Gln Ala Pro Gly Gln Gly Leu Glu Trp Met
        35                  40                  45 gga gtg atg aac ccg agc aat gga aac gtg ggc tac cca cag aag ttt     192
Gly Val Met Asn Pro Ser Asn Gly Asn Val Gly Tyr Pro Gln Lys Phe
    50                  55                  60 cag ggc cga gtc acc atg acc gca gac acg tcc acg ggc aca gtg tac     240
Gln Gly Arg Val Thr Met Thr Ala Asp Thr Ser Thr Gly Thr Val Tyr
65                  70                  75                  80 atg gtg ttg acc ggc ctt acg gct ggg gac acg gcc gtc tac tac tgt     288
Met Val Leu Thr Gly Leu Thr Ala Gly Asp Thr Ala Val Tyr Tyr Cys
```

```
                    85                  90                  95
gcc aga ggc ggg tcc acg ccg ggt cag gaa gta agg agt ccc cac gtc         336
Ala Arg Gly Gly Ser Thr Pro Gly Gln Glu Val Arg Ser Pro His Val
                   100                 105                 110 ctt gac ctc tgg ggc cag gga acc ctg gtc acc gtc tcc tcg                 378
Leu Asp Leu Trp Gly Gln Gly Thr Leu Val Thr Val Ser Ser
        115                 120                 125

<210> SEQ ID NO 48
<211> LENGTH: 126
<212> TYPE: PRT
<213> ORGANISM: Homo sapiens

<400> SEQUENCE: 48

Glu Val Gln Leu Val Glu Ser Gly Ala Glu Val Arg Lys Pro Gly Ala
1               5                   10                  15

Ser Val Arg Val Ser Cys Gln Thr Ser Gly Tyr Ser Val Thr Asp Tyr
                20                  25                  30

Tyr Leu His Trp Val Arg Gln Ala Pro Gly Gln Gly Leu Glu Trp Met
            35                  40                  45

Gly Val Met Asn Pro Ser Asn Gly Asn Val Gly Tyr Pro Gln Lys Phe
        50                  55                  60

Gln Gly Arg Val Thr Met Thr Ala Asp Thr Ser Thr Gly Thr Val Tyr
65                  70                  75                  80

Met Val Leu Thr Gly Leu Thr Ala Gly Asp Thr Ala Val Tyr Tyr Cys
                85                  90                  95

Ala Arg Gly Gly Ser Thr Pro Gly Gln Glu Val Arg Ser Pro His Val
                100                 105                 110

Leu Asp Leu Trp Gly Gln Gly Thr Leu Val Thr Val Ser Ser
            115                 120                 125

<210> SEQ ID NO 49
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NI-203.10C4-VL variable light chain (VK)
      sequence, wherein Val at postion 2 can also be Ile and Ser at
      position 7 can also be Thr
<220> FEATURE:
<221> NAME/KEY: V_region
<222> LOCATION: (70)..(117)
<223> OTHER INFORMATION: complementarity determining region (CDR)
      VK-CDR1
<220> FEATURE:
<221> NAME/KEY: V_region
<222> LOCATION: (163)..(183)
<223> OTHER INFORMATION: complementarity determining region (CDR)
      VK-CDR2
<220> FEATURE:
<221> NAME/KEY: V_region
<222> LOCATION: (280)..(306)
<223> OTHER INFORMATION: complementarity determining region (CDR)
      VK-CDR3

<400> SEQUENCE: 49 gat gtt gtg atg act cag tct ccc ctc tct ctg tcc gtc acc cct gga        48
Asp Val Val Met Thr Gln Ser Pro Leu Ser Leu Ser Val Thr Pro Gly
1               5                   10                  15 cag ccg gcc tcc atc tcc tgc agg tct gat gag agc ctc ctg cat agt        96
Gln Pro Ala Ser Ile Ser Cys Arg Ser Asp Glu Ser Leu Leu His Ser
                20                  25                  30
```

| | | |
|---|---|---|
| gat gga agg acc tat ttg tat tgg tat cta cag aag ccc ggc cag cct<br>Asp Gly Arg Thr Tyr Leu Tyr Trp Tyr Leu Gln Lys Pro Gly Gln Pro<br>35 40 45 | | 144 |
| cct cag ctc ctg atc tat gaa gtt tcc aac cgg ttc tcg gga gtg cca<br>Pro Gln Leu Leu Ile Tyr Glu Val Ser Asn Arg Phe Ser Gly Val Pro<br>50 55 60 | | 192 |
| aat agg ttc agt ggc agc ggg tca ggg aca gat ttc aca ctg aaa atc<br>Asn Arg Phe Ser Gly Ser Gly Ser Gly Thr Asp Phe Thr Leu Lys Ile<br>65 70 75 80 | | 240 |
| agc cgg gtg gag gct gag gat gtt ggc gtt tat tac tgc atg cag ggt<br>Ser Arg Val Glu Ala Glu Asp Val Gly Val Tyr Tyr Cys Met Gln Gly<br>85 90 95 | | 288 |
| gta cac ttt cct cag acg ttc ggc cag ggg acc aag ctg gag atc aaa<br>Val His Phe Pro Gln Thr Phe Gly Gln Gly Thr Lys Leu Glu Ile Lys<br>100 105 110 | | 336 |

<210> SEQ ID NO 50
<211> LENGTH: 112
<212> TYPE: PRT
<213> ORGANISM: Homo sapiens

<400> SEQUENCE: 50

Asp Val Val Met Thr Gln Ser Pro Leu Ser Leu Ser Val Thr Pro Gly
1               5                   10                  15

Gln Pro Ala Ser Ile Ser Cys Arg Ser Asp Glu Ser Leu Leu His Ser
            20                  25                  30

Asp Gly Arg Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asn Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
            85                  90                  95

Val His Phe Pro Gln Thr Phe Gly Gln Gly Thr Lys Leu Glu Ile Lys
            100                 105                 110

<210> SEQ ID NO 51
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-203.20H9-VH variable heavy chain (VH)
      sequence
<220> FEATURE:
<221> NAME/KEY: V_region
<222> LOCATION: (76)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(336)
<223> OTHER INFORMATION: complementarity determining region (CDR)
      VH-CDR3

<400> SEQUENCE: 51

| | | |
|---|---|---|
| cag gtg cag ctg gtg caa tct ggg tct gag ttg aag aag cct ggg gcc<br>Gln Val Gln Leu Val Gln Ser Gly Ser Glu Leu Lys Lys Pro Gly Ala | | 48 |

```
              1               5              10              15
tca gtg aag gtc tcc tgc aag gct tct gga tac atc ttc agt aaa cat        96
Ser Val Lys Val Ser Cys Lys Ala Ser Gly Tyr Ile Phe Ser Lys His
            20                  25                  30 ggt atc aac tgg gtg cga cag gcc cct gga caa ggc ctt gag tgg ata       144
Gly Ile Asn Trp Val Arg Gln Ala Pro Gly Gln Gly Leu Glu Trp Ile
        35                  40                  45 gga tgg atc aac acc aat acg ggg aac cca aca tat gcc cag gac ttc       192
Gly Trp Ile Asn Thr Asn Thr Gly Asn Pro Thr Tyr Ala Gln Asp Phe
    50                  55                  60 aca gga cga ttt gtc ttc tcc ttg gac acc tct gtc agc acg gca tat       240
Thr Gly Arg Phe Val Phe Ser Leu Asp Thr Ser Val Ser Thr Ala Tyr
65                  70                  75                  80 ctg gag atc agc agc cta aag gct gag gac act gcc gtg tat tac tgt       288
Leu Glu Ile Ser Ser Leu Lys Ala Glu Asp Thr Ala Val Tyr Tyr Cys
                85                  90                  95 gcg aga gaa tca gag ccg att ttt gga gtt atc tat tac atg gac gtc       336
Ala Arg Glu Ser Glu Pro Ile Phe Gly Val Ile Tyr Tyr Met Asp Val
            100                 105                 110 tgg ggc aaa ggg acc acg gtc acc gtc tcc tcg                           369
Trp Gly Lys Gly Thr Thr Val Thr Val Ser Ser
        115                 120

<210> SEQ ID NO 52
<211> LENGTH: 123
<212> TYPE: PRT
<213> ORGANISM: Homo sapiens

<400> SEQUENCE: 52

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Ser Lys His
            20                  25                  30

Gly Ile Asn Trp Val Arg Gln Ala Pro Gly Gln Gly Leu Glu Trp Ile
        35                  40                  45

Gly Trp Ile Asn Thr Asn Thr Gly Asn Pro Thr Tyr Ala Gln Asp Phe
    50                  55                  60

Thr Gly Arg Phe Val Phe Ser Leu Asp Thr Ser Val Ser Thr Ala Tyr
65                  70                  75                  80

Leu Glu Ile Ser Ser Leu Lys Ala Glu Asp Thr Ala Val Tyr Tyr Cys
                85                  90                  95

Ala Arg Glu Ser Glu Pro Ile Phe Gly Val Ile Tyr Tyr Met Asp Val
            100                 105                 110

Trp Gly Lys Gly Thr Thr Val Thr Val Ser Ser
        115                 120

<210> SEQ ID NO 53
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-203.20H9-VL variable light chain (VK)
      sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
```

```
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(291)
<223> OTHER INFORMATION: complementarity determining region (CDR)
      VK-CDR3

<400> SEQUENCE: 53 gac atc cag atg acc cag tct cca tcc tcc ctg tct gca tct gta gga      48
Asp Ile Gln Met Thr Gln Ser Pro Ser Ser Leu Ser Ala Ser Val Gly
1               5                   10                  15 gac agc gtc acc atc act tgc cgg gca agc cag agc ata agc act aat      96
Asp Ser Val Thr Ile Thr Cys Arg Ala Ser Gln Ser Ile Ser Thr Asn
            20                  25                  30 tta aat tgg tat cag aag aaa cca gga caa gcc cct acg gtc ttg atc     144
Leu Asn Trp Tyr Gln Lys Lys Pro Gly Gln Ala Pro Thr Val Leu Ile
        35                  40                  45 tat gct gcg tcc agt ttg caa ggt ggg gtc cca tca agg ttc agg ggc     192
Tyr Ala Ala Ser Ser Leu Gln Gly Gly Val Pro Ser Arg Phe Arg Gly
    50                  55                  60 cgg gga tct ggg aca tat ttc act ctc acc atc agc ggt ctt caa cct     240
Arg Gly Ser Gly Thr Tyr Phe Thr Leu Thr Ile Ser Gly Leu Gln Pro
65                  70                  75                  80 gaa gat ttt gca act tat tac tgt caa cac aat tac aat gat ttg tgg     288
Glu Asp Phe Ala Thr Tyr Tyr Cys Gln His Asn Tyr Asn Asp Leu Trp
                85                  90                  95 acg ttc ggc caa ggg acc aag gtg gaa atc aaa                         321
Thr Phe Gly Gln Gly Thr Lys Val Glu Ile Lys
            100                 105

<210> SEQ ID NO 54
<211> LENGTH: 107
<212> TYPE: PRT
<213> ORGANISM: Homo sapiens

<400> SEQUENCE: 54

Asp Ile Gln Met Thr Gln Ser Pro Ser Ser Leu Ser Ala Ser Val Gly
1               5                   10                  15

Asp Ser Val Thr Ile Thr Cys Arg Ala Ser Gln Ser Ile Ser Thr Asn
            20                  25                  30

Leu Asn Trp Tyr Gln Lys Lys Pro Gly Gln Ala Pro Thr Val Leu Ile
        35                  40                  45

Tyr Ala Ala Ser Ser Leu Gln Gly Gly Val Pro Ser Arg Phe Arg Gly
    50                  55                  60

Arg Gly Ser Gly Thr Tyr Phe Thr Leu Thr Ile Ser Gly Leu Gln Pro
65                  70                  75                  80

Glu Asp Phe Ala Thr Tyr Tyr Cys Gln His Asn Tyr Asn Asp Leu Trp
                85                  90                  95

Thr Phe Gly Gln Gly Thr Lys Val Glu Ile Lys
            100                 105

<210> SEQ ID NO 55
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-203.26D2-VH variable heavy chain (VH)
      sequence
<220> FEATURE:
```

```
<221> NAME/KEY: V_region
<222> LOCATION: (76)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(327)
<223> OTHER INFORMATION: complementarity determining region (CDR)
      VH-CDR3

<400> SEQUENCE: 55 cag gtg cag ctg gtg gag tct ggg gga ggc gtg gtc cag cct ggg ggg      48
Gln Val Gln Leu Val Glu Ser Gly Gly Gly Val Val Gln Pro Gly Gly
1               5                   10                  15 tcc ctg aga ctc tcc tgt gca gcg tct ggg ttc acg ttc aga acc tgt      96
Ser Leu Arg Leu Ser Cys Ala Ala Ser Gly Phe Thr Phe Arg Thr Cys
            20                  25                  30 ggc atg cac tgg gtc cgc cag gct cca ggc aag ggg ctg gaa tgg gtg     144
Gly Met His Trp Val Arg Gln Ala Pro Gly Lys Gly Leu Glu Trp Val
        35                  40                  45 gca ttt gtt cgg tct gat gga act act aga tat tac gca gac tcc ctg     192
Ala Phe Val Arg Ser Asp Gly Thr Thr Arg Tyr Tyr Ala Asp Ser Leu
50                  55                  60 atg ggc cgc ttc acc atc tcc aga gac aat tcc aag aac tcg ctg tat     240
Met Gly Arg Phe Thr Ile Ser Arg Asp Asn Ser Lys Asn Ser Leu Tyr
65                  70                  75                  80 ctt caa atg aac agt ctg aga cct gag gac acg gct ctt tat tac tgt     288
Leu Gln Met Asn Ser Leu Arg Pro Glu Asp Thr Ala Leu Tyr Tyr Cys
                85                  90                  95 gcg agg gaa aag gag gat cac agg gaa gct ttt gac tac tgg ggc cag     336
Ala Arg Glu Lys Glu Asp His Arg Glu Ala Phe Asp Tyr Trp Gly Gln
            100                 105                 110 gga acc ctg gtc acc gtc tcc tcg                                     360
Gly Thr Leu Val Thr Val Ser Ser
        115                 120

<210> SEQ ID NO 56
<211> LENGTH: 120
<212> TYPE: PRT
<213> ORGANISM: Homo sapiens

<400> SEQUENCE: 56

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Thr Cys
            20                  25                  30

Gly Met His Trp Val Arg Gln Ala Pro Gly Lys Gly Leu Glu Trp Val
        35                  40                  45

Ala Phe Val Arg Ser Asp Gly Thr Thr Arg Tyr Tyr Ala Asp Ser Leu
50                  55                  60

Met Gly Arg Phe Thr Ile Ser Arg Asp Asn Ser Lys Asn Ser Leu Tyr
65                  70                  75                  80

Leu Gln Met Asn Ser Leu Arg Pro Glu Asp Thr Ala Leu Tyr Tyr Cys
                85                  90                  95

Ala Arg Glu Lys Glu Asp His Arg Glu Ala Phe Asp Tyr Trp Gly Gln
            100                 105                 110

Gly Thr Leu Val Thr Val Ser Ser
        115                 120
```

```
                    115                 120

<210> SEQ ID NO 57
<211> LENGTH: 318
<212> TYPE: DNA
<213> ORGANISM: Homo sapiens
<220> FEATURE:
<221> NAME/KEY: CDS
<222> LOCATION: (1)..(318)
<223> OTHER INFORMATION: NI-203.26D2-VL variable light chain (VK)
      sequence
<220> FEATURE:
<221> NAME/KEY: V_region
<222> LOCATION: (70)..(99)
<223> OTHER INFORMATION: complementarity determining region (CDR)
      VK-CDR1
<220> FEATURE:
<221> NAME/KEY: V_region
<222> LOCATION: (145)..(165)
<223> OTHER INFORMATION: complementarity determining region (CDR)
      VK-CDR2
<220> FEATURE:
<221> NAME/KEY: V_region
<222> LOCATION: (262)..(288)
<223> OTHER INFORMATION: complementarity determining region (CDR)
      VK-CDR3

<400> SEQUENCE: 57 gaa att gtg atg aca cag tct cca gcc acc ctg tct gtg tct cca ggg        48
Glu Ile Val Met Thr Gln Ser Pro Ala Thr Leu Ser Val Ser Pro Gly
1               5                   10                  15 gaa aga gcc acc ctc tcc tgc agg gcc agt cag cgt gtt agc act gta        96
Glu Arg Ala Thr Leu Ser Cys Arg Ala Ser Gln Arg Val Ser Thr Val
            20                  25                  30 gcc tgg tac cag cag aaa cct ggc cag gct ccc agg ctc ctc atc tat       144
Ala Trp Tyr Gln Gln Lys Pro Gly Gln Ala Pro Arg Leu Leu Ile Tyr
        35                  40                  45 gat gca tcc acc agg gcc act gat atc ccc gcc agg ttc agt ggc agt       192
Asp Ala Ser Thr Arg Ala Thr Asp Ile Pro Ala Arg Phe Ser Gly Ser
    50                  55                  60 ggg tct ggg aca gac ttc act ctc acc atc agc act ctg caa tct gaa       240
Gly Ser Gly Thr Asp Phe Thr Leu Thr Ile Ser Thr Leu Gln Ser Glu
65                  70                  75                  80 gac tct gca gtt tat tac tgt cag cag tat aat agg tgg ccc ctc act       288
Asp Ser Ala Val Tyr Tyr Cys Gln Gln Tyr Asn Arg Trp Pro Leu Thr
                85                  90                  95 ttc ggc gga ggg acc aag gtg gag atc aaa                               318
Phe Gly Gly Gly Thr Lys Val Glu Ile Lys
            100                 105

<210> SEQ ID NO 58
<211> LENGTH: 106
<212> TYPE: PRT
<213> ORGANISM: Homo sapiens

<400> SEQUENCE: 58

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Arg Val Ser Thr Val
            20                  25                  30

Ala Trp Tyr Gln Gln Lys Pro Gly Gln Ala Pro Arg Leu Leu Ile Tyr
        35                  40                  45

Asp Ala Ser Thr Arg Ala Thr Asp Ile Pro Ala Arg Phe Ser Gly Ser
    50                  55                  60

Gly Ser Gly Thr Asp Phe Thr Leu Thr Ile Ser Thr Leu Gln Ser Glu
```

```
                65                  70                  75                  80
Asp Ser Ala Val Tyr Tyr Cys Gln Gln Tyr Asn Arg Trp Pro Leu Thr
                        85                  90                  95

Phe Gly Gly Gly Thr Lys Val Glu Ile Lys
                100                 105

<210> SEQ ID NO 59
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NI-203.60H3-VH variable heavy chain (VH)
      sequence
<220> FEATURE:
<221> NAME/KEY: V_region
<222> LOCATION: (76)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(327)
<223> OTHER INFORMATION: complementarity determining region (CDR)
      VH-CDR3

<400> SEQUENCE: 59 gag gtg cag ctg gtg gag tct ggg gga gga ttg gca cgc cct gga ggc      48
Glu Val Gln Leu Val Glu Ser Gly Gly Gly Leu Ala Arg Pro Gly Gly
1               5                   10                  15 tcc ctg aga ctc tcc tgt gca gtc gct gga ttc act ttc agt ggt tat      96
Ser Leu Arg Leu Ser Cys Ala Val Ala Gly Phe Thr Phe Ser Gly Tyr
            20                  25                  30 gaa atg aat tgg gtc cgc cag gca cca ggg aag ggg ctg gag tgg att     144
Glu Met Asn Trp Val Arg Gln Ala Pro Gly Lys Gly Leu Glu Trp Ile
        35                  40                  45 tca tat att agc ggt cct ggg gat gtg ata tac tac gca gac tct gtg     192
Ser Tyr Ile Ser Gly Pro Gly Asp Val Ile Tyr Tyr Ala Asp Ser Val
    50                  55                  60 aag ggc cga ttc acc atc tcc aga gac aac gcc aag aac tca ctg ttt     240
Lys Gly Arg Phe Thr Ile Ser Arg Asp Asn Ala Lys Asn Ser Leu Phe
65                  70                  75                  80 cta cag atg aac agc ctg aga gcc gag gac acg gct gtt tat tat tgt     288
Leu Gln Met Asn Ser Leu Arg Ala Glu Asp Thr Ala Val Tyr Tyr Cys
                85                  90                  95 acg aga gtc ccc cct gac atc agc tat gga ttt gat tac tgg ggc cag     336
Thr Arg Val Pro Pro Asp Ile Ser Tyr Gly Phe Asp Tyr Trp Gly Gln
                100                 105                 110 ggc acc ctg gtc acc gtc tcg tcg                                     360
Gly Thr Leu Val Thr Val Ser Ser
        115                 120

<210> SEQ ID NO 60
<211> LENGTH: 120
<212> TYPE: PRT
<213> ORGANISM: Homo sapiens

<400> SEQUENCE: 60

Glu Val Gln Leu Val Glu Ser Gly Gly Gly Leu Ala Arg Pro Gly Gly
1               5                   10                  15
```

```
Ser Leu Arg Leu Ser Cys Ala Val Ala Gly Phe Thr Phe Ser Gly Tyr
        20                  25                  30

Glu Met Asn Trp Val Arg Gln Ala Pro Gly Lys Gly Leu Glu Trp Ile
            35                  40                  45

Ser Tyr Ile Ser Gly Pro Gly Asp Val Ile Tyr Tyr Ala Asp Ser Val
        50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                85                  90                  95

Thr Arg Val Pro Pro Asp Ile Ser Tyr Gly Phe Asp Tyr Trp Gly Gln
            100                 105                 110

Gly Thr Leu Val Thr Val Ser Ser
        115                 120

<210> SEQ ID NO 61
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-203.60H3-VL variable light chain (VK)
      sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(291)
<223> OTHER INFORMATION: complementarity determining region (CDR)
      VK-CDR3

<400> SEQUENCE: 61 gac atc cag atg acc cag tct cca tct tcc ctg tct gca tct gta cga      48
Asp Ile Gln Met Thr Gln Ser Pro Ser Ser Leu Ser Ala Ser Val Arg
 1               5                  10                  15 gac agc gtc acc atc act tgc cgg gca agt cag agc att agc acc tat      96
Asp Ser Val Thr Ile Thr Cys Arg Ala Ser Gln Ser Ile Ser Thr Tyr
            20                  25                  30 tta aat tgg tat cag cag aaa cca ggg aaa gcc cct aac ctc ctg atc     144
Leu Asn Trp Tyr Gln Gln Lys Pro Gly Lys Ala Pro Asn Leu Leu Ile
        35                  40                  45 cat gat aca gac att ttg caa agt ggg gtc cca tca agg ttc agt ggc     192
His Asp Thr Asp Ile Leu Gln Ser Gly Val Pro Ser Arg Phe Ser Gly
    50                  55                  60 act gga tct ggg aca gat ttc act ctc acc atc agc ggt ctg caa cct     240
Thr Gly Ser Gly Thr Asp Phe Thr Leu Thr Ile Ser Gly Leu Gln Pro
 65                  70                  75                  80 gaa gat ttt gca act tac tac tgt caa cag agt tac agt acc cct cct     288
Glu Asp Phe Ala Thr Tyr Tyr Cys Gln Gln Ser Tyr Ser Thr Pro Pro
                85                  90                  95 act ttt ggc cag ggg acc aag ctg gag atc aaa                         321
Thr Phe Gly Gln Gly Thr Lys Leu Glu Ile Lys
            100                 105

<210> SEQ ID NO 62
```

<211> LENGTH: 107
<212> TYPE: PRT
<213> ORGANISM: Homo sapiens

<400> SEQUENCE: 62

```
Asp Ile Gln Met Thr Gln Ser Pro Ser Ser Leu Ser Ala Ser Val Arg
1               5                   10                  15

Asp Ser Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Asn Leu Leu Ile
        35                  40                  45

His Asp Thr Asp Ile Leu Gln Ser Gly Val Pro Ser Arg Phe Ser Gly
    50                  55                  60

Thr Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Leu Glu Ile Lys
            100                 105
```

<210> SEQ ID NO 63
<211> LENGTH: 381
<212> TYPE: DNA
<213> ORGANISM: Homo sapiens
<220> FEATURE:
<221> NAME/KEY: CDS
<222> LOCATION: (1)..(381)
<223> OTHER INFORMATION: NI-203.19F2-VH variable heavy chain (VH) sequence
<220> FEATURE:
<221> NAME/KEY: V_region
<222> LOCATION: (76)..(105)
<223> OTHER INFORMATION: complementarity determining region (CDR) VH-CDR1
<220> FEATURE:
<221> NAME/KEY: V_region
<222> LOCATION: (148)..(198)
<223> OTHER INFORMATION: complementarity determining region (CDR) VH-CDR2
<220> FEATURE:
<221> NAME/KEY: V_region
<222> LOCATION: (295)..(348)
<223> OTHER INFORMATION: complementarity determining region (CDR) VH-CDR3

<400> SEQUENCE: 63

```
gag gtg cag ctg gtg cag tct ggg gct gag gtg agg aag cct ggg tcc      48
Glu Val Gln Leu Val Gln Ser Gly Ala Glu Val Arg Lys Pro Gly Ser
1               5                   10                  15 tcg gtg aag gtc tcc tgc aag gct tct gga ggc aac ttc ttg agc tat      96
Ser Val Lys Val Ser Cys Lys Ala Ser Gly Gly Asn Phe Leu Ser Tyr
            20                  25                  30 tcc atc agt tgg gtg cga cag gcc cct gga caa ggg ctt gag tgg atg     144
Ser Ile Ser Trp Val Arg Gln Ala Pro Gly Gln Gly Leu Glu Trp Met
        35                  40                  45 gga ggg atc atc ccg atc ttt ggt aca cca aac tac gca cag aag ttc     192
Gly Gly Ile Ile Pro Ile Phe Gly Thr Pro Asn Tyr Ala Gln Lys Phe
    50                  55                  60 caa gga aga gtc aca att acg gcg gac aaa tcg acg agg aca gcc tac     240
Gln Gly Arg Val Thr Ile Thr Ala Asp Lys Ser Thr Arg Thr Ala Tyr
65                  70                  75                  80 atg gag ctg agc agc ctg aga ttt gat gac acg gcc gtc tat tat tgt     288
Met Glu Leu Ser Ser Leu Arg Phe Asp Asp Thr Ala Val Tyr Tyr Cys
                85                  90                  95
```

| gcg gat gcg aca aga ccg ggt aca gca gcc tct ggt ttc tat tac tac | 336 |
|---|---|
| Ala Asp Ala Thr Arg Pro Gly Thr Ala Ala Ser Gly Phe Tyr Tyr Tyr | |
| 100 105 110 | |

| ggt atg gac gtc tgg ggc caa ggg acc acg gtc acc gtc tcc tcg | 381 |
|---|---|
| Gly Met Asp Val Trp Gly Gln Gly Thr Thr Val Thr Val Ser Ser | |
| 115 120 125 | |

<210> SEQ ID NO 64
<211> LENGTH: 127
<212> TYPE: PRT
<213> ORGANISM: Homo sapiens

<400> SEQUENCE: 64

Glu Val Gln Leu Val Gln Ser Gly Ala Glu Val Arg Lys Pro Gly Ser
1               5                   10                  15

Ser Val Lys Val Ser Cys Lys Ala Ser Gly Gly Asn Phe Leu Ser Tyr
            20                  25                  30

Ser Ile Ser Trp Val Arg Gln Ala Pro Gly Gln Gly Leu Glu Trp Met
        35                  40                  45

Gly Gly Ile Ile Pro Ile Phe Gly Thr Pro Asn Tyr Ala Gln Lys Phe
    50                  55                  60

Gln Gly Arg Val Thr Ile Thr Ala Asp Lys Ser Thr Arg Thr Ala Tyr
65                  70                  75                  80

Met Glu Leu Ser Ser Leu Arg Phe Asp Asp Thr Ala Val Tyr Tyr Cys
                85                  90                  95

Ala Asp Ala Thr Arg Pro Gly Thr Ala Ala Ser Gly Phe Tyr Tyr Tyr
            100                 105                 110

Gly Met Asp Val Trp Gly Gln Gly Thr Thr Val Thr Val Ser Ser
        115                 120                 125

<210> SEQ ID NO 65
<211> LENGTH: 318
<212> TYPE: DNA
<213> ORGANISM: Homo sapiens
<220> FEATURE:
<221> NAME/KEY: CDS
<222> LOCATION: (1)..(318)
<223> OTHER INFORMATION: NI-203.19F2 -VK variable kappa light chain (VK)
      sequence
<220> FEATURE:
<221> NAME/KEY: V_region
<222> LOCATION: (70)..(102)
<223> OTHER INFORMATION: complementarity determining region (CDR)
      VK-CDR1
<220> FEATURE:
<221> NAME/KEY: V_region
<222> LOCATION: (148)..(168)
<223> OTHER INFORMATION: complementarity determining region (CDR)
      VK-CDR2
<220> FEATURE:
<221> NAME/KEY: V_region
<222> LOCATION: (265)..(288)
<223> OTHER INFORMATION: complementarity determining region (CDR)
      VK-CDR3

<400> SEQUENCE: 65

| gaa att gtg atg aca cag tct cca gac acc ctg tct gtg tct cca ggt | 48 |
|---|---|
| Glu Ile Val Met Thr Gln Ser Pro Asp Thr Leu Ser Val Ser Pro Gly | |
| 1               5                   10                  15 | |

| gaa aga gcc acc ctc tcc tgc agg gcc agt cag agt gtt aac aac aac | 96 |
|---|---|
| Glu Arg Ala Thr Leu Ser Cys Arg Ala Ser Gln Ser Val Asn Asn Asn | |
|             20                  25                  30 | |

| tta gcc tgg ttc cag cag aaa cct ggc cag gct ccc agg ctc ctc atc | 144 |
|---|---|
| Leu Ala Trp Phe Gln Gln Lys Pro Gly Gln Ala Pro Arg Leu Leu Ile | |
|         35                  40                  45 | |

```
tat ggt gca tcc acc agg gcc act ggt att cca gcc aga ttc agt ggc      192
Tyr Gly Ala Ser Thr Arg Ala Thr Gly Ile Pro Ala Arg Phe Ser Gly
    50                  55                  60 agt ggg tct ggg aca gag ttc act ctc acc atc agc agc cta cag tct      240
Ser Gly Ser Gly Thr Glu Phe Thr Leu Thr Ile Ser Ser Leu Gln Ser
65                  70                  75                  80 gaa gat ttt gca gtt tat ttc tgt cag cag agt cac aat tgg ccc act      288
Glu Asp Phe Ala Val Tyr Phe Cys Gln Gln Ser His Asn Trp Pro Thr
                85                  90                  95 ttc ggc cct ggg acc aaa gtg gat atc aaa                              318
Phe Gly Pro Gly Thr Lys Val Asp Ile Lys
                100                 105

<210> SEQ ID NO 66
<211> LENGTH: 106
<212> TYPE: PRT
<213> ORGANISM: Homo sapiens

<400> SEQUENCE: 66

Glu Ile Val Met Thr Gln Ser Pro Asp Thr Leu Ser Val Ser Pro Gly
1               5                   10                  15

Glu Arg Ala Thr Leu Ser Cys Arg Ala Ser Gln Ser Val Asn Asn Asn
                20                  25                  30

Leu Ala Trp Phe Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser His Asn Trp Pro Thr
                85                  90                  95

Phe Gly Pro Gly Thr Lys Val Asp Ile Lys
                100                 105

<210> SEQ ID NO 67
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION: NI-203.15C7-VH variable heavy chain (VH)
      sequence
<220> FEATURE:
<221> NAME/KEY: V_region
<222> LOCATION: (73)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(336)
<223> OTHER INFORMATION: complementarity determining region (CDR)
      VH-CDR3

<400> SEQUENCE: 67 gag gtg cag ctg gtg gag act ggg gga ggc gtg gtc cag cct ggg atg       48
Glu Val Gln Leu Val Glu Thr Gly Gly Gly Val Val Gln Pro Gly Met
1               5                   10                  15 tcc ctg aaa ctc tcc tgt gca gcc tct gga ttc acc ttc agt acc tat       96
```

```
              Ser Leu Lys Leu Ser Cys Ala Ala Ser Gly Phe Thr Phe Ser Thr Tyr
                          20                  25                  30 act atg cac tgg gtc cgc cag gct cca ggc aag ggg ctg gag tgg gtg         144
Thr Met His Trp Val Arg Gln Ala Pro Gly Lys Gly Leu Glu Trp Val
            35                  40                  45 tca ttt ata tca tat gat gga agg gat aaa tac tac gca gat tcc gtg         192
Ser Phe Ile Ser Tyr Asp Gly Arg Asp Lys Tyr Tyr Ala Asp Ser Val
 50                  55                  60 aag ggc cga ttc acc atc tcc aga gac aat tcc aag aac atg ttg tat         240
Lys Gly Arg Phe Thr Ile Ser Arg Asp Asn Ser Lys Asn Met Leu Tyr
 65                  70                  75                  80 ctg caa atg aac agc ctg aga gat gag gac atg gct gtg tat tac tgt         288
Leu Gln Met Asn Ser Leu Arg Asp Glu Asp Met Ala Val Tyr Tyr Cys
                    85                  90                  95 gcg act ctg caa gta tgg caa ctc tac gat tac tac gga atg gac gtc         336
Ala Thr Leu Gln Val Trp Gln Leu Tyr Asp Tyr Tyr Gly Met Asp Val
                100                 105                 110 tgg ggc caa ggg acc acg gtc acc gtc tcc tcg                             369
Trp Gly Gln Gly Thr Thr Val Thr Val Ser Ser
            115                 120
```

<210> SEQ ID NO 68
<211> LENGTH: 123
<212> TYPE: PRT
<213> ORGANISM: Homo sapiens

<400> SEQUENCE: 68

```
Glu Val Gln Leu Val Glu Thr Gly Gly Gly Val Val Gln Pro Gly Met
 1               5                  10                  15

Ser Leu Lys Leu Ser Cys Ala Ala Ser Gly Phe Thr Phe Ser Thr Tyr
                20                  25                  30

Thr Met His Trp Val Arg Gln Ala Pro Gly Lys Gly Leu Glu Trp Val
            35                  40                  45

Ser Phe Ile Ser Tyr Asp Gly Arg Asp Lys Tyr Tyr Ala Asp Ser Val
 50                  55                  60

Lys Gly Arg Phe Thr Ile Ser Arg Asp Asn Ser Lys Asn Met Leu Tyr
 65                  70                  75                  80

Leu Gln Met Asn Ser Leu Arg Asp Glu Asp Met Ala Val Tyr Tyr Cys
                    85                  90                  95

Ala Thr Leu Gln Val Trp Gln Leu Tyr Asp Tyr Tyr Gly Met Asp Val
                100                 105                 110

Trp Gly Gln Gly Thr Thr Val Thr Val Ser Ser
            115                 120
```

<210> SEQ ID NO 69
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: NI-203.15C7-VL variable light chain (VL)
      sequence
<220> FEATURE:
<221> NAME/KEY: V_region
<222> LOCATION: (67)..(105)
<223> OTHER INFORMATION: complementarity determining region (CDR)
      VL-CDR1
<220> FEATURE:
<221> NAME/KEY: V_region
<222> LOCATION: (151)..(171)
<223> OTHER INFORMATION: complementarity determining region (CDR)
      VL-CDR2

<220> FEATURE:
<221> NAME/KEY: V_region
<222> LOCATION: (268)..(300)
<223> OTHER INFORMATION: complementarity determining region (CDR)
    VL-CDR3

<400> SEQUENCE: 69

```
cag tct gtg ttg acg cag ccg ccc tca gtg tct gcg gcc cca gga cag       48
Gln Ser Val Leu Thr Gln Pro Pro Ser Val Ser Ala Ala Pro Gly Gln
1               5                   10                  15 aag gtc acc atc tcc tgc tct gga agc agc tcc aac att ggg aat aat       96
Lys Val Thr Ile Ser Cys Ser Gly Ser Ser Ser Asn Ile Gly Asn Asn
            20                  25                  30 tat gta tct tgg tat cag caa ctc cca gga aca gcc ccc aaa ctc ctc      144
Tyr Val Ser Trp Tyr Gln Gln Leu Pro Gly Thr Ala Pro Lys Leu Leu
        35                  40                  45 att tat aac agt gat aag cga ccc tca ggg att cct gac cga ttc tct      192
Ile Tyr Asn Ser Asp Lys Arg Pro Ser Gly Ile Pro Asp Arg Phe Ser
    50                  55                  60 gcc tcc aag tct ggc acg tca gcc acc ctg ggc atc acc ggg ctc cag      240
Ala Ser Lys Ser Gly Thr Ser Ala Thr Leu Gly Ile Thr Gly Leu Gln
65                  70                  75                  80 act ggg gac gag gcc gat tat tac tgc gca aca tgg gat acc aga ctg      288
Thr Gly Asp Glu Ala Asp Tyr Tyr Cys Ala Thr Trp Asp Thr Arg Leu
                85                  90                  95 agt gct ggg gta ttc ggc gga ggg acc aag ctg acc gtc ctt              330
Ser Ala Gly Val Phe Gly Gly Gly Thr Lys Leu Thr Val Leu
            100                 105                 110
```

<210> SEQ ID NO 70
<211> LENGTH: 110
<212> TYPE: PRT
<213> ORGANISM: Homo sapiens

<400> SEQUENCE: 70

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asn Ser Asp Lys Arg Pro Ser Gly Ile Pro Asp Arg Phe Ser
    50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Thr Trp Asp Thr Arg Leu
                85                  90                  95

Ser Ala Gly Val Phe Gly Gly Gly Thr Lys Leu Thr Val Leu
            100                 105                 110

<210> SEQ ID NO 71
<211> LENGTH: 10
<212> TYPE: PRT
<213> ORGANISM: Artificial Sequence
<220> FEATURE:
<223> OTHER INFORMATION: linear epitope recognized by antibody
    NI-203.15C7
<220> FEATURE:
<221> NAME/KEY: PEPTIDE
<222> LOCATION: (1)..(10)
<223> OTHER INFORMATION: unique linear epitope recognized by antibody
    NI-203.15C7

```
<400> SEQUENCE: 71

Gln Arg Leu Ala Asn Phe Leu Val His Ser
1               5                   10

<210> SEQ ID NO 72
<211> LENGTH: 10
<212> TYPE: PRT
<213> ORGANISM: Homo sapiens

<400> SEQUENCE: 72

Gly Phe Thr Phe Ser Thr Phe Ala Met Ser
1               5                   10

<210> SEQ ID NO 73
<211> LENGTH: 10
<212> TYPE: PRT
<213> ORGANISM: Homo sapiens

<400> SEQUENCE: 73

Gly Phe Thr Phe Ser Ser Tyr Gly Met His
1               5                   10

<210> SEQ ID NO 74
<211> LENGTH: 12
<212> TYPE: PRT
<213> ORGANISM: Homo sapiens

<400> SEQUENCE: 74

Gly Gly Ser Ile Ser Ser Gly Asn Tyr Tyr Trp Thr
1               5                   10

<210> SEQ ID NO 75
<211> LENGTH: 10
<212> TYPE: PRT
<213> ORGANISM: Homo sapiens

<400> SEQUENCE: 75

Gly Gly Thr Phe Ser Ser His Thr Ile Ser
1               5                   10

<210> SEQ ID NO 76
<211> LENGTH: 10
<212> TYPE: PRT
<213> ORGANISM: Homo sapiens

<400> SEQUENCE: 76

Gly Tyr Thr Phe Thr Asn Tyr Tyr Leu His
1               5                   10

<210> SEQ ID NO 77
<211> LENGTH: 10
<212> TYPE: PRT
<213> ORGANISM: Homo sapiens

<400> SEQUENCE: 77

Gly Asp Ser Val Ser Ser Gly Ser Tyr Tyr
1               5                   10

<210> SEQ ID NO 78
<211> LENGTH: 10
<212> TYPE: PRT
<213> ORGANISM: Homo sapiens

<400> SEQUENCE: 78
```

```
Gly Phe Thr Phe Ser Ser Tyr Gly Met His
1               5                   10
```

<210> SEQ ID NO 79
<211> LENGTH: 10
<212> TYPE: PRT
<213> ORGANISM: Homo sapiens

<400> SEQUENCE: 79

```
Gly Gly Asn Phe Leu Ser Tyr Ser Ile Ser
1               5                   10
```

<210> SEQ ID NO 80
<211> LENGTH: 11
<212> TYPE: PRT
<213> ORGANISM: Homo sapiens

<400> SEQUENCE: 80

```
Ser Gly Phe Thr Phe Ser Thr Tyr Thr Met His
1               5                   10
```

<210> SEQ ID NO 81
<211> LENGTH: 11
<212> TYPE: PRT
<213> ORGANISM: Homo sapiens

<400> SEQUENCE: 81

```
Arg Ala Ser Glu Ser Ile Asn Ser Trp Leu Ala
1               5                   10
```

<210> SEQ ID NO 82
<211> LENGTH: 11
<212> TYPE: PRT
<213> ORGANISM: Homo sapiens

<400> SEQUENCE: 82

```
Arg Ala Ser His Asp Ile Ser Thr Trp Leu Ala
1               5                   10
```

<210> SEQ ID NO 83
<211> LENGTH: 15
<212> TYPE: PRT
<213> ORGANISM: Homo sapiens

<400> SEQUENCE: 83

```
Lys Ser Ser Gln Ser Val Leu Tyr Ser Asn Lys Asn Phe Leu Ala
1               5                   10                  15
```

<210> SEQ ID NO 84
<211> LENGTH: 16
<212> TYPE: PRT
<213> ORGANISM: Homo sapiens

<400> SEQUENCE: 84

```
Arg Ser Ser Gln Ser Leu Val Tyr Ser Asp Gly Asn Thr Tyr Leu Asn
1               5                   10                  15
```

<210> SEQ ID NO 85
<211> LENGTH: 12
<212> TYPE: PRT
<213> ORGANISM: Homo sapiens

<400> SEQUENCE: 85

```
Thr Leu Asn Ser Gly His Ser Ser Tyr Thr Ile Ala
1               5                   10
```

<210> SEQ ID NO 86
<211> LENGTH: 11
<212> TYPE: PRT
<213> ORGANISM: Homo sapiens

<400> SEQUENCE: 86

Arg Ala Ser Gln Ser Val Ser Ser Tyr Leu Ala
1               5                   10

<210> SEQ ID NO 87
<211> LENGTH: 14
<212> TYPE: PRT
<213> ORGANISM: Homo sapiens

<400> SEQUENCE: 87

Thr Gly Thr Ser Gly Tyr Ile Tyr Gly Tyr Asn Tyr Val Ser
1               5                   10

<210> SEQ ID NO 88
<211> LENGTH: 11
<212> TYPE: PRT
<213> ORGANISM: Homo sapiens

<400> SEQUENCE: 88

Arg Ala Ser Gln Ser Val Asn Asn Asn Leu Ala
1               5                   10

<210> SEQ ID NO 89
<211> LENGTH: 13
<212> TYPE: PRT
<213> ORGANISM: Homo sapiens

<400> SEQUENCE: 89

Ser Gly Ser Ser Ser Asn Ile Gly Asn Asn Tyr Val Ser
1               5                   10

<210> SEQ ID NO 90
<211> LENGTH: 17
<212> TYPE: PRT
<213> ORGANISM: Homo sapiens

<400> SEQUENCE: 90

Thr Ile Ser Gly Ser Gly Asp Asn Thr Tyr Tyr Ala Asp Ser Leu Lys
1               5                   10                  15
Gly

<210> SEQ ID NO 91
<211> LENGTH: 17
<212> TYPE: PRT
<213> ORGANISM: Homo sapiens

<400> SEQUENCE: 91

Ile Ile Trp Tyr Asp Gly Ser Lys Glu Tyr Tyr Ala Asp Ser Leu Lys
1               5                   10                  15
Gly

<210> SEQ ID NO 92
<211> LENGTH: 16
<212> TYPE: PRT
<213> ORGANISM: Homo sapiens

<400> SEQUENCE: 92

His Ile Tyr Ser Ser Gly Thr Thr Asn Tyr Asn Pro Ser Leu Glu Ser
1               5                   10                  15

<210> SEQ ID NO 93
<211> LENGTH: 17
<212> TYPE: PRT
<213> ORGANISM: Homo sapiens

<400> SEQUENCE: 93

Gly Ile Ile Pro Ile Phe Gly Thr Ala Asn Tyr Ala Gln Lys Phe Gln
1               5                   10                  15

Asp

<210> SEQ ID NO 94
<211> LENGTH: 17
<212> TYPE: PRT
<213> ORGANISM: Homo sapiens

<400> SEQUENCE: 94

Ile Ile Asn Pro Ser Ala Gly Ser Thr Ser Tyr Ala Gln Lys Phe Gln
1               5                   10                  15

Gly

<210> SEQ ID NO 95
<211> LENGTH: 15
<212> TYPE: PRT
<213> ORGANISM: Homo sapiens

<400> SEQUENCE: 95

Ile Tyr Tyr Ser Gly Ser Thr Asn Tyr Asn Pro Ser Leu Lys Ser
1               5                   10                  15

<210> SEQ ID NO 96
<211> LENGTH: 17
<212> TYPE: PRT
<213> ORGANISM: Homo sapiens

<400> SEQUENCE: 96

Val Ile Trp Tyr Asp Gly Thr Lys Lys Tyr Tyr Ala Asp Ser Val Lys
1               5                   10                  15

Gly

<210> SEQ ID NO 97
<211> LENGTH: 17
<212> TYPE: PRT
<213> ORGANISM: Homo sapiens

<400> SEQUENCE: 97

Gly Ile Ile Pro Ile Phe Gly Thr Pro Asn Tyr Ala Gln Lys Phe Gln
1               5                   10                  15

Gly

<210> SEQ ID NO 98
<211> LENGTH: 17
<212> TYPE: PRT
<213> ORGANISM: Homo sapiens

<400> SEQUENCE: 98

Phe Ile Ser Tyr Asp Gly Arg Asp Lys Tyr Tyr Ala Asp Ser Val Lys
1               5                   10                  15

Gly

```
<210> SEQ ID NO 99
<211> LENGTH: 7
<212> TYPE: PRT
<213> ORGANISM: Homo sapiens

<400> SEQUENCE: 99

Lys Ala Ser Ser Leu Gln Ser
1               5

<210> SEQ ID NO 100
<211> LENGTH: 7
<212> TYPE: PRT
<213> ORGANISM: Homo sapiens

<400> SEQUENCE: 100

Gly Ala Ser Arg Leu Gln Ser
1               5

<210> SEQ ID NO 101
<211> LENGTH: 7
<212> TYPE: PRT
<213> ORGANISM: Homo sapiens

<400> SEQUENCE: 101

Trp Ala Ser Thr Arg Glu Ser
1               5

<210> SEQ ID NO 102
<211> LENGTH: 7
<212> TYPE: PRT
<213> ORGANISM: Homo sapiens

<400> SEQUENCE: 102

Lys Val Ser Asn Arg Asp Ser
1               5

<210> SEQ ID NO 103
<211> LENGTH: 7
<212> TYPE: PRT
<213> ORGANISM: Homo sapiens

<400> SEQUENCE: 103

Val Glu His Asn Gly Asn Tyr
1               5

<210> SEQ ID NO 104
<211> LENGTH: 7
<212> TYPE: PRT
<213> ORGANISM: Homo sapiens

<400> SEQUENCE: 104

Asp Ala Ser Asn Arg Ala Thr
1               5

<210> SEQ ID NO 105
<211> LENGTH: 7
<212> TYPE: PRT
<213> ORGANISM: Homo sapiens

<400> SEQUENCE: 105

Glu Val Thr Lys Arg Pro Ser
1               5

<210> SEQ ID NO 106
```

```
<211> LENGTH: 7
<212> TYPE: PRT
<213> ORGANISM: Homo sapiens

<400> SEQUENCE: 106

Gly Ala Ser Thr Arg Ala Thr
1               5

<210> SEQ ID NO 107
<211> LENGTH: 7
<212> TYPE: PRT
<213> ORGANISM: Homo sapiens

<400> SEQUENCE: 107

Asn Ser Asp Lys Arg Pro Ser
1               5

<210> SEQ ID NO 108
<211> LENGTH: 12
<212> TYPE: PRT
<213> ORGANISM: Homo sapiens

<400> SEQUENCE: 108

Ser Pro Ser Ser Leu Leu Ala Thr Tyr Phe Asp Tyr
1               5                   10

<210> SEQ ID NO 109
<211> LENGTH: 13
<212> TYPE: PRT
<213> ORGANISM: Homo sapiens

<400> SEQUENCE: 109

Thr Ile Ala Ser Ala Thr Val Asp His Gly Met Asp Val
1               5                   10

<210> SEQ ID NO 110
<211> LENGTH: 11
<212> TYPE: PRT
<213> ORGANISM: Homo sapiens

<400> SEQUENCE: 110

Pro Leu Ala Thr Val Pro Asp Ala Phe Asn Ile
1               5                   10

<210> SEQ ID NO 111
<211> LENGTH: 15
<212> TYPE: PRT
<213> ORGANISM: Homo sapiens

<400> SEQUENCE: 111

Gly Glu Leu Glu Pro Arg Ile Leu Tyr Tyr Tyr Gly Met Asp Val
1               5                   10                  15

<210> SEQ ID NO 112
<211> LENGTH: 15
<212> TYPE: PRT
<213> ORGANISM: Homo sapiens

<400> SEQUENCE: 112

Asp Ser Ala Gly Ile Gln Ile Trp Phe Arg Asp Ala Phe Asp Ile
1               5                   10                  15

<210> SEQ ID NO 113
<211> LENGTH: 18
<212> TYPE: PRT
```

-continued

<213> ORGANISM: Homo sapiens

<400> SEQUENCE: 113

Val Pro Tyr Gly Tyr Gly Tyr Arg Gly Tyr Asp Gly Ala Trp Tyr Phe
1               5                   10                  15

Asp Tyr

<210> SEQ ID NO 114
<211> LENGTH: 10
<212> TYPE: PRT
<213> ORGANISM: Homo sapiens

<400> SEQUENCE: 114

Gly Phe Ser Ser Ser Trp Glu Phe Gly Phe
1               5                   10

<210> SEQ ID NO 115
<211> LENGTH: 18
<212> TYPE: PRT
<213> ORGANISM: Homo sapiens

<400> SEQUENCE: 115

Ala Thr Arg Pro Gly Thr Ala Ala Ser Gly Phe Tyr Tyr Tyr Gly Met
1               5                   10                  15

Asp Val

<210> SEQ ID NO 116
<211> LENGTH: 14
<212> TYPE: PRT
<213> ORGANISM: Homo sapiens

<400> SEQUENCE: 116

Leu Gln Val Trp Gln Leu Tyr Asp Tyr Tyr Gly Met Asp Val
1               5                   10

<210> SEQ ID NO 117
<211> LENGTH: 8
<212> TYPE: PRT
<213> ORGANISM: Homo sapiens

<400> SEQUENCE: 117

Gln Gln His Asn Ser Tyr Trp Thr
1               5

<210> SEQ ID NO 118
<211> LENGTH: 9
<212> TYPE: PRT
<213> ORGANISM: Homo sapiens

<400> SEQUENCE: 118

Gln Gln Thr Asn Asn Phe Pro Pro Thr
1               5

<210> SEQ ID NO 119
<211> LENGTH: 9
<212> TYPE: PRT
<213> ORGANISM: Homo sapiens

<400> SEQUENCE: 119

Gln Gln Tyr Tyr Ser Asn Pro Asn Thr
1               5

<210> SEQ ID NO 120

```
<211> LENGTH: 9
<212> TYPE: PRT
<213> ORGANISM: Homo sapiens

<400> SEQUENCE: 120

Met Gln Gly Ser Asn Trp Pro Gly Thr
1               5

<210> SEQ ID NO 121
<211> LENGTH: 9
<212> TYPE: PRT
<213> ORGANISM: Homo sapiens

<400> SEQUENCE: 121

Glu Thr Trp Asp Thr Ser Thr Arg Val
1               5

<210> SEQ ID NO 122
<211> LENGTH: 8
<212> TYPE: PRT
<213> ORGANISM: Homo sapiens

<400> SEQUENCE: 122

Gln Gln Arg Ser Asn Arg Phe Thr
1               5

<210> SEQ ID NO 123
<211> LENGTH: 10
<212> TYPE: PRT
<213> ORGANISM: Homo sapiens

<400> SEQUENCE: 123

Ala Ser Tyr Ala Gly Ser Asn Asn Val Val
1               5                   10

<210> SEQ ID NO 124
<211> LENGTH: 8
<212> TYPE: PRT
<213> ORGANISM: Homo sapiens

<400> SEQUENCE: 124

Gln Gln Ser His Asn Trp Pro Thr
1               5

<210> SEQ ID NO 125
<211> LENGTH: 11
<212> TYPE: PRT
<213> ORGANISM: Homo sapiens

<400> SEQUENCE: 125

Ala Thr Trp Asp Thr Arg Leu Ser Ala Gly Val
1               5                   10

<210> SEQ ID NO 126
<211> LENGTH: 10
<212> TYPE: PRT
<213> ORGANISM: Homo sapiens

<400> SEQUENCE: 126

Gly Tyr Ser Phe Thr Asn Ser Trp Ile Ala
1               5                   10

<210> SEQ ID NO 127
<211> LENGTH: 10
<212> TYPE: PRT
```

<213> ORGANISM: Homo sapiens

<400> SEQUENCE: 127

Gly Phe Thr Phe Ser Ser Tyr Gly Met His
1               5                   10

<210> SEQ ID NO 128
<211> LENGTH: 10
<212> TYPE: PRT
<213> ORGANISM: Homo sapiens

<400> SEQUENCE: 128

Gly Tyr Ser Val Thr Asp Tyr Tyr Leu His
1               5                   10

<210> SEQ ID NO 129
<211> LENGTH: 10
<212> TYPE: PRT
<213> ORGANISM: Homo sapiens

<400> SEQUENCE: 129

Gly Tyr Ile Phe Ser Lys His Gly Ile Asn
1               5                   10

<210> SEQ ID NO 130
<211> LENGTH: 10
<212> TYPE: PRT
<213> ORGANISM: Homo sapiens

<400> SEQUENCE: 130

Gly Phe Thr Phe Arg Thr Cys Gly Met His
1               5                   10

<210> SEQ ID NO 131
<211> LENGTH: 10
<212> TYPE: PRT
<213> ORGANISM: Homo sapiens

<400> SEQUENCE: 131

Gly Phe Thr Phe Ser Gly Tyr Glu Met Asn
1               5                   10

<210> SEQ ID NO 132
<211> LENGTH: 16
<212> TYPE: PRT
<213> ORGANISM: Homo sapiens

<400> SEQUENCE: 132

Arg Ser Ser Gln Ser Leu Leu His Pro Asn Gly Asn Asp Tyr Leu Asp
1               5                   10                  15

<210> SEQ ID NO 133
<211> LENGTH: 10
<212> TYPE: PRT
<213> ORGANISM: Homo sapiens

<400> SEQUENCE: 133

Arg Ala Ser Gln Arg Val Thr Thr Ile Ala
1               5                   10

<210> SEQ ID NO 134
<211> LENGTH: 16
<212> TYPE: PRT
<213> ORGANISM: Homo sapiens

```
<400> SEQUENCE: 134

Arg Ser Asp Glu Ser Leu Leu His Ser Asp Gly Arg Thr Tyr Leu Tyr
1               5                   10                  15

<210> SEQ ID NO 135
<211> LENGTH: 11
<212> TYPE: PRT
<213> ORGANISM: Homo sapiens

<400> SEQUENCE: 135

Arg Ala Ser Gln Ser Ile Ser Thr Asn Leu Asn
1               5                   10

<210> SEQ ID NO 136
<211> LENGTH: 10
<212> TYPE: PRT
<213> ORGANISM: Homo sapiens

<400> SEQUENCE: 136

Arg Ala Ser Gln Arg Val Ser Thr Val Ala
1               5                   10

<210> SEQ ID NO 137
<211> LENGTH: 11
<212> TYPE: PRT
<213> ORGANISM: Homo sapiens

<400> SEQUENCE: 137

Arg Ala Ser Gln Ser Ile Ser Thr Tyr Leu Asn
1               5                   10

<210> SEQ ID NO 138
<211> LENGTH: 16
<212> TYPE: PRT
<213> ORGANISM: Homo sapiens

<400> SEQUENCE: 138

Ile Tyr Pro Gly Asp Ser Asp Thr Lys Tyr Gly Pro Ser Phe Gln Gly
1               5                   10                  15

<210> SEQ ID NO 139
<211> LENGTH: 17
<212> TYPE: PRT
<213> ORGANISM: Homo sapiens

<400> SEQUENCE: 139

Phe Val Arg Tyr Asp Gly Ser Asn Lys Tyr Tyr Ala Asp Ser Val Lys
1               5                   10                  15

Gly

<210> SEQ ID NO 140
<211> LENGTH: 17
<212> TYPE: PRT
<213> ORGANISM: Homo sapiens

<400> SEQUENCE: 140

Val Met Asn Pro Ser Asn Gly Asn Val Gly Tyr Pro Gln Lys Phe Gln
1               5                   10                  15

Gly

<210> SEQ ID NO 141
<211> LENGTH: 17
<212> TYPE: PRT
```

<213> ORGANISM: Homo sapiens

<400> SEQUENCE: 141

Trp Ile Asn Thr Asn Thr Gly Asn Pro Thr Tyr Ala Gln Asp Phe Thr
1               5                   10                  15

Gly

<210> SEQ ID NO 142
<211> LENGTH: 17
<212> TYPE: PRT
<213> ORGANISM: Homo sapiens

<400> SEQUENCE: 142

Phe Val Arg Ser Asp Gly Thr Thr Arg Tyr Tyr Ala Asp Ser Leu Met
1               5                   10                  15

Gly

<210> SEQ ID NO 143
<211> LENGTH: 17
<212> TYPE: PRT
<213> ORGANISM: Homo sapiens

<400> SEQUENCE: 143

Tyr Ile Ser Gly Pro Gly Asp Val Ile Tyr Tyr Ala Asp Ser Val Lys
1               5                   10                  15

Gly

<210> SEQ ID NO 144
<211> LENGTH: 7
<212> TYPE: PRT
<213> ORGANISM: Homo sapiens

<400> SEQUENCE: 144

Met Gly Ser Asn Arg Ala Ala
1               5

<210> SEQ ID NO 145
<211> LENGTH: 7
<212> TYPE: PRT
<213> ORGANISM: Homo sapiens

<400> SEQUENCE: 145

Gly Ala Ser Ser Arg Ala Thr
1               5

<210> SEQ ID NO 146
<211> LENGTH: 7
<212> TYPE: PRT
<213> ORGANISM: Homo sapiens

<400> SEQUENCE: 146

Glu Val Ser Asn Arg Phe Ser
1               5

<210> SEQ ID NO 147
<211> LENGTH: 7
<212> TYPE: PRT
<213> ORGANISM: Homo sapiens

<400> SEQUENCE: 147

Ala Ala Ser Ser Leu Gln Gly
1               5

<210> SEQ ID NO 148
<211> LENGTH: 7
<212> TYPE: PRT
<213> ORGANISM: Homo sapiens

<400> SEQUENCE: 148

Asp Ala Ser Thr Arg Ala Thr
1               5

<210> SEQ ID NO 149
<211> LENGTH: 7
<212> TYPE: PRT
<213> ORGANISM: Homo sapiens

<400> SEQUENCE: 149

Asp Thr Asp Ile Leu Gln Ser
1               5

<210> SEQ ID NO 150
<211> LENGTH: 11
<212> TYPE: PRT
<213> ORGANISM: Homo sapiens

<400> SEQUENCE: 150

Arg Ala Ala Ala Ala Ile Asn Trp Phe Asp Ser
1               5                   10

<210> SEQ ID NO 151
<211> LENGTH: 11
<212> TYPE: PRT
<213> ORGANISM: Homo sapiens

<400> SEQUENCE: 151

Glu Gln Glu Asp His Lys Glu Ala Phe Asp Tyr
1               5                   10

<210> SEQ ID NO 152
<211> LENGTH: 17
<212> TYPE: PRT
<213> ORGANISM: Homo sapiens

<400> SEQUENCE: 152

Gly Gly Ser Thr Pro Gly Gln Glu Val Arg Ser Pro His Val Leu Asp
1               5                   10                  15

Leu

<210> SEQ ID NO 153
<211> LENGTH: 14
<212> TYPE: PRT
<213> ORGANISM: Homo sapiens

<400> SEQUENCE: 153

Glu Ser Glu Pro Ile Phe Gly Val Ile Tyr Tyr Met Asp Val
1               5                   10

<210> SEQ ID NO 154
<211> LENGTH: 11
<212> TYPE: PRT
<213> ORGANISM: Homo sapiens

<400> SEQUENCE: 154

Glu Lys Glu Asp His Arg Glu Ala Phe Asp Tyr
1               5                   10

<210> SEQ ID NO 155
<211> LENGTH: 11
<212> TYPE: PRT
<213> ORGANISM: Homo sapiens

<400> SEQUENCE: 155

Val Pro Pro Asp Ile Ser Tyr Gly Phe Asp Tyr
1               5                   10

<210> SEQ ID NO 156
<211> LENGTH: 8
<212> TYPE: PRT
<213> ORGANISM: Homo sapiens

<400> SEQUENCE: 156

Leu Gln Ala Leu Arg Gly Tyr Thr
1               5

<210> SEQ ID NO 157
<211> LENGTH: 9
<212> TYPE: PRT
<213> ORGANISM: Homo sapiens

<400> SEQUENCE: 157

Gln Gln Tyr Asn Gln Trp Pro Leu Thr
1               5

<210> SEQ ID NO 158
<211> LENGTH: 9
<212> TYPE: PRT
<213> ORGANISM: Homo sapiens

<400> SEQUENCE: 158

Met Gln Gly Val His Phe Pro Gln Thr
1               5

<210> SEQ ID NO 159
<211> LENGTH: 9
<212> TYPE: PRT
<213> ORGANISM: Homo sapiens

<400> SEQUENCE: 159

Gln His Asn Tyr Asn Asp Leu Trp Thr
1               5

<210> SEQ ID NO 160
<211> LENGTH: 9
<212> TYPE: PRT
<213> ORGANISM: Homo sapiens

<400> SEQUENCE: 160

Gln Gln Tyr Asn Arg Trp Pro Leu Thr
1               5

<210> SEQ ID NO 161
<211> LENGTH: 9
<212> TYPE: PRT
<213> ORGANISM: Homo sapiens

<400> SEQUENCE: 161

Gln Gln Ser Tyr Ser Thr Pro Pro Thr
1               5

<210> SEQ ID NO 162

<211> LENGTH: 121
<212> TYPE: PRT
<213> ORGANISM: Homo sapiens

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Ala Met Ser Trp Val Arg Gln Ala Pro Gly Lys Gly Leu Glu Trp Val
        35                  40                  45

Ser Thr Ile Ser Gly Ser Gly Asp Asn Thr Tyr Tyr Ala Asp Ser Leu
50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Pro Glu Asp Thr Ala Val Tyr Tyr Cys
                85                  90                  95

Ala Lys Ser Pro Ser Ser Leu Leu Ala Thr Tyr Phe Asp Tyr Trp Gly
            100                 105                 110

Gln Gly Thr Leu Val Thr Val Ser Ser
        115                 120

<210> SEQ ID NO 163
<211> LENGTH: 102
<212> TYPE: PRT
<213> ORGANISM: Homo sapiens

<400> SEQUENCE: 163

Thr Gln Ser Pro Ser Thr Leu Ser Ala Ser Val Gly Asp Arg Val Thr
1               5                   10                  15

Ile Thr Cys Arg Ala Ser Glu Ser Ile Asn Ser Trp Leu Ala Trp Tyr
            20                  25                  30

Gln Gln Lys Pro Gly Lys Gly Pro Lys Leu Leu Ile Tyr Lys Ala Ser
        35                  40                  45

Ser Leu Gln Ser Gly Val Pro Ser Arg Phe Ser Gly Ser Gly Ser Gly
50                  55                  60

Thr Glu Phe Thr Leu Thr Ile Ser Ser Leu Gln Pro Asp Asp Phe Ala
65                  70                  75                  80

Thr Tyr Tyr Cys Gln Gln His Asn Ser Tyr Trp Thr Phe Gly Gln Gly
                85                  90                  95

Thr Lys Val Glu Ile Lys
            100

<210> SEQ ID NO 164
<211> LENGTH: 126
<212> TYPE: PRT
<213> ORGANISM: Homo sapiens

<400> SEQUENCE: 164

Gln Val Gln Leu Val Gln Ser Gly Ala Glu Val Arg Lys Pro Gly Ala
1               5                   10                  15

Ser Val Arg Val Ser Cys Gln Thr Ser Gly Tyr Ser Val Thr Asp Tyr
            20                  25                  30

Tyr Leu His Trp Val Arg Gln Ala Pro Gly Gln Gly Leu Glu Trp Met
        35                  40                  45

Gly Val Met Asn Pro Ser Asn Gly Asn Val Gly Tyr Pro Gln Lys Phe
50                  55                  60

```
Gln Gly Arg Val Thr Met Thr Ala Asp Thr Ser Thr Gly Thr Val Tyr
65                  70                  75                  80

Met Val Leu Thr Gly Leu Thr Ala Gly Asp Thr Ala Val Tyr Tyr Cys
                85                  90                  95

Ala Arg Gly Gly Ser Thr Pro Gly Gln Glu Val Arg Ser Pro His Val
            100                 105                 110

Leu Asp Leu Trp Gly Gln Gly Thr Leu Val Thr Val Ser Ser
            115                 120                 125

<210> SEQ ID NO 165
<211> LENGTH: 112
<212> TYPE: PRT
<213> ORGANISM: Homo sapiens

<400> SEQUENCE: 165

Asp Ile Val Met Thr Gln Thr Pro Leu Ser Leu Ser Val Thr Pro Gly
1               5                   10                  15

Gln Pro Ala Ser Ile Ser Cys Arg Ser Asp Glu Ser Leu Leu His Ser
            20                  25                  30

Asp Gly Arg Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asn Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Val His Phe Pro Gln Thr Phe Gly Gln Gly Thr Lys Leu Glu Ile Lys
            100                 105                 110
```

HUMAN ISLET AMYLOID POLYPEPTIDE (HIAPP) SPECIFIC ANTIBODIES AND USES THEREOF

RELATED APPLICATIONS

This application is a continuation application of U.S. patent application Ser. No. 15/258,883, filed Sep. 7, 2016, which is a divisional application of U.S. patent application Ser. No. 14/427,575, filed Mar. 11, 2015, which is the National Stage Entry of PCT/EP2013/068907, filed Sep. 12, 2013, which claims priority to, and the benefit of, U.S. Provisional Patent Application No. 61/700,110, filed Sep. 12, 2012 and European Patent Application Number EP 12184134.0, filed Sep. 12, 2012, the entire contents of which are hereby incorporated by reference.

REFERENCE TO A SEQUENCE LISTING

The content of the electronically submitted sequence listing in ASCII text file (Name: sequence listing.txt; Size: 123,742 bytes; and Date of Creation: Aug. 6, 2018) filed with the application is incorporated herein by reference in its entirety.

FIELD OF THE INVENTION

The present invention generally relates to novel molecules specifically binding to human islet amyloid polypeptide (hIAPP) also known as amylin and/or to its precursor proislet amyloid polypeptide (proIAPP), particularly human antibodies as well as fragments, derivatives and variants thereof that recognize the IAPP, proIAPP proteins, aggregated forms of IAPP, aggregated forms of proIAPP, and/or IAPP fibrils. In addition, the present invention relates to pharmaceutical and diagnostic compositions comprising such binding molecules, antibodies and mimics thereof valuable both as a diagnostic tool to identify IAPP, proIAPP, aggregated IAPP, proIAPP species and/or IAPP fibrils in plasma and also in passive vaccination strategies for treating disorders related to aggregated IAPP, aggregated proIAPP, and IAPP fibrils such as diabetes mellitus type 2 (T2D) and islet rejection following clinical pancreatic islet transplantation into individuals with diabetes mellitus type 1 (T1D).

BACKGROUND OF THE INVENTION

Protein accumulation, modifications and aggregation are pathological aspects of numerous metabolic diseases including well known neurodegenerative diseases such as Huntington's, Alzheimer's (AD) and Parkinson's diseases (PD) (Taylor et al., Science 296 (2005), 1991-1995). Pathological protein aggregation is also involved in metabolic diseases such as diabetes mellitus type 2 (T2D) and islet rejection following clinical pancreatic islet transplantation into individuals with diabetes mellitus type 1 (T1D). Misfolding and aggregation of proteins lead to the development of amyloid deposits and seem to be directly related to cell toxicity in these diseases. Islet amyloid polypeptide (IAPP or amylin), a physiological peptide co-secreted with insulin by β-cells in the pancreas, forms fibrillar aggregates in pancreatic islets (also called islets of Langerhans) of T2D patients and has been suggested to play a role in the development of the disease (Westermark et al. (2011), Physiol. Rev. 91(3): 795-826). Furthermore, as mentioned before, IAPP aggregates have been found in pancreatic islets upon transplantation of isolated islets in patients with diabetes mellitus type 1 (T1D).

Human IAPP (hIAPP) is a peptide hormone that consists of 37 amino acids, with a disulfide bridge between cysteine residues 2 and 7 and an amidated C-terminus. Pancreatic islets are composed of 65 to 80% β-cells, which produce and secrete insulin and IAPP essential for regulation of blood glucose levels and cell metabolism. IAPP is processed from preprohormone preproIAPP, a 89 amino acid precursor produced in pancreatic β-cells.

PreproIAPP is rapidly cleaved after translation into proislet amyloid polypeptide, a 67 amino acid peptide, which undergoes additional proteolysis and post-translational modifications to generate hIAPP. hIAPP expression is regulated together with insulin, as increased insulin production leads to increased hIAPP levels. hIAPP is released from pancreatic β-cells into the blood circulation and is involved in glycemic regulation through gastric emptying and satiety control, in synergy with insulin.

While hIAPP acts as a regulator of cell metabolism under physiological conditions, hIAPP can aggregate and form amyloid fibrils (IAPP amyloidosis) associated with β-cell failure, increased β-cell death and reduced β-cell mass. Several evidences point toward hIAPP amyloidosis as a major trigger for T2D pathogenesis. First, deposition of hIAPP fibrils is found in more than 90% of type-2 diabetes patients (Zraika et al. (2010), Diabetologia 53(6): 1046-1056). Second, hIAPP aggregation is toxic to β-cells and correlates with the reduction in insulin producing β-cells (Butler et al. (2003), Diabetes 52(9): 2304-2314; Ritzel et al. (2007), Diabetes 56(1): 65-71; Jurgens et al. (2011), Am. J. Pathol. 178(6): 2632-2640). Third, transgenic murine models expressing hIAPP show pancreatic islet amyloid deposits and spontaneously develop T2D (Janson et al. (1996), Proc. Natl. Acad. Sci. USA 93(14): 7283-7288; Hoppener et al. (1999), Diabetologia 42(4): 427-434; Hull et al. (2003), Diabetes 52(2): 372-379; Butler et al. (2004), Diabetes 53(6): 1509-1516; Matveyenko et al. (2006), ILAR J. 47(3): 225-233; Hoppener et al. (2008), Exp. Diabetes Res. 697035). They recapitulate the human disease with β-cell dysfunction, β-cell mass deficiency and β-cell loss, comparable to what observed in the tissues from T2D patients. hIAPP expression and amyloid formation directly correlate with β-cell apoptosis and diabetes development in these models, thus providing evidence for the contribution of human IAPP in the development of the disease. Moreover, treatment interfering with hIAPP aggregation ameliorated the diabetic phenotype and increased animal life span (Aitken et al. (2009), Diabetes 59(1): 161-171). hIAPP aggregation and amyloidosis is a prerequisite for toxicity. The non-amyloidogenic rodent IAPP (rIAPP), which is unable to form fibrils as a result of six amino acid substitution, is nontoxic to β-cells. In the development of the disease, pathological hIAPP aggregation found in human pancreatic islets may cause β-cell dysfunction and death associated with impairment of insulin secretion. In addition, compensatory increase in β-cell mass and insulin and amylin secretion to maintain normal blood glucose levels may favor the formation of toxic hIAPP oligomers and deposition of hIAPP fibrils. While initial hIAPP oligomers are considered as the main cytotoxic species, the hIAPP fibril end product may also play a role in β-cell loss (Meier et al. (2006), Am. J. Physiol. Endocrinol. Metab. 291(6): E1317-1324; Haataja et al. (2008), Endocr. Rev. 29(3): 303-316; Engel et al. (2008), Proc. Natl. Acad. Sci. USA 105(16): 6033-6038). hIAPP fibrils have also been observed in isolated pancreatic islets from donors and associated to β-cell loss following clinical pancreatic islets transplantation into individuals with type-1 diabetes (Andersson et al. (2008), Exp. Diabetes Res. 562985; Udayasankar et al. (2009), Diabetologia 52(1): 145-153; Bohman et al. (2012), Amyloid 19(2): 87-93). The exact mechanism leading to hIAPP aggregation and amyloidosis in T2D is unknown. Insulin resistance in T2D increases insulin secretion demand together with proIAPP cell content and hIAPP release, what may elicit amyloidosis as hIAPP fibril formation is concentration dependent. Another proposed mechanism is the accumulation and aggregation of N-terminal unprocessed proIAPP caused by proteolysis failure in the setting of insulin resistance, as partially processed forms of proIAPP are found in amyloid deposits, in particular the 48 residue intermediate proIAPP$_{1-48}$ (Marzban et al. (2006), Diabetes 55(8): 2192-2201). In this context, abnormal processing of proIAPP may act as a seed for hIAPP amyloidosis and increase amyloid formation (Paulsson et al. (2005), Diabetes 54(7): 2117-2125; Paulsson et al. (2006), Diabetologia 49(6): 1237-1246; Marzban et al. (2006), Diabetes 55(8): 2192-2201). ProIAPP is therefore also considered as an appropriate therapeutic target.

Clinical features of T2D are high blood glucose levels and insulin resistance and/or deficiency. Diabetes mellitus is a group of metabolic diseases including T1D, T2D, and gestational diabetes. T2D, also named adult-onset diabetes, obesity-related diabetes, and noninsulin-dependent diabetes mellitus (NIDDM) is the most common form of diabetes, accounting for about 90% of all cases (Gerich et al. (1998), Endocr. Rev. 19(4): 491-503). T2D is characterized by a decrease in the number of functional insulin-producing β-cells. While the pathology progresses, it can lead to long-term complications such as cardiovascular disease, diabetic retinopathy leading to blindness, kidney failure, frequent infections, and amputations caused by poor circulation. As a consequence, T2D is associated with a shorter life expectancy. The disease affects more than 300 million people worldwide resulting in more than a million deaths annually. Both genetic determinants and environmental factors lead to the development of the disease, with obesity, physical inactivity and aging thought to be the primary cause (Kahn et al. (2006), Nature 444(7121): 840-846).

Current treatments for T2D include lifestyle management (diet and exercise) and pharmacological intervention such as metformin and insulin supply to decrease blood glucose levels by either stimulating the pancreas to release insulin or increasing insulin response. These treatments are based on symptomatic improvement of diabetes, with the consequence of a lack of durability. Indeed, none of the available treatments have been shown to counteract the aggregation of hIAPP and the loss of pancreatic β-cells. New treatment strategies involving analogues of glucagon-peptide 1 (GLP-1) (Butler et al. (2009), Diabetologia 53(1): 1-6) and inhibitors of GLP-1 inactivating enzyme dipeptidyl-peptidase 4 (DDP4) are based on the potent insulinotropic effect of GLP-1 and its effect to enhance β-cell proliferation. Importantly, increased insulin release is also coupled to increased amylin release. Experimentally, stimulated insulin secretion has been shown to promote the development of islet amyloidosis in animal models and similar effects can be expected in humans (Aston-Mourney et al. (2011), Diabetologia 54(7): 1756-1765). These treatments could therefore potentially aggravate islet amyloidosis. More recent and promising strategies involve the development of anti-inflammatory drugs or antibodies targeting the IL-1β pathway (Donath et al. (2008), Nat. Clin. Pract. Endocrinol. Metab. 4(5): 240-241; Ehes et al. (2009), Proc. Natl. Acad. Sci. USA 106(33): 13998-14003; Owyang et al. (2010), Endocrinology 151(6): 2515-2527; Dinarello et al. (2010), Curr. Opin. Endocrinol. Diabetes Obes. 17(4): 314-321; Boni-Schnetzler et al. (2011), J. Clin. Endocrinol. Metab. 93(10): 4065-4074; Boni-Schnetzler et al. (2012), Br. J. Clin. Pharmacol.; Cavelti-Weder et al. (2012), Diabetes Care). Of important note, recent studies show that hIAPP specifically induce the inflammasome—IL-1β system leading to activation of the innate immune system (Masters et al. (2010), Nat. Immunol. 11(10): 897-904; Mandrup-Poulsen et al. (2010), Nat. Immunol. 11(10): 881-883), thus supporting a therapeutic strategy targeting hIAPP aggregation.

These findings highlight the potential benefit associated with active or passive immunotherapy approaches targeting hIAPP and/or proIAPP.

Summarizing the above, novel therapeutic strategies are urgently needed addressing aggregated hIAPP, proIAPP proteins and/or hIAPP oligomers and/or fibrils with efficacious and safe therapy.

Passive immunization with human antibodies which are evolutionarily optimized and affinity matured by the human immune system would provide a promising new therapeutic avenue with a high probability for excellent efficacy and safety.

SUMMARY OF THE INVENTION

The present invention makes use of the hIAPP-specific immune response of healthy human subjects for the isolation of natural anti-hIAPP specific human monoclonal antibodies. In particular, experiments performed in accordance with the present invention were successful in the isolation of monoclonal hIAPP and/or proIAPP-specific antibodies from a pool of healthy human subjects or from pools of obese patients and other patients groups with enhanced risk to develop T2D, which at the time of antibody isolation showed no signs of T2D.

The present invention is thus directed to human antibodies, antigen-binding fragments and similar antigen-binding molecules which are capable of specifically recognizing IAPP and/or proIAPP. If not indicated otherwise, by "specifically recognizing IAPP and/or proIAPP", "antibody specific to/for IAPP and/or proIAPP" and "anti-IAPP and/or anti-proIAPP antibody" is meant specifically, generally, and collectively antibodies to the native monomeric form of IAPP; antibodies to the proIAPP precursor form of IAPP; antibodies binding specifically to either forms, IAPP and proIAPP; antibodies binding to aggregated, oligomeric, fibrillar and/or non-fibrillar IAPP and/or proIAPP species. Provided herein are human antibodies selective for full-length, and/or aggregated forms, such as oligomeric, fibrillar and non-fibrillar aggregated forms of IAPP and/or proIAPP.

In a particularly preferred embodiment of the present invention, the human antibody or antigen-binding fragment thereof demonstrates the immunological binding characteristics of an antibody characterized by the variable regions $V_H$ and/or $V_L$ as set forth in FIG. 1 or FIG. 2.

The antigen-binding fragment of the antibody can be a single chain Fv fragment, an F(ab') fragment, an F(ab) fragment, and an F(ab')2 fragment, or any other antigen-binding fragment. In a specific embodiment, infra, the antibody or fragment thereof is a human IgG isotype antibody. Alternatively, the antibody is a chimeric human-rodent or rodentized antibody such as murine or murinized, rat or ratinized antibody, the rodent versions being particularly useful for diagnostic methods and studies in animals.

Furthermore, the present invention relates to compositions comprising the antibody of the present invention or active fragments thereof and to immunotherapeutic and immunodiagnostic methods using such compositions in the prevention, diagnosis or treatment of disorders related to IAPP, such as T2D, wherein an effective amount of the composition is administered to a patient in need thereof.

Naturally, the present invention extends to the immortalized human B memory lymphocyte and B cell, respectively, that produces the antibody or an antigen binding fragment thereof having the distinct and unique characteristics as defined below.

The present invention also relates to polynucleotides encoding at least a variable region of an immunoglobulin chain of the antibody of the invention. Preferably, said variable region comprises at least one complementarity determining region (CDR) of the $V_H$ and/or $V_L$ of the variable region as set forth in FIG. 1 or in FIG. 2.

Accordingly, the present invention also encompasses vectors comprising said polynucleotides and host cells transformed therewith as well as their use for the production of an antibody and equivalent binding molecules which are specific for IAPP and/or proIAPP. Means and methods for the recombinant production of antibodies and mimics thereof as well as methods of screening for competing binding molecules, which may or may not be antibodies, are known in the art. However, as described herein, in particular with respect to therapeutic applications in human the antibody of the present invention is a human antibody in the sense that application of said antibody is substantially free of an immune response directed against such antibody otherwise observed for chimeric and even humanized antibodies.

Furthermore, disclosed herein are compositions and methods that can be used to identify IAPP and/or proIAPP in samples and/or in vivo. The disclosed anti-IAPP and/or proIAPP antibodies or IAPP and/or proIAPP binding fragments thereof can be used to screen human blood, plasma, serum, saliva, peritoneal fluid, cerebrospinal fluid ("CSF"), and urine for the presence of IAPP and/or proIAPP in samples, for example, by using ELISA-based or surface adapted assay. In one embodiment the present invention relates to a method of diagnosing or monitoring the progression of a disorder related to IAPP and/or proIAPP in a subject, the method comprising determining the presence of IAPP and/or proIAPP oligomers, aggregates or fibrils in a sample from the subject to be diagnosed with at least one antibody of the present invention or an IAPP and/or proIAPP binding molecule having substantially the same binding specificities of any one thereof, wherein the presence of IAPP and/or proIAPP oligomers, aggregates or fibrils is indicative of the disorder.

Furthermore, in one embodiment of the present invention the disclosed anti-IAPP and/or proIAPP antibodies or IAPP and/or proIAPP binding fragments thereof and/or IAPP and/or proIAPP binding molecules comprising at least one CDR of an antibody of the present invention are provided for the preparation of a composition for in vivo detection (also called in vivo imaging) of or targeting a therapeutic and/or diagnostic agent to IAPP and/or proIAPP in the human or animal body. The methods and compositions disclosed herein can aid in disorders related to IAPP and characterized, e.g., by the occurrence of oligomeric, fibrillar and non-fibrillar aggregated forms of IAPP and/or proIAPP such as T2D diagnosis and can be used to monitor disease progression and therapeutic efficacy of the therapy provided to the subject, for example in in vivo imaging related diagnostic methods. Therefore, in one embodiment the IAPP and/or proIAPP binding molecule of the present invention is provided, wherein said in vivo detection (imaging) comprises positron emission tomography (PET), single photon emission tomography (SPECT), near infrared (NIR) optical imaging or magnetic resonance imaging (MRI).

Hence, it is a particular object of the present invention to provide methods for treating, diagnosing or preventing a disease related to fibrillar and/or non-fibrillar oligomeric and/or aggregated, IAPP and/or proIAPP such as Type 2 Diabetes (T2D). The methods comprise administering an effective concentration of a human antibody or antibody derivative to the subject where the antibody targets IAPP and/or proIAPP.

In a further aspect the present invention provides a peptide having an epitope of IAPP and/or proIAPP specifically recognized by an antibody of the present invention. Said peptide comprises or consists of an amino acid sequence as indicated below in the detailed description and in the examples or a modified sequence thereof in which one or more amino acids are substituted, deleted and/or added. Additionally, the present invention provides a method for diagnosing T2D or the risk to develop T2D in a subject, comprising a step of determining the presence of an antibody that binds to said peptide in a biological sample of said subject. Further embodiments of the present invention will be apparent from the description and Examples that follow.

BRIEF DESCRIPTION OF THE DRAWINGS

FIG. 1: Amino acid and nucleotide sequences of the variable region, i.e. heavy chain and kappa/lambda light chain of human IAPP antibodies NI-203.9A2 (A), NI-203.19H8 (B), NI-203.26C11 (C), NI-203.8E3 (D), NI-203.11B12 (E), NI-203.205F8 (F), NI-203.9B3 (G), NI-203.19F2 (H), and NI-203.15C7 (I). Framework (FR) and complementarity determining regions (CDRs) are indicated with the CDRs being underlined. The heavy chain joining region (JH) and light chain joining region (JK) are indicated as well. Due to the cloning strategy the amino acid sequence at the N-terminus of the heavy chain and light chain may potentially contain primer-induced alterations in FR1, which however do not substantially affect the biological activity of the antibody. In order to provide a consensus human antibody, the nucleotide and amino acid sequences of the original clone were aligned with and tuned in accordance with the pertinent human germ line variable region sequences in the database; see, e.g., Vbase (http://vbase.mrc-cpe.cam.ac.uk/) hosted by the MRC Centre for Protein Engineering (Cambridge, UK). The amino acid sequence of human antibodies is indicated when N-terminus amino acids are considered to potentially deviate from the consensus germ line sequence due to the PCR primer and thus have been replaced by primer-induced mutation correction (PIMC). PIMC-modified amino acids are indicated in bold on the sequences.

FIG. 2: Amino acid and nucleotide sequences of the variable region, i.e. heavy chain and kappa/lambda light chain of human proIAPP antibodies NI-203.1D10 (A), NI-203.2A11 (B), NI-203.10C4 (C), NI-203.20H9 (D), NI-203.26D2 (E) and NI-203.60H3 (F). Framework (FR) and complementarity determining regions (CDRs) are indicated with the CDRs being underlined. The heavy chain joining region (JH) and light chain joining region (JK) are indicated as well. Due to the cloning strategy the amino acid sequence at the N-terminus of the heavy chain and light chain may potentially contain primer-induced alterations in FR1, which however do not substantially affect the biological activity of the antibody. In order to provide a consensus human antibody, the nucleotide and amino acid sequences of the original clone were aligned with and tuned in accordance with the pertinent human germ line variable region sequences in the database; see, e.g., Vbase (http://vbase.mrc-cpe.cam.ac.uk/) hosted by the MRC Centre for Protein Engineering (Cambridge, UK). The amino acid sequence of human antibodies is indicated when N-terminus amino acids are considered to potentially deviate from the consensus germ line sequence due to the PCR primer and thus have been replaced by primer-induced mutation correction (PIMC). PIMC-modified amino acids are indicated in bold on the sequences.

FIG. 3: IAPP-binding specificity of human recombinant antibodies assessed by direct ELISA. (A) Electron microscopy image of the IAPP solution (2 mg/ml) used for ELISA plate coating. Scale bar represents 1 (B) Recombinant NI-203.9A2, NI-203.19H8, NI-203.26C11 and NI-203.8E3 showed a specific binding to human IAPP (10 µg/ml). BSA (10 µg/ml) was used as a control to determine unspecific binding. Data are expressed as OD values at 450 nm.

FIG. 4: $EC_{50}$ determination of the recombinant human-derived anti-IAPP antibodies for IAPP and proIAPP. (A) Electron microscopy images of the IAPP and proIAPP solutions (2 mg/ml) used for ELISA plate coating. Scale bar represents 1 (B) Plates were incubated with the indicated concentrations of recombinant human-derived antibodies NI-203.9A2, NI-203.19H8, NI-203.26C11 or NI-203.8E3. The antibodies NI-203.9A2, NI-203.19H8, NI-203.26C11 and NI-203.8E3 bind with high affinity to human IAPP (■, 10 µg/ml) with an $EC_{50}$ of 9 nM, 22 nM, 6 nM and 4 nM, respectively. NI-203.26C11 also binds proIAPP (□, 10 µg/ml) with an $EC_{50}$ of 260 nM. Measurements were made in duplicate and background signal on BSA was subtracted. Data are expressed as mean OD values at 450 nm.

FIG. 5: Human-derived anti-IAPP antibodies are specific to IAPP fibrils. (A) Electron microscopy images of IAPP (2 mg/ml) and nonfibrillar IAPP (500 µg/ml) solutions used for ELISA plate coating. While the IAPP solution contains fibrils, IAPP fibrils are lacking in the nonfibrillar IAPP solution. Scale bar represents 1 (B) Plates were incubated with the indicated concentrations of recombinant human-derived antibodies NI-203.9A2, NI-203.19H8, NI-203.26C11 or NI-203.8E3. NI-203.9A2, NI-203.19H8, NI-203.26C11 and NI-203.8E3 antibodies bind with high affinity to IAPP fibrils (IAPP solution, ■, 10 µg/ml) and with very low affinity to nonfibrillar IAPP (Δ, 10 µg/ml), suggesting specificity toward IAPP fibrils. Measurements were made in duplicate and background signal on BSA was subtracted. Data are expressed as mean OD values at 450 nm.

FIG. 6: IAPP binding epitopes of human recombinant antibodies assessed by pepscan analysis. (A) Pepscan images of recombinant NI-203.19H8 and NI-203.26C11 human-derived antibodies (1 µg/ml). NI-203.19H8 binding occurred at peptides 6 and 7 (row A) covering amino acids 19-25 (peptide 6: 16-LVHSSNNFGA-25 SEQ ID NO: 6, peptide 7: 19-SSNNFGAILS-28 SEQ ID NO: 8, consensus binding sequence: 19-SSNNFGA-25 SEQ ID NO: 4). NI-203.26C11 binding occurred at peptide 1 (row A) covering amino acids 1-10 (peptide 1: 1-KCNTATCATQ-10 SEQ ID NO: 9) but not at peptide 2 covering amino acids 4-13 (peptide 2: 4-TATCATQRLA-13 SEQ ID NO: 10). Alanine substitution or replacement at residues 2-8 on peptides 33-39 and 41 (row C) impaired NI-203.26C11 binding (peptide 33 mutation: C2A, peptide 34 mutation: N3A, peptide 35 mutation: T4A, peptide 36 mutation: ASG, peptide 37 mutation: A5P, peptide 38 mutation: T6A, peptide 39 mutation: C7A, peptide 41 mutation: A8P). Secondary HRP-conjugated donkey anti-human IgG Fcγ only (1:20000; IIary Ab) was used as a control. (B) Identified binding epitopes of the different human-derived IAPP-specific antibodies within the indicated amino acids of the human IAPP protein sequence. Upper panel: amino acid sequence of the full-length human IAPP (amino acids 1-37). NI: binding epitope not identified.

DETAILED DESCRIPTION OF THE INVENTION

Figure 7:
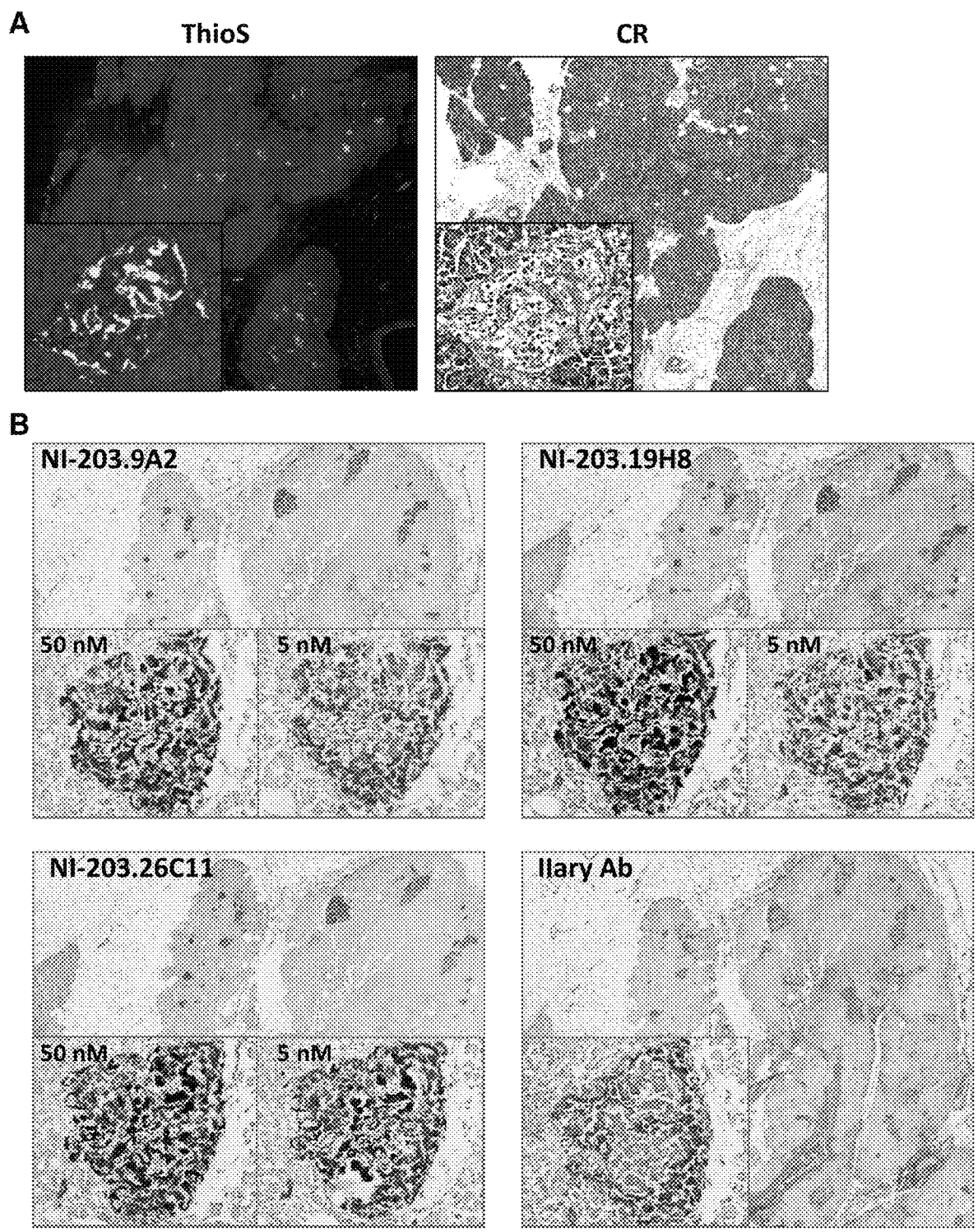
FIG. 7: NI-203.9A2, NI-203.19H8 and NI-203.26C11 antibodies specifically recognize pathological IAPP amyloid in the pancreas of patients diagnosed with diabetes mellitus type 2 (T2D). NI-203.9A2, NI-203.19H8 and NI-203.26C11 antibodies show a staining in T2D pancreatic islets loaded with IAPP fibrils (amyloid) (A, B) but not in T2D pancreatic islets lacking IAPP fibrils (C, D). (A) Thioflavin S (ThioS, left panel) and Congo red (CR, right panel) staining of amyloid in pancreatic islets of a T2D patient. (B) Detection of IAPP fibrils on amyloid positive T2D pancreatic islets with NI-203.9A2, NI-203.19H8 and NI-203.26C11 antibodies (brown-CR) at 50 nM (large panel and bottom left inset) and 5 nM (bottom right inset). (C) Absence of amyloid in pancreatic islets of a T2D patient, as shown by negative thioflavin S (ThioS, left panel) and Congo red (CR, right panel) staining. (D) Absence of staining on amyloid negative T2D pancreatic islets with NI-203.9A2, NI-203.19H8 and NI-203.26C11 antibodies at 50 nM. Secondary donkey anti-human antibody only (IIary Ab) was used as a control. Bottom insets: high magnification images of individual human pancreatic islets. Human pancreatic islets were stained with anti-insulin antibody (blue in original (i.o.), strong staining here) and counterstaining was performed to visualize cell nuclei (faint blue i.o., faint staining here).
Figure 7:
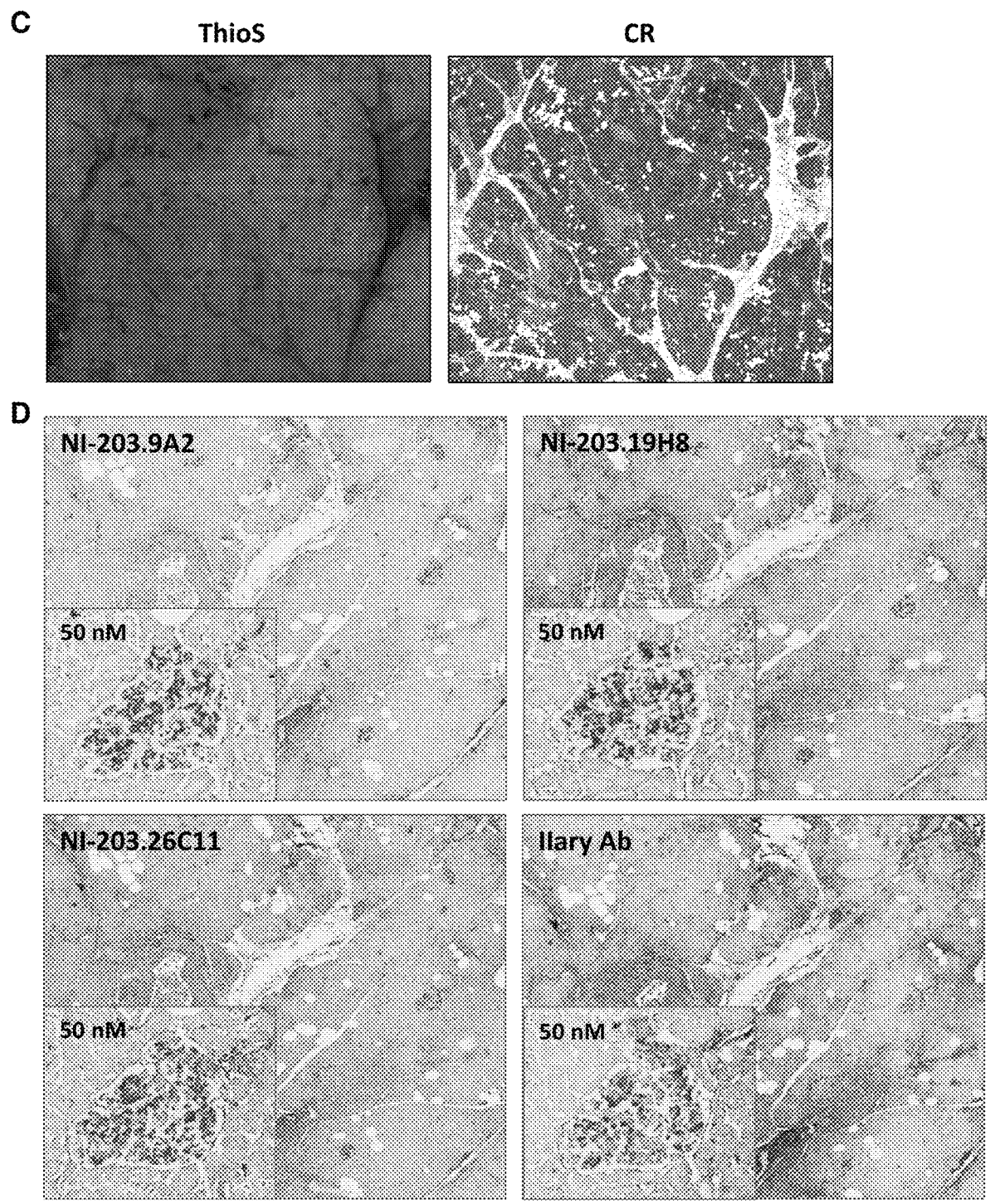

In type-2 diabetes (T2D) genetic determinants and environmental factors lead to the development of insulin resistance followed by a compensatory increase in beta-cell mass and insulin and amylin (hIAPP) secretion to maintain normal blood glucose levels. The resulting high concentrations of amylin favor the formation of toxic human islet amyloid polypeptide (hIAPP) oligomers and deposition of hIAPP fibrils which is found in more than 90% of type-2 diabetes patients. The deposition of hIAPP correlates with the reduction in insulin producing beta-cells and has also been proposed to play a role for the loss of β-cells in pancreatic islets transplanted into individuals with type-1 diabetes. Several human-derived antibodies from pools of healthy or obese donors with high risk for type-2 diabetes but absence of disease have been identified and characterized in vitro, cloned and produced recombinantly by Neurimmune's RTM™ technology as described in detail in international application WO2008/081008 and are provided herein. Lead candidates are validated in transgenic mice expressing hIAPP and exposed to high fat diet. Therapeutic efficacy is assessed by determining the beta-cell mass and hIAPP amyloid load in the pancreas as well as plasma levels of hIAPP, and functional tests of glucose metabolism and insulin secretion.

Type-2 diabetes is the most common form of diabetes, accounting for about 90% of all cases. The disease affects more than 200 million people worldwide resulting in more than a million deaths from diabetes annually. More than 300.000 patients are affected in Switzerland. The prevalence of diabetes is increasing dramatically in both developed and developing countries due to population growth, aging, urbanization, and increasing prevalence of obesity and physical inactivity. The global type-2 diabetes market at USD 25 billion is forecast to reach USD 35 billion by 2016 with a compound annual growth rate of 6.4% between 2009 and 2016. Current treatments include dietary management and pharmacological intervention acting on different pathways to decrease blood glucose levels by either improving insulin sensitivity or stimulating the pancreas to release insulin. None of the available treatments can however counteract the aggregation of hIAPP and the loss of pancreatic beta-cells. New treatment strategies for type-2 diabetes involve analogues of glucagon-peptide 1 (GLP-1) and inhibitors of dipeptidyl-peptidase 4 (DPP 4), the enzyme which inactivates endogenous GLP-1. These strategies are based on the potent insulinotropic effect of GLP-1 and its effect to enhance beta-cell proliferation. Importantly, increased insulin release is also coupled to increased amylin release. Experimentally, stimulated insulin secretion has been shown to promote the development of islet amyloidosis in animal models and similar effects can be expected in humans. Besides the particular use of IAPP binding molecules of the present invention a further proposed therapeutic approach might therefore be an attractive combination therapy of these molecules and the above indicated novel treatments.

I. Definitions

Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

If not specifically indicated otherwise, the term "IAPP", is used interchangeable to specifically refer to the native monomeric, oligomeric, non-fibrillar and fibrillar form of islet amyloid polypeptide (IAPP). The term "IAPP" is also used to generally identify other conformers of IAPP, for example, oligomers and/or aggregates of IAPP such as IAPP-fibrils. The term "IAPP" is also used to refer collectively to all types and forms of IAPP. The term proIAPP is used interchangeable to specifically refer to the native monomeric, oligomeric, fibrillar and/or aggregated form of the precursor peptide of the islet amyloid polypeptide (proIAPP). Added letters in front of the terms IAPP or proIAPP are used to indicate the organism the particular ortholog is originating from, e.g. hIAPP for human IAPP or mIAPP for murine origin.

The amino acid sequence of 37 aa for human IAPP is: KCNTATCATQRLANFLVHSSNNFGAILSSTNVGSNTY (SEQ ID NO: 1) with a disulfide bridge between cysteine residues 2 and 7 and an amidated C-terminus.

IAPP is processed from preprohormone preproIAPP, a 89 amino acid precursor produced in pancreatic β-cells. The protein sequence for human preproIAPP is: MGILKLQVFLIVLSVALNHLKATPIESHQVEKRKCN-TATCATQRLANFLVHSSNNF GAILSSTNVGSN-TYGKRNAVEVLKREPLNYLPL (SEQ ID NO: 2), which sequence may be found as well in pertinent databases, e.g., in the UniProt database: UniProtID: P10997 (IAPP_HUMAN).

PreproIAPP is rapidly cleaved after translation into proislet amyloid polypeptide. The protein sequence for human proIAPP is: TPIESHQVEKRKCNTATCATQRLAN-FLVHSSNNFGAILSSTNVGSNTYGKRNAVEV LKREPLNYLPL (SEQ ID NO: 3), which undergoes additional proteolysis and post-translational modifications to generate hIAPP.

The "wild type" or recombinant human IAPP, proIAPP and preproIAPP amino acid sequences are represented by the above mentioned sequences according to SEQ ID NOs: 1-3.

The human anti-IAPP and anti-proIAPP antibodies disclosed herein specifically bind IAPP and/or proIAPP and epitopes thereof and to various conformations of IAPP and/or proIAPP and epitopes thereof. For example, disclosed herein are antibodies that specifically bind pathologically aggregated IAPP and/or proIAPP forms, such as non-fibrillar oligomers and/or fibrillar oligomers/fibrils and/or aggregates consisting of mixed forms thereof. The term (pathologically) aggregated/aggregates of IAPP and/or proIAPP is used interchangeable to specifically refer to the aforementioned forms. The term (pathological) "aggregated forms" or "aggregates" as used herein describes the products of an accumulation or cluster formation due to an IAPP and/or proIAPP erroneous/pathological interaction with one another. These aggregates, accumulations or cluster forms may be, substantially consist or consist of both IAPP and/or proIAPP and of non-fibrillar oligomers and/or fibrillar oligomers and fibrils thereof. As used herein, reference to an antibody that "specifically binds", "selectively binds", or "preferentially binds" IAPP and/or proIAPP refers to an antibody that does not bind other unrelated proteins. In one example, an IAPP and/or proIAPP antibody disclosed herein can bind IAPP and/or proIAPP or an epitope thereof and show no binding above about 2 times background for other proteins. An antibody that "specifically binds" or "selectively binds" an IAPP and/or proIAPP conformer refers to an antibody that does not bind all conformations of IAPP and/or proIAPP, i.e., does not bind at least one other IAPP and/or proIAPP conformer. For example, disclosed herein are antibodies that can preferentially bind to aggregated forms of IAPP and/or proIAPP both in vitro and in tissues obtained from patients with overt T2D or with a risk to develop T2D. Since the human IAPP and/or proIAPP antibodies of the present invention have been isolated from a pool of healthy human subjects or from pools of obese patients and other patients groups with enhanced risk to develop T2D, which at the time of antibody isolation showed no signs of T2D, exhibiting an IAPP and/or proIAPP specific immune response, the IAPP and/or proIAPP antibodies of the present invention may also be called "human auto-antibodies" in order to emphasize that those antibodies were indeed expressed by the subjects and have not been isolated from, for example a human immunoglobulin expressing phage library, which hitherto represented one common method for trying to provide human-like antibodies.

The term "peptide" is understood to include the terms "polypeptide" and "protein" (which, at times, may be used interchangeably herein) within its meaning. Similarly, fragments of proteins and polypeptides are also contemplated and may be referred to herein as "peptides". Nevertheless, the term "peptide" preferably denotes an amino acid polymer including at least 5 contiguous amino acids, preferably at least 10 contiguous amino acids, more preferably at least 15 contiguous amino acids, still more preferably at least 20 contiguous amino acids, and particularly preferred at least 25 contiguous amino acids. In addition, the peptide in accordance with present invention typically has no more than 100 contiguous amino acids, preferably less than 80 contiguous amino acids and more preferably less than 50 contiguous amino acids.

Polypeptides:

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation and derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

"Recombinant peptides, polypeptides or proteins" refer to peptides, polypeptides or proteins produced by recombinant DNA techniques, i.e. produced from cells, microbial or mammalian, transformed by an exogenous recombinant DNA expression construct encoding the fusion protein including the desired peptide. Proteins or peptides expressed in most bacterial cultures will typically be free of glycan. Proteins or polypeptides expressed in yeast may have a glycosylation pattern different from that expressed in mammalian cells.

Included as polypeptides of the present invention are fragments, derivatives, analogs or variants of the foregoing polypeptides and any combinations thereof as well. The terms "fragment," "variant," "derivative" and "analog" include peptides and polypeptides having an amino acid sequence sufficiently similar to the amino acid sequence of the natural peptide. The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the preferred peptides of the present invention, in particular to IAPP and/or proIAPP or fragments, variants, derivatives or analogs of either of them. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

Furthermore, the terms "fragment," "variant," "derivative" and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of IAPP and/or proIAPP specific binding molecules, e.g., antibodies and antibody polypeptides of the present invention, are polypeptides which have been altered so as to exhibit additional features not found on the native polypeptide. Examples include fusion proteins. Variant polypeptides may also be referred to herein as "polypeptide analogs". As used herein a "derivative" of a binding molecule or fragment thereof, an antibody, or an antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Determination of Similarity and/or Identity of Molecules:

"Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: -Ala, Pro, Gly, Gln, Asn, Ser, Thr; -Cys, Ser, Tyr, Thr; -Val, Ile, Leu, Met, Ala, Phe; -Lys, Arg, His; -Phe, Tyr, Trp, His; and -Asp, Glu.

"Similarity" between two polynucleotides is determined by comparing the nucleic acid sequence of one polynucleotide to the sequence of a polynucleotide. A nucleic acid of one polynucleotide is similar to the corresponding nucleic acid of a second polynucleotide if it is identical or, if the nucleic acid is part of a coding sequence, the respective triplet comprising the nucleic acid encodes for the same amino acid or for a conservative amino acid substitution.

The determination of percent identity or similarity between two sequences is preferably accomplished using the mathematical algorithm of Karlin and Altschul (1993) Proc. Natl. Acad. Sci USA 90: 5873-5877. Such an algorithm is incorporated into the BLASTn and BLASTp programs of Altschul et al. (1990) J. Mol. Biol. 215: 403-410 available at NCBI (http://www.ncbi.nlmnih.gov/blast/Blast.cge).

The determination of percent identity or similarity is performed with the standard parameters of the BLASTn and BLASTp programs, as recommended on the NCBI webpage and in the "BLAST Program Selection Guide" in respect of sequences of a specific length and composition.

BLAST polynucleotide searches are performed with the BLASTn program.

For the general parameters, the "Max Target Sequences" box may be set to 100, the "Short queries" box may be ticked, the "Expect threshold" box may be set to 1000 and the "Word Size" box may be set to 7 as recommended for short sequences (less than 20 bases) on the NCBI webpage. For longer sequences the "Expect threshold" box may be set to 10 and the "Word Size" box may be set to 11. For the scoring parameters the "Match/mismatch Scores" may be set to 1,-2 and the "Gap Costs" box may be set to linear. For the Filters and Masking parameters, the "Low complexity regions" box may not be ticked, the "Species-specific repeats" box may not be ticked, the "Mask for lookup table only" box may be ticked, the "DUST Filter Settings" may be ticked and the "Mask lower case letters" box may not be ticked. In general the "Search for short nearly exact matches" may be used in this respect, which provides most of the above indicated settings. Further information in this respect may be found in the "BLAST Program Selection Guide" published on the NCBI webpage.

BLAST protein searches are performed with the BLASTp program. For the general parameters, the "Max Target Sequences" box may be set to 100, the "Short queries" box may be ticked, the "Expect threshold" box may be set to 10 and the "Word Size" box may be set to "3". For the scoring parameters the "Matrix" box may be set to "BLOSUM62", the "Gap Costs" Box may be set to "Existence: 11 Extension: 1", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked.

Modifications of both programs, e.g., in respect of the length of the searched sequences, are performed according to the recommendations in the "BLAST Program Selection Guide" published in a HTML and a PDF version on the NCBI webpage.

Polynucleotides:

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a binding molecule, an antibody, or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operable associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operable associated" or "operable linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operable associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operable associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operable associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

A "binding molecule" as used in the context of the present invention relates primarily to antibodies, and fragments thereof, but may also refer to other non-antibody molecules that bind to IAPP and/or proIAPP including but not limited to hormones, receptors, ligands, major histocompatibility complex (MHC) molecules, chaperones such as heat shock proteins (HSPs) as well as cell-cell adhesion molecules such as members of the cadherin, intergrin, C-type lectin and immunoglobulin (Ig) superfamilies. Thus, for the sake of clarity only and without restricting the scope of the present invention most of the following embodiments are discussed with respect to antibodies and antibody-like molecules which represent the preferred binding molecules for the development of therapeutic and diagnostic agents.

Antibodies:

The terms "antibody" and "immunoglobulin" are used interchangeably herein. An antibody or immunoglobulin is an IAPP and/or proIAPP-binding molecule which comprises at least the variable domain of a heavy chain, and normally comprises at least the variable domains of a heavy chain and a light chain. Basic immunoglobulin structures in vertebrate systems are relatively well understood; see, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the $V_H$ and $V_L$ chains. Any antibody or immunoglobulin fragment which contains sufficient structure to specifically bind to IAPP and/or proIAPP is denoted herein interchangeably as a "binding fragment" or an "immunospecific fragment."

In naturally occurring antibodies, an antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three dimensional configuration in an aqueous environment. The "CDRs" are flanked by four relatively conserved "framework" regions or "FRs" which show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest," Kabat, E., et al., U.S. Department of Health and Human Services, (1983); and Chothia and Lesk, J. Mol. Biol., 196 (1987), 901-917, which are incorporated herein by reference in their entireties.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia and Lesk, J. Mol. Biol., 196 (1987), 901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE I

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table I is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system, which however is theoretical and may not equally apply to every antibody of the present invention. For example, depending on the position of the first CDR the following CDRs might be shifted in either direction.

Antibodies or antigen-binding fragments, immunospecific fragments, variants, or derivatives thereof of the invention include, but are not limited to, polyclonal, monoclonal, multispecific, human, humanized, primatized, murinized or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019 Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In one embodiment, the antibody of the present invention is not IgM or a derivative thereof with a pentavalent structure. Particular, in specific applications of the present invention, especially therapeutic use, IgMs are less useful than IgG and other bivalent antibodies or corresponding binding molecules since IgMs due to their pentavalent structure and lack of affinity maturation often show unspecific cross-reactivities and very low affinity.

In a particularly preferred embodiment, the antibody of the present invention is not a polyclonal antibody, i.e. it substantially consists of one particular antibody species rather than being a mixture obtained from a plasma immunoglobulin sample.

Antibody fragments, including single-chain antibodies, may comprise the variable region(s) alone or in combination with the entirety or a portion of the following: hinge region, CH1, CH2, and CH3 domains. Also included in the invention are IAPP and/or proIAPP binding fragments which comprise any combination of variable region(s) with a hinge region, CH1, CH2, and CH3 domains. Antibodies or immunospecific fragments thereof of the present invention may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

In one aspect, the antibody of the present invention is a human monoclonal antibody isolated from a human. Optionally, the framework region of the human antibody is aligned and adopted in accordance with the pertinent human germ line variable region sequences in the database; see, e.g., Vbase (http://vbase.mrc-cpe.cam.ac.uk/) hosted by the MRC Centre for Protein Engineering (Cambridge, UK). For example, amino acids considered to potentially deviate from the true germ line sequence could be due to the PCR primer sequences incorporated during the cloning process. Compared to artificially generated human-like antibodies such as single chain antibody fragments (scFvs) from a phage displayed antibody library or xenogeneic mice the human monoclonal antibody of the present invention is characterized by (i) being obtained using the human immune response rather than that of animal surrogates, i.e. the antibody has been generated in response to natural IAPP or proIAPP in its relevant conformation in the human body, (ii) having protected the individual or is at least significant for the presence of IAPP and/or proIAPP, and (iii) since the antibody is of human origin the risks of cross-reactivity against self-antigens is minimized Thus, in accordance with the present invention the terms "human monoclonal antibody", "human monoclonal autoantibody", "human antibody" and the like are used to denote an IAPP and/or proIAPP binding molecule which is of human origin, i.e. which has been isolated from a human cell such as a B cell or hybridoma thereof or the cDNA of which has been directly cloned from mRNA of a human cell, for example a human memory B cell. A human antibody is still "human" even if amino acid substitutions are made in the antibody, e.g., to improve binding characteristics.

Antibodies derived from human immunoglobulin libraries or from animals transgenic for one or more human immunoglobulins and that do not express endogenous immunoglobulins, as described infra and, for example in, U.S. Pat. No. 5,939,598 by Kucherlapati et al., are denoted human-like antibodies in order distinguish them from truly human antibodies of the present invention.

For example, the paring of heavy and light chains of human-like antibodies such as synthetic and semi-synthetic antibodies typically isolated from phage display do not necessarily reflect the original paring as it occurred in the original human B cell. Accordingly Fab and scFv fragments obtained from recombinant expression libraries as commonly used in the prior art can be considered as being artificial with all possible associated effects on immunogenicity and stability.

In contrast, the present invention provides isolated affinity-matured antibodies from selected human subjects, which are characterized by their therapeutic utility and their tolerance in man.

As used herein, the term "rodentized antibody" or "rodentized immunoglobulin" refers to an antibody comprising one or more CDRs from a human antibody of the present invention; and a human framework region that contains amino acid substitutions and/or deletions and/or insertions that are based on a rodent antibody sequence. When referred to rodents, preferably sequences originating in mice and rats are used, wherein the antibodies comprising such sequences are referred to as "murinized" or "ratinized" respectively. The human immunoglobulin providing the CDRs is called the "parent" or "acceptor" and the rodent antibody providing the framework changes is called the "donor". Constant regions need not be present, but if they are, they are usually substantially identical to the rodent antibody constant regions, i.e. at least about 85-90%, preferably about 95% or more identical. Hence, in some embodiments, a full-length murinized human heavy or light chain immunoglobulin contains a mouse constant region, human CDRs, and a substantially human framework that has a number of "murinizing" amino acid substitutions. Typically, a "murinized antibody" is an antibody comprising a murinized variable light chain and/or a murinized variable heavy chain. For example, a murinized antibody would not encompass a typical chimeric antibody, e.g., because the entire variable region of a chimeric antibody is non-mouse. A modified antibody that has been "murinized" by the process of "murinization" binds to the same antigen as the parent antibody that provides the CDRs and is usually less immunogenic in mice, as compared to the parent antibody. The above explanations in respect of "murinized" antibodies apply analogously for oder "rodentized" antibodies, such as "ratinized antibodies", wherein rat sequences are used instead of the murine.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody or diabody.

In another embodiment, the antibodies, or antigen-binding fragments, variants, or derivatives thereof disclosed herein are composed of a single polypeptide chain such as scFvs and are to be expressed intracellularly (intrabodies) for potential in vivo therapeutic and diagnostic applications.

The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a $V_L$ or CL domain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of IAPP or proIAPP.

By "specifically binding", or "specifically recognizing", used interchangeably herein, it is generally meant that a binding molecule, e.g., an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D".

Where present, the term "immunological binding characteristics," or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, a binding molecule, e.g., an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, a binding molecule, e.g., an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

A binding molecule, e.g., an antibody or antigen-binding fragment, variant, or derivative disclosed herein may be said to bind IAPP and/or proIAPP or a fragment, variant or specific conformation thereof with an off rate (k(off)) of less than or equal to $5\times10^{-2}$ $\sec^{-1}$, $10^{-2}$ $\sec^{-1}$, $5\times10^{-3}$ $\sec^{-1}$ or $10^{-3}$ $\sec^{-1}$. More preferably, an antibody of the invention may be said to bind IAPP and/or proIAPP or a fragment, variant or specific conformation thereof with an off rate (k(off)) less than or equal to $5\times10^{-4}$ $\sec^{-1}$, $10^{-4}$ $\sec^{-1}$, $5\times10^{-5}$ $\sec^{-1}$, or $10^{-5}$ $\sec^{-1}$ $5\times10^{-6}$ $\sec^{-1}$, $10^{-6}$ $\sec^{-1}$, $5\times10^{-7}$ $\sec^{-7}$ or $10^{-7}$ $\sec^{-1}$.

A binding molecule, e.g., an antibody or antigen-binding fragment, variant, or derivative disclosed herein may be said to bind IAPP and/or proIAPP or a fragment, variant or specific conformation thereof with an on rate (k(on)) of greater than or equal to $10^3$ $M^{-1}$ $\sec^{-1}$, $5\times10^3$ $M^{-1}$ $\sec^{-1}$, $10^4$ $M^{-1}$ $\sec^{-1}$ or $5\times10^4$ $M^{-1}$ $\sec^{-1}$. More preferably, an antibody of the invention may be said to bind IAPP and/or proIAPP or a fragment, variant or specific conformation thereof with an on rate (k(on)) greater than or equal to $10^{-5}$ $M^{-1}$ $\sec^{-1}$, $5\times10^{-5}$ $M^{-1}$ $\sec^{-1}$, $10^{-6}$ $M^{-1}$ $\sec^{-1}$, or $5\times10^{-6}$ $M^{-1}$ $\sec^{-1}$ or $10^{-7}$ $M^{-1}$ $\sec^{-1}$.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valences of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In *Fundamental Immunology*, Paul, W. E., Ed., Raven Press New York, N Y (1984), Kuby, Janis Immunology, W. H. Freeman and Company New York, N Y (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

Binding molecules, e.g., antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Binding molecules, e.g., antibodies or antigen-binding fragments, variants or derivatives thereof of the invention may also be described or specified in terms of their binding affinity to IAPP and/or proIAPP. Preferred binding affinities include those with a dissociation constant or Kd less than $5\times10^{-2}$ M, $10^{-3}$ M, $5\times10^{-3}$M, $10^{-3}$M, $5\times10^{-4}$M, $10^{-4}$M, $5\times10^{-5}$M, $10^{-5}$M, $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$ M, $10^{-10}$ M, $5\times10^{-11}$ M, $10^{-11}$ M, $5\times10^{-12}$M, $10^{-12}$M, $5\times10^{-13}$M, $10^{-13}$M, $5\times10^{-14}$M, $10^{-14}$M, $5\times10^{-15}$ M, or $10^{-15}$ M.

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "CH1 domain" includes the first (most amino terminal) constant region domain of an immunoglobulin heavy chain. The CH1 domain is adjacent to the $V_H$ domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al., J. Immunol. 161 (1998), 4083-4090.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked", "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the term "sample" refers to any biological material obtained from a subject or patient. In one aspect, a sample can comprise blood, peritoneal fluid, CSF, saliva or urine. In other aspects, a sample can comprise whole blood, blood plasma, blood serum, B cells enriched from blood samples, and cultured cells (e.g., B cells from a subject). A sample can also include a biopsy or tissue sample including neural tissue. In still other aspects, a sample can comprise whole cells and/or a lysate of the cells. Blood samples can be collected by methods known in the art. In one aspect, the pellet can be resuspended by vortexing at 4° C. in 200 µl buffer (20 mM Tris, pH. 7.5, 0.5% Nonidet, 1 mM EDTA, 1 mM PMSF, 0.1M NaCl, IX Sigma Protease Inhibitor, and IX Sigma Phosphatase Inhibitors 1 and 2). The suspension can be kept on ice for 20 minutes with intermittent vortexing. After spinning at 15,000×g for 5 minutes at about 4° C., aliquots of supernatant can be stored at about −70° C.

Diseases:

Unless stated otherwise, the terms "disorder" and "disease" are used interchangeably herein and comprise any undesired physiological change in a subject, an animal, an isolated organ, tissue or cell/cell culture.

In T2D genetic determinants and environmental factors lead to the development of insulin resistance followed by a compensatory increase in beta-cell mass and insulin and amylin (IAPP) secretion to maintain normal blood glucose levels. The resulting high concentrations of amylin favor the formation of toxic hIAPP oligomers and deposition of hIAPP fibrils which is found in more than 90% of T2D patients. The deposition of hIAPP correlates with the reduction in insulin producing beta-cells and has also been proposed to play a role for the loss of β-cells in pancreatic islets transplanted into individuals with T1D. The present application provides several human-derived antibodies from pools of healthy donors or obese donors with high risk for T2D but absence of disease, which were cloned and produced recombinantly as described herein below in more detail.

However, in one embodiment of the present invention the antibodies of the present invention, binding molecules having substantially the same binding specificities of any one thereof, the polynucleotides, the vectors or the cells of the present invention are used for the preparation of a pharmaceutical or diagnostic composition for prophylactic and therapeutic treatment, monitoring the progression or a response to treatment and/or diagnosis of diseases from the group of Diabetes mellitus diseases, comprising type 1 diabetes (T1D), gestational diabetes, pre-diabetes, latent autoimmune diabetes of adults (LADA; type 1,5 diabetes) and/or type 2 diabetes (T2D).

In a preferred embodiment the antibodies of the present invention, binding molecules having substantially the same binding specificities of any one thereof, the polynucleotides, the vectors or the cells of the present invention are used for the preparation of a pharmaceutical or diagnostic composition for prophylactic and therapeutic treatment, monitoring the progression or a response to treatment and/or diagnosis of a group of disorders generally characterized by symptoms such as metabolic changes preceding, causing, and/or connected/associated with or linked to T2D comprising diseases that cause damage to the pancreas and could therefore lead to diabetes comprising chronic pancreatitis, cystic fibrosis, pancreatic cancer; in diseases that increase the risk of T2D comprising Alzheimer's disease, Huntington's disease; and/or in cardiovascular diseases linked or not with obesity and T2D. In one preferred embodiment, symptoms generally characterizing the above-mentioned diseases comprise disturbed insulin sensitivity and increased secretion of insulin and/or hIAPP in a subject.

In one embodiment, the above-mentioned specific symptoms associated group of disorders comprises gestational diabetes, pre-diabetes (when high blood glycaemia is not reaching the T2D threshold or insulin resistance); metabolic syndrome in general as a risk factor for developing diabetes or as a condition that could exist prior diabetes; Islet amyloidosis in general as a risk factor for developing diabetes or as a condition that could exist prior diabetes; obesity in general as a risk factor for developing diabetes or as a condition that could exist prior diabetes and/or beta-cell failure following clinical pancreatic islet transplantation.

Furthermore, the antibodies of the present invention, binding molecules having substantially the same binding specificities of any one thereof, the polynucleotides, the vectors or the cells of the present invention are used for the preparation of a composition for detection of a changed, i.e. increased or decreased secretion of amylin as compared to amylin secretion in a healthy subject in differential diagnostic of type 1 diabetes, latent autoimmune diabetes of adults (LADA, Type 1,5 diabetes) in comparison to T2D forms, or in disorders preceding an overt T2D, such as gestational diabetes or pre-diabetes; in diseases that cause damage to the pancreas and could therefore lead to diabetes such as chronic pancreatitis, cystic fibrosis, pancreatic cancer; in diseases that increase the risk of T2D such as Alzheimer's disease, Huntington's disease; and/or in cardiovascular diseases linked or not with obesity and T2D Disorders such as obesity and insulin resistance/hyperinsulinemia are observed often as a predisposition and/or as a symptom of T2D which can lead to elevated circulating levels of islet amyloid polypeptide (IAPP) already ahead the overt form of T2D. Amylin (hIAPP) oligomers, fibrils, and plaques have been found accumulating not only within pancreas and kidneys but as well within the heart in patients with obesity and insulin resistance. This accumulation has been observed in connection of an altered cellular $Ca^{2+}$ homeostasis which in turn may contribute to cardiac dysfunction in such patients.

Therefore, in one embodiment the antibodies of the present invention, binding molecules having substantially the same binding specificities of any one thereof, the polynucleotides, the vectors or the cells of the present invention are used for the preparation of a pharmaceutical or diagnostic composition for prophylactic and therapeutic treatment, amelioration, monitoring the progression or a response to treatment and/or for diagnosis of a group of disorders following to T2D or resulting from the metabolic changes preceding and/or causing T2D, i.e. the metabolic changes occurring in the pre-diabetic state, wherein the group of disorders comprises heart disease, strokes, diabetic retinopathy, kidney failure, renal failure, ketoacidosis and nonketotic hyperosmolar coma.

More than 20 neurodegenerative disorders (see, e.g., Table 1 on page 511 in M. Ristow, J. Mol. Med 82 (2004), 510-529) are known to be associated with diabetes mellitus, increased insulin resistance and obesity, disturbed insulin sensitivity, and excessive or impaired insulin secretion. Therefore, in one embodiment of the present invention the antibodies of the present invention, binding molecules having substantially the same binding specificities of any one thereof, the polynucleotides, the vectors or the cells of the present invention are used for the preparation of a pharmaceutical or diagnostic composition for prophylactic and therapeutic treatment, monitoring the progression or a response to treatment and/or diagnosis of neurodegenerative disorders comprising Alzheimer disease (AD), ataxia-telangiectasia (AT), Bardet-Biedl syndrome (BBS), Friedreich ataxia (FRDA), Huntington disease, myotonic dystrophy, narcolepsy, Parkinson disease, Prader-Willi syndrome, and Werner syndrome.

The impaired glucose tolerance scarcely induces complications being characteristic for diabetes mellitus, but has a higher risk of the onset of diabetes mellitus than normal-type, which may be a cause for macrovascular diseases.

The "insulin resistance" means conditions of reduced sensitivity to insulin. Insulin has been known to exhibit a wider range of effects such as, in addition to an effect on the glucose metabolism, an effect on lipid metabolism or effects on the blood vessel and the kidney. Once the sensitivity to insulin is reduced, not only glucose metabolic abnormality but also lipid metabolic abnormality such as hypertriglycemia, decreased HDL plasma level, or hypertension as an abnormality of insulin effects on the blood vessel or the kidney may be induced.

As used herein, the term "diabetic" in a human generally and currently means a random plasma or blood glucose concentration of ≥200 mg/dL (≥11.1 mmol/L) or a fasting plasma glucose≥126 mg/dL (≥7.0 mmol/L) or a 2 hour post-load glucose≥200 mg/dL (≥11.1 mmol/L) during an oral glucose tolerance test. In addition or alternatively the term "diabetic" is used for subjects showing one or more of the clinical symptoms of diabetes including increased thirst (polydipsia), frequent urination (polyuria), extreme hunger, unexplained weight loss, fatigue and blurry vision, vulnerability to slow-healing sores and frequent infection, including those of the bladder, vagina and gums and/or areas of darkened skin (acanthosis *nigricans*).

As used herein, the term "non-diabetic" in a human generally and currently means a fasting plasma glucose level of <100 mg/dL (5.6 mmol/dL) or a 2 hour post-load glucose<140 mg/dL (<7.8 mmol/dL) during an oral glucose tolerance test.

As used herein, the term "pre-diabetic" in a human generally and currently means a fasting plasma glucose level of 100-125 mg/dL (5.6-6.9 mmol/L) or a 2 hour post-load glucose 140-199 mg/L (7.8-11.1 mmol/L) during an oral glucose tolerance test. Unless stated otherwise, the terms "pre-diabetic," "prodromal" and "presymptomatic" are used interchangeably herein and describing the pre-clinical phase of T2D.

In addition or alternatively levels of glycosylated hemoglobin (HbA1c) may be used in diagnosing diabetes in a subject. At elevated HbA1c levels at or beyond the threshold of 6.5% a diagnosis of diabetes is made, i.e. the term "diabetic" is generally and currently used in a human, while levels from 5.7% to 6.4% point to high risk for developing both diabetes and cardiovascular disease and are a marker of "pre-diabetes," or a "pre-diabetic/presymptomatic" state in a human. The term "non-diabetic" in a human generally and currently means then HbA1c levels below the threshold of 5.7%.

Rodent Models of Type II Diabetes Mellitus in Drug Discovery

Examples of conventionally reported model animals which spontaneously develop Type II diabetes include KK-Ay mice (Nishimura M., Exp. Anim 18, 147-157, 1969), NSY mice (Ueda H., et al., Diabetologia 38, 503-508, 1995), db/db mice (Hummel K. P., et al., Science 153, 1127-1128, 1966), ob/ob mice (Herberg L. & Kley H K, Horm. Metab. Res. 7, 410-5, 1975), and AKITA mice (Yoshioka M., et al., Diabetes 46, 887-894, 1997).

Of these animals, KK-Ay mice and NSY mice are models with obesity and db/db mice and ob/ob mice are models with obesity due to an abnormality in leptin receptors or in leptin production. On the other hand, AKITA mice are a model for diabetes caused by an abnormality in pancreatic β cells.

As a non-obese Type II diabetes model animal, for example, a model mouse is so far reported in Japanese Patent Application No. 2004-65181. This mouse exhibits abnormal insulin secretion.

However, the antibodies of the present invention are preferably tested and characterized in transgenic animals, e.g., rodents expressing hIAPP such as rats transgenic for human amylin in the pancreatic β-cells (HIP rats) as described in Butler et al., *Diabetes* 53 (2004), 1509-1516 and in Matveyenko and Butler, *Diabetes* 55 (2006), 2106-2114. More preferably, type 2 diabetes mouse models overexpressing human IAPP are used as described in Matveyenko and Butler (2006), ILAR J. 47(3): 225-233, and summarized in Table 2 on page 228 therein. Because of the hIAPP-overexpression such model animals validly display T2D-symptoms such as the hyperglycamic state. In general, the term "hyperglycemia" or "hyperglycemic state" refers to significantly increased fasting plasma glucose levels on two consecutive measurements taken at different time intervals and when compared to non-transgenic control littermates. Absolute values measured in hyperglycemic animals might depend from the particular animal model used, e.g., in h-IAPP (hemizygous)/ob/+ mice, ≥~15-20 mM glucose; in h-IAPP (homozygous)/FVB/N mice≥~11 mM glucose.

Methods for studying diabetes include measurement of physiological changes and analysis of blood or plasma of diabetic in comparison to healthy, non-diabetic animals. These measurements include, but are not limited to, growth dynamics, body mass index (BMI), lean mass index (LMI), food and water intake, sex differences, fasting and random blood glucose, triglycerides (TG), lipoproteins, cholesterol, liver weight and liver lipids, kidney size and function, a glucose tolerance test (GTT), insulin tolerance test (ITT), blood insulin concentration, pancreatic islet cell morphology, high-fat diets, and caloric restriction.

As used herein, the terms "random" and "non-fasting" generally means at any time during the day or night without regard to time since the last meal.

As used herein, the term "fasting" generally means no caloric intake for at least 12 hours.

It is appreciated that these definitions are the currently accepted guidelines practitioners generally follow according to the American Diabetes Association (ADA) and the German Diabetes Association (GDA). Guidelines may change over time and vary by region or country and depend upon the group or institution (e.g. ADA, World Health Organization, NIDDK/NIH, CDC, GDA etc.) providing the guidelines, known to those skilled in the art. Physicians may also use clinical experience, the patient's past medical history, and/or other information when deciding on a diagnosis and treatment. These definitions may therefore change over time according to advances in science and medicine.

Treatment:

As used herein, the terms "treat" or "treatment" refer to both therapeutic treatment and prophylactic or preventative measures, wherein the object is to prevent or slow down (lessen) an undesired physiological change or disorder, such as the development of diabetes. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

If not stated otherwise the term "drug," "medicine," or "medicament" are used interchangeably herein and shall include but are not limited to all (A) articles, medicines and preparations for internal or external use, and any substance or mixture of substances intended to be used for diagnosis, cure, mitigation, treatment, or prevention of disease of either man or other animals; and (B) articles, medicines and preparations (other than food) intended to affect the structure or any function of the body of man or other animals; and (C) articles intended for use as a component of any article specified in clause (A) and (B). The term "drug," "medicine," or "medicament" shall include the complete formula of the preparation intended for use in either man or other animals containing one or more "agents," "compounds", "substances" or "(chemical) compositions" as and in some other context also other pharmaceutically inactive excipients as fillers, disintegrants, lubricants, glidants, binders or ensuring easy transport, disintegration, disaggregation, dissolution and biological availability of the "drug," "medicine," or "medicament" at an intended target location within the body of man or other animals, e.g., at the skin, in the stomach or the intestine. The terms "agent," "compound", or "substance" are used interchangeably herein and shall include, in a more particular context, but are not limited to all pharmacologically active agents, i.e. agents that induce a desired biological or pharmacological effect or are investigated or tested for the capability of inducing such a possible pharmacological effect by the methods of the present invention.

By "subject" or "individual" or "animal" or "patient" or "mammal," is meant any subject, particularly a mammalian subject, e.g., a human patient, for whom diagnosis, prognosis, prevention, or therapy is desired.

Pharmaceutical Carriers:

Pharmaceutically acceptable carriers and administration routes can be taken from corresponding literature known to the person skilled in the art. The pharmaceutical compositions of the present invention can be formulated according to methods well known in the art; see for example Remington: The Science and Practice of Pharmacy (2000) by the University of Sciences in Philadelphia, ISBN 0-683-306472, Vaccine Protocols. 2nd Edition by Robinson et al., Humana Press, Totowa, N.J., USA, 2003; Banga, Therapeutic Peptides and Proteins: Formulation, Processing, and Delivery Systems. 2nd Edition by Taylor and Francis (2006), ISBN: 0-8493-1630-8. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. Aerosol formulations such as nasal spray formulations include purified aqueous or other solutions of the active agent with preservative agents and isotonic agents. Such formulations are preferably adjusted to a pH and isotonic state compatible with the nasal mucous membranes. Pharmaceutical compositions for oral administration, such as single domain antibody molecules (e.g., "Nanobodies™") etc. are also envisaged in the present invention. Such oral formulations may be in tablet, capsule, powder, liquid or semi-solid form. A tablet may comprise a solid carrier, such as gelatin or an adjuvant. Formulations for rectal or vaginal administration may be presented as a suppository with a suitable carrier; see also O'Hagan et al., Nature Reviews, Drug Discovery 2(9) (2003), 727-735. Further guidance regarding formulations that are suitable for various types of administration can be found in Remington's Pharmaceutical Sciences, Mace Publishing Company, Philadelphia, Pa., 17th ed. (1985) and corresponding updates. For a brief review of methods for drug delivery see Langer, Science 249 (1990), 1527-1533.

II. Antibodies of the Present Invention

The present invention generally relates to human anti-IAPP antibodies and antigen-binding fragments thereof, which preferably demonstrate the immunological binding characteristics and/or biological properties as outlined for the antibodies illustrated in the Examples. In accordance with the present invention human monoclonal antibodies specific for IAPP and/or proIAPP were cloned from a pool of healthy human subjects.

In the course of the experiments performed in accordance with the present invention antibodies in conditioned media of human memory B cell cultures were screened in parallel for binding to aggregated oligomeric, fibrillar and/or non-fibrillar IAPP and/or proIAPP protein—and bovine serum albumin (BSA). Only B-cell cultures positive for aggregated IAPP and/or proIAPP protein but not for BSA were subjected to antibody cloning.

Figure 8:
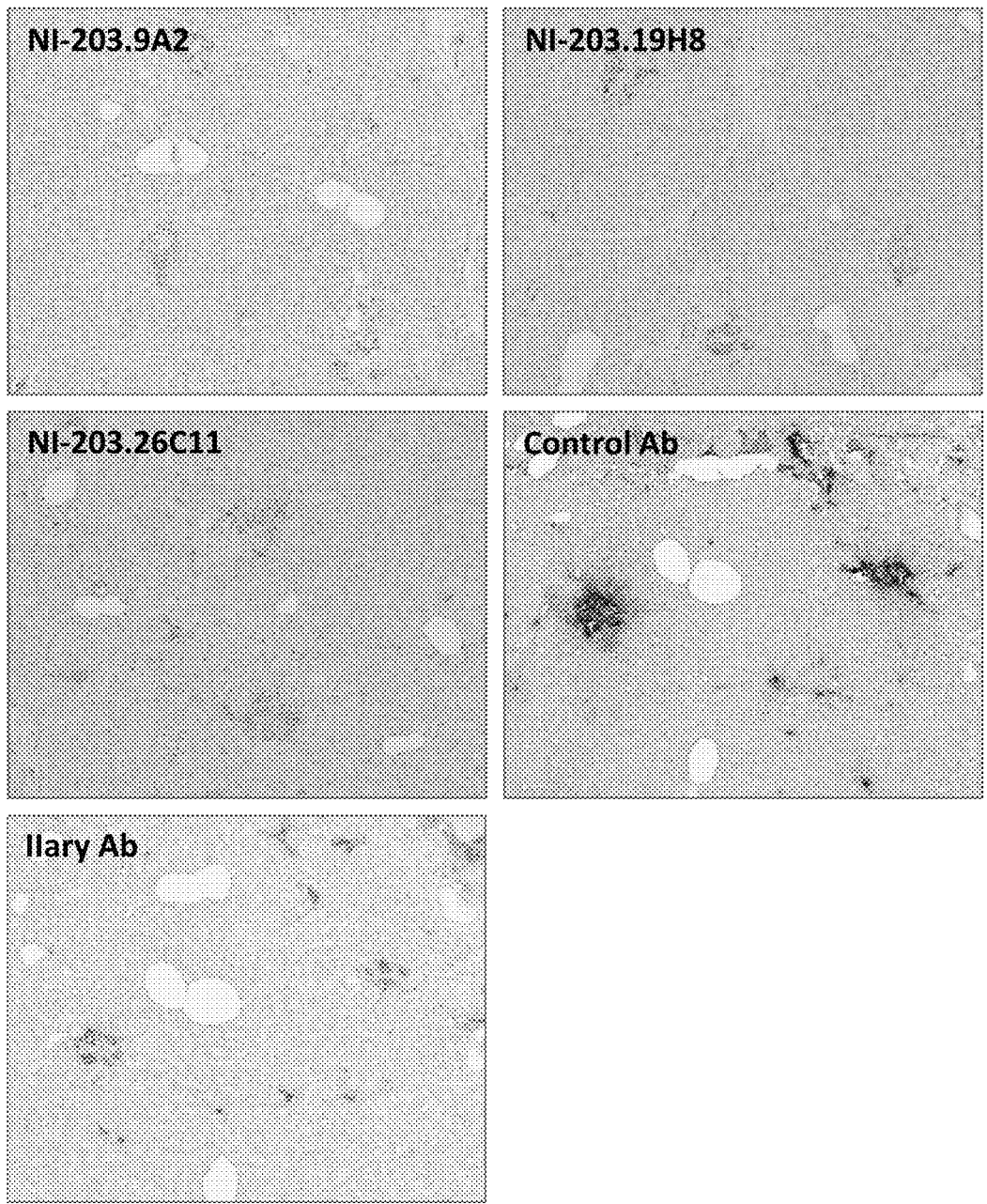
FIG. 8: NI-203.9A2, NI-203.19H8 and NI-203.26C11 antibodies do not recognize physiological IAPP on human control pancreas. NI-203.9A2, NI-203.19H8 and NI-203.26C11 antibodies (50 nM) show weak staining on human control islets when compared to the IAPP control antibody (1:100; control Ab). Secondary donkey anti-human antibody only (IIary Ab) was used as a control. Human pancreatic islets were stained with anti-insulin antibody (blue in original (i.o.), strong staining here) and counterstaining was performed to visualize cell nuclei (faint blue i.o., faint staining here).
Figure 9:
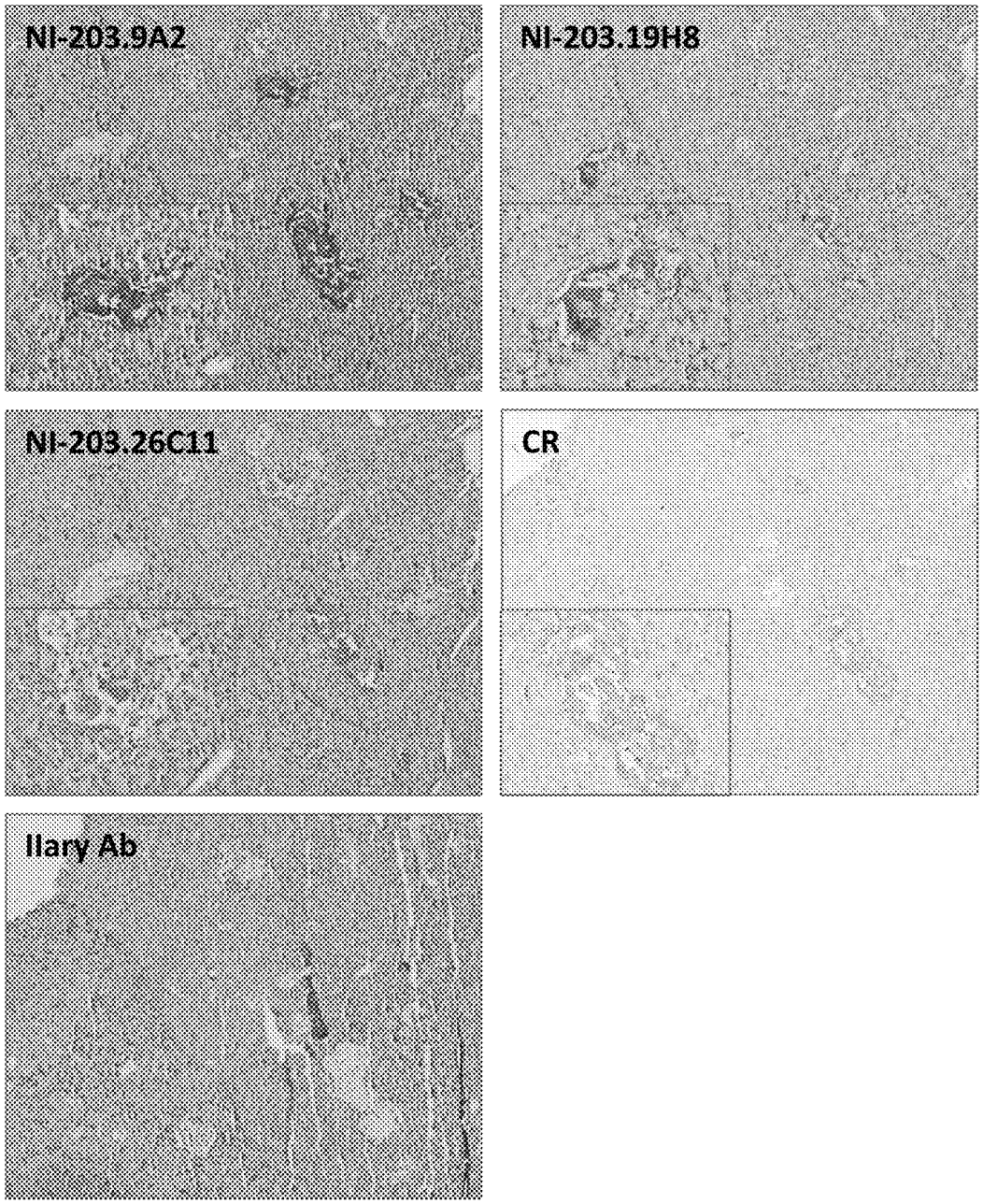
FIG. 9: NI-203.9A2, NI-203.19H8 and NI-203.26C11 antibodies recognize pathological IAPP fibrils on a diabetic cat pancreas. Detection of IAPP fibrils on pancreatic islets of a T2D cat with NI-203.9A2, NI-203.19H8 and NI-203.26C11 antibodies (50 nM, brown-CR). IAPP fibrils (amyloid) were stained with Congo red (CR). Secondary donkey anti-human antibody only (IIary Ab) was used as a control. Bottom left insets: high magnification images of individual cat pancreatic islets. Cat pancreatic islets were stained with anti-insulin antibody (blue in original (i.o.), strong staining here) and counterstaining was performed to visualize cell nuclei (faint blue i.o., faint staining here).
Figure 11:
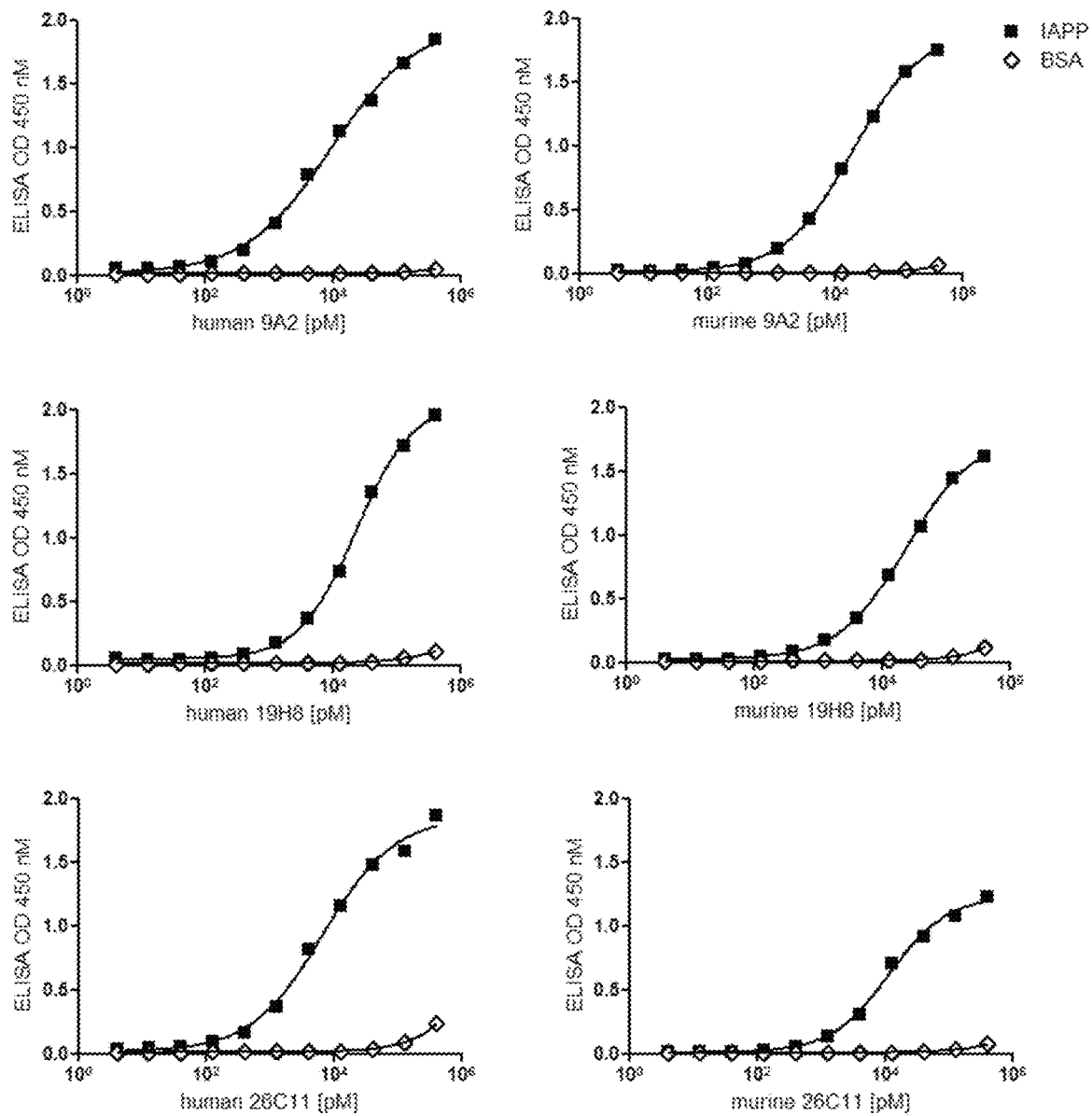
FIG. 11: Recombinant human and mouse chimeric antibody NI-203.9A2, NI-203.19H8 and NI-203.26C11 bind with equal affinity to human IAPP. (A) EC$_{50}$ determination of the recombinant human and mouse chimeric anti-IAPP antibodies for IAPP (□, 10 µg/ml) and BSA (◇, 10 µg/ml). Plates were incubated with the indicated concentrations of antibodies. Measurements were made in duplicate. Data are expressed as mean OD values at 450 nm. (B, C) EC$_{50}$ values of human and mouse chimeric antibodies.
Figure 12:
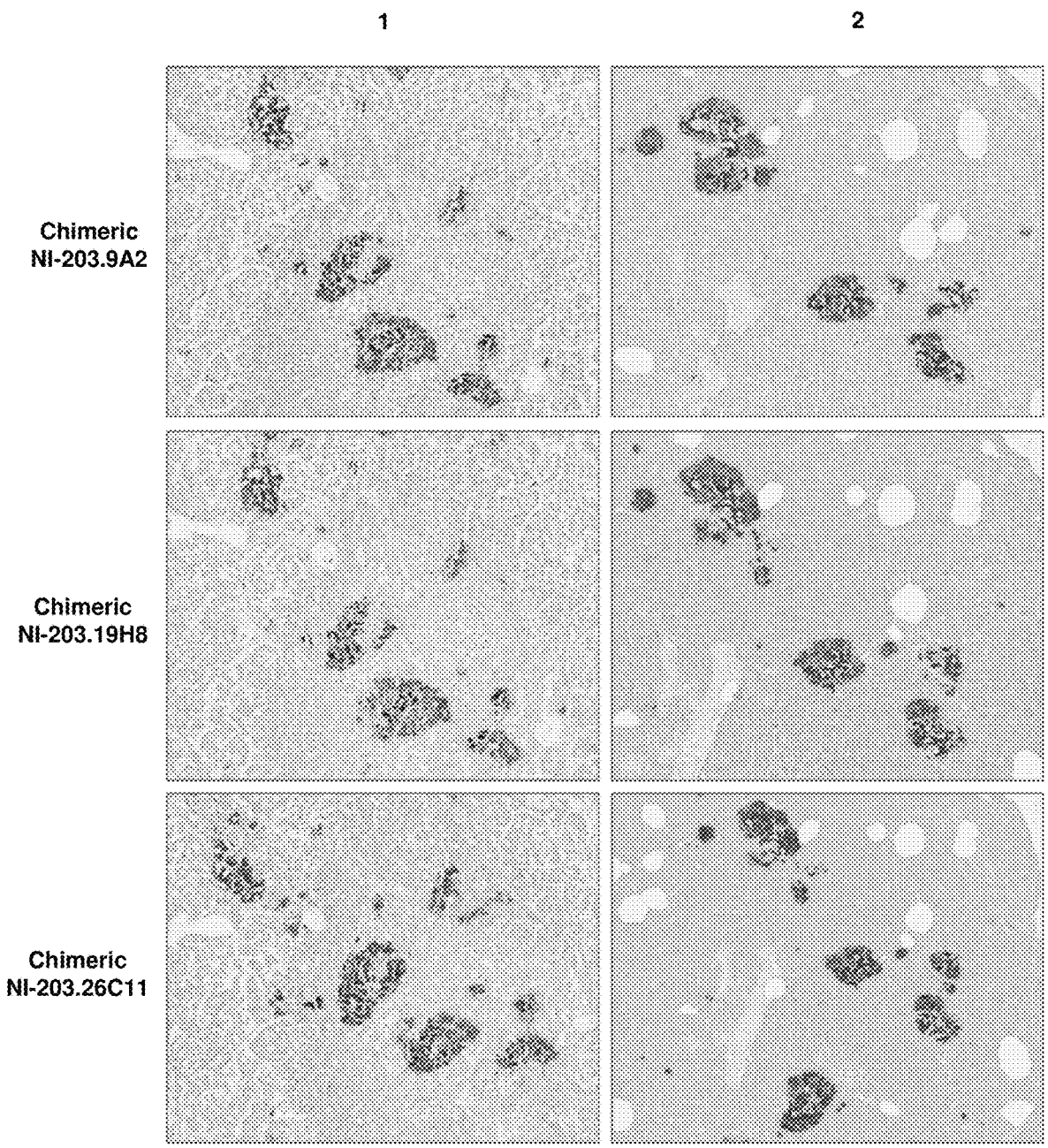
FIG. 12: Recombinant mouse chimeric antibody NI-203.9A2, NI-203.19H8 and NI-203.26C11 recognize pathological IAPP fibrils in the pancreas of patients diagnosed with diabetes mellitus type 2 (T2D). Detection of IAPP fibrils on pancreatic islets of two human T2D patients (1 and 2) with chimeric NI-203.9A2, NI-203.19H8 and NI-203.26C11 antibodies at 50 nM (brown i.o., strong dark to black staining here). Human pancreatic islets were stained with anti-insulin antibody (blue i.o., strong staining here) and counterstaining was performed to visualize cell nuclei (faint blue i.o., faint staining here).

Due to this measure, several antibodies could be isolated. Selected antibodies were further analyzed for class and light chain subclass determination. Selected relevant antibody messages from memory B cell cultures are then transcribed by RT-PCR, cloned and combined into expression vectors for recombinant production; see the appended Examples. Recombinant expression of the human antibodies in HEK293 or CHO cells and the subsequent characterization of their binding specificities towards human IAPP and/or proIAPP protein (FIGS. 3 and 4; Example 1), and their distinctive binding to pathologically aggregated forms thereof (FIG. 5; Example 2) confirmed that for the first time human antibodies have been cloned that are highly specific for IAPP and/or proIAPP protein and distinctively recognize the pathologically aggregated forms of IAPP and/or proIAPP protein, such as IAPP fibrils. A second round of experiments confirmed the above findings as shown in FIGS. 7-9 and in Example 4. Furthermore, mouse chimeric antibodies generated according to the present invention and comprising CDR domains of the human antibodies of the present invention have shown equal binding affinity to human IAPP as the human antibodies as shown in FIGS. 11 and 12 and in Example 6.

Thus, the present invention generally relates to an isolated naturally occurring human monoclonal anti-islet amyloid polypeptide (IAPP) antibody and binding fragments, derivatives and variants thereof. In one embodiment of the invention, the antibody is capable of binding human IAPP and/or proIAPP.

In one embodiment, the present invention is directed to an anti-IAPP and/or anti-proIAPP antibody, or antigen-binding fragment, variant or derivatives thereof, where the antibody specifically binds to the same epitope of IAPP as a reference antibody selected from the group consisting of NI-203.9A2, NI-203.19H8, NI-203.26C11, NI-203.8E3, NI-203.11B12, NI-203.205F8, NI-203.9B3, NI-203.19F2, and NI-203.15C7. Epitope mapping identified a sequence within the human IAPP including aa 19-SSNNFGA-25 (SEQ ID NO: 4) as the unique linear epitope recognized by antibody NI-203.19H8 of this invention, a sequence within the human IAPP including aa 2-CNTATCA-8 (SEQ ID NO: 5) as the unique linear epitope recognized by antibody NI-203.26C11 of this invention, and a sequence within the human IAPP including aa 10-QRLANFLVHS-19 (SEQ ID NO: 71) as the unique linear epitope recognized by antibody NI-203.15C7 of this invention (see FIGS. 5A and 5B and Example 3). Therefore, in one embodiment the antibody of the present invention is provided, wherein the antibody specifically binds an IAPP epitope which comprises the amino acid sequence SSNNFGA (SEQ ID NO: 4), CNTATCA (SEQ ID NO: 5) or QRLANFLVHS (SEQ ID NO: 71). As described in detail in Example 3 the epitopes of recombinant IAPP antibodies NI-203.9A2, NI-203.8E3, and NI-203.19F2 antibodies could not be identified so far, indicating that these antibodies probably bind nonlinear epitopes.

Furthermore, in one embodiment, the present invention is directed to an anti-IAPP and/or anti-proIAPP antibody, or antigen-binding fragment, variant or derivatives thereof, where the antibody specifically binds to the same epitope of proIAPP as a reference antibody selected from the group consisting of antibodies NI-203.1D10, NI-203.2A11, NI-203.10C4, NI-203.20H9, NI-203.26D2, NI-203.60H3 and NI-203.26C11.

Furthermore, without intending to be bound by initial experimental observations as demonstrated in the Example 4 and shown in FIG. 7, the human monoclonal NI-203.9A2, NI-203.19H8, NI-203.26C11 and NI-203.8E3 anti-IAPP antibodies of the present invention are preferably characterized in specifically binding to pathological IAPP aggregates (fibrils in this Example) and not substantially recognizing IAPP in the physiological form in the pancreas. The same is expected to apply to human monoclonal NI-203.19F2 and NI-203.15C7 anti-IAPP antibodies. Hence, the present invention provides a set of human anti-IAPP and/or anti-proIAPP antibodies with binding specificities, which are thus particularly useful for diagnostic and therapeutic purposes. Thus, in one embodiment the present invention provides antibodies, which are capable of specifically binding pathologically aggregated forms of IAPP and/or proIAPP (see FIG. 5 and FIGS. 7-9, and Examples 2 and 4). For further details and a summarizing overview in respect of binding specificities of the present invention see also FIGS. 7 and 8 and the description below.

In one embodiment, the antibody of the present invention exhibits the binding properties of the exemplary NI-203.9A2, NI-203.19H8, NI-203.26C11, NI-203.8E3, NI-203.19F2, and NI-203.15C7 antibodies as described in the Examples. In addition, or alternatively, the anti-IAPP and/or anti-proIAPP antibody of the present invention preferentially recognizes pathologically aggregated anti-IAPP and/or anti-proIAPP, such as IAPP fibrils rather than physiological IAPP and/or proIAPP monomers, in particular when analyzed according to Examples 2 to 4. In one embodiment thus, the antibody of the present invention does not substantially recognize physiological IAPP. The term "does not substantially recognize" when used in the present application to describe the binding affinity of an molecule of a group comprising an antibody, a fragment thereof or a binding molecule for a specific target molecule, antigen and/or conformation of the target molecule and/or antigen means that the molecule of the aforementioned group binds said molecule, antigen and/or conformation with a binding affinity which is at least 2-fold, 3-fold, 4-fold, 5-fold, 6-fold, 7-fold, 8-fold or 9-fold less than the dissociation constant (KD) of the molecule of the aforementioned group for binding another molecule, antigen and/or conformation. Preferably the term "does not substantially recognize" when used in the present application means that the molecule of the aforementioned group binds said molecule, antigen and/or conformation with a binding affinity which is at least or 10-fold, 20-fold, 50-fold, 100-fold, 1000-fold or 10000-fold less than the dissociation constant (KD) of said molecule of the aforementioned group for binding to another molecule, antigen and/or conformation. In addition, or alternatively, the anti-IAPP and/or anti-proIAPP antibody of the present invention binds to disease causing aggregated forms of human anti-IAPP and/or anti-proIAPP, in particular those described in Example 4. In this context, the binding specificities may be in the range as shown for the exemplary NI-203.9A2, NI-203.19H8, NI-203.26C11 and NI-203.8E3 antibodies in FIG. 4, respective FIG. 5, i.e. having half maximal effective concentrations (EC50) of about 1 pM to 500 nM, preferably an EC50 of about 10 pM to 100 nM, most preferably an EC50 of about 100 pM to 50 nM for human IAPP as shown for NI-203.19H8, or an EC50 of about 100 pM to 10 nM for human IAPP as shown for NI-203.9A2, NI-203.26C11 and NI-203.8E3. In this context, the experimental results as provided in Example 4 and shown FIG. 4, respective FIG. 5, also indicate that in addition or alternatively some of the anti-IAPP antibodies of the present invention do not substantially recognize proIAPP as shown for the exemplary antibodies NI-203.9A2, NI-203.19H8 and NI-203.8E3. In one embodiment thus, the antibody of the present invention does not substantially recognize proIAPP.

In addition, or alternatively, the anti-IAPP antibody of the present invention binds specifically besides to mature IAPP to the precursor form of IAPP, i.e. proIAPP as well, in particular as described in Example 1. In this context, the binding specificities may be in the range as shown for the exemplary NI-203.26C11 antibody in FIG. 3, respective FIG. 4, i.e. having half maximal effective concentrations (EC50) of about 1 pM to 500 nM, preferably an EC50 of about 10 pM to 400 nM, more preferably an EC50 of about 100 pM to 400 nM or an EC50 of about 100 pM to 300 nM, most preferably an EC50 of about 1 nM to 300 nM for aggregated pro-IAPP as shown for NI-203.26C11.

In addition, or alternatively, the anti-IAPP antibody of the present invention binds specifically to mature IAPP and does not or does not substantially bind to the precursor form of IAPP, i.e. proIAPP, in particular as described in Example 1. In this context, the binding specificities may be in the range as shown for the exemplary NI-203.9A2, NI-203.19H8 and NI-203.8E3 antibodies in FIG. 4, respective FIG. 5 and indicated above.

In one embodiment, the antibody of the present invention exhibits the binding properties of exemplary antibodies NI-203.1D10, NI-203.2A11, NI-203.10C4, NI-203.20H9, NI-203.26D2 and NI-203.60H3 preferably binding proIAPP over proIAPP. However, the proIAPP antibodies have been obtained by a screening for antibodies specifically binding to the N-terminal flanking region of proIAPP which is not present in IAPP, as there is some evidence for the role of N-terminal unprocessed proIAPP rather than the full-length proIAPP peptide in amyloid formation and cell death. Thereby, in one embodiment the anti-proIAPP antibody of the present invention, such as exemplary antibodies NI-203.1D10, NI-203.2A11, NI-203.10C4, NI-203.20H9, NI-203.26D2 and NI-203.60H3 does not bind substantially or does not bind IAPP.

Some purified antibodies bind to a wide array of biomolecules, e.g., proteins. As the skilled artisan will appreciate, the term specific is used herein to indicate that other biomolecules than IAPP and/or proIAPP proteins or fragments thereof do not significantly bind to the antigen-binding molecule, e.g., one of the antibodies of the present invention. Preferably, the level of binding to a biomolecule other than IAPP and/or proIAPP results in a binding affinity which is at most only 20% or less, 10% or less, only 5% or less, only 2% or less or only 1% or less (i.e. at least 5, 10, 20, 50 or 100 fold lower) of the affinity to IAPP and/or proIAPP, respectively; see e.g., Example 1 and FIG. 3. Furthermore, the anti-IAPP and/or anti-proIAPP antibodies of the present invention binding specifically to IAPP and/or proIAPP aggregates as validated by experiments showing that the antibodies of the present invention do not recognize pathological Aβ amyloid in Alzheimer's disease human brain and have only minimal cross-reactive binding qualities to several protein candidates with misfolding/aggregation propensities, as shown with the exemplary antibodies NI-203.9A2, NI-203.19H8 and NI-203.26C11 on paraffin-embedded brain sections of a patient diagnosed with Alzheimer's disease and by direct ELISA experiments; see Example 5 and FIG. 10. Therefore, in one embodiment the antibody of the present invention is provided, which does not substantially recognize amyloid-β peptide ($A\beta_{1-42}$).

In one embodiment the anti-IAPP and/or anti-proIAPP antibody of the present invention preferably binds preferentially to aggregated forms of IAPP and/or proIAPP, IAPP and/or proIAPP fibrils and/or oligomers; see experimental results by direct ELISA in Example 2 and in pancreas of patients diagnosed with T2D and on diabetic cat pancreases by immunohistochemical staining described in Example 4 and shown in FIGS. 7 and 9 respectively. In one embodiment the antibody of the present invention preferentially binds to aggregated forms of IAPP and/or proIAPP, wherein the aggregates comprise, essentially consist of or consist of fibrillar forms of and/or fibrillar oligomers of IAPP. In another embodiment the antibody of the present invention preferentially binds to aggregated forms of IAPP and/or proIAPP, wherein the aggregates comprise, essentially consist of or consist of non-fibrillar forms of and/or non-fibrillar oligomers of IAPP. In yet another embodiment the antibody of the present invention preferentially binds to aggregated forms of IAPP and/or proIAPP, wherein the aggregates comprise, essentially consist of or consist of either fibrillar and non-fibrillar forms of IAPP and/or proIAPP and/or fibrillar and non-fibrillar oligomers of IAPP and/or proIAPP. In still another embodiment the anti-IAPP and/or anti-proIAPP antibody of the present invention preferentially binds to both native IAPP and/or proIAPP and pathologically aggregated forms of IAPP and/or proIAPP; see experimental results as exemplified in Example 2 and Example 3 by direct ELISA.

As mentioned before, aggregates comprising IAPP and/or proIAPP can also be found associated with amyloid deposits in pancreatic islets of T2D patients. Therefore, in one embodiment the antibody of the present invention may be useful in treatment of the T2D.

The present invention is also drawn to an antibody, or antigen-binding fragment, variant or derivatives thereof, where the antibody comprises an antigen-binding domain identical to that of an antibody selected from the group consisting of NI-203.9A2, NI-203.19H8, NI-203.26C11, NI-203.8E3, NI-203.11B12, NI-203.205F8, NI-203.9B3, NI-203.19F2, NI-203.15C7, NI-203.1D10, NI-203.2A11, NI-203.10C4, NI-203.20H9, NI-203.26D2, and NI-203.60H3.

The present invention further exemplifies several such binding molecules, e.g., antibodies and binding fragments thereof, which may be characterized by comprising in their variable region, e.g., binding domain at least one complementarity determining region (CDR) of the $V_H$ and/or $V_L$ variable region comprising any one of the amino acid sequences depicted in FIG. 1 or in FIG. 2. The corresponding nucleotide sequences encoding the above-identified variable regions are set forth in Table II respective Table III below. Exemplary sets of CDRs of the above amino acid sequences of the $V_H$ and/or $V_L$ region are depicted in FIG. 1 and in FIG. 2. However, as discussed in the following the person skilled in the art is well aware of the fact that in addition or alternatively CDRs may be used, which differ in their amino acid sequence from those set forth in FIG. 1 respective in FIG. 2 by one, two, three or even more amino acids in case of CDR2 and CDR3. Therefore, in one embodiment the antibody of the present invention or an IAPP and/or proIAPP binding fragment thereof is provided comprising in its variable region at least one complementarity determining region (CDR) as depicted in FIG. 1 and/or one or more CDRs thereof comprising one or more amino acid substitutions.

In one embodiment, the antibody of the present invention is any one of the antibodies comprising an amino acid sequence of the $V_H$ and/or $V_L$ region as depicted in FIG. 1 or a $V_H$ and/or $V_L$ region thereof comprising one or more amino acid substitutions. Preferably, the antibody of the present invention is characterized by the preservation of the cognate pairing of the heavy and light chain as was present in the human B-cell.

Alternatively, the antibody of the present invention is an antibody or antigen-binding fragment, derivative or variant thereof, which competes for binding to IAPP and/or proIAPP with at least one of the antibodies having the $V_H$ and/or $V_L$ region as depicted in FIG. 1.

Experimental results provided in Example 4 suggest that some of the anti-IAPP and/or anti-proIAPP antibodies of the present invention preferentially bind to disease causing aggregated forms of human anti-IAPP and/or anti-proIAPP over the physiological forms of the proteins. In one embodiment thus, the antibody of the present invention preferentially recognizes IAPP and/or proIAPP aggregates over physiological IAPP and/or proIAPP. Furthermore, in one embodiment, the antibody of the present invention preferentially recognizes IAPP aggregates comprising IAPP oligomers and/or fibrils over physiological IAPP. In another embodiment, the antibody of the present invention preferentially recognizes IAPP aggregates comprising non-fibrillar IAPP and/or non-fibrillar IAPP oligomers over physiological IAPP.

As already indicated before, some of the antibodies of the present invention have been shown to be capable of binding both, IAPP and its precursor form proIAPP. Furthermore, some of the antibodies of the present invention have been isolated from human patients because of their capability to bind proIAPP. Therefore, in one embodiment the antibody of the present invention is capable of binding proIAPP.

Therefore, alternatively or in addition to the above, in one embodiment the antibody of the present invention or an IAPP and/or proIAPP binding fragment thereof is provided comprising in its variable region at least one complementarity determining region (CDR) as depicted in FIG. 2 and/or one or more CDRs thereof comprising one or more amino acid substitutions.

In one embodiment, the antibody of the present invention is any one of the antibodies comprising an amino acid sequence of the $V_H$ and/or $V_L$ region as depicted in FIG. 2 or a $V_H$ and/or $V_L$ region thereof comprising one or more amino acid substitutions. Preferably, the antibody of the present invention is characterized by the preservation of the cognate pairing of the heavy and light chain as was present in the human B-cell.

Alternatively, the antibody of the present invention is an antibody or antigen-binding fragment, derivative or variant thereof, which competes for binding to IAPP and/or proIAPP with at least one of the antibodies having the $V_H$ and/or $V_L$ region as depicted in FIG. 2.

The antibody of the present invention may be human, in particular for therapeutic applications. Alternatively, the antibody of the present invention is a rodent, rodentized or chimeric rodent-human antibody, preferably a murine, murinized or chimeric murine-human antibody or a rat, ratinized or chimeric rat-human antibody which are particularly useful for diagnostic methods and studies in animals. In one embodiment the antibody of the present invention is a chimeric rodent-human or a rodentized antibody.

Furthermore, in one embodiment, the chimeric antibody of the present invention exhibits the binding properties of the exemplary NI-203.9A2, NI-203.19H8 and NI-203.26C11 murine chimeric antibodies as described in the Examples. Further, the mouse chimeric antibodies of the present invention bind with a high affinity to human IAPP fibrils as described in Example 6. Preferably, the binding affinity of chimeric antibodies is similar to their human counterparts. In this context, the binding specificities may be in the range as shown for the exemplary NI-203.9A2, NI-203.19H8 and NI-203.26C11 murine chimeric antibodies with an $EC_{50}$ of 18.6 nM, 23.9 nM and 11.5 nM respectively as described in Example 6 and shown in FIG. 11 and Table C therein. No binding was observed on BSA.

In one embodiment the antibody of the present invention is provided by cultures of single or oligoclonal B-cells that are cultured and the supernatant of the culture, which contains antibodies produced by said B-cells, is screened for presence and affinity of anti-IAPP and/or proIAPP antibodies therein. The screening process comprises screening for binding to native monomeric, fibrillar or non-fibrillar aggregates like oligomers of hIAPP derived from a synthetic full-length hIAPP peptide of the amino acid sequence represented by SEQ ID NO: 1; and/or a separate and independent screening for binding to a synthetic peptide derived from human proIAPP (N-terminal fragment) of the amino acid sequence TPIESHQVEKRKCNTATCATQR represented by SEQ ID NO: 7.

In addition or alternatively the screening process for presence and affinity of anti-IAPP and/or proIAPP antibodies may comprise the steps of a sensitive tissue amyloid plaque immunoreactivity (TAPIR) assay such as described in international application WO2004/095031, the disclosure content of which is incorporated herein by reference, performed here in analogy for amyloid deposits on pancreatic islets. Furthermore or alternatively, screens on pancreas sections for binding to anti-IAPP and/or proIAPP such as described in analogy in international application WO2008/081008 for brain and spinal cord sections may be performed.

As mentioned above, due to its generation upon a human immune response the human monoclonal antibody of the present invention will recognize epitopes which are of particular pathological relevance and which might not be accessible or less immunogenic in case of immunization processes for the generation of, for example, mouse monoclonal antibodies and in vitro screening of phage display libraries, respectively. Accordingly, it is prudent to stipulate that the epitope of the human anti-IAPP and/or proIAPP antibody of the present invention is unique and no other antibody which is capable of binding to the epitope recognized by the human monoclonal antibody of the present invention exists; see also FIG. 5A and which show the unique epitope of antibody NI-203.19H8 respective antibody NI-203.26C11 of this invention. A further indication for the uniqueness of the antibodies of the present invention is the fact that, as indicated in Example 3, antibodies NI-203.9A2 and NI-203.8E3 of the present invention bind assumable conformational epitopes of IAPP aggregates, which as indicated above, are of particular pathological relevance and might be as well not obtainable by the usual processes for antibody generation, such as immunization or in vitro library screenings.

Therefore, in one embodiment the present invention also extends generally to anti-IAPP antibodies and IAPP binding molecules which compete with the human monoclonal antibody of the present invention for specific binding to IAPP. The present invention is more specifically directed to an antibody, or antigen-binding fragment, variant or derivatives thereof, where the antibody specifically binds to the same epitope of IAPP as a reference antibody selected from the group consisting of NI-203.9A2, NI-203.19H8, NI-203.26C11, NI-203.8E3, NI-203.19F2, and NI-203.15C7.

Furthermore, in one embodiment the present invention also extends generally to anti-IAPP and/or anti-proIAPP antibodies and IAPP and/or anti-proIAPP binding molecules which compete with the human monoclonal antibody of the present invention for specific binding to proIAPP. The present invention is therefore, more specifically also directed to an antibody, or antigen-binding fragment, variant or derivatives thereof, where the antibody specifically binds to the same epitope of proIAPP as a reference antibody selected from the group consisting of NI-203.1D10, NI-203.2A11, NI-203.10C4, NI-203.20H9, NI-203.26D2, NI-203.60H3 and NI-203.26C11.

In addition, or alternatively the present invention also extends generally to bispecific anti-IAPP and/or anti-proIAPP antibodies and IAPP and/or anti-proIAPP binding molecules which compete with the human monoclonal antibody of the present invention for specific binding to both IAPP and proIAPP. The present invention is therefore, more specifically also directed to an antibody, or antigen-binding fragment, variant or derivatives thereof, where the antibody specifically binds to the same epitope of IAPP and proIAPP as the exemplary antibody NI-203.26C11. In view of the above thus, in one embodiment the present invention also relates to an antibody or antigen-binding molecule which competes with an antibody of the present invention for specific binding to IAPP and/or proIAPP.

Competition between antibodies is determined by an assay in which the immunoglobulin under test inhibits specific binding of a reference antibody to a common antigen, such as IAPP and/or proIAPP. Numerous types of competitive binding assays are known, for example: solid phase direct or indirect radioimmunoassay (RIA), solid phase direct or indirect enzyme immunoassay (EIA), sandwich competition assay; see Stahli et al., Methods in Enzymology 9 (1983), 242-253; solid phase direct biotin-avidin EIA; see Kirkland et al., J. Immunol. 137 (1986), 3614-3619 and Cheung et al., Virology 176 (1990), 546-552; solid phase direct labeled assay, solid phase direct labeled sandwich assay; see Harlow and Lane, Antibodies, A Laboratory Manual, Cold Spring Harbor Press (1988); solid phase direct label RIA using $I^{125}$ label; see Morel et al., Molec. Immunol. 25 (1988), 7-15 and Moldenhauer et al., Scand. J. Immunol. 32 (1990), 77-82. Typically, such an assay involves the use of purified IAPP and/or proIAPP or aggregates, such as oligomers and/or fibrils thereof bound to a solid surface or cells bearing either of these, an unlabeled test immunoglobulin and a labeled reference immunoglobulin, i.e. the human monoclonal antibody of the present invention. Competitive inhibition is measured by determining the amount of label bound to the solid surface or cells in the presence of the test immunoglobulin. Usually the test immunoglobulin is present in excess. Preferably, the competitive binding assay is performed under conditions as described for the ELISA assay in the appended Examples. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% or 75%. Hence, the present invention is further drawn to an antibody, or antigen-binding fragment, variant or derivatives thereof, where the antibody competitively inhibits a reference antibody selected from the group consisting of NI-203.9A2, NI-203.19H8, NI-203.26C11, NI-203.8E3, NI-203.19F2, and NI-203.15C7 from binding to IAPP.

In addition, the present invention is further drawn to an antibody, or antigen-binding fragment, variant or derivatives thereof, where the antibody competitively inhibits a reference antibody selected from the group consisting of NI-203.1D10, NI-203.2A11, NI-203.10C4, NI-203.20H9, NI-203.26D2, NI-203.60H3 and NI-203.26C11 from binding to proIAPP.

Further in addition or alternatively the present invention is further drawn to a bispecific antibody, or antigen-binding fragment, variant or derivatives thereof, where the antibody competitively inhibits a reference antibody such as the exemplary antibody NI-203.26C11 from binding to either IAPP and proIAPP.

In another embodiment, the present invention provides an isolated polypeptide comprising, consisting essentially of, or consisting of an immunoglobulin heavy chain variable region ($V_H$), where at least one of $V_H$-CDRs of the heavy chain variable region or at least two of the $V_H$-CDRs of the heavy chain variable region are at least 80%, 85%, 90% or 95% identical to reference heavy chain $V_H$-CDR1, $V_H$-CDR2 or $V_H$-CDR3 amino acid sequences from the antibodies disclosed herein. Alternatively, the $V_H$-CDR1, $V_H$-CDR2 and $V_H$-CDR3 regions of the $V_H$ are at least 80%, 85%, 90% or 95% identical to reference heavy chain $V_H$-CDR1, $V_H$-CDR2 and $V_H$-CDR3 amino acid sequences from the antibodies disclosed herein. Thus, according to this embodiment a heavy chain variable region of the invention has $V_H$-CDR1, $V_H$-CDR2 and $V_H$-CDR3 polypeptide sequences related to the groups shown in FIG. 1 or in FIG. 2 respectively. While FIGS. 1 and 2 show $V_H$-CDRs defined by the Kabat system, other CDR definitions, e.g., $V_H$-CDRs defined by the Chothia system, are also included in the present invention, and can be easily identified by a person of ordinary skill in the art using the data presented in FIG. 1 and FIG. 2.

In another embodiment, the present invention provides an isolated polypeptide comprising, consisting essentially of, or consisting of an immunoglobulin heavy chain variable region ($V_H$) in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in FIG. 1 or in FIG. 2 respectively.

In another embodiment, the present invention provides an isolated polypeptide comprising, consisting essentially of, or consisting of an immunoglobulin heavy chain variable region ($V_H$) in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in FIG. 1 or in FIG. 2 respectively, except for one, two, three, four, five, or six amino acid substitutions in any one $V_H$-CDR. In certain embodiments the amino acid substitutions are conservative.

In another embodiment, the present invention provides an isolated polypeptide comprising, consisting essentially of, or consisting of an immunoglobulin light chain variable region ($V_L$), where at least one of the $V_L$-CDRs of the light chain variable region or at least two of the $V_L$-CDRs of the light chain variable region are at least 80%, 85%, 90% or 95% identical to reference light chain $V_L$-CDR1, $V_L$-CDR2 or $V_L$-CDR3 amino acid sequences from antibodies disclosed herein. Alternatively, the $V_L$-CDR1, $V_L$-CDR2 and $V_L$-CDR3 regions of the $V_L$ are at least 80%, 85%, 90% or 95% identical to reference light chain $V_L$-CDR1, $V_L$-CDR2 and $V_L$-CDR3 amino acid sequences from antibodies disclosed herein. Thus, according to this embodiment a light chain variable region of the invention has $V_L$-CDR1, $V_L$-CDR2 and $V_L$-CDR3 polypeptide sequences related to the polypeptides shown in FIG. 1 or in FIG. 2 respectively. While FIGS. 1 and 2 show $V_L$-CDRs defined by the Kabat system, other CDR definitions, e.g., $V_L$-CDRs defined by the Chothia system, are also included in the present invention.

In another embodiment, the present invention provides an isolated polypeptide comprising, consisting essentially of, or consisting of an immunoglobulin light chain variable region ($V_L$) in which the $V_L$-CDR1, $V_L$-CDR2 and $V_L$-CDR3 regions have polypeptide sequences which are identical to the $V_L$-CDR1, $V_L$-CDR2 and $V_L$-CDR3 groups shown in FIG. 1 or in FIG. 2 respectively.

In another embodiment, the present invention provides an isolated polypeptide comprising, consisting essentially of, or consisting of an immunoglobulin heavy chain variable region ($V_L$) in which the $V_L$-CDR1, $V_L$-CDR2 and $V_L$-CDR3 regions have polypeptide sequences which are identical to the $V_L$-CDR1, $V_L$-CDR2 and $V_L$-CDR3 groups shown in FIG. 1 or in FIG. 2 respectively, except for one, two, three, four, five, or six amino acid substitutions in any one $V_L$-CDR. In certain embodiments the amino acid substitutions are conservative.

An immunoglobulin or its encoding cDNA may be further modified. Thus, in a further embodiment the method of the present invention comprises any one of the step(s) of producing a chimeric antibody, murinized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988). When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO89/09622. Methods for the production of humanized antibodies are described in, e.g., European application EP-A1 0 239 400 and international application WO90/07861. Further sources of antibodies to be utilized in accordance with the present invention are so-called xenogeneic antibodies. The general principle for the production of xenogeneic antibodies such as human-like antibodies in mice is described in, e.g., international applications WO91/10741, WO94/02602, WO96/34096 and WO 96/33735. As discussed above, the antibody of the invention may exist in a variety of forms besides complete antibodies; including, for example, Fv, Fab and F(ab)$_2$, as well as in single chains; see e.g. international application WO88/09344. In one embodiment therefore, the antibody of the present invention is provided, which is selected from the group consisting of a single chain Fv fragment (scFv), an F(ab') fragment, an F(ab) fragment, and an F(ab')$_2$ fragment.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, *Molecular Cloning A Laboratory Manual*, Cold Spring Harbor Laboratory (1989) N.Y. and Ausubel, *Current Protocols in Molecular Biology*, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO00/30680 for corresponding technical details.

Additionally, the present invention encompasses peptides including those containing a binding molecule as described above, for example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides may easily be synthesized or produced by recombinant means to produce a binding agent useful according to the invention. Such methods are well known to those of ordinary skill in the art. Peptides can be synthesized for example, using automated peptide synthesizers which are commercially available. The peptides can also be produced by recombinant techniques by incorporating the DNA expressing the peptide into an expression vector and transforming cells with the expression vector to produce the peptide.

Hence, the present invention relates to any binding molecule, e.g., an antibody or binding fragment thereof which is oriented towards the human anti-IAPP and/or anti-proIAPP antibodies of the present invention and displays the mentioned properties, i.e. which specifically recognizes IAPP and/or proIAPP. Such antibodies and binding molecules can be tested for their binding specificity and affinity by ELISA and immunohistochemistry as described herein, see, e.g., the Examples. These characteristics of the antibodies and binding molecules can be tested by Western Blot as well. Preliminary results of subsequent experiments performed in accordance with the present invention revealed that the human anti-IAPP and/or anti-proIAPP antibody of the present invention, in particular antibodies NI-203.9A2, NI-203.19H8, NI-203.26C11 and NI-203.8E3 were able to differentially bind to IAPP-fibrils in ELISA tests. Furthermore, 203.9A2, NI-203.19H8 and NI-203.26C11 antibodies of the present invention have been shown to preferentially bind to pathologies in human, such as large amyloid deposits in pancreatic islets corresponding to pathological IAPP fibrils, as visualized by ThioS and Congo red staining (see FIG. 7A). The same properties are expected to apply to antibodies NI-203.19F2 and NI-203.15C7.

Human antibodies NI-203.9A2, NI-203.19H8 and NI-203.26C11 showed prominent pancreatic islet staining on amyloid-positive sections but were not showing any staining on pancreatic islets from a T2D patient lacking amyloid deposits and from a control patient not diagnosed with T2D (see Example 4 and FIG. 7). The antibodies of the present invention also gave positive results on diabetic cat pancreases showing islet amyloid deposits; see FIG. 9. This binding specificity towards pathological forms of IAPP and/or proIAPP in human and animal tissue emphasizes besides the biochemical experiments showed herein (see Examples 2 and FIG. 5) the usability of the antibodies of the present invention in treatment and diagnosis of diseases associated with occurrence of aggregated IAPP and/or proIAPP in the pancreas.

As an alternative to obtaining immunoglobulins directly from the culture of B cells or B memory cells, the cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells may be used; for efficient processing, however, mammalian cells are preferred. Typical mammalian cell lines useful for this purpose include, but are not limited to, CHO cells, HEK 293 cells, or NSO cells.

The production of the antibody or analog is then undertaken by culturing the modified recombinant host under culture conditions appropriate for the growth of the host cells and the expression of the coding sequences. The antibodies are then recovered by isolating them from the culture. The expression systems are preferably designed to include signal peptides so that the resulting antibodies are secreted into the medium; however, intracellular production is also possible.

In accordance with the above, the present invention also relates to a polynucleotide encoding the antibody or equivalent binding molecule of the present invention, in case of the antibody preferably at least a variable region of an immunoglobulin chain of the antibody described above. Typically, said variable region encoded by the polynucleotide comprises at least one complementarity determining region (CDR) of the $V_H$ and/or $V_L$ of the variable region of the said antibody.

The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat; see, e.g., Riechmann, et al, Nature 332 (1988), 323-327. Thus, the present invention also relates to antibodies wherein one or more of the mentioned CDRs comprise one or more, preferably not more than two amino acid substitutions. Preferably, the antibody of the invention comprises in one or both of its immunoglobulin chains two or all three CDRs of the variable regions as set forth in FIG. 1 or respectively in FIG. 2.

Binding molecules, e.g., antibodies, or antigen-binding fragments, variants, or derivatives thereof of the invention, as known by those of ordinary skill in the art, can comprise a constant region which mediates one or more effector functions. For example, binding of the C1 component of complement to an antibody constant region may activate the complement system. Activation of complement is important in the opsonization and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the present invention include an antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of IAPP and/or proIAPP aggregation and deposition, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted. In other embodiments, certain antibodies for use in the diagnostic and treatment methods described herein have a constant region, e.g., an IgG heavy chain constant region, which is altered to eliminate glycosylation, referred to elsewhere herein as aglycosylated or "agly" antibodies. Such "agly" antibodies may be prepared enzymatically as well as by engineering the consensus glycosylation site(s) in the constant region. While not being bound by theory, it is believed that "agly" antibodies may have an improved safety and stability profile in vivo. Methods of producing aglycosylated antibodies, having desired effector function are found for example in international application WO2005/018572, which is incorporated by reference in its entirety.

In certain antibodies, or antigen-binding fragments, variants, or derivatives thereof described herein, the Fc portion may be mutated to decrease effector function using techniques known in the art. For example, the deletion or inactivation (through point mutations or other means) of a constant region domain may reduce Fc receptor binding of the circulating modified antibody thereby increasing IAPP and/or proIAPP localization. In other cases it may be that constant region modifications consistent with the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as IAPP and/or proIAPP localization, biodistribution and serum half-life, may easily be measured and quantified using well know immunological techniques without undue experimentation.

In certain antibodies, or antigen-binding fragments, variants, or derivatives thereof described herein, the Fc portion may be mutated or exchanged for alternative protein sequences to increase the cellular uptake of antibodies by way of example by enhancing receptor-mediated endocytosis of antibodies via Fcγ receptors, LRP, or Thy1 receptors or by 'SuperAntibody Technology', which is said to enable antibodies to be shuttled into living cells without harming them (Expert Opin. Biol. Ther. (2005), 237-241). For example, the generation of fusion proteins of the antibody binding region and the cognate protein ligands of cell surface receptors or bi- or multi-specific antibodies with a specific sequences biding to IAPP and/or proIAPP as well as a cell surface receptor may be engineered using techniques known in the art.

In certain antibodies, or antigen-binding fragments, variants, or derivatives thereof described herein, the Fc portion may be mutated or exchanged for alternative protein sequences or the antibody may be chemically modified to increase its blood brain barrier penetration.

Modified forms of antibodies, or antigen-binding fragments, variants, or derivatives thereof of the invention can be made from whole precursor or parent antibodies using techniques known in the art. Exemplary techniques are discussed in more detail herein. Antibodies, or antigen-binding fragments, variants, or derivatives thereof of the invention can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

Antibodies, or antigen-binding fragments, variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In particular preferred embodiments, antibodies, or antigen-binding fragments, variants, or derivatives thereof of the invention will not elicit a deleterious immune response in the animal to be treated, e.g., in a human. In certain embodiments, binding molecules, e.g., antibodies, or antigen-binding fragments thereof of the invention are derived from a patient, e.g., a human patient, and are subsequently used in the same species from which they are derived, e.g., human, alleviating or minimizing the occurrence of deleterious immune responses.

De-immunization can also be used to decrease the immunogenicity of an antibody. As used herein, the term "de-immunization" includes alteration of an antibody to modify T cell epitopes; see, e.g., international applications WO98/52976 and WO00/34317. For example, $V_H$ and $V_L$ sequences from the starting antibody are analyzed and a human T cell epitope "map" from each V region showing the location of epitopes in relation to complementarity determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., IAPP and/or proIAPP-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: *Monoclonal Antibodies and T-Cell Hybridomas* Elsevier, N.Y., 563-681 (1981), said references incorporated by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. In certain embodiments, antibodies of the present invention are derived from human B cells which have been immortalized via transformation with Epstein-Barr virus, as described herein.

In the well-known hybridoma process (Kohler et al., Nature 256 (1975), 495) the relatively short-lived, or mortal, lymphocytes from a mammal, e.g., B cells derived from a human subject as described herein, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and re-growth with each individual strain comprising specific genes for the formation of a single antibody. They produce antibodies, which are homogeneous against a desired antigen and, in reference to their pure genetic parentage, are termed "monoclonal".

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (ELISA) as described herein. After hybridoma cells are identified that produce antibodies of the desired specificity, affinity and/or activity, the clones may be subcloned by limiting dilution procedures and grown by standard methods; see, e.g., Goding, *Monoclonal Antibodies: Principles and Practice*, Academic Press, pp. 59-103 (1986). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, lymphocytes can be selected by micromanipulation and the variable genes isolated. For example, peripheral blood mononuclear cells can be isolated from an immunized or naturally immune mammal, e.g., a human, and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibody fragments that recognize specific epitopes may be generated by known techniques. For example, Fab and F(ab')$_2$ fragments may be produced recombinantly or by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes.

Human antibodies, such as described herein, are particularly desirable for therapeutic use in human patients. Human antibodies of the present invention are isolated, e.g., from healthy human subjects who because of their overweight or obesity may be suspected to be at risk of developing a metabolic disorder, e.g., T2D, or a patient with the disorder but with an unusually stable disease course or unusually mild form of the disease. However, the healthy human subject suspected to be at risk to develop a metabolic disorder, e.g., T2D from whom antibodies, such as described herein may be isolated, may as well be selected on the basis of the presence of other risks known to enhance the chance of a person to develop a metabolic disorder, e.g., T2D. Said risks may be deduced from an examination of the person for risk factors associated with the development of a metabolic disorder, e.g., T2D, such as age 45 or older; overweight or obesity; close family relatives with diabetes; family background is African American, Alaska Native, American Indian, Asian American, Hispanic/Latino, Pacific Islander American, Asian or Arabic; history of gestational diabetes; giving birth to at least one baby weighing more than 4.5 kg; blood pressure of 140/90 or higher; cholesterol levels higher than normal, with, e.g., High-density lipoprotein (HDL) level below 40 mg/dL (equivalent to below 1 mmol/L), or triglyceride level above 200-499 mg/dL (equivalent to above 2.3-5.6 mmol/L); sedentary lifestyle; diagnosis of polycystic ovary syndrome (PCOS); diagnosis of prediabetes on previous testing—an A1C (also called HbA1c or glycohaemoglobin) level of 5.7 to 6.4 percent, impaired fasting glucose (IFG), or impaired glucose tolerance (IGT); diagnosis of other clinical conditions associated with insulin resistance, such as a acanthosis *nigricans*; history of cardiovascular disease.

In case obesity or overweight of a person is used as an indicator of a person to develop a metabolic disease, e.g., T2D, though it is prudent to expect that obese healthy and symptom-free subjects, respectively, more regularly will have developed protective anti-IAPP and/or anti-proIAPP antibodies than subjects who are diagnosed with a less risk, e.g., because they are not classified as obese but as overweight, or even as persons of a normal weight, subjects belonging to the latter two classifications may be used as well as source for obtaining a human antibody of the present invention as well.

A subject may be classified as having normal weight, being overweight or obese based on measurements of the subjects height and weight, and calculating the subjects Body Mass Index by the following calculation: BMI=weight [kg]/(height[m])$^2$. Based on the result, the subjects are classified as of normal weight (BMI 18.5-24.9 kg/m2), overweight (25.0-29.9 kg/m2), or obese (≥30 kg/m2) based on current World Health Organization criteria (World Health Organization (2000) "Obesity: preventing and managing the global epidemic. Report of a WHO consultation." World Health Organ Tech Rep Ser 894: 1.253). Alternatively or in addition, the waist circumference (WC) of a subject may be measured, and used based on sex-specific cut-offs to define WC as normal (<94 cm [<34.6 inches] in men and <80 cm [31.5 inches] in women), moderately increased (94-102 cm [34.6-40 inches] in men and 80-88 cm [31.5-35 inches] in women), or large (≥102 cm [≥40 inches] in men and >88 cm [≥35 inches] in women) as described in InterAct Consortium, Langenberg et al., PLoS Med. 2012 June; 9(6): e1001230, wherein a healthy subject with a high waist circumference (large WC) more regularly will have developed protective anti-IAPP and/or anti-proIAPP antibodies comparable with the classification as obese the highest risk to develop T2D and may be used preferably for the isolation of these antibodies, but persons with a moderately increased or normal WC may be used for the isolation of anti-IAPP and/or anti-proIAPP antibodies as well.

In one embodiment, an antibody of the invention comprises at least one heavy or light chain CDR of an antibody molecule. In another embodiment, an antibody of the invention comprises at least two CDRs from one or more antibody molecules. In another embodiment, an antibody of the invention comprises at least three CDRs from one or more antibody molecules. In another embodiment, an antibody of the invention comprises at least four CDRs from one or more antibody molecules. In another embodiment, an antibody of the invention comprises at least five CDRs from one or more antibody molecules. In another embodiment, an antibody of the invention comprises at least six CDRs from one or more antibody molecules. Exemplary antibody molecules comprising at least one CDR that can be included in the subject antibodies are described herein.

Antibodies of the present invention can be produced by any method known in the art for the synthesis of antibodies, in particular, by chemical synthesis or preferably by recombinant expression techniques as described herein.

In one embodiment, an antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody. Domain deleted constructs can be derived using a vector encoding an IgG$_1$ human constant domain, see, e.g., international applications WO02/060955 and WO02/096948A2. This vector is engineered to delete the CH2 domain and provide a synthetic vector expressing a domain deleted IgG$_1$ constant region.

In certain embodiments, antibodies, or antigen-binding fragments, variants, or derivatives thereof of the present invention are minibodies. Minibodies can be made using methods described in the art, see, e.g., U.S. Pat. No. 5,837,821 or international application WO94/09817.

In one embodiment, an antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the CH2 domain may be enough to substantially reduce Fc binding and thereby increase IAPP and/or proIAPP localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as an effector function or provide for more cytotoxin or carbohydrate attachment. In such embodiments it may be desirable to insert or replicate specific sequences derived from selected constant region domains.

The present invention also provides antibodies that comprise, consist essentially of, or consist of, variants (including derivatives) of antibody molecules (e.g., the V$_H$ regions and/or V$_L$ regions) described herein, which antibodies or fragments thereof immunospecifically bind to IAPP and/or proIAPP. Standard techniques known to those of skill in the art can be used to introduce mutations in the nucleotide sequence encoding an antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference V$_H$ region, V$_H$-CDR1, V$_H$-CDR2, V$_H$-CDR3, V$_L$ region, V$_L$-CDR1, V$_L$-CDR2, or V$_L$-CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind IAPP and/or proIAPP).

For example, it is possible to introduce mutations only in framework regions or only in CDR regions of an antibody molecule. Introduced mutations may be silent or neutral missense mutations, e.g., have no, or little, effect on an antibody's ability to bind antigen, indeed some such mutations do not alter the amino acid sequence whatsoever. These types of mutations may be useful to optimize codon usage, or improve a hybridoma's antibody production. Codon-optimized coding regions encoding antibodies of the present invention are disclosed elsewhere herein. Alternatively, non-neutral mis sense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity). Following mutagenesis, the encoded protein may routinely be expressed and the functional and/or biological activity of the encoded protein, (e.g., ability to immunospecifically bind at least one epitope of IAPP and/or proIAPP) can be determined using techniques described herein or by routinely modifying techniques known in the art.

III. Polynucleotides Encoding Antibodies

A polynucleotide encoding an antibody, or antigen-binding fragment, variant, or derivative thereof can be composed of any polyribonucleotide or polydeoxribonucleotide, which may be unmodified RNA or DNA or modified RNA or DNA. For example, a polynucleotide encoding an antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an antibody, or antigen-binding fragment, variant, or derivative thereof can be composed of triple-stranded regions comprising RNA or DNA or both RNA and DNA. A polynucleotide encoding an antibody, or antigen-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

As is well known, RNA may be isolated from the original B cells, hybridoma cells or from other transformed cells by standard techniques, such as a guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art. In one embodiment, cDNAs that encode the light and the heavy chains of the antibody may be made, either simultaneously or separately, using reverse transcriptase and DNA polymerase in accordance with well-known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as human constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

In this context, the present invention also relates to a polynucleotide encoding at least the binding domain or variable region of an immunoglobulin chain of the antibody of the present invention. In one embodiment, the present invention provides an isolated polynucleotide comprising, consisting essentially of, or consisting of a nucleic acid encoding an immunoglobulin heavy chain variable region ($V_H$), where at least one of the CDRs of the heavy chain variable region or at least two of the $V_H$-CDRs of the heavy chain variable region are at least 80%, 85%, 90% or 95% identical to reference heavy chain $V_H$-CDR1, $V_H$-CDR2, or $V_H$-CDR3 amino acid sequences from the antibodies disclosed herein. Alternatively, the $V_H$-CDR1, $V_H$-CDR2, or $V_H$-CDR3 regions of the $V_H$ are at least 80%, 85%, 90% or 95% identical to reference heavy chain $V_H$-CDR1, $V_H$-CDR2, and $V_H$-CDR3 amino acid sequences from the antibodies disclosed herein. Thus, according to this embodiment a heavy chain variable region of the invention has $V_H$-CDR1, $V_H$-CDR2, or $V_H$-CDR3 polypeptide sequences related to the polypeptide sequences shown in FIG. 1, or respectively has $V_H$-CDR1, $V_H$-CDR2, or $V_H$-CDR3 polypeptide sequences related to the polypeptide sequences shown in FIG. 2.

In another embodiment, the present invention provides an isolated polynucleotide comprising, consisting essentially of, or consisting of a nucleic acid encoding an immunoglobulin light chain variable region ($V_L$), where at least one of the $V_L$-CDRs of the light chain variable region or at least two of the $V_L$-CDRs of the light chain variable region are at least 80%, 85%, 90% or 95% identical to reference light chain $V_L$-CDR1, $V_L$-CDR2, or $V_L$-CDR3 amino acid sequences from the antibodies disclosed herein. Alternatively, the $V_L$-CDR1, $V_L$-CDR2, or $V_L$-CDR3 regions of the $V_L$ are at least 80%, 85%, 90% or 95% identical to reference light chain $V_L$-CDR1, $V_L$-CDR2, and $V_L$-CDR3 amino acid sequences from the antibodies disclosed herein. Thus, according to this embodiment a light chain variable region of the invention has $V_L$-CDR1, $V_L$-CDR2, or $V_L$-CDR3 polypeptide sequences related to the polypeptide sequences shown in FIG. 1, or respectively has $V_L$-CDR1, $V_L$-CDR2, or $V_L$-CDR3 polypeptide sequences related to the polypeptide sequences shown in FIG. 2.

In another embodiment, the present invention provides an isolated polynucleotide comprising, consisting essentially of, or consisting of a nucleic acid encoding an immunoglobulin heavy chain variable region ($V_H$) in which the $V_H$-CDR1, $V_H$-CDR2, and $V_H$-CDR3 regions have polypeptide sequences which are identical to the $V_H$-CDR1, $V_H$-CDR2, and $V_H$-CDR3 groups shown in FIG. 1 or respectively are identical to the $V_H$-CDR1, $V_H$-CDR2, and $V_H$-CDR3 groups as shown in FIG. 2.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2 (1981), 482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

In a preferred embodiment of the present invention, the polynucleotide comprises, consists essentially of, or consists of a nucleic acid having a polynucleotide sequence of the $V_H$ or $V_L$ region of an anti-IAPP and/or anti-proIAPP antibody as depicted in Table II or in Table III. In this respect, the person skilled in the art will readily appreciate that the polynucleotides encoding at least the variable domain of the light and/or heavy chain may encode the variable domain of both immunoglobulin chains or only one. In one embodiment therefore, the polynucleotide comprises, consists essentially of, or consists of a nucleic acid having a polynucleotide sequence of the $V_H$ and the $V_L$ region of an anti-IAPP and/or anti-proIAPP antibody as depicted in Table II or the sequence of the $V_H$ and the $V_L$ region of an anti-IAPP and/or anti-proIAPP antibody as depicted in Table III.

TABLE II

Nucleotide sequences of the $V_H$ and $V_L$ region of IAPP antibodies.

| Antibody | Nucleotide sequences of variable heavy (VH) and variable light (VL/VK) chains |
|---|---|
| NI-203.9A2-$V_H$ | GAGGTGCAGCTGGTGGAGTCTGGGGGAGGCTTGGTACAGCCTGGGGGG<br>TCCCTGAGGCTCTCCTGTGCAGCCTCTGGATTCACGTTTAGCACCTTT<br>GCCATGAGCTGGGTCCGCCAGGCTCCAGGGAAGGGGCTGGAGTGGGTC<br>TCAACTATTAGTGGTAGTGGTGATAATACATACTATGCAGACTCCCTG<br>AAGGGCCGGTTCACCATCTCCAGAGACAATTCCAAGAACACACTATAT<br>CTGCAAGTGAACAGCCTGAGACCCGAGGACACGGCCGTTTATTACTGT<br>GCGAAAAGTCCCTCGTCACTTCTGGCCACCTACTTTGACTACTGGGGC<br>CAGGGAACCCTGGTCACCGTCTCCTCG SEQ ID NO: 11 |
| NI-203.9A2-$V_K$ | GAAATTGTGTTGACACAGTCTCCTTCCACCCTGTCTGCATCTGTAGGA<br>GACAGAGTCACCATCACTTGCCGGGCCAGTGAGAGTATTAATAGCTGG<br>TTGGCCTGGTATCAGCAGAAACCAGGGAAAGGCCCTAAGCTCCTGATC<br>TATAAGGCGTCTAGTTTACAAAGTGGGGTCCCATCAAGGTTCAGCGGC<br>AGTGGATCTGGGACAGAATTCACTCTCACCATCAGCAGCCTGCAGCCT<br>GATGATTTTGCAACTTATTACTGCCAACAGCACAATAGTTATTGGACG<br>TTCGGCCAAGGGACCAAGGTGGAAATCAAA SEQ ID NO: 13 |
| NI-203.19H8-$V_H$ | GAGGTGCAGCTGGTGGAGTCTGGGGGAGGCGTGGTCCAGCCTGGGACG<br>TCCCTGAGACTCTCCTGTGCAGCGTCTGGGTTCACCTTCAGCAGTTAT<br>GGCATGCACTGGGTCCGCCAGGCTCCAGGCAAGGGCCTGGAGTGGGTG<br>GCAATTATATGGTATGATGGAAGTAAGGAATATTATGCAGACTCCCTG<br>AAGGGCCGAGTCACCATCTCCAGAGACAATTCCGAGAACACTCTCTAT<br>CTGCAACTGCACACCCTGAGAGTCGAGGACACGGCTGTGTATTTCTGT<br>GCGAGGACAATCGCATCGGCCACCGTGGACCACGGTATGGACGTCTGG<br>GGCCAAGGCACCCTGGTCACCGTCTCCTCG SEQ ID NO: 15 |
| NI-203.19H8-$V_K$ | GATGTTGTGATGACTCAGTCTCCTTCGTCCGTGTCTGCATCTGTAGGA<br>GACAGAGTCACCATCACTTGTCGGGCGAGTCACGATATTAGCACCTGG<br>TTAGCCTGGTATCAGCAGAGACCAGGGAAAGCCCCTAACCTCCTGATC<br>TTTGGAGCATCGAGGTTGCAAAGTGGGGTCTCACCAAGGTTCAGCGGC<br>AGTGGATCTGGGACAGATTTCACTCTCACCATCAGCAGCCTGCAGCCT<br>GAAGATTTTGCAACTTACTATTGTCAACAGACTAACAATTTCCCTCCC<br>ACCTTCGGCCAAGGGACACGACTGGAGATTAAA<br>SEQ ID NO: 17 |
| N1-203.26C11-$V_H$ | CAGGTGCAGCTGCAGGAGTCGGGCCCAGGATTGGTGAAGCCTTCTCAG<br>ACCCTGTCCCTCACCTGCACTGTCTCTGGTGGCTCCATCAGCAGTGGT<br>AATTACTACTGGACCTGGATCCGGCAGCCCGCCGGGAAGGGACTGGAG<br>TGGATTGGGCATATCTATTCCAGTGGGACCACCAATTACAACCCCTCC<br>CTCGAGAGTCGAGTCACCATTTCAGTAGACACGTCCAAGAACCAGTTC<br>TCCCTGAGCCTGAACTCTGTGACCGCCGCAGACACGGCCGTTTATTAC<br>TGTGCGAGACCACTGGCTACAGTTCCGGATGCTTTTAATATCTGGGGC<br>CAAGGGACAATGGTCACCGTCTCTTCG SEQ ID NO: 19 |
| NI-203.26C11-$V_K$ | GAAATTGTGATGACTCAGTCTCCAGACTCCCTGGCTGTGTCTCTGGGC<br>GAGAGGGCCACCATCAAGTGCAAGTCCAGCCAGAGTGTTTTATACAGC<br>AATAAGAACTTCTTAGCTTGGTACCAGCAGAAACCAGGACAGCCTCCT<br>AAATTACTCATTTACTGGGCATCTACTCGGGAATCCGGGGTCCCTGAC<br>CGATTCAGTGGCAGCGGGTCTGGGACAGATTTCACTCTCACCATCAGC<br>AGCCTGCAGGCTGAAGATGTGGCAGTTTATTACTGTCAGCAGTATTAT<br>AGTAATCCTAACACTTTTGGCCAGGGGACCAAGGTGGAGATCAAA<br>SEQ ID NO: 21 |

TABLE II-continued

Nucleotide sequences of the $V_H$ and $V_L$ region of IAPP antibodies.

| Antibody | Nucleotide sequences of variable heavy (VH) and variable light (VL/VK) chains |
|---|---|
| NI-203.8E3-$V_H$ | CAGGTGCAGCTGGTGCAGTCTGGGGCTGAAGTGAAGAAACCTGGGTCC<br>TCGGTGAAGGTCTCCTGCAAGGCTTCTGGAGGCACCTTCAGTAGTCAC<br>ACTATCAGCTGGGTGCGACAGGCCCCTGGGCAAGGGCTTGAGTGGATG<br>GGAGGGATCATCCCCATCTTTGGTACAGCAAACTACGCACAGAAGTTT<br>CAGGACAGAGTCACGGTTACCGCGGACAAATCCACGAATACAGCCTAC<br>ATGGAGTTGAGTAGCCTCAGACCTGAGGACACGGCCGTGTATTACTGT<br>GCGAAGGGGGAACTGGAACCACGAATCCTCTACTACTACGGTATGGAC<br>GTCTGGGGCCGAGGGACCACGGTCACCGTCTCCTCG<br>SEQ ID NO: 23 |
| NI-203.8E3-$V_K$ | GATGTTGTGATGACTCAGTCTCCACTCTCCCTGCCCGTCACCCTTGGA<br>CAGCCGGCCTCCATCTCCTGCAGGTCTAGTCAAAGCCTCGTATACAGT<br>GATGGAAACACCTACTTGAATTGGTTTCACCAGAGGCCAGGCCAATCT<br>CCAAGGCGGCTAATTTATAAGGTTTCTAATCGTGACTCTGGGGTCCCA<br>GACAGATTCAGCGGCAGTGGGTCAGGCACTGATTTCACACTGAAAATC<br>AGCAGGGTGGAGGCTGAGGATGTTGGGGTTTATTACTGCATGCAAGGT<br>TCAAATTGGCCAGGGACGTTCGGCCAAGGGACCAAGGTGGAAATCAAA<br>SEQ ID NO: 25 |
| NI-203.11B12-$V_H$ | CAGGTGCAGCTGGTGCAATCTGGGGCTGAGGTGAAGAAGCCTGGGGCC<br>TCAATGAAGGTTTCCTGCAAGGCATCTGGATACACCTTCACCAACTAC<br>TATTTACACTGGGTGCGACAGGCCCCTGGACAAGGACTTGAGTGGATG<br>GGAATAATCAACCCTAGTGCTGGTAGCACAAGCTACGCACAGAAGTTC<br>CAGGGCAGAGTCACCATGACCAGGGACACGTCCACGAGCACAGTCTAC<br>ATGGAACTGAGCAGCCTGAAATCTGAAGACACGGCCGTCTATTACTGT<br>GCGAGAGATTCCGCTGGGATACAGATATGGTTCAGGGATGCTTTTGAT<br>ATCTGGGGCCAAGGGACAATGGTCACCGTCTCTTCG<br>SEQ ID NO: 27 |
| NI-203.11B12-$V_H$ | CAGCCTGTGCTGACTCAGCCACCCTCTGCCTCTGCTTCCCTGGGATCC<br>TCGGTCAAGCTCACCTGCACTCTGAACAGTGGGCACAGTAGCTACACC<br>ATCGCATGGCATCAGCAGCAGCCAGGGAAGGCCCCTCGGTACTTGATG<br>AAGGTTGAACATAATGGAAACTACAACAAGGGGAGCGGACTTCCTGAT<br>CGCTTCTCAGGCTCCAGCTCTGGGGCTGACCGCTACCTCGCCATCTCC<br>AACCTCCAGTCTGAGGATGAGGCTGATTATTACTGTGAGACCTGGGAC<br>ACTAGCACTAGGGTCTTCGGCGGAGGGACCAAGCTGACCGTCCTA<br>SEQ ID NO: 29 |
| NI-203.205F8-$V_H$ | CAGGTGCAGCTGCAGGAGTCGGGCCCCGGACTGGTGAAGCCTTCGGAG<br>ACCCTGTCCCTCACCTGCACTGTCTCTGGTGACTCCGTCAGCAGTGGT<br>AGTTACTACTGGAGCTGGATCCGGCAGCCCCCAGGGAAGGGACTGGAG<br>TGGATTGGGTATATCTATTACAGTGGGAGCACCAACTACAACCCCTCC<br>CTCAAGAGTCGAGTCACCATATCAGTAGACACGTCCAAGAACCAGTTC<br>TCCCTGAAGCTGAGCTCTGTGACCGCTGCGGACACGGCCGTATATTCC<br>TGTGCGAGAGTCCCCTATGGTTACGGATATAGGGGCTACGATGGGGCT<br>TGGTACTTTGACTACTGGGGCCAGGGAACCCTGGTCACCGTCTCCTCG<br>SEQ ID NO: 31 |
| NI-203.205F8-$V_K$ | GAAATTGTGTTGACACAGTCTCCAGCCACCCTGTCTTTGTCTCCAGGG<br>GAAAGAGCCACCCTCTCCTGCAGGGCCAGTCAGAGTGTTAGCAGCTAC<br>TTAGCCTGGTACCAACAGAAACCTGGCCAGGCTCCCAGGCTCCTCATC<br>TATGATGCATCCAACAGGGCCACTGGCATCCCAGCCAGGTTCAGTGGC<br>AGTGGGTCTGGGACAGACTTCACTCTCACCATCAGCAGCCTAGAGCCT<br>GAAGATTTTGCAGTTTATTACTGTCAGCAGCGTAGCAACCGGTTCACT<br>TTCGGCCCTGGGACCAAAGTGGATATCAAA SEQ ID NO:33 |
| NI-203.9B3-$V_H$ | GAGGTGCAGCTGGTGGAGTCTGGGGGAGGCGTGGTCCAGCCTGGGGGG<br>TCCCTGAGACTCTCCTGTGCAGCGTCAGGATTCACCTTCAGTAGCTAT<br>GGCATGCACTGGGTCCGCCAGGCTCCAGGCAAGGGGCTGGAGTGGGTG<br>GCAGTTATCTGGTATGATGGAACTAAGAAGTACTATGCAGACTCCGTG<br>AAGGGCCGATTCACCACCTCCAGAGACAATTCCAAGAATACGCTGTCT<br>CTGCAAATGAACAGCCTGAGAGCCGAGGACTCGGCTGTGTATTACTGT<br>GCGAGAGGCTTTAGCAGCAGCTGGGAGTTTGGGTTCTGGGGCCAGGGA<br>ACCCTGGTCACCGTCTCCTCG SEQ ID NO: 35 |
| NI-203.9B3-$V_L$ | CAGTCTGCCCTGACTCAGCCTCCCTCCGCGTCGGGTCTCCTGGACAG<br>TCAGTCACCATCTCCTGCACTGGAACCAGCGGTTACATTTATGGTTAT<br>AACTATGTCTCCTGGTACCAACAGCACCCCGGCAAAGCCCCCAAAGTC<br>ATGATTTATGAGGTCACTAAGCGGCCCTCAGGGGTCCCTGATCGCTTC<br>TCTGGCTCCAAGTCTGGCAACACGGCCTCCCTGACCGTCTCTGGGCTC<br>CAGGCTGAGGATGAGGCTGTTTATTACTGCGCCTCATATGCAGGCAGC<br>AACAATGTAGTATTCGGCGGAGGGACCAAGCTGACCGTCCTA<br>SEQ ID NO: 37 |

TABLE II-continued

Nucleotide sequences of the V_H and V_L region of IAPP antibodies.

| Antibody | Nucleotide sequences of variable heavy (VH) and variable light (VL/VK) chains |
|---|---|
| NI-203.19F2-V_H | GAGGTGCAGCTGGTGCAGTCTGGGGCTGAGGTGAAGAAGCCTGGGTCC<br>TCGGTGAAGGTCTCCTGCAAGGCTTCTGGAGGCAACTTCTTGAGCTAT<br>TCCATCAGTTGGGTGCGACAGGCCCCTGGACAAGGGCTTGAGTGGATG<br>GGAGGGATCATCCCGATCTTTGGTACACCAAACTACGCACAGAAGTTC<br>CAAGGAAGAGTCACAATTACGGCGGACAAATCGACGAGGACAGCCTAC<br>ATGGAGCTGAGCAGCCTGAGATTTGATGACACGGCCGTCTATTATTGT<br>GCGGATGCGACAAGACCGGGTACAGCAGCCTCTGGTTTCTATTACTAC<br>GGTATGGACGTCTGGGGCCAAGGGACCACGGTCACCGTCTCCTCG<br>SEQ ID NO: 63 |
| NI-203.19F2-V_K | GAAATTGTGATGACACAGTCTCCAGACACCCTGTCTGTGTCTCCAGGT<br>GAAAGAGCCACCCTCTCCTGCAGGGCCAGTCAGAGTGTTAACAACAAC<br>TTAGCCTGGTTCCAGCAGAAACCTGGCCAGGCTCCCAGGCTCCTCATC<br>TATGGTGCATCCACCAGGGCCACTGGTATTCCAGCCAGATTCAGTGGC<br>AGTGGGTCTGGGACAGAGTTCACTCTCACCATCAGCAGCCTACAGTCT<br>GAAGATTTTGCAGTTTATTTCTGTCAGCAGAGTCACAATTGGCCCACT<br>TTCGGCCCTGGGACCAAAGTGGATATCAAA SEQ ID NO: 65 |
| NI-203.15C7-V_H | GAGGTGCAGCTGGTGGAGACTGGGGGAGGCGTGGTCCAGCCTGGGATG<br>TCCCTGAAACTCTCCTGTGCAGCCTCTGGATTCACCTTCAGTACCTAT<br>ACTATGCACTGGGTCCGCCAGGCTCCAGGCAAGGGGCTGGAGTGGGTG<br>TCATTTATATCATATGATGGAAGGGATAAATACTACGCAGATTCCGTG<br>AAGGGCCGATTCACCATCTCCAGAGACAATTCCAAGAACATGTTGTAT<br>CTGCAAATGAACAGCCTGAGAGATGAGGACATGGCTGTGTATTACTGT<br>GCGACTCTGCAAGTATGGCAACTCTACGATTACTACGGAATGGACGTC<br>TGGGGCCAAGGGACCACGGTCACCGTCTCCTCG SEQ ID NO: 67 |
| NI-203.15C7-V_L | CAGTCTGTGTTGACGCAGCCGCCCTCAGTGTCTGCGGCCCCAGGACAG<br>AAGGTCACCATCTCCTGCTCTGGAAGCAGCTCCAACATTGGGAATAAT<br>TATGTATCTTGGTATCAGCAACTCCCAGGAACAGCCCCCAAACTCCTC<br>ATTTATAACAGTGATAAGCGACCCTCAGGGATTCCTGACCGATTCTCT<br>GCCTCCAAGTCTGGCACGTCAGCCACCCTGGGCATCACCGGGCTCCAG<br>ACTGGGGACGAGGCCGATTATTACTGCGCAACATGGGATACCAGACTG<br>AGTGCTGGGGTATTCGGCGGAGGGACCAAGCTGACCGTCCTT<br>SEQ ID NO: 69 |

TABLE III

Nucleotide sequences of the VH and VL region of proIAPP antibodies.

| Antibody | Nucleotide sequences of variable heavy (VH) and variable light (VL/VK) chains |
|---|---|
| NI-203.1D10-V_H | GAGGTGCAGCTGGTGCAGTCTGGCGCAGAAGTGAAGAAGCCCGGGGAGT<br>CTCTCAGAATCTCCTGTAAGGCTTCTGGATACAGCTTCACCAACTCTTG<br>GATCGCCTGGGTGCGCCAGATGCCCGGGAAAGGCCTGGACTACGTGGGT<br>ATCATCTATCCTGGTGACTCTGATACCAAGTATGGCCCGTCCTTCCAAG<br>GCCACGTCACTATCTCAGCCGACAACTTCGCCAACACCGCCTACCTGCA<br>GTGGAGCAGCCTGAAGGCCTCCGACACCGCCATCTATTATTGTGCGAGA<br>CGGGCAGCAGCGGCTATTAACTGGTTCGACTCCTGGGGCCAGGGAACCC<br>TGGTCACCGTCTCCTCG SEQ ID NO: 39 |
| NI-203.1D10-V_K | GACATCCAGTTGACCCAGTCTCCACTCTCCCTGTCCGTCACCCCTGGAG<br>AGCCGGCCTCCATCTCCTGCAGGTCTAGCCAGAGCCTCCTGCATCCTAA<br>TGGAAACGACTATTTGGATTGGTACGTGCAGAAGCCAGGGCAGTCTCCA<br>CAGATCGTGATCTACATGGGTTCTAATCGGGCCGCCGGGGTCCCTGACA<br>GGTTCAGTGGCAGTGGATCAGGCACAGATTTTACACTGAAAATCAGCAG<br>AGTGGAGGCTGAGGATGTTGGGACTTATTACTGCCTGCAAGCTCTACGC<br>GGGTACACTTTTGGCCAGGGGACCAAGGTGGAAATCAAA<br>SEQ ID NO: 41 |
| NI-203.2A11-V_H | CAGGTGCAGCTGGTGGAGTCTGGGGGAGGCGTGGTCCAGCCTGGGGGGT<br>CCCTGAGACTCTCCTGTGTAGCGTCTGGATTCACCTTCAGCAGTTATGG<br>CATGCACTGGGTCCGCCAGGCTCCAGGCAAGGGGCTGGAGTGGGTGGCA<br>TTTGTACGGTATGATGGAAGTAATAAGTACTATGCAGACTCCGTGAAGG<br>GCCGATTCACCATCTCCAGAGACAATTCCAAGAACTCGCTGTCTCTTCA<br>AATGAACAGTCTGAGAACTGAAGACACGGCTGTATATTACTGCGCGAAA<br>GAACAGGAGGACCACAAGGAAGCTTTTGACTACTGGGGCCAGGGAACCC<br>TGGTCACCGTCTCCTCG SEQ ID NO: 43 |
| NI-203.2A11-V_K | GAAATTGTGATGACACAGTCTCCAGCCACCCTGTCTGTGTCTCCAGGGG<br>AAAGAGCCACCCTCTCCTGCAGGGCCAGTCAGAGAGTTACCACCATAGC |

TABLE III-continued

Nucleotide sequences of the VH and VL region of proIAPP antibodies.

| Antibody | Nucleotide sequences of variable heavy (VH) and variable light (VL/VK) chains |
|---|---|
| | CTGGTACCAGCAGAAACCTGGCCAGGCTCCCAGGCTCCTCATCTATGGT<br>GCATCCAGCAGGGCCACTGATATTCCCGCCAGGTTCAGTGGCAGTGGGT<br>CTGGGACAGACTTCACTCTCACCATCAGCAGTCTGCAGTCTGAAGACTT<br>TGCAGTTTATTACTGTCAGCAGTATAACCAGTGGCCCCTCACTTTCGGC<br>GGAGGGACCAAGCTGGAGATCAAA SEQ ID NO: 45 |
| NI-203.10C4-$V_H$ | GAGGTGCAGCTGGTGGAGTCTGGGGCTGAAGTGAGGAAGCCTGGGGCCT<br>CAGTGAGGGTCTCCTGCCAGACATCTGGATACAGCGTCACCGACTACTA<br>TCTACACTGGGTGCGACAGGCCCCTGGACAGGGCCTTGAGTGGATGGGA<br>GTGATGAACCCGAGCAATGGAAACGTGGGCTACCCACAGAAGTTTCAGG<br>GCCGAGTCACCATGACCGCAGACACGTCCACGGGCACAGTGTACATGGT<br>GTTGACCGGCCTTACGGCTGGGGACACGGCCGTCTACTACTGTGCCAGA<br>GGCGGGTCCACGCCGGGTCAGGAAGTAAGGAGTCCCCACGTCCTTGACC<br>TCTGGGGCCAGGGAACCCTGGTCACCGTCTCCTCG SEQ ID NO: 47 |
| NI-203.10C4-$V_K$ | GATGTTGTGATGACTCAGTCTCCCCTCTCTCTGTCCGTCACCCCTGGAC<br>AGCCGGCCTCCATCTCCTGCAGGTCTGATGAGAGCCTCCTGCATAGTGA<br>TGGAAGGACCTATTTGTATTGGTATCTACAGAAGCCCGGCCAGCCTCCT<br>CAGCTCCTGATCTATGAAGTTTCCAACCGGTTCTCGGGAGTGCCAAATA<br>GGTTCAGTGGCAGCGGGTCAGGGACAGATTTCACACTGAAAATCAGCCG<br>GGTGGAGGCTGAGGATGTTGGCGTTTATTACTGCATGCAGGGTGTACAC<br>TTTCCTCAGACGTTCGGCCAGGGGACCAAGCTGGAGATCAAA<br>SEQ ID NO: 49 |
| NI-203.20H9-$V_H$ | CAGGTGCAGCTGGTGCAATCTGGGTCTGAGTTGAAGAAGCCTGGGGCCT<br>CAGTGAAGGTCTCCTGCAAGGCTTCTGGATACATCTTCAGTAAACATGG<br>TATCAACTGGGTGCGACAGGCCCCTGGACAAGGCCTTGAGTGGATAGGA<br>TGGATCAACACCAATACGGGGAACCCAACATATGCCCAGGACTTCACAG<br>GACGATTTGTCTTCTCCTTGGACACCTCTGTCAGCACGGCATATCTGGA<br>GATCAGCAGCCTAAAGGCTGAGGACACTGCCGTGTATTACTGTGCGAGA<br>GAATCAGAGCCGATTTTTGGAGTTATCTATTACATGGACGTCTGGGGCA<br>AAGGGACCACGGTCACCGTCTCCTCG SEQ ID NO: 51 |
| NI-203.20H9-$V_K$ | GACATCCAGATGACCCAGTCTCCATCCTCCCTGTCTGCATCTGTAGGAG<br>ACAGCGTCACCATCACTTGCCGGGCAAGCCAGAGCATAAGCACTAATTT<br>AAATTGGTATCAGAAGAAACCAGGACAAGCCCCTACGGTCTTGATCTAT<br>GCTGCGTCCAGTTTGCAAGGTGGGGTCCCATCAAGGTTCAGGGGCCGGG<br>GATCTGGGACATATTTCACTCTCACCATCAGCGGTCTTCAACCTGAAGA<br>TTTTGCAACTTATTACTGTCAACACAATTACAATGATTGTGGACGTTC<br>GGCCAAGGGACCAAGGTGGAAATCAAA SEQ ID NO: 53 |
| NI-203.26D2-$V_H$ | CAGGTGCAGCTGGTGGAGTCTGGGGGAGGCGTGGTCCAGCCTGGGGGGT<br>CCCTGAGACTCTCCTGTGCAGCGTCTGGGTTCACGTTCAGAACCTGTGG<br>CATGCACTGGGTCCGCCAGGCTCCAGGCAAGGGGCTGGAATGGGTGGCA<br>TTTGTTCGGTCTGATGGAACTACTAGATATTACGCAGACTCCCTGATGG<br>GCCGCTTCACCATCTCCAGAGACAATTCCAAGAACTCGCTGTATCTTCA<br>AATGAACAGTCTGAGACCTGAGGACACGGCTCTTTATTACTGTGCGAGG<br>GAAAAGGAGGATCACAGGGAAGCTTTTGACTACTGGGGCCAGGGAACCC<br>TGGTCACCGTCTCCTCG SEQ ID NO: 55 |
| NI-203.26D2-$V_K$ | GAAATTGTGATGACACAGTCTCCAGCCACCCTGTCTGTGTCTCCAGGGG<br>AAAGAGCCACCCTCTCCTGCAGGGCCAGTCAGCGTGTTAGCACTGTAGC<br>CTGGTACCAGCAGAAACCTGGCCAGGCTCCCAGGCTCCTCATCTATGAT<br>GCATCCACCAGGGCCACTGATATTCCCGCCAGGTTCAGTGGCAGTGGGT<br>CTGGGACAGACTTCACTCTCACCATCAGCACTCTGCAATCTGAAGACTC<br>TGCAGTTTATTACTGTCAGCAGTATAATAGGTGGCCCCTCACTTTCGGC<br>GGAGGGACCAAGGTGGAGATCAAA SEQ ID NO: 57 |
| NI-203.60H3-$V_H$ | GAGGTGCAGCTGGTGGAGTCTGGGGGAGGATTGGCACGCCCTGGAGGCT<br>CCCTGAGACTCTCCTGTGCAGTCGCTGGATTCACTTTCAGTGGTTATGA<br>AATGAATTGGGTCCGCCAGGCACCAGGGAAGGGGCTGGAGTGGATTTCA<br>TATATTAGCGGTCCTGGGGATGTGATATACTACGCAGACTCTGTGAAGG<br>GCCGATTCACCATCTCCAGAGACAACGCCAAGAACTCACTGTTTCTACA<br>GATGAACAGCCTGAGAGCCGAGGACACGGCTGTTTATTATTGTACGAGA<br>GTCCCCCCTGACATCAGCTATGGATTTGATTACTGGGGCCAGGGCACCC<br>TGGTCACCGTCTCCTCG SEQ ID NO: 59 |
| NI-203.60H3-$V_K$ | GACATCCAGATGACCCAGTCTCCATCTTCCCTGTCTGCATCTGTACGAG<br>ACAGCGTCACCATCACTTGCCGGGCAAGTCAGAGCATTAGCACCTATTT<br>AAATTGGTATCAGCAGAAACCAGGGAAAGCCCCTAACCTCCTGATCCAT<br>GATACAGACATTTTGCAAAGTGGGGTCCCATCAAGGTTCAGTGGCACTG<br>GATCTGGGACAGATTTCACTCTCACCATCAGCGGTCTGCAACCTGAAGA<br>TTTTGCAACTTACTACTGTCAACAGAGTTACAGTACCCCTCCTACTTTT<br>GGCCAGGGGACCAAGCTGGAGATCAAA SEQ ID NO: 61 |

The present invention also includes fragments of the polynucleotides of the invention, as described elsewhere. Additionally polynucleotides which encode fusion polynucleotides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides, e.g., as described in Kutmeier et al., BioTechniques 17 (1994), 242, which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody, or antigen-binding fragment, variant, or derivative thereof may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably polyA+ RNA, isolated from, any tissue or cells expressing the IAPP and/or proIAPP-specific antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody Amplified nucleic acids generated by PCR may then be cloned into replicable cloning vectors using any method well known in the art.

Once the nucleotide sequence and corresponding amino acid sequence of the antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning, A Laboratory Manual*, 2d Ed., Cold Spring Harbor Laboratory, Cold Spring Harbor, N.Y. (1990) and Ausubel et al., eds., *Current Protocols in Molecular Biology*, John Wiley & Sons, NY (1998), which are both incorporated by reference herein in their entireties), to generate antibodies having a different amino acid sequence, for example to create amino acid substitutions, deletions, and/or insertions.

IV. Expression of Antibody Polypeptides

Following manipulation of the isolated genetic material to provide antibodies, or antigen-binding fragments, variants, or derivatives thereof of the invention, the polynucleotides encoding the antibodies are typically inserted in an expression vector for introduction into host cells that may be used to produce the desired quantity of antibody. Recombinant expression of an antibody, or fragment, derivative or analog thereof, e.g., a heavy or light chain of an antibody which binds to a target molecule is described herein. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art.

Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operable linked to a promoter. Such vectors may include the nucleotide sequence encoding the constant region of the antibody molecule (see, e.g., international applications WO 86/05807 and WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells. For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) as discussed above. In one embodiment, this is accomplished using a proprietary expression vector of Biogen IDEC, Inc., referred to as NEOSPLA, and disclosed in U.S. Pat. No. 6,159,730. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/

His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the antibodies, or antigen-binding fragments, variants, or derivatives thereof of the invention may be expressed using polycistronic constructs such as those disclosed in US patent application publication no. 2003-0157641 A1 and incorporated herein in its entirety. In these expression systems, multiple gene products of interest such as heavy and light chains of antibodies may be produced from a single polycistronic construct. These systems advantageously use an internal ribosome entry site (IRES) to provide relatively high levels of antibodies. Compatible IRES sequences are disclosed in U.S. Pat. No. 6,193,980 which is also incorporated herein. Those skilled in the art will appreciate that such expression systems may be used to effectively produce the full range of antibodies disclosed in the instant application. Therefore, in one embodiment the present invention provides a vector comprising the polynucleotide encoding at least the binding domain or variable region of an immunoglobulin chain of the antibody, optionally in combination with a polynucleotide that encodes the variable region of the other immunoglobulin chain of said binding molecule.

More generally, once the vector or DNA sequence encoding a monomeric subunit of the antibody has been prepared, the expression vector may be introduced into an appropriate host cell. Introduction of the plasmid into the host cell can be accomplished by various techniques well known to those of skill in the art. These include, but are not limited to, transfection including lipotransfection using, e.g., Fugene® or lipofectamine, protoplast fusion, calcium phosphate precipitation, cell fusion with enveloped DNA, microinjection, and infection with intact virus. Typically, plasmid introduction into the host is via standard calcium phosphate co-precipitation method. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells comprising a polynucleotide encoding an antibody of the invention, or a heavy or light chain thereof, or at least the binding domain or variable region of an immunoglobulin thereof, which preferably are operable linked to a heterologous promoter. In addition or alternatively the invention also includes host cells comprising a vector, as defined hereinabove, comprising a polynucleotide encoding at least the binding domain or variable region of an immunoglobulin chain of the antibody, optionally in combination with a polynucleotide that encodes the variable region of the other immunoglobulin chain of said binding molecule. In preferred embodiments for the expression of double-chained antibodies, a single vector or vectors encoding both the heavy and light chains may be co-expressed in the host cell for expression of the entire immunoglobulin molecule, as detailed below.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain; see Proudfoot, Nature 322 (1986), 52; Kohler, Proc. Natl. Acad. Sci. USA 77 (1980), 2197. The coding sequences for the heavy and light chains may comprise cDNA or genomic DNA.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, NSO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese Hamster Ovary (CHO) cells, in conjunction with a vector such as the major intermediate early gene promoter element from human cytomegalovirus is an effective expression system for antibodies; see, e.g., Foecking et al., Gene 45 (1986), 101; Cockett et al., Bio/Technology 8 (1990), 2.

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAH (human lymphocyte) and 293 (human kidney). CHO and 293 cells are particularly preferred. Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., Cell 11 (1977), 223), hypoxanthine-guanine phosphoribosyltransferase (Szybalska & Szybalski, Proc. Natl. Acad. Sci. USA 48 (1992), 202), and adenine phosphoribosyltransferase (Lowy et al., Cell 22 (1980), 817) genes can be employed in tk-, hgprt- or aprt-cells, respectively. Also, anti-metabolite resistance can be used as the basis of selection for the following genes: dhfr, which confers resistance to methotrexate (Wigler et al., Natl. Acad. Sci. USA 77 (1980), 357; O'Hare et al., Proc. Natl. Acad. Sci. USA 78 (1981), 1527); gpt, which confers resistance to mycophenolic acid (Mulligan & Berg, Proc. Natl. Acad. Sci. USA 78 (1981), 2072); neo, which confers resistance to the aminoglycoside G-418 Goldspiel et al., Clinical Pharmacy 12 (1993), 488-505; Wu and Wu, Biotherapy 3 (1991), 87-95; Tolstoshev, Ann. Rev. Pharmacol. Toxicol. 32 (1993), 573-596; Mulligan, Science 260 (1993), 926-932; and Morgan and Anderson, Ann. Rev. Biochem. 62 (1993), 191-217; TIB TECH 11 (1993), 155-215; and hygro, which confers resistance to hygromycin (Santerre et al., Gene 30 (1984), 147. Methods commonly known in the art of recombinant DNA technology which can be used are described in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds), *Current Protocols in Human Genetics*, John Wiley & Sons, N Y (1994); Colberre-Garapin et al., J. Mol. Biol. 150:1 (1981), which are incorporated by reference herein in their entireties.

The expression levels of an antibody molecule can be increased by vector amplification, for a review, see Bebbington and Hentschel, *The use of vectors based on gene amplification for the expression of cloned genes in mammalian cells in DNA cloning*, Academic Press, New York, Vol. 3. (1987). When a marker in the vector system expressing antibody is amplifiable, increase in the level of inhibitor present in culture of host cell will increase the number of copies of the marker gene. Since the amplified region is associated with the antibody gene, production of the antibody will also increase; see Crouse et al., Mol. Cell. Biol. 3 (1983), 257. In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-) affinity chromatography, e.g., after preferential biosynthesis of a synthetic hinge region polypeptide or prior to or subsequent to the HIC chromatography step described herein.

Genes encoding antibodies, or antigen-binding fragments, variants or derivatives thereof of the invention can also be expressed in non-mammalian cells such as bacteria or insect or yeast or plant cells. Bacteria which readily take up nucleic acids include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies; see, e.g., international application WO02/096948.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2 (1983), 1791), in which the antibody coding sequence may be ligated individually into the vector in frame with the lacZ coding region so that a fusion protein is produced; pIN vectors (Inouye & Inouye, Nucleic Acids Res. 13 (1985), 3101-3109; Van Heeke & Schuster, J. Biol. Chem. 24 (1989), 5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*. For expression in *Saccharomyces*, the plasmid YRp7, for example, (Stinchcomb et al., Nature 282 (1979), 39; Kingsman et al., Gene 7 (1979), 141; Tschemper et al., Gene 10 (1980), 157) is commonly used. This plasmid already contains the TRP1 gene which provides a selection marker for a mutant strain of yeast lacking the ability to grow in tryptophan, for example ATCC No. 44076 or PEP4-1 (Jones, Genetics 85 (1977), 12). The presence of the trpl lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, the whole antibodies, their dimers, individual light and heavy chains, or other immunoglobulin forms of the present invention, can be purified according to standard procedures of the art, including for example, by chromatography (e.g., ion exchange, affinity, particularly by affinity for the specific antigen after Protein A, and sizing column chromatography), centrifugation, differential solubility, e g ammonium sulfate precipitation, or by any other standard technique for the purification of proteins; see, e.g., Scopes, "Protein Purification", Springer Verlag, N.Y. (1982). Alternatively, a preferred method for increasing the affinity of antibodies of the invention is disclosed in US patent publication 2002-0123057 A1. In one embodiment therefore, the present invention also provides a method for preparing an anti-IAPP or an anti-proIAPP antibody or immunoglobulin chain(s) thereof, said method comprising:
(a) culturing the host cell as defined hereinabove, which cell comprised a polynucleotide or a vector as defined hereinbefore; and
(b) isolating said antibody or immunoglobulin chain(s) thereof from the culture.

Furthermore, in one embodiment the present invention also relates to an antibody or immunoglobulin chain(s) thereof encoded by a polynucleotide as defined hereinabove or obtainable by said method for preparing an anti-IAPP or an anti-proIAPP antibody or immunoglobulin chain(s) thereof.

V. Fusion Proteins and Conjugates

In certain embodiments, the antibody polypeptide comprises an amino acid sequence or one or more moieties not normally associated with an antibody. Exemplary modifications are described in more detail below. For example, a single-chain Fv antibody fragment of the invention may comprise a flexible linker sequence, or may be modified to add a functional moiety (e.g., PEG, a drug, a toxin, or a label such as a fluorescent, radioactive, enzyme, nuclear magnetic, heavy metal and the like)

An antibody polypeptide of the invention may comprise, consist essentially of, or consist of a fusion protein. Fusion proteins are chimeric molecules which comprise, for example, an immunoglobulin IAPP and/or proIAPP-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

As discussed in more detail elsewhere herein, antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, antibodies may be recombinantly fused or conjugated to molecules useful as labels in detection assays and effector molecules such as heterologous polypeptides, drugs, radionuclides, or toxins; see, e.g., international applications WO92/08495; WO91/14438; WO89/12624; U.S. Pat. No. 5,314,995; and European patent application EP 0 396 387.

Antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. Antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification may be present in the same or varying degrees at several sites in a given antibody. Also, a given antibody may contain many types of modifications. Antibodies may be branched, for example, as a result of ubiquitination, and they may be cyclic, with or without branching. Cyclic, branched, and branched cyclic antibodies may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., Meth. Enzymol. 182 (1990), 626-646; Rattan et al., Ann. NY Acad. Sci. 663 (1992), 48-62).

The present invention also provides for fusion proteins comprising an antibody, or antigen-binding fragment, variant, or derivative thereof, and a heterologous polypeptide. In one embodiment, a fusion protein of the invention comprises, consists essentially of, or consists of, a polypeptide having the amino acid sequence of any one or more of the $V_H$ regions of an antibody of the invention or the amino acid sequence of any one or more of the $V_L$ regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the $V_H$-CDRs of an antibody, or fragments, variants, or derivatives thereof, or the amino acid sequence of any one, two, three of the $V_L$-CDRs of an antibody, or fragments, variants, or derivatives thereof, and a heterologous polypeptide sequence. In one embodiment, the fusion protein comprises a polypeptide having the amino acid sequence of a $V_H$-CDR3 of an antibody of the present invention, or fragment, derivative, or variant thereof, and a heterologous polypeptide sequence, which fusion protein specifically binds to IAPP and/or proIAPP. In another embodiment, a fusion protein comprises a polypeptide having the amino acid sequence of at least one $V_H$ region of an antibody of the invention and the amino acid sequence of at least one $V_L$ region of an antibody of the invention or fragments, derivatives or variants thereof, and a heterologous polypeptide sequence. Preferably, the $V_H$ and $V_L$ regions of the fusion protein correspond to a single source antibody (or scFv or Fab fragment) which specifically binds IAPP and/or proIAPP. In yet another embodiment, a fusion protein for use in the diagnostic and treatment methods disclosed herein comprises a polypeptide having the amino acid sequence of any one, two, three or more of the $V_H$ CDRs of an antibody and the amino acid sequence of any one, two, three or more of the $V_L$ CDRs of an antibody, or fragments or variants thereof, and a heterologous polypeptide sequence. Preferably, two, three, four, five, six, or more of the $V_H$-CDR(s) or $V_L$-CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., Proc. Natl. Acad. Sci. USA 84 (1987), 2936-2940; CD4 (Capon et al., Nature 337 (1989), 525-531; Traunecker et al., Nature 339 (1989), 68-70; Zettmeissl et al., DNA Cell Biol. USA 9 (1990), 347-353; and Byrn et al., Nature 344 (1990), 667-670); L-selectin (homing receptor) (Watson et al., J. Cell. Biol. 110 (1990), 2221-2229; and Watson et al., Nature 349 (1991), 164-167); CD44 (Aruffo et al., Cell 61 (1990), 1303-1313); CD28 and B7 (Linsley et al., J. Exp. Med. 173 (1991), 721-730); CTLA-4 (Lisley et al., J. Exp. Med. 174 (1991), 561-569); CD22 (Stamenkovic et al., Cell 66 (1991), 1133-1144); TNF receptor (Ashkenazi et al., Proc. Natl. Acad. Sci. USA 88 (1991), 10535-10539; Lesslauer et al., Eur. J. Immunol. 27 (1991), 2883-2886; and Peppel et al., J. Exp. Med. 174 (1991), 1483-1489 (1991); and IgE receptor a (Ridgway and Gorman, J. Cell. Biol. 115 (1991), Abstract No. 1448).

As discussed elsewhere herein, antibodies, or antigen-binding fragments, variants, or derivatives thereof of the invention may be fused to heterologous polypeptides to increase the in vivo half-life of the polypeptides or for use in immunoassays using methods known in the art. For example, in one embodiment, PEG can be conjugated to the antibodies of the invention to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512.

Moreover, antibodies, or antigen-binding fragments, variants, or derivatives thereof of the invention can be fused to marker sequences, such as a peptide to facilitate their purification or detection. In preferred embodiments, the marker amino acid sequence is a hexa-histidine peptide (HIS), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86 (1989), 821-824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37 (1984), 767), GST, c-mycand the "flag" tag; see, e.g., Bill Brizzard, BioTechniques 44 (2008) 693-695 for a review of epitope tagging techniques, and Table 1 on page 694 therein listing the most common epitope tags usable in the present invention, the subject matter of which is hereby expressly incorporated by reference.

Fusion proteins can be prepared using methods that are well known in the art; see for example U.S. Pat. Nos. 5,116,964 and 5,225,538. The precise site at which the fusion is made may be selected empirically to optimize the secretion or binding characteristics of the fusion protein. DNA encoding the fusion protein is then transfected into a host cell for expression, which is performed as described hereinbefore.

Antibodies of the present invention may be used in non-conjugated form or may be conjugated to at least one of a variety of molecules, e.g., to improve the therapeutic properties of the molecule, to facilitate target detection, or for imaging or therapy of the patient. Antibodies, or antigen-binding fragments, variants, or derivatives thereof of the invention can be labeled or conjugated either before or after purification, when purification is performed. In particular, antibodies, or antigen-binding fragments, variants, or derivatives thereof of the invention may be conjugated to therapeutic agents, prodrugs, peptides, proteins, enzymes, viruses, lipids, biological response modifiers, pharmaceutical agents, or PEG.

Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

Those skilled in the art will appreciate that conjugates may also be assembled using a variety of techniques depending on the selected agent to be conjugated. For example, conjugates with biotin are prepared, e.g., by reacting an IAPP and/or proIAPP binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, preferably fluorescein-isothiocyanate. Conjugates of the antibodies, or antigen-binding fragments, variants or derivatives thereof of the invention are prepared in an analogous manner.

The present invention further encompasses antibodies, or antigen-binding fragments, variants, or derivatives thereof of the invention conjugated to a diagnostic or therapeutic agent. The antibodies can be used diagnostically to, for example, demonstrate presence of a metabolic disease, e.g., T2D to indicate the risk of getting a metabolic disease, to monitor the development or progression of a metabolic disease, i.e. a disease showing the occurrence of, or related to aggregated IAPP and/or proIAPP as part of a clinical testing procedure to, e.g., determine the efficacy of a given treatment and/or prevention regimen. In one embodiment thus, the present invention relates to an antibody, which is detectably labeled. Furthermore, in one embodiment, the present invention relates to an antibody, which is attached to a drug. Detection can be facilitated by coupling the antibody, or antigen-binding fragment, variant, or derivative thereof to a detectable substance. The detectable substances or label may be in general an enzyme; a heavy metal, preferably gold; a dye, preferably a fluorescent or luminescent dye; or a radioactive label. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions; see, e.g., U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$ or $^{99}Tc$. Therefore, in one embodiment the present invention provides an detectably labeled antibody, wherein the detectable label is selected from the group consisting of an enzyme, a radioisotope, a fluorophore and a heavy metal An antibody, or antigen-binding fragment, variant, or derivative thereof also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, Meth. Enzymol. 73 (1981), 482-523; Maggio, E. (ed.), *Enzyme Immunoassay*, CRC Press, Boca Raton, Fla., (1980); Ishikawa, E. et al., (eds.), *Enzyme Immunoassay*, Kgaku Shoin, Tokyo (1981). The enzyme, which is bound to the antibody, will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibody, or antigen-binding fragment, variant, or derivative thereof, it is possible to detect the antibody through the use of a radioimmunoassay (RIA) (see, for example, Weintraub, B., *Principles of Radioimmunoassays, Seventh Training Course on Radioligand Assay Techniques*, The Endocrine Society, (March, 1986)), which is incorporated by reference herein). The radioactive isotope can be detected by means including, but not limited to, a gamma counter, a scintillation counter, or autoradiography.

An antibody, or antigen-binding fragment, variant, or derivative thereof can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody, or antigen-binding fragment, variant, or derivative thereof are well known, see, e.g., Anion et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. (1985); Hellstrom et al., "Antibodies For Drug Delivery", in *Controlled Drug Delivery* (2nd Ed.), Robinson et al. (eds.), Marcel Dekker, Inc., pp. 623-53 (1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press pp. 303-16 (1985), and Thorpe et al., "The Preparation And Cytotoxic Properties Of Antibody-Toxin Conjugates", Immunol. Rev. 62 (1982), 119-158.

As mentioned, in certain embodiments, a moiety that enhances the stability or efficacy of a binding molecule, e.g., a binding polypeptide, e.g., an antibody or immunospecific fragment thereof can be conjugated. For example, in one embodiment, PEG can be conjugated to the binding molecules of the invention to increase their half-life in vivo. Leong et al., Cytokine 16 (2001), 106; Adv. in Drug Deliv. Rev. 54 (2002), 531; or Weir et al., Biochem. Soc. Transactions 30 (2002), 512.

VI. Compositions and Methods of Use

The present invention relates to compositions comprising the aforementioned IAPP and/or proIAPP binding molecule, e.g., antibody or antigen-binding fragment thereof of the present invention or derivative or variant thereof, or the polynucleotide, vector or cell of the invention as defined hereinbefore. In one embodiment, the composition of the present invention is a pharmaceutical composition and further comprises a pharmaceutically acceptable carrier. Furthermore, the pharmaceutical composition of the present invention may comprise further agents such as interleukins or interferons depending on the intended use of the pharmaceutical composition. For use in the treatment of a metabolic disease showing the occurrence of, or related to aggregated IAPP and/or proIAPP, e.g., of T2D, the additional agent may be selected from the group consisting of small organic molecules, anti-IAPP and/or anti-proIAPP antibodies, and combinations thereof. Hence, in a particular preferred embodiment the present invention relates to the use of the IAPP and/or proIAPP binding molecule, e.g., antibody or antigen-binding fragment thereof of the present invention or of a binding molecule having substantially the same binding specificities of any one thereof, the polynucleotide, the vector or the cell of the present invention for the preparation of a pharmaceutical or diagnostic composition for prophylactic and therapeutic treatment of a metabolic disease, monitoring the progression of a metabolic disease or a response to a metabolic disease treatment in a subject or for determining a subject's risk for developing a metabolic disease.

Hence, in one embodiment the present invention relates to a method of treating a metabolic disorder characterized by abnormal accumulation and/or deposition of IAPP and/or proIAPP in islets of Langerhans, which method comprises administering to a subject in need thereof a therapeutically effective amount of any one of the afore-described IAPP and/or proIAPP binding molecules, antibodies, polynucleotides, vectors or cells of the instant invention. The terms "metabolic disorder" includes but is not limited to the group of disorders generally characterized by symptoms such as metabolic changes preceding, causing, and/or connected/associated with or linked to T2D comprising diseases that cause damage to the pancreas and could therefore lead to diabetes comprising chronic pancreatitis, cystic fibrosis, pancreatic cancer; in diseases that increase the risk of T2D comprising Alzheimer's disease, Huntington's disease; in cardiovascular diseases linked or not with obesity and T2D; and/or to T2D itself.

A particular advantage of the therapeutic approach of the present invention lies in the fact that the antibodies of the present invention are derived from B cells or B memory cells from healthy human subjects with no signs of a disease showing the occurrence of, or related to aggregated IAPP and/or proIAPP such as T2D and thus are, with a certain probability, capable of preventing a clinically manifest disease related to aggregated IAPP and/or proIAPP, or of diminishing the risk of the occurrence of the clinically manifest disease, or of delaying the onset or progression of the clinically manifest disease. Typically, the antibodies of the present invention also have already successfully gone through somatic maturation, i.e. the optimization with respect to selectivity and effectiveness in the high affinity binding to the target IAPP and/or proIAPP molecule by means of somatic variation of the variable regions of the antibody.

The knowledge that such cells in vivo, e.g. in a human, have not been activated by means of related or other physiological proteins or cell structures in the sense of an autoimmunological or allergic reaction is also of great medical importance since this signifies a considerably increased chance of successfully living through the clinical test phases. So to speak, efficiency, acceptability and tolerability have already been demonstrated before the preclinical and clinical development of the prophylactic or therapeutic antibody in at least one human subject. It can thus be expected that the human anti-IAPP and/or anti-proIAPP antibodies of the present invention, both its target structure-specific efficiency as therapeutic agent and its decreased probability of side effects significantly increase its clinical probability of success.

The present invention also provides a pharmaceutical and diagnostic, respectively, pack or kit comprising one or more containers filled with one or more of the above described ingredients, e.g. anti-IAPP and/or anti-proIAPP antibody, binding fragment, derivative or variant thereof, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, e.g. kit of the present invention is of course particularly suitable for the risk assessment, diagnosis, prevention and treatment of a disorder which is accompanied with the presence of aggregated IAPP and/or proIAPP, and in particular applicable for the treatment of disorders generally characterized by symptoms such as metabolic changes preceding, causing, and/or connected/associated with or linked to T2D comprising diseases that cause damage to the pancreas and could therefore lead to diabetes comprising chronic pancreatitis, cystic fibrosis, pancreatic cancer; in diseases that increase the risk of T2D comprising Alzheimer's disease, Huntington's disease; in cardiovascular diseases linked or not with obesity and T2D; and/or to T2D itself, for example.

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways, e.g., by intravenous, intraperitoneal, subcutaneous, intramuscular, intranasal, topical or intradermal administration or spinal or brain delivery. Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringers dextrose), and the like. Preservatives and other additives may also be present such as, for example, antimicrobials, anti-oxidants, chelating agents, and inert gases and the like. Furthermore, the pharmaceutical composition of the invention may comprise further agents such as dopamine or psychopharmacologic drugs, depending on the intended use of the pharmaceutical composition.

Furthermore, in a preferred embodiment of the present invention the pharmaceutical composition may be formulated as a vaccine, for example, if the pharmaceutical composition of the invention comprises an anti-IAPP and/or anti-proIAPP antibody or binding fragment, derivative or variant thereof for passive immunization. As mentioned in the background section, several lines of evidence have been shown indicating that aggregated IAPP and/or proIAPP species are a major trigger for T2D pathogenesis (Zraika et al. (2010), Diabetologia 53(6): 1046-1056; Westermark et al. (2011), Physiol. Rev. 91(3): 795-826; Jurgens et al. (2011), Am. J. Pathol. 178(6): 2632-2640; Hoppener et al. (2008), Exp. Diabetes Res. 697035) and treatment interfering with hIAPP aggregation ameliorated the diabetic phenotype and increased animal life span (Aitken et al. (2009), Diabetes 59(1): 161-171). Accordingly, it is prudent to expect that passive immunization with human anti-IAPP and/or anti-proIAPP antibodies and equivalent IAPP and/or proIAPP binding molecules of the present invention will help to circumvent several adverse effects of active immunization therapy concepts as already discussed in the background section. Therefore, the present anti-IAPP and/or anti-proIAPP antibodies and their equivalents of the present invention will be particularly useful as a vaccine for the prevention or amelioration of diseases showing the presence of, or caused by aggregated IAPP and/or pro/IAPP such as metabolic changes preceding, causing, and/or connected/associated with or linked to T2D comprising diseases that cause damage to the pancreas and could therefore lead to diabetes comprising chronic pancreatitis, cystic fibrosis, pancreatic cancer; in diseases that increase the risk of T2D comprising Alzheimer' s disease, Huntington's disease; in cardiovascular diseases linked or not with obesity and T2D; and/or to T2D itself, for example.

In one embodiment, it may be beneficial to use recombinant bispecific or multispecific constructs of the antibody of the present invention. For a reference see Fischer and Leger, Pathobiology 74 (2007), 3-14. Such bispecific molecule might be designed to target IAPP with one binding arm and another entity known in pathogenesis of diabetes with the second arm, e.g., proIAPP (besides antibodies of the present invention which are bispecific against IAPP and proIAPP as indicated above for the exemplary antibody NI-203.26C11). Or such a bispecific molecule might be designed to bind with the second binding arm other entities known in pathogenesis of diabetes such as IL-1β and IL-6, or by blocking sodium-glucose cotransporter-2 (SGLT2) or CD33, which intervention is thought to reverse diabetes in NOD mice by induction of adaptive regulatory T cells (Ablamunits et al., Diabetes 61 (2012), 145-154; Belghith et al., Nat Med 9 (2003), 1202-1208).

In one embodiment, it may be beneficial to use recombinant Fab (rFab) and single chain fragments (scFvs) of the antibody of the present invention, which might more readily penetrate a cell membrane. For example, Robert et al., Protein Eng. Des. Sel. (2008) October 16; S1741-0134, published online ahead, describe the use of chimeric recombinant Fab (rFab) and single chain fragments (scFvs) of monoclonal antibody WO-2 which recognizes an epitope in the N-terminal region of Aβ. The engineered fragments were able to (i) prevent amyloid fibrillization, (ii) disaggregate preformed A131-42 fibrils and (iii) inhibit A131-42 oligomer-mediated neurotoxicity in vitro as efficiently as the whole IgG molecule. The perceived advantages of using small Fab and scFv engineered antibody formats which lack the effector function include more efficient passage across the blood-brain barrier and minimizing the risk of triggering inflammatory side reactions. Furthermore, besides scFv and single-domain antibodies retain the binding specificity of full-length antibodies, they can be expressed as single genes and intracellularly in mammalian cells as intrabodies, with the potential for alteration of the folding, interactions, modifications, or subcellular localization of their targets; see for review, e.g., Miller and Messer, Molecular Therapy 12 (2005), 394-401.

In a different approach Muller et al., Expert Opin. Biol. Ther. (2005), 237-241, describe a technology platform, so-called 'SuperAntibody Technology', which is said to enable antibodies to be shuttled into living cells without harming them. Such cell-penetrating antibodies open new diagnostic and therapeutic windows. The term 'TransMabs' has been coined for these antibodies.

In a further embodiment, co-administration or sequential administration of other antibodies useful for treating a disease related to the occurrence of aggregated IAPP and/or proIAPP may be desirable. In one embodiment, the additional antibody is comprised in the pharmaceutical composition of the present invention. Examples of antibodies which can be used to treat a subject include, but are not limited to, antibodies targeting CD33, SGLT2, IL-6 and IL-1.

In a further embodiment, co-administration or sequential administration of other agents useful for treating a disease related to aggregated IAPP and/or proIAPP, and/or to diabetes may be desirable. In one embodiment, the additional agent is comprised in the pharmaceutical composition of the present invention. Examples of agents which can be used to treat a subject include, but are not limited to: Insulin and insulin analogues; insulin signaling pathway modulators, such as inhibitors of protein tyrosine phosphatases (PTPases), non-small molecule mimetic compounds and inhibitors of glutamine-fructose-6-phosphate amidotransferase (GFAT), DPP-IV inhibitors, agents influencing a deregulated hepatic glucose production, like inhibitors of glucose-6-phosphatase (G6Pase), inhibitors of fructose-1,6-bisphosphatase (F-1,6-BPase), inhibitors of glycogen phosphorylase (GP), glucagon receptor antagonists, inhibitors of phosphoenolpyruvate carboxykinase (PEPCK), pyruvate dehydrogenase kinase (PDHK) inhibitors, insulin sensitivity enhancers, insulin secretion enhancers, α-glucosidase inhibitors, inhibitors of gastric emptying; Glucagon-Like-Peptide-1 (GLP-1) receptor agonists; Sulfonylurea agents; Biguanide agents such as Metformin; Alpha-glucosidase inhibitors; peroxisome proliferator-activated receptor (PPAR)-Agonists; Meglitinide agents; Dipeptidyl-peptidase (DPP) IV inhibitors; PDE1, PDE5, PDE9, PDE10 or PDE11 (PDE=Phosphodiesterase) inhibitors; Amylin agonists (e.g., pramlintide and other amylin analogues); Cinnamon; Glucagon receptor antagonists; Glycogen-Phosphorylase inhibitors; Fructose-1,6-Bisphosphate inhibitors; Cannabinoid (CB1) receptor antagonists; Anti-obesity drugs such as appetite suppressors, satiety increasing substances, and energy expenditure increasing drugs; anti-inflammatory agents or any combination thereof. Examples of agents which may be used for treating or preventing islet rejection following clinical pancreatic islet transplantation include but are not limited to the agents of the group comprising sirolimus (rapamycin), Calcineurin inhibitors (e.g., tacrolimus), cyclosporine, mycophenolate mofetil, FTY 720, cyclosporine, corticosteroids and anti-IL2-receptor monoclonal antibodies (e.g., daclizumab), glucagon-like peptide-1 (GLP-1) receptor agonists (see, e.g., Noguchi et al., Acta Med. Okayama, 60 (2006), and the international application WO2012088157). Therefore, in one embodiment a composition is provided further comprising an additional agent useful for treating diabetes mellitus type 2 (T2D) and/or in treating or preventing islet rejection following clinical pancreatic islet transplantation. Examples of other agents that may be used concomitantly with a pharmaceutical composition of the present invention are described in the art; see, e.g. international applications WO2009005672, WO2010128092, WO2012088157 or European application EP11158212.8.

A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Preferably, the therapeutic agent in the composition is present in an amount sufficient to restore or preserve normal blood sugar control and/or insulin response in case of metabolic disorders such as T2D.

From the foregoing, it is evident that the present invention encompasses any use of an IAPP and/or proIAPP binding molecule comprising at least one CDR of the above described antibody, in particular for diagnosing and/or treatment of a disease related to aggregated IAPP and/or proIAPP as mentioned above, such as T2D. Preferably, said binding molecule is an antibody of the present invention or an immunoglobulin chain thereof. In addition, the present invention relates to anti-idiotypic antibodies of any one of the mentioned antibodies described hereinbefore. These are antibodies or other binding molecules which bind to the unique antigenic peptide sequence located on an antibody's variable region near the antigen-binding site and are useful, e.g., for the detection of anti-IAPP and/or anti-proIAPP antibodies in a sample obtained from a subject. In one embodiment thus, the present invention provides an antibody as defined hereinabove and below or an IAPP and/or proIAPP binding molecule having substantially the same binding specificities of any one thereof, the polynucleotide, the vector or the cell as defined herein or a pharmaceutical or diagnostic composition comprising any one thereof for use in prophylactic treatment, therapeutic treatment and/or monitoring the progression or a response to treatment of a disorder related to IAPP and/or proIAPP, preferably wherein the disorder is selected from the group comprising all types of diabetes, such as type 1 diabetes, gestational diabetes, prediabetes (when high blood glycemia is not reaching the T2D threshold or insulin resistance) and latent autoimmune diabetes of adults (LADA); any disease that causes damage to the pancreas and could therefore lead to diabetes such as chronic pancreatitis, cystic fibrosis and pancreatic cancer; any disease that increases the risk of T2D such as Alzheimer's disease and Huntington's disease or other neurodegenerative diseases which have been defined herein as associated with diabetes; metabolic syndrome in general as a risk factor for developing diabetes or as a condition that could exist prior diabetes; islet amyloidosis in general as a risk factor for developing diabetes or as a condition that could exist prior diabetes; obesity in general as a risk factor for developing diabetes or as a condition that could exist prior diabetes; any cardiovascular disease linked or not with obesity and T2D; all the consequences of T2D that may also increase the risk of developing diabetes such heart disease, strokes, diabetic retinopathy, kidney failure, renal failure, ketoacidosis and nonketotic hyperosmolar coma. The above group of disorders will be referred to as the group of disorders related to IAPP and/or proIAPP.

In another embodiment the present invention relates to a diagnostic composition comprising any one of the above described IAPP and/or proIAPP binding molecules, antibodies, antigen-binding fragments, polynucleotides, vectors or cells of the invention and optionally suitable means for detection such as reagents conventionally used in immuno- or nucleic acid-based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry and the Western blot assay. The antigens and antibodies of the invention can be bound to many different carriers and used to isolate cells specifically bound thereto. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the IAPP and/or proIAPP binding molecules, in particular antibodies of the present invention may also be used in a method for the diagnosis of a disorder in an individual by obtaining a body fluid sample from the tested individual which may be a blood sample, a plasma sample, a serum sample, a lymph sample or any other body fluid sample, such as a saliva or a urine sample and contacting the body fluid sample with an antibody of the instant invention under conditions enabling the formation of antibody-antigen complexes. The level of such complexes is then determined by methods known in the art, a level significantly higher than that formed in a control sample indicating the disease in the tested individual. In the same manner, the specific antigen bound by the antibodies of the invention may also be used. Thus, the present invention relates to an in vitro immunoassay comprising the binding molecule, e.g., antibody or antigen-binding fragment thereof of the invention.

In this context, the present invention also relates to means specifically designed for this purpose. For example, an antibody-based array may be used, which is for example loaded with antibodies or equivalent antigen-binding molecules of the present invention which specifically recognize IAPP and/or proIAPP. Design of microarray immunoassays is summarized in Kusnezow et al., Mol. Cell Proteomics 5 (2006), 1681-1696. Accordingly, the present invention also relates to microarrays loaded with IAPP and/or proIAPP binding molecules identified in accordance with the present invention.

In one embodiment, the present invention relates to a method of diagnosing a disease related to aggregated IAPP and/or proIAPP in a subject, the method comprising determining the presence of IAPP and/or proIAPP and/or aggregated IAPP and/or proIAPP in a sample from the subject to be diagnosed with at least one antibody of the present invention, an IAPP and/or proIAPP binding fragment thereof or an IAPP and/or proIAPP-binding molecule having substantially the same binding specificities of any one thereof, wherein the presence of pathologically aggregated IAPP and/or proIAPP is indicative of a metabolic disorder, such as T2D and an increase of the level of the pathologically aggregated IAPP and/or proIAPP in comparison to the level of the physiological IAPP and/or proIAPP monomeric forms is indicative for progression of a metabolic disorder in said subject.

The subject to be diagnosed may be asymptomatic or preclinical for the disease. Preferably, the control subject has a disease related to aggregated IAPP and/or proIAPP, for example, metabolic changes preceding, causing, and/or connected/associated with or linked to T2D comprising diseases that cause damage to the pancreas and could therefore lead to diabetes comprising chronic pancreatitis, cystic fibrosis, pancreatic cancer; in diseases that increase the risk of T2D comprising Alzheimer's disease, Huntington's disease; in cardiovascular diseases linked or not with obesity and T2D; and/or to T2D itself, wherein a similarity between the level of pathologically aggregated IAPP and/or proIAPP and the reference standard indicates that the subject to be diagnosed has a metabolic or is at risk to develop a metabolic disease. Alternatively, or in addition as a second control the control subject does not have a metabolic disease, wherein a difference between the level of physiological IAPP and/or proIAPP monomers and/or of aggregated IAPP and/or proIAPP and the reference standard indicates that the subject to be diagnosed has a metabolic disease or is at risk to develop a metabolic disease. Preferably, the subject to be diagnosed and the control subject(s) are age-matched. The sample to be analyzed may be any body fluid suspected to contain pathologically aggregated IAPP and/or proIAPP, for example a blood, blood plasma, blood serum, urine, peritoneal fluid, saliva or cerebral spinal fluid (CSF).

The level of physiological IAPP and/or proIAPP monomers and/or of pathologically aggregated IAPP and/or proIAPP may be assessed by any suitable method known in the art comprising, e.g., analyzing IAPP and/or proIAPP by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry. Preferably, said in vivo imaging of IAPP and/or proIAPP comprises positron emission tomography (PET), single photon emission tomography (SPECT), near infrared (NIR) optical imaging or magnetic resonance imaging (MRI).

Antibody based methods for detection of IAPP and/or proIAPP and for diagnosing or monitoring the progression of a disease related to aggregated IAPP and/or proIAPP such as T2D, and monitoring the treatment of such a disease using antibodies and related means which may be adapted in accordance with the present invention are also described in international application WO2003092619 the disclosure content of which being incorporated herein by reference. Those methods may be applied as described but with an IAPP and/or proIAPP specific antibody, binding fragment, derivative or variant of the present invention.

In one embodiment thus, an antibody of the present invention or an IAPP and/or proIAPP binding molecule having substantially the same binding specificities of any one thereof, the polynucleotide, the vector or the cell as defined hereinabove or a pharmaceutical or diagnostic composition comprising any one thereof is provided for use in prophylactic treatment, therapeutic treatment and/or monitoring the progression or a response to treatment of a disorder related to IAPP and/or proIAPP. In general thus, the present invention also relates to a method of diagnosing or monitoring the progression of a disorder related to IAPP and/or proIAPP (such as islet amyloidosis and T2D which is usually preceded by islet amyloidosis) in a subject, the method comprising determining the presence of IAPP and/or proIAPP oligomers, aggregates or fibrils in a sample from the subject to be diagnosed with at least one antibody of the present invention or an IAPP and/or proIAPP binding molecule having substantially the same binding specificities of any one thereof, wherein the presence of IAPP and/or proIAPP oligomers, aggregates or fibrils is indicative of the disorder. In one embodiment said method of diagnosing or monitoring the progression of islet amyloidosis in a subject is provided, the method comprising determining the presence of IAPP and/or proIAPP oligomers, aggregates or fibrils in a sample from the subject to be diagnosed with at least one antibody of the present invention or an IAPP and/or proIAPP binding molecule having substantially the same binding specificities of any one thereof, wherein the presence of IAPP and/or proIAPP oligomers, aggregates or fibrils is indicative of presymptomatic, prodromal or clinical diabetes mellitus type 2 (T2D) and/or of beta-cell failure following clinical pancreatic islet transplantation and an increase of the level of IAPP and/or proIAPP oligomers, aggregates or fibrils in comparison to the level of the physiological IAPP or in comparison to a reference sample derived from a healthy control subject or a control sample from the same subject is indicative for progression of presymptomatic, prodromal or established diabetes mellitus type 2 (T2D) and/or of islet failure following clinical pancreatic islet transplantation in said subject. It would be appreciated by any person skilled in the art that in one embodiment said method is used as well for the diagnosing or monitoring the progression of any other disorder from the group of disorders related to IAPP and/or proIAPP as defined hereinabove.

As indicated above, the antibodies of the present invention, fragments thereof and molecules of the same binding specificity as the antibodies and fragments thereof may be used not only in vitro but in vivo as well, wherein besides diagnostic, therapeutic applications as well may be pursued. In one embodiment thus, the present invention also relates to an IAPP and/or proIAPP binding molecule comprising at least one CDR of an antibody of the present invention for the preparation of a composition for in vivo detection of or targeting a therapeutic and/or diagnostic agent to IAPP and/or proIAPP in the human or animal body. Potential therapeutic and/or diagnostic agents may be chosen from the nonexhaustive enumerations of the therapeutic agents useful in treatment of metabolic diseases, such as T2D and potential labels as indicated hereinbefore. In respect of the in vivo imaging, in one preferred embodiment the present invention provides said IAPP and/or proIAPP binding molecule comprising at least one CDR of an antibody of the present invention, wherein said in vivo imaging comprises positron emission tomography (PET), single photon emission tomography (SPECT), near infrared (NIR) optical imaging or magnetic resonance imaging (MRI). In a further embodiment the present invention also provides said IAPP and/or proIAPP binding molecule comprising at least one CDR of an antibody of the present invention, or said molecule for the preparation of a composition for the above specified in vivo imaging methods, for the use in the method of diagnosing or monitoring the progression of a disorder related to IAPP and/or proIAPP in a subject, as defined hereinabove.

VII. Peptides with Aggregation Specific IAPP Epitopes

In a further aspect the present invention relates to peptides having an epitope of IAPP and/or proIAPP specifically recognized by any antibody of the present invention. Preferably, such peptide comprises or consists of an amino acid sequence as indicated in SEQ ID NO: 4, in SEQ ID NO: 5, or in SEQ ID NO: 71 as the unique linear epitope recognized by the antibody or a modified sequence thereof in which one or more amino acids are substituted, deleted and/or added, wherein the peptide is recognized by any antibody of the present invention, preferably by antibody NI-203.19H8 respective by antibody NI-203.26C11 or by antibody NI-203.15C7.

In one embodiment of this invention such a peptide may be used for diagnosing or monitoring a disease related to aggregated IAPP and/or proIAPP in a subject, such as T2D comprising a step of determining the presence of an antibody that binds to a peptide in a biological sample of said subject, and being used for diagnosis of such a disease in said subject by measuring the levels of antibodies which recognize the above described peptide of the present invention and comparing the measurements to the levels which are found in healthy subjects of comparable age and gender. Thus in one embodiment the present invention relates to a method for diagnosing islet amyloidosis indicative of presymptomatic or clinical diabetes mellitus type 2 (T2D) and/or of beta-cell failure following clinical pancreatic islet transplantation in a subject, comprising a step of determining the presence of an antibody that binds to a peptide as defined above in a biological sample of said subject. According to this method, an elevated level of measured antibodies specific for said peptide of the present invention is indicative for diagnosing in said subject presymptomatic or clinical diabetes mellitus type 2 (T2D) and/or of beta-cell failure following clinical pancreatic islet transplantation or for diagnosing in said subject any other disease from the group of disorders related to IAPP and/or proIAPP as defined hereinabove. The peptide of the present invention may be formulated in an array, a kit and composition, respectively, as described hereinbefore. In this context, the present invention also relates to a kit useful in the diagnosis or monitoring the progression of islet amyloidosis, said kit comprising at least one antibody of the present invention or an IAPP and/or proIAPP binding molecule having substantially the same binding specificities of any one thereof, the polynucleotide, the vector or the cell and/or the peptide as respectively defined hereinbefore, optionally with reagents and/or instructions for use.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19

850673 2. Several documents are cited throughout the text of this specification. Full bibliographic citations may be found at the end of the specification immediately preceding the claims. The contents of all cited references (including literature references, issued patents, published patent applications as cited throughout this application and manufacturer's specifications, instructions, etc.) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

Example 1: Validation of Target and Binding Specificity of Human IAPP Antibodies To validate IAPP as a recognized target of isolated antibodies, direct ELISA assays were performed. For the exemplary recombinant human NI-203.9A2, NI-203.19H8, NI-203.26C11 and NI-203.8E3 antibodies, 96-well microplates (Costar, Corning, USA) were coated with human IAPP solution or with BSA (Sigma-Aldrich, Buchs, Switzerland) diluted to a concentration of 10 µg/ml in carbonate ELISA coating buffer (15 mM $Na_2CO_3$, 35 mM $NaHCO_3$, pH 9.42) and binding efficiency of the antibody was tested. Importantly, the human IAPP solution used for ELISA assay contained IAPP fibrils, as shown by electron microscopy; see FIG. 3A. The exemplary NI-203.9A2, NI-203.19H8, NI-203.26C11 and NI-203.8E3 antibodies specifically bind to human IAPP fibrils by ELISA. No binding is observed to BSA; see FIG. 3B. The same characteristics seem to apply to the antibodies NI-203.19F2 and NI-203.15C7.

For a determination of the half maximal effective concentration ($EC_{50}$) of the exemplary antibodies NI-203.9A2, NI-203.19H8, NI-203.26C11 and NI-203.8E3, additional direct ELISA experiments with varying antibody concentrations were performed. 96-well microplates (Costar, Corning, USA) were coated with human IAPP and human proIAPP solutions diluted to a concentration of 10 µg/ml in carbonate ELISA coating buffer (15 mM $Na_2CO_3$, 35 mM $NaHCO_3$, pH 9.42) and binding efficiency of the antibody was tested. While the human IAPP solution used for ELISA assay contains IAPP fibrils, human proIAPP formed large aggregates in solution, as revealed by electron microscopy; see FIG. 4A. Binding was determined using a donkey anti-human IgGγ antibody (Jackson ImmunoResearch, Newmarket, UK) conjugated with HRP, followed by measurement of HRP activity in a standard colorimetric assay.

The $EC_{50}$ values were estimated by a non-linear regression using GraphPad Prism (San Diego, USA) software. Recombinant human-derived antibodies NI-203.9A2, NI-203.19H8, NI-203.26C11 and NI-203.8E3 bind with a high affinity to human IAPP fibrils with an $EC_{50}$ of 9 nM, 22 nM, 6 nM and 4 nM, respectively. Antibody NI-203.26C11 also binds to aggregated human proIAPP with an $EC_{50}$ in the nanomolar range (260 nM); see FIG. 4B.

Example 2: Antibody Specificity to Human IAPP Fibrils and not to Nonfibrillar Human IAPP Thus Preferably Binding to Conformational Epitopes To determine the binding capacity of the exemplary NI-203.9A2, NI-203.19H8, NI-203.26C11 and NI-203.8E3 antibodies to conformational epitopes, direct ELISA experiments were performed with human IAPP and nonfibrillar IAPP solutions diluted to a concentration of 10 µg/ml in carbonate ELISA coating buffer (15 mM $Na_2CO_3$, 35 mM $NaHCO_3$, pH 9.42) and binding capacity of the antibody was tested. While the human IAPP solution used for ELISA assay contains IAPP fibrils, human nonfibrillar IAPP solution was lacking IAPP fibrils and only showed small amorphous aggregates, as revealed by electron microscopy; see FIG. 5A. Binding was determined using a donkey anti-human IgGγ antibody (Jackson immunoResearch, Newmarket, UK) conjugated with HRP, followed by measurement of HRP activity in a standard colorimetric assay.

Recombinant NI-203.9A2, NI-203.19H8, NI-203.26C11 and NI-203.8E3 antibodies showed high affinity binding to IAPP fibrils upon coating with the IAPP solution (FIG. 5B), as previously observed (FIG. 4). A loss in affinity was observed on nonfibrillar IAPP when compared to IAPP fibrils (FIG. 5B), thus demonstrating preferential binding of NI-203.9A2, NI-203.19H8, NI-203.26C11 and NI-203.8E3 antibodies to IAPP fibrils. Preliminary results show the same effects as described above for antibodies NI-203.19F2 and NI-203.15C7.

These findings strongly point to NI-203.9A2, NI-203.19H8, NI-203.26C11, NI-203.8E3, NI-203.19F2 and NI-203.15C7 antibody binding epitopes that are predominantly exposed and accessible upon IAPP fibril formation, in contrast to linear epitopes that are present in the physiological human IAPP protein conformation. Pathological IAPP fibrils are observed in pancreatic islets of T2D patients. Since NI-203.9A2, NI-203.19H8, NI-203.26C11, NI-203.8E3, NI-203.19F2 and NI-203.15C7 antibodies show prominent binding to therapeutically relevant pathological human IAPP fibrils, these human-derived antibodies are of therapeutic potential in T2D.

Example 3: Assessment of the Binding Epitope of NI-203.9A2, NI-203.19H8, NI-203.26C11, NI-203.8E3, NI-203.19F2, and NI-203.15C7 Antibodies To determine the binding epitope of the exemplary NI-203.9A2, NI-203.19H8, NI-203.26C11, NI-203.8E3, NI-203.19F2, and NI-203.15C7 antibodies, pepscan and alanine scan analysis was performed with overlapping peptides mapping the entire human IAPP amino acid sequence and with alanine substitution on the first 22 amino acids of proIAPP. Binding capacity of the antibody was tested on these peptides spotted onto a nitrocellulose membrane (JPT Peptide Technologies, Berlin, Germany) and using HRP-conjugated donkey anti-human IgGγ secondary antibody (Jackson immunoResearch, Newmarket, UK) followed by detection of HRP activity (FIG. 6A).

Recombinant NI-203.19H8, NI-203.26C11, and NI-203.15C7 antibodies (1 µg/ml) showed binding to the sequence 19-SSNNFGA-25 (SEQ ID NO: 4), 2-CN-TATCA-8 (SEQ ID NO: 5), and 10-QRLANFLVHS-19 (SEQ ID NO: 71) on human IAPP (FIGS. 6A and 6B), thus corresponding to the putative binding epitope sequences of these antibodies. The epitope of recombinant NI-203.9A2, NI-203.8E3, and NI-203.19F2 antibodies (1 and 10 µg/ml) have not been identified.

Example 4: Binding of NI-203.9A2, NI-203.19H8 and NI-203.26C11 Antibodies to Pathological IAPP Fibrils in the Pancreas of Patients Diagnosed with Diabetes Mellitus Type 2 but not in Control Patients Paraffin-embedded pancreas sections of two patients diagnosed with diabetes mellitus type 2 (T2D) were selected based on amyloid load in pancreatic islets observed upon ThioS and Congo red staining, and subsequently used for the exemplary NI-203.9A2, NI-203.19H8 and NI-203.26C11 antibody binding characterization. Paraffin-embedded pancreas sections of a patient not diagnosed with diabetes mellitus type 2 were used as control. After formic acid pretreatment, sections were incubated with human NI-203.9A2, NI-203.19H8 and NI-203.26C11 antibodies (5 and 50 nM) or mouse monoclonal anti-IAPP antibody (1:100; Abcam, Cambridge, UK), followed by incubation with biotinylated donkey anti-human secondary antibody (1:500; Jackson ImmunoResearch, Newmarket, UK) or biotinylated goat anti-mouse secondary antibody (1:500; Jackson ImmunoResearch, Newmarket, UK). Antibody signal was amplified with the Vectastain ABC-AP kit (Vector Laboratories, USA) and detected with diaminobenzidine substrate (Thermo Fisher Scientific, USA). Upon avidin/biotin blocking (Avidin/Biotin blocking kit, Vector Laboratories, USA), pancreatic islet β-cells were visualized using a polyclonal guinea pig anti-insulin antibody (1:5; Dako, USA) coupled to a biotinylated donkey anti-guinea pig secondary antibody (1:500; Jackson ImmunoResearch Laboratories, USA) and antibody signal was amplified with the Vectastain ABC-AP kit (Vector Laboratories, USA) and detected with alkaline phosphatase substrate (Vector Laboratories, USA).

The first T2D patient showed large amyloid deposits in pancreatic islets corresponding to pathological IAPP fibrils, as visualized by ThioS and Congo red staining (FIG. 7A). NI-203.9A2, NI-203.19H8 and NI-203.26C11 human antibodies showed prominent pancreatic islet staining on these amyloid-positive sections (FIG. 7B). The antibody staining was observed at 5 nM and increased at 50 nM, with no staining observed with the secondary antibody only, suggesting specific binding of the human IAPP antibodies. These findings were confirmed on a second T2D patient showing amyloid deposits in pancreatic islets (data not shown). In contrast, NI-203.9A2, NI-203.19H8 and NI-203.26C11 human antibodies were not showing any staining on pancreatic islets from a third T2D patient lacking amyloid deposits (FIGS. 7C and D) and from a control patient not diagnosed with T2D (FIG. 8). The commercially available mouse monoclonal anti-IAPP antibody stained physiological IAPP on pancreatic islets from the non-diabetic control patient; see FIG. 8. The antibodies of the present invention also gave positive results on diabetic cat pancreases showing islet amyloid deposits; see FIG. 9. The same binding properties seem to apply to antibodies NI-203.19F2 and NI-203.15C7.

These data demonstrate that NI-203.9A2, NI-203.19H8, NI-203.26C11, NI-203.19F2 and NI-203.15C7 antibodies specifically recognize pathological IAPP fibrils and are in accordance with the biochemical binding properties of these antibodies, which show strong binding specificity to IAPP fibrils in vitro (FIG. 5).

Example 5: NI-203.9A2, NI-203.19H8 and NI-203.26C11 Antibodies do not Cross-React to Pathological Aβ Amyloid in the Brain of Patient Diagnosed with Alzheimer's Disease Paraffin-embedded brain sections of a patient diagnosed with Alzheimer's disease was used to assess cross-reactivity of the exemplary NI-203.9A2, NI-203.19H8 and NI-203.26C11 antibodies. After formic acid pretreatment, sections were incubated with human NI-203.9A2, NI-203.19H8 and NI-203.26C11 antibodies (50 nM) or mouse monoclonal anti-β amyloid antibody 6E10 (1:2000; Covance, Allschwill, Switzerland), followed by incubation with biotinylated donkey anti-human secondary antibody (1:500; Jackson ImmunoResearch, Newmarket, UK) or biotinylated goat anti-mouse secondary antibody (1:500; Jackson ImmunoResearch, Newmarket, UK). Antibody signal was amplified with the Vectastain ABC-AP kit (Vector Laboratories, USA) and detected with diaminobenzidine substrate (Thermo Fisher Scientific, USA).

Figure 10:
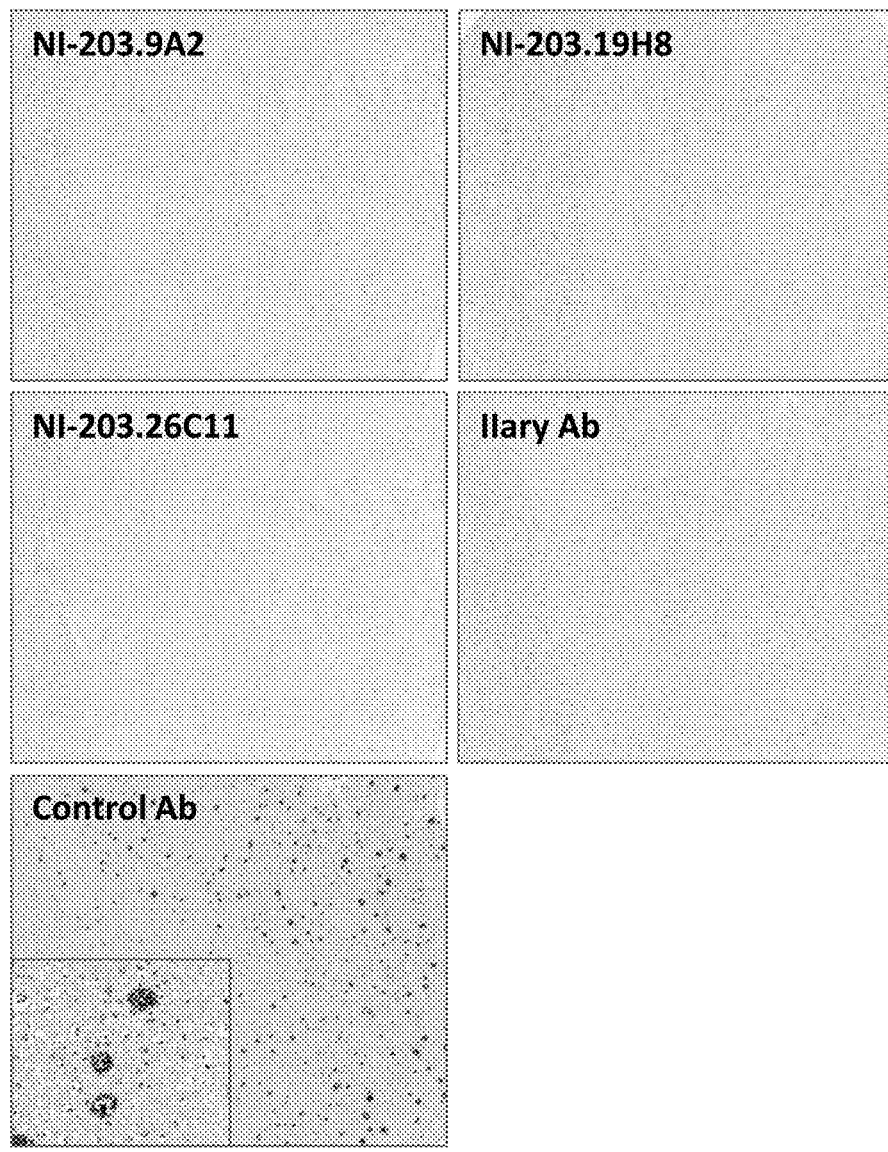
FIG. 10: NI-203.9A2, NI-203.19H8 and NI-203.26C11 antibodies do not recognize pathological Aβ deposits in a human brain with Alzheimer's disease. Absence of staining with NI-203.9A2, NI-203.19H8 and NI-203.26C11 antibodies (50 nM), in opposition to the AP-specific antibody 6E10 (1:2000; control Ab). Secondary donkey anti-human antibody only (IIary Ab) was used as a control. Counterstaining was performed to visualize cell nuclei (faint blue i.o., faint staining here).

NI-203.9A2, NI-203.19H8 and NI-203.26C11 antibodies did not recognize pathological Aβ amyloid in Alzheimer's disease human brain, in contrast to the anti-β amyloid specific antibody 6E10 (FIG. 10). The same seems to apply to antibodies NI-203.19F2 and NI-203.15C7.

These data demonstrate that NI-203.9A2, NI-203.19H8 and NI-203.26C11 antibodies are not cross-reactive to pathological Aβ amyloid. Accordingly, also minimal cross-reactive binding of NI-203.9A2, NI-203.19H8 and NI-203.26C11 antibodies to several protein candidates with misfolding/aggregation propensities by direct ELISA has been demonstrated, including the most prominent amyloid-forming proteins including, but not restricted to, alpha-synuclein, superoxide dismutase 1 (SOD1), Tau and TAR-binding protein 43 (TDP-43).

Example 6: Quality Control of Mouse Chimeric NI-203.9A2, NI-203.19H8 and NI-203.26C11 Antibodies To validate the exemplary mouse chimeric NI-203.9A2, NI-203.19H8 and NI-203.26C11 antibodies, direct ELISA assays were performed as described above. Chimeric antibodies were compared to corresponding human antibodies. For the exemplary recombinant chimeric NI-203.9A2, NI-203.19H8 and NI-203.26C11 antibodies, and their corresponding human antibodies, 96-well microplates (Costar, Corning, USA) were coated with human IAPP solution or with BSA (Sigma-Aldrich, Buchs, Switzerland) diluted to a concentration of 10 µg/ml in carbonate ELISA coating buffer (15 mM $Na_2CO_3$, 35 mM $NaHCO_3$, pH 9.42) and binding efficiency of the chimeric and human antibodies was tested. Binding was determined using a donkey anti-human IgGγ antibody (Jackson immunoResearch, Newmarket, UK) conjugated with HRP, followed by measurement of HRP activity in a standard colorimetric assay. Importantly, the human IAPP solution used for ELISA assay contained IAPP fibrils, as shown by electron microscopy; see FIG. 3A. The $EC_{50}$ values were estimated by a non-linear regression using GraphPad Prism (San Diego, USA) software.

NI-203.9A2, NI-203.19H8 and NI-203.26C11 mouse chimeric antibodies bind with a high affinity to human IAPP fibrils with an $EC_{50}$ of 18.6 nM, 23.9 nM and 11.5 nM, respectively. No binding was observed on BSA. The binding affinity of chimeric antibodies was similar to their human counterparts, with an $EC_{50}$ of 9.4 nM, 22.9 nM and 6.8 nM for human NI-203.9A2, NI-203.19H8 and NI-203.26C11 antibodies, respectively; see FIG. 11.

The exemplary mouse chimeric NI-203.9A2, NI-203.19H8 and NI-203.26C11 antibodies were further validated on paraffin-embedded pancreas sections of two selected patients diagnosed with diabetes mellitus type 2 (T2D), and showing islet amyloid deposits. After formic acid pretreatment, sections were incubated with chimeric NI-203.9A2, NI-203.19H8 and NI-203.26C11 antibodies (50 nM), followed by incubation with biotinylated donkey anti-human secondary antibody (1:500; Jackson ImmunoResearch, Newmarket, UK). Antibody signal was amplified with the Vectastain ABC-AP kit (Vector Laboratories, USA) and detected with diaminobenzidine substrate (Thermo Fisher Scientific, USA). Upon avidin/biotin blocking (Avidin/Biotin blocking kit, Vector Laboratories, USA), pancreatic islet β-cells were visualized using a polyclonal guinea pig anti-insulin antibody (1:5; Dako, USA) coupled to a biotinylated donkey anti-guinea pig secondary antibody (1:500; Jackson ImmunoResearch, Newmarket, UK) and antibody signal was amplified with the Vectastain ABC-AP kit (Vector Laboratories, USA) and detected with alkaline phosphatase substrate (Vector Laboratories, USA).

NI-203.9A2, NI-203.19H8 and NI-203.26C11 chimeric antibodies showed prominent pancreatic islet staining on amyloid-positive sections from two T2D patients (FIG. 12).

These data demonstrate that chimeric NI-203.9A2, NI-203.19H8 and NI-203.26C11 antibodies specifically recognize pathological IAPP fibrils with efficiency comparable to their human counterparts (FIG. 12).

Example 7: In Vivo Validation of the Therapeutic Effect of the IAPP and/or proIAPP Antibodies in T2D Animal Models Lead antibody candidates are validated in two transgenic mice models and in a rat model expressing hIAPP: 1) h-IAPP (hemizygous)/C57BL/6/DBA mice exposed to high fat diet (Hull et al. (2003), Diabetes 52: 372-379); 2) h-IAPP (hemizygous)/A$^{vy}$/A mice exposed to standard diet (Butler et al. (2003), Diabetes 52: 2304-2314); 3) h-IAPP (homozygous)/CD rats exposed to standard diet (Butler et al. (2004), Diabetes 53: 1509-1516). Therapeutic efficacy is assessed by determining the beta-cell mass and hIAPP amyloid load in the pancreas as well as plasma levels of hIAPP, and functional tests of glucose metabolism and insulin secretion.

1) Physiological Characteristics

The following physiological characteristics (i) to (vii) of the type II diabetes animal models are tested to see whether the application of the antibodies of the present application show preventive and/or therapeutic effect.

(i) Blood Glucose:

The blood glucose level of the T2D animal models is tested and compared to non-treated animals and a normal (not T2D model) strain animals.

The "normal strain mouse" herein is not particularly limited and can be any mouse as long as it shows no abnormality in the blood glucose level, urea sugar, insulin secretion and the like. Preferred examples of the "normal strain mouse" include a KOR mouse, NC mouse, and laboratory mouse which is used as a recurrent parent in generating a congenic mouse (e.g., C3H/He mouse, BALB/c mouse, and C57BL/6 mouse).

The "normal strain rat" herein is not particularly limited and can be any rat as long as it shows no abnormality in the blood glucose level, urea sugar, insulin secretion and the like.

As diabetes in the mouse and rat models is preferably induced by transgenic expression of hIAPP, preferably the same strains are used as controls as those which were originally used for the generation of the transgenic animals.

The expression "having a higher blood glucose level as compared to a normal strain mouse/rat" means that the blood glucose level (glucose concentration in the blood) at fasting is higher than that of a normal strain mouse/rat at fasting. Blood glucose levels of the diabetic animals of 130 mg/dl or higher, more preferably 140 mg/dl or higher, further preferably 200 mg/dl and further more preferably 300 mg/dl or higher is classified as higher blood glucose. Further, the term "fasting" as used herein means a condition about 12 hours after the start of fasting of a mouse/rat.

In the present invention, the "blood glucose level" can be measured by a conventional method known to the person skilled in the art, for example, using a commercial measuring apparatus (e.g., Medisafe Reader; Terumo Co., Ltd.) according to the method described in Example hereinafter.

Exemplary Method of Measurement of Blood Glucose Level

The blood glucose level (blood glucose concentration) of a subject animal is measured using a commercial measuring apparatus (Medisafe Reader, Terumo Co., Ltd.). Measurement principle of this apparatus will be explained as follows. The measurement is based on colorimetric analysis. A measuring chip is prepared, and onto the chip are placed glucose oxidase and peroxidase as catalysts and 4-aminoantipyrine and N-ethyl-N(2-hydroxy-3-sulfopropyl)-m-toluidine as chromogenic agents. When a blood sample absorbed through capillary phenomenon is placed on this chip and then glucose in the blood is oxidized by glucose oxidase. Then, the chromogenic agents on the chip are oxidized by hydrogen peroxide generated at this moment and peroxidase, which yields a red-purple color. The amount of glucose in the blood is calculated by measuring the degree of this color tone.

Here, 4 µl of the whole blood is obtained from a subject animal as a blood sample and measured using a measurement time of 18 seconds.

(ii) Glycosylated Hemoglobin (HbA1c) Concentration:

The Type II diabetes animal models are tested for increased blood glycosylated hemoglobin concentration and compared to non-treated T2D model animals and normal, non-T2D model animals. Concentrations of 2.5% or higher, 2.6% or higher, further 2.8% or higher, and further 3.0% or higher are classified as increased.

The "glycosylated hemoglobin concentration" as used herein means the proportion of hemoglobin molecules with glucose attached to them in a red blood cell. The glycosylated hemoglobin concentration can be used as an index to judge appropriateness of therapeutic control for diabetes patients and is known to correlate better with the blood sugar level at 1 to 2 months earlier than with that at the present time.

The "glycosylated hemoglobin concentration" can be measured by a conventional method known to the person skilled in the art, for example, using a commercial measuring apparatus (e.g., DCA 2000 System; Bayer Medical Ltd.) according to the method described in Example hereinafter. More specifically, for example, when the abovementioned DCA 2000 System is used as a measuring apparatus, the amount of total hemoglobin is measured by the thiocyanmethemoglobin method and the amount of glycosylated hemoglobin is measured by the latex coagulation inhibition reaction.

(iii) Urine Sugar:

Urine sugar of the control animals and of the T2D model animals is tested herein.

The term "positive in test for urine sugar" as used herein means that the glucose concentration in the urine excreted by the animals is 100 mg/dl or higher. The urine glucose concentration can be measured by a conventional method, for example, by the method described in Example hereinafter using a commercial kit (e.g., Pretest; Wako Pure Chemical Industries, Ltd.). Specifically, for example, when the Pretest is used as a measuring kit, a animal urine sample is first put on a test paper of the Pretest, and after 30 seconds a judgment is made according to the specified color table in this kit for the classification into five grades ranging from − to +4. Urine glucose concentrations estimated from the result of the judgment are 100-250 mg/dl for +1, 250-500 mg/dl for +2, 500-2000 mg/dl for +3, and 2000 mg/dl or higher for +4. The judging results of +1 and higher are assessed as "positive in test for urine sugar".

Exemplary Method of Measurement of Urine Sugar

Urine glucose (urine sugar) of a subject animal is measured by methods known to the person skilled in the art, e.g., using a commercial kit (Pretest; Wako Pure Chemical Industries, Ltd.). First, an animal urine sample is blotted into a test paper of the abovementioned Pretest, and after 30 seconds judgment is made according to a color table specified for the classification into five grades ranging from – to +4. Urine glucose concentrations estimated from the results of the judgment are 100-250 mg/dl for +1, 250-500 mg/dl for +2, 500-2000 mg/dl for +3, and 2000 mg/dl or higher for +4. The judging results of +1 and higher are assessed as "positive in test for urine sugar".

(iv) Blood Insulin Concentration:

It is tested whether the blood insulin concentration of the Type II diabetes animal models is compared to the levels in is equivalent to or higher than that of a non-treated and that of non-diabetic control animals (normal strain animals).

The expression that the blood insulin concentration is "equivalent to or higher than that of a normal strain animal" means that the blood insulin concentration at fasting is equivalent to or higher than that of a normal strain animal at fasting, e.g., 90 pg/ml or higher, or 110 pg/ml or higher.

In the present invention, the "blood insulin concentration" can be measured by a conventional method, for example, using a Levis insulin assay kit U-type (Shibayagi Co.) according to the method described in Example hereinafter. More specifically, for example, an anti-insulin monoclonal antibody (mouse) is immobilized onto a plate, insulin in a sample is bound thereto, after which a biotin-labeled anti-insulin monoclonal antibody which recognizes another site of insulin is reacted therewith, a peroxidase-avidin conjugate is further added thereto to bind to biotin, and finally a chromogenic substance is added to measure insulin by color development.

Exemplary Method of Measurement of Blood Insulin Concentration

The blood insulin concentration of a subject mouse is measured using a method known to the person skilled in the art, e.g., incorporated into a commercial kit (*Levis* insulin assay kit U-type; Shibayagi Co.). The insulin concentration is measured in the following manner. An anti-insulin monoclonal antibody is immobilized onto a plate, insulin in a sample is bound to it, after which a biotin-labeled anti-insulin monoclonal antibody, which recognizes another portion of insulin, is reacted, a peroxidase-avidin conjugate is further added thereto to bind to biotin, and finally a chromogenic substance is added to measure insulin by color development. The range of measurement is generally from 39 to 2,500 pg/ml for a normal animal (mouse).

(v) Glucose Tolerance:

The treated and non-treated T2D model animals and normal animals are tested for abnormal glucose tolerance.

Whether the glucose tolerance of an animal is normal or abnormal can be confirmed by a glucose tolerance test. The glucose tolerance test can be carried out according to a conventional procedure known to the person skilled in the art, for example, by intraperitoneally administering glucose to a fasting (at least 12 hours) animal at 2 mg per gram of bodyweight and measuring the blood glucose level of the animal at certain times during the glucose tolerance test (for example, every 15 minutes over 240 minutes). When the result shows that the blood glucose level shows no tendency to decrease with time as compared with that for a normal mouse, the glucose tolerance is assessed as abnormal. When the result in the treated animals shows tendency to decrease with time as compared with that for non-treated animals, the treatment with the antibodies of the present invention is classified as effective.

Exemplary Method of Evaluation of Glucose Tolerance

The glucose tolerance of subject animals is evaluated by the glucose tolerance test.

The glucose tolerance test is carried out by first administering glucose intraperitoneally to a 12-hour fasting animal at 2 mg per gram of bodyweight and then measuring the glucose level in the blood (peripheral blood) of the animal, every 15 minutes over 240 minutes. The blood glucose level is measured by the abovementioned method. When the result shows that the blood glucose level exhibits no tendency to decrease with time as compared with that for a normal animal, the glucose tolerance is assessed as abnormal. A faster decrease with time in treated compared to non-treated T2D model animals is assessed as a sign of efficiency of the treatment of the present invention.

(vi) Insulin Sensitivity:

The treated and non-treated T2D model animals and normal animals are tested for abnormal insulin sensitivity.

Whether the insulin sensitivity of an animal is normal or abnormal can be confirmed by an insulin sensitivity test. The insulin sensitivity test can be carried out according to a conventional procedure known to the person skilled in the art, for example, by intraperitoneally administering insulin to a fasting animal at 0.5-0.85 U per kg of bodyweight and measuring the blood glucose level of the animal at certain times during the insulin sensitivity test (for example, every 15 minutes over 240 minutes). When the result shows that the blood glucose level shows no tendency to decrease with time as compared with that for a normal mouse, the insulin sensitivity is assessed as abnormal. When the result in the treated animals shows tendency to decrease with time as compared with that for non-treated animals, the treatment with the antibodies of the present invention is classified as effective.

Exemplary Method of Evaluation of Insulin Sensitivity

The insulin sensitivity of subject animals is evaluated by the insulin sensitivity test.

The insulin sensitivity test is carried out by first administering insulin intraperitoneally to an 12-hour fasting animal at 0.5-0.85 U per kg of bodyweight and then measuring the glucose level in the blood (peripheral blood) of the animal every 15 minutes over 240 minutes. The blood glucose level is measured by the abovementioned method. When the result shows that the blood glucose level exhibits no tendency to decrease with time as compared with that for a normal animal, the insulin sensitivity is assessed as abnormal. A faster decrease with time in treated compared to non-treated T2D model animals is assessed as a sign of efficiency of the treatment of the present invention.

(vii) Others:

Assessment of Polydipsia and Polyuria

The Type II diabetes model animals are tested for showing tendencies of increased water drinking and increased urination, after the onset of diabetes and during the treatment of the antibodies of the present invention. The tendency of increased water drinking can be confirmed, for example, by carefully monitoring the rate of decrease in the water volume in a water bottle placed in a rearing cage and comparing it with that for a normal strain animal and with that of non-treated animals. Further, the tendency of increased urination can be confirmed, for example, by observing the extent of wetting of a floor sheet in the rearing cage and comparing it as indicated before.

Judgment of the Presence or Absence of Obese Tendency in Mice

The body weights of treated, non-treated T2D model animals and normal animals are measured and compared. Decreased weight of treated animals in comparison to non-treated animals and/or comparable weight of treated and normal animals is assessed as a sign of efficiency of the treatment of the present invention.

2) Histopathological Examination

The pancreatic tissue of Type II diabetes animals, of the non-treated T2D model controls and of normal animals is fixed, embedded in paraffin and stained and analyzed according to the methods of Example 4 for amyloid deposits of amylin on pancreatic islet (Langerhans islet) β-cells. Similarly, β-cell apoptosis and β-cell survival is assessed by immunostaining using appropriate markers (e.g., TUNEL and cleaved caspase-3 staining for apoptosis and insulin staining for β-cell area). A decrease of amyloid deposits and/or β-cell apoptosis and/or an increase in β-cell survival in pancreatic islets in treated animals in comparison with non-treated animals or comparable levels in treated animals and in normal animals is assessed as a sign of the efficiency of the preventive and/or therapeutic methods of the present inventions.

3) Housing of the Animals

The Type II diabetes animal models are maintained under SPF conditions and accordingly to what previously described (Hull et al. (2003), Diabetes 52: 372-379; Butler et al. (2003), Diabetes 52: 2304-2314; Butler et al. (2004), Diabetes 53: 1509-1516). At 6 weeks of age, h-IAPP (hemizygous)/C57BL/6/DBA mice are assigned to a high fat diet shown to promote islet amyloid formation (Hull et al. (2003), Diabetes 52: 372-379).

The invention claimed is:

1. An anti-islet amyloid polypeptide (IAPP) antibody or antigen-binding fragment thereof comprising a variable region comprising:
   (a) a CDR-H1 comprising the amino acid sequence of SEQ ID NO: 76 or a variant thereof, wherein the variant comprises two or fewer amino acid substitutions,
   (b) a CDR-H2 comprising the amino acid sequence of SEQ ID NO: 94 or a variant thereof, wherein the variant comprises two or fewer amino acid substitutions,
   (c) a CDR-H3 comprising the amino acid sequence of SEQ ID NO: 112 or a variant thereof, wherein the variant comprises two or fewer amino acid substitutions,
   (d) a CDR-L1 comprising the amino acid sequence of SEQ ID NO: 85 or a variant thereof, wherein the variant comprises two or fewer amino acid substitutions,
   (e) a CDR-L2 comprising the amino acid sequence of SEQ ID NO: 103 or a variant thereof, wherein the variant comprises two or fewer amino acid substitutions, and
   (f) a CDR-L3 comprising the amino acid sequence of SEQ ID NO: 121 or a variant thereof, wherein the variant comprises two or fewer amino acid substitutions.

2. The anti-IAPP antibody or antigen-binding fragment thereof of claim 1 comprising a variable region comprising the amino acid sequence of SEQ ID NO: 28 or SEQ ID NO: 30, or a variable region comprising an amino acid sequence at least 90% identical to SEQ ID NO: 28 or SEQ ID NO: 30.

3. The anti-IAPP antibody or antigen-binding fragment thereof of claim 1, which
   (a) is capable of binding human IAPP;
   (b) does not substantially recognize amyloid-6 peptide ($A\beta_{1-42}$); and/or
   (c) does not substantially recognize physiological IAPP.

4. The anti-IAPP antibody or antigen-binding fragment thereof of claim 1, which specifically binds an IAPP epitope that comprises the amino acid sequence KCNTATCATQ (SEQ ID NO: 9).

5. The anti-IAPP antibody or antigen-binding fragment thereof of claim 1, which preferentially recognizes IAPP aggregates comprising IAPP oligomers and/or fibrils over physiological IAPP.

6. The anti-IAPP antibody or antigen-binding fragment thereof of claim 1, which is a chimeric rodent-human or a rodentized antibody or antigen-binding fragment thereof.

7. The anti-IAPP antibody or antigen-binding fragment thereof of claim 1, which is selected from the group consisting of a single chain Fv fragment (scFv), an F(ab') fragment, an F(ab) fragment, and an F(ab')$_2$ fragment.

8. The anti-IAPP antibody or antigen-binding fragment thereof of claim 1, which (i) comprises a detectable label selected from the group consisting of an enzyme, a radioisotope, a fluorophore, and a heavy metal; or (ii) is attached to a drug.

9. An anti-IAPP antibody or antigen-binding fragment thereof comprising the following complementarity determining regions (CDRs):
- (a) a CDR-H1 comprising the amino acid sequence of any one of SEQ ID NO: 76,
- (b) a CDR-H2 comprising the amino acid sequence of any one of SEQ ID NO: 94,
- (c) a CDR-H3 comprising the amino acid sequence of any one of SEQ ID NO: 112,
- (d) a CDR-L1 comprising the amino acid sequence of any one of SEQ ID NO: 85,
- (e) a CDR-L2 comprising the amino acid sequence of any one of SEQ ID NO: 103,
- (f) a CDR-L3 comprising the amino acid sequence of any one of SEQ ID NO: 121.

10. The anti-IAPP antibody or antigen-binding fragment thereof of claim 9 comprising a variable region comprising the amino acid sequences of SEQ ID NO: 28 and SEQ ID NO: 30.

11. The antibody or antigen-binding fragment thereof of claim 1, which is a fusion protein comprising a polypeptide sequence which is heterologous to the $V_H$ region and/or $V_L$ region.

12. The antibody or antigen-binding fragment thereof of claim 11, wherein the polypeptide sequence comprises a constant domain.

13. The antibody or antigen-binding fragment thereof of claim 12, wherein the constant domain is a constant domain of the IgG type.

14. The antibody or antigen-binding fragment thereof of claim 9, which is a fusion protein comprising a polypeptide sequence which is heterologous to the $V_H$ region and/or $V_L$ region.

15. The antibody or antigen-binding fragment thereof of claim 14, wherein the polypeptide sequence comprises a constant domain.

16. The antibody or antigen-binding fragment thereof of claim 15, wherein the constant domain is a constant domain of the IgG type.

* * * * *